US008993728B2

(12) United States Patent
Ono et al.

(10) Patent No.: US 8,993,728 B2
(45) Date of Patent: Mar. 31, 2015

(54) ANTI-HUMAN CLCP1 ANTIBODY AND USE THEREOF

(75) Inventors: Ken-ichiro Ono, Nagano (JP); Takashi Takahashi, Aichi (JP)

(73) Assignees: Medical and Biological Laboratories Co., Ltd. (JP); Oncomics Co., Ltd. (JP)

( * ) Notice: Subject to any disclaimer, the term of this patent is extended or adjusted under 35 U.S.C. 154(b) by 1092 days.

(21) Appl. No.: 13/054,554

(22) PCT Filed: Jul. 16, 2009

(86) PCT No.: PCT/JP2009/062901
§ 371 (c)(1),
(2), (4) Date: Aug. 15, 2011

(87) PCT Pub. No.: WO2010/008051
PCT Pub. Date: Jan. 21, 2010

(65) Prior Publication Data
US 2011/0293618 A1     Dec. 1, 2011

(30) Foreign Application Priority Data
Jul. 16, 2008   (JP) ................................ 2008-185305

(51) Int. Cl.
| A61K 39/395 | (2006.01) |
| G01N 33/574 | (2006.01) |
| C07K 16/30 | (2006.01) |
| G01N 33/50 | (2006.01) |
| A61K 39/00 | (2006.01) |

(52) U.S. Cl.
CPC .......... *G01N 33/574* (2013.01); *C07K 16/3023* (2013.01); *G01N 33/5011* (2013.01); *A61K 2039/505* (2013.01); *C07K 2317/24* (2013.01); *C07K 2317/56* (2013.01); *C07K 2317/565* (2013.01); *C07K 2317/73* (2013.01); *C07K 2317/732* (2013.01); *C07K 2317/77* (2013.01); *C07K 2317/92* (2013.01)
USPC ................ 530/387.9; 530/387.7; 530/388.85; 435/7.23; 424/138.1; 424/139.1; 424/155.1; 424/156.1

(58) Field of Classification Search
None
See application file for complete search history.

(56) References Cited

U.S. PATENT DOCUMENTS

| 6,900,031 B2 | 5/2005 | Honjo et al. |
| 7,537,891 B2 | 5/2009 | Huang et al. |
| 7,998,491 B2 * | 8/2011 | Honjo et al. ................ 424/277.1 |
| 2003/0129697 A1 | 7/2003 | Honjo et al. |

FOREIGN PATENT DOCUMENTS

| EP | 2322610 A1 | 5/2011 |
| JP | 2002-523076 A | 7/2002 |
| JP | 2003-189872 A | 7/2003 |
| JP | 2006-515742 A | 6/2006 |
| JP | 2007-130024 A | 5/2007 |
| WO | WO-00/12532 A1 | 3/2000 |
| WO | WO-2004/020583 A2 | 3/2004 |
| WO | WO-2004/023973 A2 | 3/2004 |
| WO | WO-2004/047853 A2 | 6/2004 |
| WO | WO-2006/138275 A2 | 12/2006 |

OTHER PUBLICATIONS

Balmana et al. Ann Oncol 2009; 20(supp 4):iv19-20.*
Kataja et al., Ann Oncol 2009; 20(sup 4): iv10-14.*
Nelson et al., Ann. Intern Med. 2009; 151:727-737.*
"International Application Serial No. PCT/JP2009/062901, International Search Report mailed Oct. 13, 2009", 5 pgs.
"Machine Translation of JP 2007-130024A, published May 31, 2007", 16 pgs.
Kim, M., et al., "Epigenetic Down-Regulation and Suppressive Role of DCBLD2 in Gastric Cell Proliferation and Invasion", *Molecular Cancer Research*, 6(2), (2008), 222-230.
Kobuke, K., et al., "ESDN, a Novel Neuropilin-like Membrane Protein Cloned from Vascular Cells with the Longest Secretory Signal Sequence among Eukaryotes, Is Up-regulated after Vascular Injury", *The Journal of Biological Chemistry*, 276(36), (2001), 34105-34114.
Koshikawa, K., et al., "Hitoohaigan ni okeru Shinkitenikanrenidenshi CLCP no Tanri to Sonokaiseki", *Journal of the Japanese Surgical Society*, vol. 104, Special Issue, (Abstract PS3102-8) (w/English Translation), (2007), p. 520.
Koshikawa, K., et al., "Significant up-regulation of a novel gene, CLCP1, in a highly metastatic lung cancer subline as well as in lung cancers in vivo", *Oncogene*, 21(18), (2002), 2822-2828.
Nadadur, S. S., et a. "A novel TNF-inducible message with putative growth suppressor function", *Biochimica et Biophysica Acta*, 1489(2-3), (1999), 433-439.
Nagai, H., et al., "CLCP1 interacts with semaphorin 4B and regulates motility of lung cancer cells", *Oncogene*, 26, (2007), 4025-4031.

(Continued)

*Primary Examiner* — Sheela J Huff
(74) *Attorney, Agent, or Firm* — Schwegman Lundberg & Woessner, P.A.

(57) ABSTRACT

The present invention provides novel antibodies that recognize the extracellular domain of a human CLCP1 antigen; nucleic acids encoding the antibodies; vectors carrying the nucleic acids in an expressible manner; transformed cells containing the vectors; methods for producing the antibodies; diagnostic methods for cancer or prognosis of cancer, immunohistological or immunocytological assay methods, and kits for determining the expression level of CLCP1 in cells or tissues, all of which use the antibodies; pharmaceutical compositions comprising the antibodies; agents for treating or preventing CLCP1-expressing cancer; agents for inhibiting growth, migration, invasion, or metastasis of CLCP1-expressing cancer cells; immunostaining agents for staining CLCP1-expressing cancer cells; and agents for treating or preventing CLCP1-expressing tumor. The present invention also provides methods of screening for candidate substances that inhibit cancer cell growth, invasion, migration, or metastasis, or candidate substances having cytotoxicity against cancer cells.

34 Claims, 44 Drawing Sheets

(56) References Cited

OTHER PUBLICATIONS

Sadeghi, M. M., et al., "ESDN is a Marker of Vascular Remodeling and Regulator of Cell Proliferation in Graft Arteriosclerois", *American Journal of Transplantation*, 7(9), (2007), 2098-2105.

"European Application Serial No. 09797975.1, Supplementary European Search Report mailed Nov. 9, 2012", 7 pgs.

"International Application Serial No. PCT/JP2009/062901, International Preliminary Report on Patentability dated Feb. 8, 2011", 10 pgs.

"International Application Serial No. PCT/JP2009/062901, Written Opinion mailed Oct. 13, 2009", (w/ English Translation), 15 pgs.

Hofsli, E., et al., "Identification of novel neuroendocrine-specific tumour genes", *British Journal of Cancer*, 99(8), (2008), 1330-1339.

"European Application Serial No. 09797975.1, Office Action mailed Nov. 11, 2013", 5 pgs.

"European Application Serial No. 09797975.1, Office Action mailed Nov. 27, 2012", 1 pg.

"European Application Serial No. 09797975.1, Reply filed Mar. 11, 2014 to Office Action mailed Nov. 11, 2013", 3 pgs.

"European Application Serial No. 09797975.1, Response filed May 29, 2013 to Office Action mailed Nov. 27, 2012", 18 pgs.

\* cited by examiner

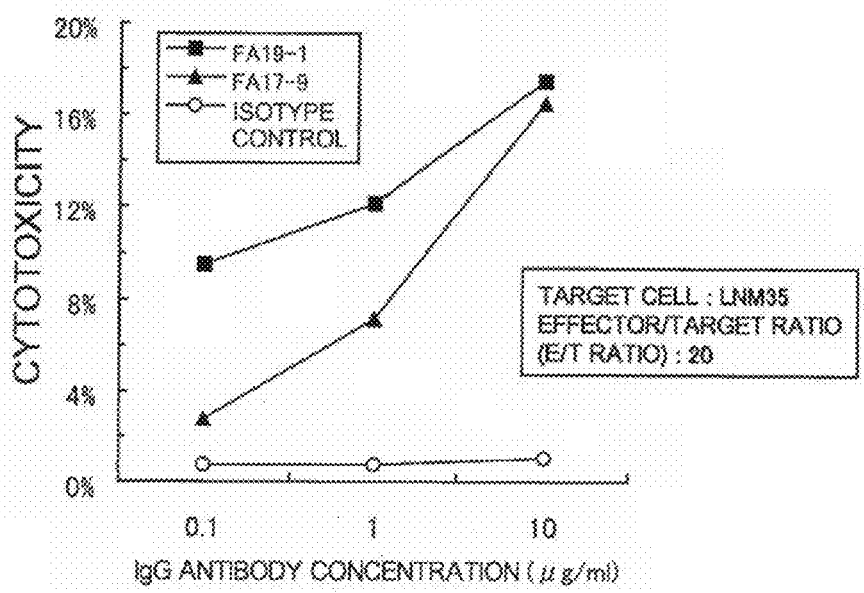
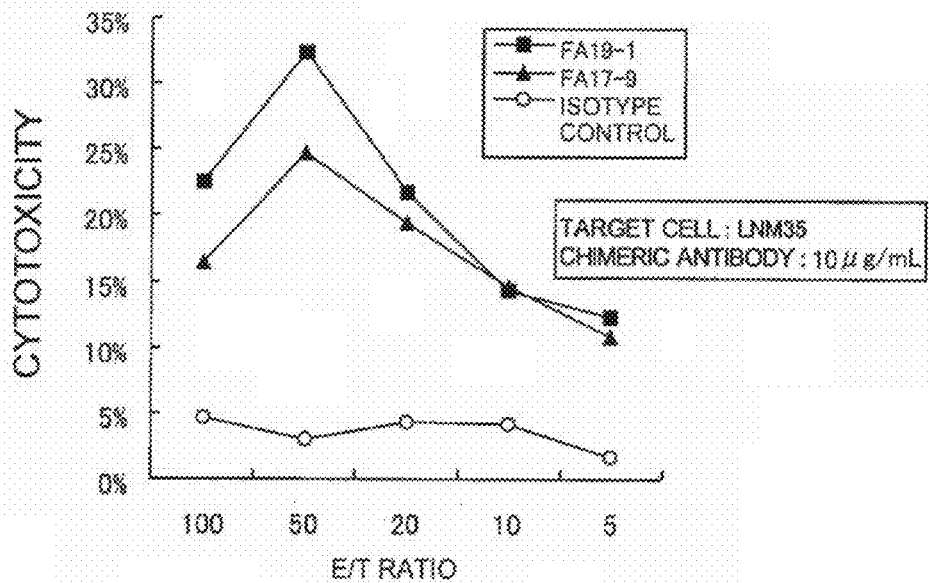
FIG. 22

| Kabat number | 1 0123456789 | 2 0123456789 | 3 0123456789ABCDEF | 4 0123456789 | 5 0123456789 | 6 0123456789 | 7 0123456789 | 8 0123456789 | 9 0123456789ABCDEF | 10 0123456A78 |
|---|---|---|---|---|---|---|---|---|---|---|
| CDR | | | ==L1== | | ==L2== | | | | ==L3== | |
| FA19 VK | -DIQMTQSPSSLSASLGGKVTITCRASQ | | DINKYIAWYQHKPGKGPRLLIHH | TSTLQPGIPSRFSGSGRDYSFSISNLEPEDIATYYC | | | | | QYDYL------ | WTFGGGTKL |
| FA19 CDR | | RASQ----- | DINKYIA | | HTSTLQP | | | | LQYDYL----- | WT |
| FA19RKA | -DIQMTQSPSSLSASVGDRVTITCRASQ | | DINKYIAWYQQKPGKAPKLLIY | HTSTLQPGVPSRFSGSGSGTDFTLTISSLQPEDFATYYC | | | | | LQYDYL------ | WTFGGGTKVEIK |
| U96396FW | -DIQMTQSPSSLSASVGDRVTITC | | | WYQQKPGKAPKLLIY | | GVPSRFSGSGSGTDFTLTISSLQPEDFATYYC | | | | FGGGTKVEIK |
| U96396 | -DIQMTQSPSSLSASVGDRVTITCRASQ | | SISSYLNWYQQKPGKAPKLLIY | AASSLQSGVPSRFSGSGSGTDFTLTISSLQPEDFATYYCQQSYST----- | | | | | | LTFGGGTKVEIK |

(B)

```
                    <==CDR1==>
FA19-1: DIQMTQSPSSLSASLGGKVTITCRASQDINKYIAWYQHKPGKGPRLLIHHTSTLQPGIPSRF
RKA   : .............V.DR...........Q.......A.K...Y.........V......

<==CDR2==>                    <==CDR3==>
FA19-1: SGSGSGRDYSFSISNLEPEDIATYYCLQYDYLWTFGGGTKL
RKA   : .......T.FTLT..S.Q...F.................VEIK

FR= 63 AMINO ACIDS/80 AMINO ACIDS HOMOLOGY 78.8%
```

FIG. 41

SEQUENCE LISTING

<160> NUMBER OF SEQ ID NOS: 112

<210> SEQ ID NO 1
<211> LENGTH: 2328
<212> TYPE: DNA
<213> ORGANISM: Homo sapiens

<400> SEQUENCE: 1

| | | | | | | |
|---|---|---|---|---|---|---|
| atggcgagcc | gggcggtggt | gagagccagg | cgctgcccgc | agtgtcccca | agtccgggcc | 60 |
| gcggccgccg | ccccgcctg | ggccgcgctc | ccctctccc | gctccctccc | tccctgctcc | 120 |
| aactcctcct | ccttctccat | gcctctgttc | ctcctgctct | tacttgtcct | gctcctgctg | 180 |
| ctcgaggacg | ctggagccca | gcaaggtgat | ggatgtggac | acactgtact | aggccctgag | 240 |
| agtggaaccc | ttacatccat | aaactaccca | cagacctatc | ccaacagcac | tgtttgtgaa | 300 |
| tgggagatcc | gtgtaaagat | gggagagaga | gttcgcatca | aatttggtga | ctttgacatt | 360 |
| gaagattctg | attcttgtca | ctttaattac | ttgagaattt | ataatggaat | tggagtcagc | 420 |
| agaactgaaa | taggcaaata | ctgtggtctg | gggttgcaaa | tgaaccattc | aattgaatca | 480 |
| aaaggcaatg | aaatcacatt | gctgttcatg | agtggaatcc | atgtttctgg | acgcggattt | 540 |
| ttggcctcat | actctgttat | agataaacaa | gatctaatta | cttgtttgga | cactgcatcc | 600 |
| aatttttgg | aacctgagtt | cagtaagtac | tgcccagctg | gttgtctgct | tccttttgct | 660 |
| gagatatctg | gaacaattcc | tcatggatat | agagattcct | cgccattgtg | catggctggt | 720 |
| gtgcatgcag | gagtagtgtc | aaacacgttg | gcggccaaa | tcagtgttgt | aattagtaaa | 780 |
| ggtattccct | attatgaaag | ttctttggct | aacaacgtca | catctgtggt | gggacactta | 840 |
| tctacaagtc | tttttacatt | taagacaagt | ggatgttatg | gaacactggg | gatggagtct | 900 |
| ggtgtgatcg | cggatcctca | aataacagca | tcatctgtgc | tggagtggac | tgaccacaca | 960 |
| gggcaagaga | acagttggaa | acccaaaaaa | gccaggctga | aaaaacctgg | accgccttgg | 1020 |
| gctgcttttg | ccactgatga | ataccagtgg | ttacaaatag | atttgaataa | ggaaaagaaa | 1080 |
| ataacaggca | ttataaccac | tggatccacc | atggtggagc | acaattacta | tgtgtctgcc | 1140 |
| tacagaatcc | tgtacagtga | tgatgggcag | aaatggactg | tgtacagaga | gcctggtgtg | 1200 |
| gagcaagata | agatatttca | aggaaacaaa | gattatcacc | aggatgtgcg | taataacttt | 1260 |
| ttgccaccaa | ttattgcacg | ttttattaga | gtgaatccta | cccaatggca | gcagaaaatt | 1320 |
| gccatgaaaa | tggagctgct | cggatgtcag | tttattccta | aaggtcgtcc | tccaaaactt | 1380 |
| actcaacctc | cacctcctcg | gaacagcaat | gacctcaaaa | acactacagc | cctccaaaa | 1440 |
| atagccaaag | tcgtgccccc | aaaatttacg | caaccactac | aacctcgcag | tagcaatgaa | 1500 |
| tttcctgcac | agacagaaca | aacaactgcc | agtcctgata | tcagaaatac | taccgtaact | 1560 |
| ccaaatgtaa | ccaaagatgt | agcgctggct | gcagttcttg | tccctgtgct | ggtcatggtc | 1620 |
| ctcactactc | tcattctcat | attagtgtgt | gcttggcact | ggagaaacag | aaagaaaaaa | 1680 |
| actgaaggca | cctatgactt | accttactgg | gaccgggcag | gttggtggaa | aggaatgaag | 1740 |
| cagtttcttc | ctgcaaaagc | agtggaccat | gaggaaaccc | cagttcgcta | tagcagcagc | 1800 |
| gaagttaatc | acctgagtcc | aagagaagtc | accacagtgc | tgcaggctga | ctctgcagag | 1860 |
| tatgctcagc | cactggtagg | aggaattgtt | ggtacacttc | atcaaagatc | tacctttaaa | 1920 |
| ccagaagaag | gaaaagaagc | aggctatgca | gacctagatc | cttacaactc | accagggcag | 1980 |
| gaagtttatc | atgcctatgc | tgaaccactc | ccaattacgg | ggcctgagta | tgcaaccccca | 2040 |
| atcatcatgg | acatgtcagg | gcaccccaca | acttcagttg | gtcagcccctc | cacatccact | 2100 |

```
ttcaaggcta cggggaacca acctccccca ctagtgggaa cttacaatac acttctctcc    2160
aggactgaca gctgctcctc agcccaggcc cagtatgata ccccgaaagc tgggaagcca    2220
ggtctacctg ccccagacga attggtgtac caggtgccac agagcacaca agaagtatca    2280
ggagcaggaa gggatgggga atgtgatgtt tttaaagaaa tcctttga                 2328
```

<210> SEQ ID NO 2
<211> LENGTH: 775
<212> TYPE: PRT
<213> ORGANISM: Homo sapiens

<400> SEQUENCE: 2

```
Met Ala Ser Arg Ala Val Val Arg Ala Arg Arg Cys Pro Gln Cys Pro
1               5                   10                  15

Gln Val Arg Ala Ala Ala Ala Pro Ala Trp Ala Ala Leu Pro Leu
            20                  25                  30

Ser Arg Ser Leu Pro Pro Cys Ser Asn Ser Ser Phe Ser Met Pro
        35                  40                  45

Leu Phe Leu Leu Leu Leu Val Leu Leu Leu Leu Glu Asp Ala
    50                  55                  60

Gly Ala Gln Gln Gly Asp Gly Cys Gly His Thr Val Leu Gly Pro Glu
65                  70                  75                  80

Ser Gly Thr Leu Thr Ser Ile Asn Tyr Pro Gln Thr Tyr Pro Asn Ser
                85                  90                  95

Thr Val Cys Glu Trp Glu Ile Arg Val Lys Met Gly Glu Arg Val Arg
            100                 105                 110

Ile Lys Phe Gly Asp Phe Asp Ile Glu Asp Ser Asp Ser Cys His Phe
        115                 120                 125

Asn Tyr Leu Arg Ile Tyr Asn Gly Ile Gly Val Ser Arg Thr Glu Ile
    130                 135                 140

Gly Lys Tyr Cys Gly Leu Gly Leu Gln Met Asn His Ser Ile Glu Ser
145                 150                 155                 160

Lys Gly Asn Glu Ile Thr Leu Leu Phe Met Ser Gly Ile His Val Ser
                165                 170                 175

Gly Arg Gly Phe Leu Ala Ser Tyr Ser Val Ile Asp Lys Gln Asp Leu
            180                 185                 190

Ile Thr Cys Leu Asp Thr Ala Ser Asn Phe Leu Glu Pro Glu Phe Ser
        195                 200                 205

Lys Tyr Cys Pro Ala Gly Cys Leu Leu Pro Phe Ala Glu Ile Ser Gly
    210                 215                 220

Thr Ile Pro His Gly Tyr Arg Asp Ser Ser Pro Leu Cys Met Ala Gly
225                 230                 235                 240

Val His Ala Gly Val Val Ser Asn Thr Leu Gly Gly Gln Ile Ser Val
                245                 250                 255

Val Ile Ser Lys Gly Ile Pro Tyr Tyr Glu Ser Ser Leu Ala Asn Asn
            260                 265                 270

Val Thr Ser Val Val Gly His Leu Ser Thr Ser Leu Phe Thr Phe Lys
        275                 280                 285

Thr Ser Gly Cys Tyr Gly Thr Leu Gly Met Glu Ser Gly Val Ile Ala
    290                 295                 300

Asp Pro Gln Ile Thr Ala Ser Ser Val Leu Glu Trp Thr Asp His Thr
305                 310                 315                 320

Gly Gln Glu Asn Ser Trp Lys Pro Lys Lys Ala Arg Leu Lys Lys Pro
                325                 330                 335
```

```
Gly Pro Pro Trp Ala Ala Phe Ala Thr Asp Glu Tyr Gln Trp Leu Gln
            340                 345                 350

Ile Asp Leu Asn Lys Glu Lys Lys Ile Thr Gly Ile Thr Thr Gly
        355                 360                 365

Ser Thr Met Val Glu His Asn Tyr Tyr Val Ser Ala Tyr Arg Ile Leu
    370                 375                 380

Tyr Ser Asp Asp Gly Gln Lys Trp Thr Val Tyr Arg Glu Pro Gly Val
385                 390                 395                 400

Glu Gln Asp Lys Ile Phe Gln Gly Asn Lys Asp Tyr His Gln Asp Val
                405                 410                 415

Arg Asn Asn Phe Leu Pro Pro Ile Ile Ala Arg Phe Ile Arg Val Asn
            420                 425                 430

Pro Thr Gln Trp Gln Gln Lys Ile Ala Met Lys Met Glu Leu Leu Gly
        435                 440                 445

Cys Gln Phe Ile Pro Lys Gly Arg Pro Lys Leu Thr Gln Pro Pro
    450                 455                 460

Pro Pro Arg Asn Ser Asn Asp Leu Lys Asn Thr Ala Pro Pro Lys
465                 470                 475                 480

Ile Ala Lys Gly Arg Ala Pro Lys Phe Thr Gln Pro Leu Gln Pro Arg
                485                 490                 495

Ser Ser Asn Glu Phe Pro Ala Gln Thr Glu Gln Thr Thr Ala Ser Pro
            500                 505                 510

Asp Ile Arg Asn Thr Thr Val Thr Pro Asn Val Thr Lys Asp Val Ala
        515                 520                 525

Leu Ala Ala Val Leu Val Pro Val Leu Val Met Val Leu Thr Thr Leu
530                 535                 540

Ile Leu Ile Leu Val Cys Ala Trp His Trp Arg Asn Arg Lys Lys Lys
545                 550                 555                 560

Thr Glu Gly Thr Tyr Asp Leu Pro Tyr Trp Asp Arg Ala Gly Trp Trp
                565                 570                 575

Lys Gly Met Lys Gln Phe Leu Pro Ala Lys Ala Val Asp His Glu Glu
            580                 585                 590

Thr Pro Val Arg Tyr Ser Ser Glu Val Asn His Leu Ser Pro Arg
        595                 600                 605

Glu Val Thr Thr Val Leu Gln Ala Asp Ser Ala Glu Tyr Ala Gln Pro
610                 615                 620

Leu Val Gly Gly Ile Val Gly Thr Leu His Gln Arg Ser Thr Phe Lys
625                 630                 635                 640

Pro Glu Glu Gly Lys Glu Ala Gly Tyr Ala Asp Leu Asp Pro Tyr Asn
                645                 650                 655

Ser Pro Gly Gln Glu Val Tyr His Ala Tyr Ala Glu Pro Leu Pro Ile
            660                 665                 670

Thr Gly Pro Glu Tyr Ala Thr Pro Ile Ile Met Asp Met Ser Gly His
        675                 680                 685

Pro Thr Thr Ser Val Gly Gln Pro Ser Thr Ser Thr Phe Lys Ala Thr
        690                 695                 700

Gly Asn Gln Pro Pro Leu Val Gly Thr Tyr Asn Thr Leu Leu Ser
705                 710                 715                 720

Arg Thr Asp Ser Cys Ser Ser Ala Gln Ala Gln Tyr Asp Thr Pro Lys
                725                 730                 735

Ala Gly Lys Pro Gly Leu Pro Ala Pro Asp Glu Leu Val Tyr Gln Val
            740                 745                 750
```

```
Pro Gln Ser Thr Gln Glu Val Ser Gly Ala Gly Arg Asp Gly Glu Cys
            755                 760                 765

Asp Val Phe Lys Glu Ile Leu
            770             775

<210> SEQ ID NO 3
<211> LENGTH: 526
<212> TYPE: PRT
<213> ORGANISM: Homo sapiens

<400> SEQUENCE: 3

Met Ala Ser Arg Ala Val Val Arg Ala Arg Arg Cys Pro Gln Cys Pro
1               5                   10                  15

Gln Val Arg Ala Ala Ala Ala Pro Ala Trp Ala Ala Leu Pro Leu
                20                  25                  30

Ser Arg Ser Leu Pro Pro Cys Ser Asn Ser Ser Phe Ser Met Pro
                35                  40                  45

Leu Phe Leu Leu Leu Leu Val Leu Leu Leu Leu Glu Asp Ala
    50                  55                  60

Gly Ala Gln Gln Gly Asp Gly Cys Gly His Thr Val Leu Gly Pro Glu
65              70                  75                  80

Ser Gly Thr Leu Thr Ser Ile Asn Tyr Pro Gln Thr Tyr Pro Asn Ser
                85                  90                  95

Thr Val Cys Glu Trp Glu Ile Arg Val Lys Met Gly Leu Arg Val Arg
                100                 105                 110

Ile Lys Phe Gly Asp Phe Asp Ile Glu Asp Ser Asp Ser Cys His Phe
                115                 120                 125

Asn Tyr Leu Arg Ile Tyr Asn Gly Ile Gly Val Ser Arg Thr Glu Ile
    130                 135                 140

Gly Lys Tyr Cys Gly Leu Gly Leu Gln Met Asn His Ser Ile Glu Ser
145                 150                 155                 160

Lys Gly Asn Glu Ile Thr Leu Leu Phe Met Ser Gly Ile His Val Ser
                165                 170                 175

Gly Arg Gly Phe Leu Ala Ser Tyr Ser Val Ile Asp Lys Gln Asp Leu
                180                 185                 190

Ile Thr Cys Leu Asp Thr Ala Ser Asn Phe Leu Glu Pro Glu Phe Ser
    195                 200                 205

Lys Tyr Cys Pro Ala Gly Cys Leu Leu Pro Phe Ala Glu Ile Ser Gly
                210                 215                 220

Thr Ile Pro His Gly Tyr Arg Asp Ser Ser Pro Leu Cys Met Ala Gly
225                 230                 235                 240

Val His Ala Gly Val Val Ser Asn Thr Leu Gly Gly Gln Ile Ser Val
                245                 250                 255

Val Ile Ser Lys Gly Ile Pro Tyr Tyr Glu Ser Ser Leu Ala Asn Asn
                260                 265                 270

Val Thr Ser Val Val Gly His Leu Ser Thr Ser Leu Phe Thr Phe Lys
                275                 280                 285

Thr Ser Gly Cys Tyr Gly Thr Leu Gly Met Glu Ser Gly Val Ile Ala
    290                 295                 300

Asp Pro Gln Ile Thr Ala Ser Ser Val Leu Glu Trp Thr Asp His Thr
305                 310                 315                 320

Gly Gln Glu Asn Ser Trp Lys Pro Lys Lys Ala Arg Leu Lys Lys Pro
                325                 330                 335

Gly Pro Pro Trp Ala Ala Phe Ala Thr Asp Glu Tyr Gln Trp Leu Gln
                340                 345                 350
```

Ile Asp Leu Asn Lys Glu Lys Ile Thr Gly Ile Ile Thr Thr Gly
            355                 360                 365

Ser Thr Met Val Glu His Asn Tyr Tyr Val Ser Ala Tyr Arg Ile Leu
370                 375                 380

Tyr Ser Asp Asp Gly Gln Lys Trp Thr Val Tyr Arg Glu Pro Gly Val
385                 390                 395                 400

Glu Gln Asp Lys Ile Phe Gln Gly Asn Lys Asp Tyr His Gln Asp Val
                405                 410                 415

Arg Asn Asn Phe Leu Pro Pro Ile Ile Ala Arg Phe Ile Arg Val Asn
            420                 425                 430

Pro Thr Gln Trp Gln Gln Lys Ile Ala Met Lys Met Glu Leu Leu Gly
            435                 440                 445

Cys Gln Phe Ile Pro Lys Gly Arg Pro Pro Lys Leu Thr Gln Pro Pro
            450                 455                 460

Pro Pro Arg Asn Ser Asn Asp Leu Lys Asn Thr Thr Ala Pro Pro Lys
465                 470                 475                 480

Ile Ala Lys Gly Arg Ala Pro Lys Phe Thr Gln Pro Leu Gln Pro Arg
                485                 490                 495

Ser Ser Asn Glu Phe Pro Ala Gln Thr Glu Gln Thr Thr Ala Ser Pro
            500                 505                 510

Asp Ile Arg Asn Thr Thr Val Thr Pro Asn Val Thr Lys Asp
            515                 520                 525

<210> SEQ ID NO 4
<211> LENGTH: 243
<212> TYPE: PRT
<213> ORGANISM: Homo sapiens

<400> SEQUENCE: 4

Leu Phe Thr Phe Lys Thr Ser Gly Cys Tyr Gly Thr Leu Gly Met Glu
1               5                   10                  15

Ser Gly Val Ile Ala Asp Pro Gln Ile Thr Ala Ser Ser Val Leu Glu
            20                  25                  30

Trp Thr Asp His Thr Gly Gln Glu Asn Ser Trp Lys Pro Lys Lys Ala
        35                  40                  45

Arg Leu Lys Lys Pro Gly Pro Pro Trp Ala Ala Phe Ala Thr Asp Glu
50                  55                  60

Tyr Gln Trp Leu Gln Ile Asp Leu Asn Lys Glu Lys Lys Ile Thr Gly
65                  70                  75                  80

Ile Ile Thr Thr Gly Ser Thr Met Val Glu His Asn Tyr Tyr Val Ser
                85                  90                  95

Ala Tyr Arg Ile Leu Tyr Ser Asp Asp Gly Gln Lys Trp Thr Val Tyr
            100                 105                 110

Arg Glu Pro Gly Val Glu Gln Asp Lys Ile Phe Gln Gly Asn Lys Asp
        115                 120                 125

Tyr His Gln Asp Val Arg Asn Asn Phe Leu Pro Pro Ile Ile Ala Arg
    130                 135                 140

Phe Ile Arg Val Asn Pro Thr Gln Trp Gln Gln Lys Ile Ala Met Lys
145                 150                 155                 160

Met Glu Leu Leu Gly Cys Gln Phe Ile Pro Lys Gly Arg Pro Pro Lys
                165                 170                 175

Leu Thr Gln Pro Pro Pro Pro Arg Asn Ser Asn Asp Leu Lys Asn Thr
            180                 185                 190

Thr Ala Pro Pro Lys Ile Ala Lys Gly Arg Ala Pro Lys Phe Thr Gln

```
                195                 200                 205
Pro Leu Gln Pro Arg Ser Ser Asn Glu Phe Pro Ala Gln Thr Glu Gln
    210                 215                 220

Thr Thr Ala Ser Pro Asp Ile Arg Asn Thr Thr Val Thr Pro Asn Val
225                 230                 235                 240

Thr Lys Asp

<210> SEQ ID NO 5
<211> LENGTH: 372
<212> TYPE: DNA
<213> ORGANISM: Mus musculus

<400> SEQUENCE: 5
gaggtccagc tgcagcagtc tggacctgag ctggtaaagc ctggggcttc agtgaagatg      60
tcctgcaagg cttctggata cacattcact acctatgtta tgcactgggt gaagcagaag     120
cctgggcagg gccttgagtg gattggatat attaatcctt acaatgatgg tactaagtac     180
aatgagaagt tcaaaggcaa ggccacactg acttcagaca atcctccag cacagcctac      240 atggagctca gcagcctgac ctctgaggac tctgcggtct attactgtgc aagaggggcc     300
aattactacg gtagtagcta caactggtcc ttcgatgtct ggggcgcagg gaccacggtc     360
accgtctcct ca                                                         372

<210> SEQ ID NO 6
<211> LENGTH: 124
<212> TYPE: PRT
<213> ORGANISM: Mus musculus

<400> SEQUENCE: 6

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ala Asn Tyr Tyr Gly Ser Ser Tyr Asn Trp Ser Phe Asp
            100                 105                 110

Val Trp Gly Ala Gly Thr Thr Val Thr Val Ser Ser
        115                 120

<210> SEQ ID NO 7
<211> LENGTH: 5
<212> TYPE: PRT
<213> ORGANISM: Mus musculus

<400> SEQUENCE: 7

Thr Tyr Val Met His
1               5

<210> SEQ ID NO 8
<211> LENGTH: 17
<212> TYPE: PRT
```

<213> ORGANISM: Mus musculus

<400> SEQUENCE: 8

Tyr Ile Asn Pro Tyr Asn Asp Gly Thr Lys Tyr Asn Glu Lys Phe Lys
1               5                   10                  15

Gly

<210> SEQ ID NO 9
<211> LENGTH: 15
<212> TYPE: PRT
<213> ORGANISM: Mus musculus

<400> SEQUENCE: 9

Gly Ala Asn Tyr Tyr Gly Ser Ser Tyr Asn Trp Ser Phe Asp Val
1               5                   10                  15

<210> SEQ ID NO 10
<211> LENGTH: 309
<212> TYPE: DNA
<213> ORGANISM: Mus musculus

<400> SEQUENCE: 10

```
gacatccaga tgacacagtc tccatcctca ctgtctgcat ctctgggagg caaagtcacc      60
atcacttgca aggcaagcca agacattaac aagtatatag cttggtacca acacaagcct    120
ggagaaggtc ctaggctact catacattac acatctacat tacagccagg catcccatca    180
aggttcagtg gaagtgggtc tgggagagat tattccttca gcatcagcaa cctggagcct    240
gaagatattg caacttatta ttgtctacag tatgattatc tgtggacgtt cggtggaggc    300
accaagctg                                                           309
```

<210> SEQ ID NO 11
<211> LENGTH: 103
<212> TYPE: PRT
<213> ORGANISM: Mus musculus

<400> SEQUENCE: 11

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Glu Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Tyr Leu Trp Thr
                85                  90                  95

Phe Gly Gly Gly Thr Lys Leu
            100

<210> SEQ ID NO 12
<211> LENGTH: 11
<212> TYPE: PRT
<213> ORGANISM: Mus musculus

<400> SEQUENCE: 12

Lys Ala Ser Gln Asp Ile Asn Lys Tyr Ile Ala
1               5                   10

<210> SEQ ID NO 13
<211> LENGTH: 8
<212> TYPE: PRT
<213> ORGANISM: Mus musculus

<400> SEQUENCE: 13

Leu Gln Tyr Asp Tyr Leu Trp Thr
1               5

<210> SEQ ID NO 14
<211> LENGTH: 372
<212> TYPE: DNA
<213> ORGANISM: Mus musculus

<400> SEQUENCE: 14

```
gaggtccagc tgcagcagtc tggacctgag ctggtaaagc ctggggcttc agtgaagatg      60
tcctgcaagg cttctggata cacattcact acctatatta tgcactgggt gaagcagaag     120
cctgggcagg gccttgagtg gattggatat attaatcctt acaatgatgg tactaagtac     180
aatgagaagt tcaaaggcga ggccacactg acttcagaca atcctccag tacagcctac      240 atggagctca gcagcctgac ctctgaggac tctgcggtct attactgtgc aagaggggcc     300
aattactacg gtagtaacta caactggtcc ttcgatgtct ggggcgcagg gaccacggtc     360
accgtctcct ca                                                         372
```

<210> SEQ ID NO 15
<211> LENGTH: 124
<212> TYPE: PRT
<213> ORGANISM: Mus musculus

<400> SEQUENCE: 15

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Glu Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ala Asn Tyr Tyr Gly Ser Asn Tyr Asn Trp Ser Phe Asp
            100                 105                 110

Val Trp Gly Ala Gly Thr Thr Val Thr Val Ser Ser
        115                 120

<210> SEQ ID NO 16
<211> LENGTH: 5
<212> TYPE: PRT
<213> ORGANISM: Mus musculus

<400> SEQUENCE: 16

Thr Tyr Ile Met His
1               5

<210> SEQ ID NO 17

```
<211> LENGTH: 17
<212> TYPE: PRT
<213> ORGANISM: Mus musculus

<400> SEQUENCE: 17

Tyr Ile Asn Pro Tyr Asn Asp Gly Thr Lys Tyr Asn Glu Lys Phe Lys
1               5                   10                  15

Gly

<210> SEQ ID NO 18
<211> LENGTH: 15
<212> TYPE: PRT
<213> ORGANISM: Mus musculus

<400> SEQUENCE: 18

Gly Ala Asn Tyr Tyr Gly Ser Asn Tyr Asn Trp Ser Phe Asp Val
1               5                   10                  15

<210> SEQ ID NO 19
<211> LENGTH: 309
<212> TYPE: DNA
<213> ORGANISM: Mus musculus

<400> SEQUENCE: 19
gacatccaga tgacacagtc tccatcctca ctgtctgcat ctctgggagg caaagtcacc      60
atcacttgca gggcaagcca agacattaac aagtatatag cttggtacca acacaagcct     120
ggaaaaggtc ctaggctgct catacatcac acatgtacat tacagccagg catcccatca     180
aggttcagtg gaagtgggtc tgggagagat tattccttca gcatcagcaa cctggagcct     240
gaagatattg caacttatta ttgtctacag tatgattatc tgtggacgtt cggtggaggc     300
accaagctg                                                             309

<210> SEQ ID NO 20
<211> LENGTH: 103
<212> TYPE: PRT
<213> ORGANISM: Mus musculus

<400> SEQUENCE: 20

Asp Ile Gln Met Thr Gln Ser Pro Ser Ser Leu Ser Ala Ser Leu Gly
1               5                   10                  15

Gly Lys Val Thr Ile Thr Cys Arg Ala Ser Gln Asp Ile Asn Lys Tyr
                20                  25                  30

Ile Ala Trp Tyr Gln His Lys Pro Gly Lys Gly Pro Arg Leu Leu Ile
            35                  40                  45

His His Thr Cys Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Tyr Leu Trp Thr
                85                  90                  95

Phe Gly Gly Gly Thr Lys Leu
            100

<210> SEQ ID NO 21
<211> LENGTH: 11
<212> TYPE: PRT
<213> ORGANISM: Mus musculus

<400> SEQUENCE: 21
```

```
Arg Ala Ser Gln Asp Ile Asn Lys Tyr Ile Ala
1               5                   10
```

<210> SEQ ID NO 22
<211> LENGTH: 8
<212> TYPE: PRT
<213> ORGANISM: Mus musculus

<400> SEQUENCE: 22

```
Leu Gln Tyr Asp Tyr Leu Trp Thr
1               5
```

<210> SEQ ID NO 23
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 23

```
Gly Gly Gly Gly Ser
1               5
```

<210> SEQ ID NO 24
<211> LENGTH: 21
<212> TYPE: DNA
<213> ORGANISM: Homo sapiens

<400> SEQUENCE: 24

```
ctatgcaggc agactgccgg c                                          21
```

<210> SEQ ID NO 25
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 25

```
cccaagcttt gcaggcagac tgccggc                                    27
```

<210> SEQ ID NO 26
<211> LENGTH: 34
<212> TYPE: DNA
<213> ORGANISM: Artificial
<220> FEATURE:
<223> OTHER INFORMATION: An artificially synthesized primer sequence

<400> SEQUENCE: 26

```
cgaggtacca aggatttctt taaaaacatc acat                            34
```

<210> SEQ ID NO 27
<211> LENGTH: 21
<212> TYPE: PRT
<213> ORGANISM: Artificial
<220> FEATURE:
<223> OTHER INFORMATION: An artificially synthesized peptide sequence

<400> SEQUENCE: 27

```
Met Arg Ser Leu Leu Ile Leu Val Leu Cys Phe Leu Pro Leu Ala Ala
1               5                   10                  15
Leu Gly Ala Ala Ala
                20
```

<210> SEQ ID NO 28

```
<211> LENGTH: 63
<212> TYPE: DNA
<213> ORGANISM: Artificial
<220> FEATURE:
<223> OTHER INFORMATION: An artificially synthesized nucleotide sequence

<400> SEQUENCE: 28
atgaggtctt tgctaatctt ggtgctttgc ttcctgcccc tggctgctct gggggcggcc    60
gcc                                                                 63

<210> SEQ ID NO 29
<211> LENGTH: 33
<212> TYPE: DNA
<213> ORGANISM: Artificial
<220> FEATURE:
<223> OTHER INFORMATION: An artificially synthesized primer sequence

<400> SEQUENCE: 29
aatagcggcc gcaccatggc gagccgggcg gtg                                 33

<210> SEQ ID NO 30
<211> LENGTH: 37
<212> TYPE: DNA
<213> ORGANISM: Artificial
<220> FEATURE:
<223> OTHER INFORMATION: An artificially synthesized primer sequence

<400> SEQUENCE: 30
acgcgtcgac aaggatttct ttaaaaacat cacattc                             37

<210> SEQ ID NO 31
<211> LENGTH: 33
<212> TYPE: DNA
<213> ORGANISM: Artificial
<220> FEATURE:
<223> OTHER INFORMATION: An artificially synthesized primer sequence

<400> SEQUENCE: 31
acgcgtcgac tacatctttg gttacatttg gag                                 33

<210> SEQ ID NO 32
<211> LENGTH: 36
<212> TYPE: DNA
<213> ORGANISM: Artificial
<220> FEATURE:
<223> OTHER INFORMATION: An artificially synthesized primer sequence

<400> SEQUENCE: 32
aatagcggcc gctctttta catttaagac aagtgg                               36

<210> SEQ ID NO 33
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 33
cgactggagc acgaggacac tga                                            23

<210> SEQ ID NO 34
<211> LENGTH: 19
<212> TYPE: DNA
<213> ORGANISM: Artificial
<220> FEATURE:
<223> OTHER INFORMATION: An artificially synthesized primer sequence
```

```
<400> SEQUENCE: 34
aattttcttg tccacctgg                                                    19

<210> SEQ ID NO 35
<211> LENGTH: 26
<212> TYPE: DNA
<213> ORGANISM: Artificial
<220> FEATURE:
<223> OTHER INFORMATION: An artificially synthesized primer sequence

<400> SEQUENCE: 35
ctaacactca ttcctgttga agctct                                            26

<210> SEQ ID NO 36
<211> LENGTH: 30
<212> TYPE: PRT
<213> ORGANISM: Mus musculus

<400> SEQUENCE: 36

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr
            20                  25                  30

<210> SEQ ID NO 37
<211> LENGTH: 14
<212> TYPE: PRT
<213> ORGANISM: Mus musculus

<400> SEQUENCE: 37

Trp Val Lys Gln Lys Pro Gly Gln Gly Leu Glu Trp Ile Gly
1               5                   10

<210> SEQ ID NO 38
<211> LENGTH: 32
<212> TYPE: PRT
<213> ORGANISM: Mus musculus

<400> SEQUENCE: 38

Glu Ala Thr Leu Thr Ser Asp Lys Ser Ser Ser Thr Ala Tyr Met Glu
1               5                   10                  15

Leu Ser Ser Leu Thr Ser Glu Asp Ser Ala Val Tyr Tyr Cys Ala Arg
            20                  25                  30

<210> SEQ ID NO 39
<211> LENGTH: 11
<212> TYPE: PRT
<213> ORGANISM: Mus musculus

<400> SEQUENCE: 39

Trp Gly Ala Gly Thr Thr Val Thr Val Ser Ser
1               5                   10

<210> SEQ ID NO 40
<211> LENGTH: 121
<212> TYPE: PRT
<213> ORGANISM: Homo sapiens

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
```

```
            20                  25                  30

Ala Ile His Trp Val Arg Gln Ala Pro Gly Gln Arg Leu Glu Trp Ile
        35                  40                  45

Gly Trp Ile Asn Thr Ala Ser Ala Asn Thr Lys Cys Ser Gln Asn Phe
    50                  55                  60

Gln Gly Arg Val Thr Val Thr Arg Asp Thr Ser Ala Asn Thr Ala Tyr
65                  70                  75                  80

Met Glu Leu Ser Ser Leu Lys Ser Glu Asp Thr Ala Val Tyr Tyr Cys
                85                  90                  95

Ala Arg Cys Ser Gly Asp Thr Cys Tyr Gln Gly Ser Asp Tyr Trp Gly
            100                 105                 110

Gln Gly Thr Leu Val Thr Val Ser Ser
        115                 120

<210> SEQ ID NO 41
<211> LENGTH: 30
<212> TYPE: PRT
<213> ORGANISM: Homo sapiens

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 42
<211> LENGTH: 14
<212> TYPE: PRT
<213> ORGANISM: Homo sapiens

<400> SEQUENCE: 42

Trp Val Arg Gln Ala Pro Gly Gln Arg Leu Glu Trp Ile Gly
1               5                   10

<210> SEQ ID NO 43
<211> LENGTH: 32
<212> TYPE: PRT
<213> ORGANISM: Homo sapiens

<400> SEQUENCE: 43

Arg Val Thr Val Thr Arg Asp Thr Ser Ala Asn Thr Ala Tyr Met Glu
1               5                   10                  15

Leu Ser Ser Leu Lys Ser Glu Asp Thr Ala Val Tyr Tyr Cys Ala Arg
            20                  25                  30

<210> SEQ ID NO 44
<211> LENGTH: 11
<212> TYPE: PRT
<213> ORGANISM: Homo sapiens

<400> SEQUENCE: 44

Trp Gly Gln Gly Thr Leu Val Thr Val Ser Ser
1               5                   10

<210> SEQ ID NO 45
<211> LENGTH: 124
<212> TYPE: PRT
<213> ORGANISM: Artificial
<220> FEATURE:
<223> OTHER INFORMATION: An artificially synthesized amino acid sequence

<400> SEQUENCE: 45
```

-continued

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Thr Tyr
                20                  25                  30

Ile Met His Trp Val Arg Gln Ala Pro Gly Gln Arg Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Arg Val Thr Val Thr Arg Asp Thr Ser Ala Asn Thr Ala Tyr
65                  70                  75                  80

Met Glu Leu Ser Ser Leu Lys Ser Glu Asp Thr Ala Val Tyr Tyr Cys
                85                  90                  95

Ala Arg Gly Ala Asn Tyr Tyr Gly Ser Asn Tyr Asn Trp Ser Phe Asp
            100                 105                 110

Val Trp Gly Gln Gly Thr Leu Val Thr Val Ser Ser
        115                 120
```

<210> SEQ ID NO 46
<211> LENGTH: 23
<212> TYPE: PRT
<213> ORGANISM: Mus musculus

<400> SEQUENCE: 46

```
Asp Ile Gln Met Thr Gln Ser Pro Ser Ser Leu Ser Ala Ser Leu Gly
1               5                   10                  15

Gly Lys Val Thr Ile Thr Cys
            20
```

<210> SEQ ID NO 47
<211> LENGTH: 15
<212> TYPE: PRT
<213> ORGANISM: Mus musculus

<400> SEQUENCE: 47

```
Trp Tyr Gln His Lys Pro Gly Lys Gly Pro Arg Leu Leu Ile His
1               5                   10                  15
```

<210> SEQ ID NO 48
<211> LENGTH: 32
<212> TYPE: PRT
<213> ORGANISM: Mus musculus

<400> SEQUENCE: 48

```
Gly Ile Pro Ser Arg Phe Ser Gly Ser Gly Ser Gly Arg Asp Tyr Ser
1               5                   10                  15

Phe Ser Ile Ser Asn Leu Glu Pro Glu Asp Ile Ala Thr Tyr Tyr Cys
                20                  25                  30
```

<210> SEQ ID NO 49
<211> LENGTH: 10
<212> TYPE: PRT
<213> ORGANISM: Mus musculus

<400> SEQUENCE: 49

```
Phe Gly Gly Gly Thr Lys Leu Glu Ile Lys
1               5                   10
```

<210> SEQ ID NO 50
<211> LENGTH: 106
<212> TYPE: PRT

<213> ORGANISM: Homo sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Thr
                85                  90                  95

Phe Gly Gly Gly Thr Lys Val Glu Ile Lys
            100                 105

<210> SEQ ID NO 51
<211> LENGTH: 23
<212> TYPE: PRT
<213> ORGANISM: Homo sapiens

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 52
<211> LENGTH: 15
<212> TYPE: PRT
<213> ORGANISM: Homo sapiens

<400> SEQUENCE: 52

Trp Tyr Gln Gln Lys Pro Gly Lys Ala Pro Lys Leu Leu Ile Tyr
1               5                   10                  15

<210> SEQ ID NO 53
<211> LENGTH: 32
<212> TYPE: PRT
<213> ORGANISM: Homo sapiens

<400> SEQUENCE: 53

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 54
<211> LENGTH: 10
<212> TYPE: PRT
<213> ORGANISM: Homo sapiens

<400> SEQUENCE: 54

Phe Gly Gly Gly Thr Lys Val Glu Ile Lys
1               5                   10

<210> SEQ ID NO 55
<211> LENGTH: 106
<212> TYPE: PRT

<210> SEQ ID NO 55 (continued)
<213> ORGANISM: Artificial
<220> FEATURE:
<223> OTHER INFORMATION: An artificially synthesized amino acid sequence

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Lys Tyr
            20                  25                  30

Ile Ala Trp Tyr Gln Gln Lys Pro Gly Lys Ala Pro Lys Leu Leu Ile
        35                  40                  45

Tyr His Thr Ser Thr Leu Gln Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Tyr Leu Trp Thr
                85                  90                  95

Phe Gly Gly Gly Thr Lys Val Glu Ile Lys
            100                 105
```

<210> SEQ ID NO 56
<211> LENGTH: 7
<212> TYPE: PRT
<213> ORGANISM: Mus musculus

<400> SEQUENCE: 56

```
Tyr Thr Ser Thr Leu Gln Pro
1               5
```

<210> SEQ ID NO 57
<211> LENGTH: 7
<212> TYPE: PRT
<213> ORGANISM: Mus musculus

<400> SEQUENCE: 57

```
His Thr Cys Thr Leu Gln Pro
1               5
```

<210> SEQ ID NO 58
<211> LENGTH: 363
<212> TYPE: DNA
<213> ORGANISM: Mus musculus

<400> SEQUENCE: 58

```
gaggttcagc tgcagcagtc tggggctgag cttgtgaggc caggggcctt agtcaagttg      60
tcctgcaaag cttctggctt caacattaaa gactactata tgcactgggt gaagcagagg     120
cctgaacagg gcctggagtg gattggatgg attgatcctg agaatgataa tactatatat     180
gacccgaagt tccagggcaa ggccagtata acagcagaca cgtcctccaa cacagcctac     240
ctgcacctca gcagcctgac atctgaggac actgccgtct attactgtgc tagagcctat     300
ggttacgacg attactatgc tatggaatac tggggtcaag gaacctcagt caccgtctcc     360
tca                                                                    363
```

<210> SEQ ID NO 59
<211> LENGTH: 121
<212> TYPE: PRT
<213> ORGANISM: Mus musculus

<400> SEQUENCE: 59

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Asp Asn Thr Ile Tyr Asp Pro Lys Phe
    50                  55                  60

Gln Gly Lys Ala Ser Ile Thr Ala Asp Thr Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Ala Tyr Gly Tyr Asp Asp Tyr Tyr Ala Met Glu Tyr Trp Gly
            100                 105                 110

Gln Gly Thr Ser Val Thr Val Ser Ser
            115                 120

<210> SEQ ID NO 60
<211> LENGTH: 5
<212> TYPE: PRT
<213> ORGANISM: Mus musculus

<400> SEQUENCE: 60

Asp Tyr Tyr Met His
1               5

<210> SEQ ID NO 61
<211> LENGTH: 17
<212> TYPE: PRT
<213> ORGANISM: Mus musculus

<400> SEQUENCE: 61

Trp Ile Asp Pro Glu Asn Asp Asn Thr Ile Tyr Asp Pro Lys Phe Gln
1               5                   10                  15

Gly

<210> SEQ ID NO 62
<211> LENGTH: 12
<212> TYPE: PRT
<213> ORGANISM: Mus musculus

<400> SEQUENCE: 62

Ala Tyr Gly Tyr Asp Asp Tyr Tyr Ala Met Glu Tyr
1               5                   10

<210> SEQ ID NO 63
<211> LENGTH: 327
<212> TYPE: DNA
<213> ORGANISM: Mus musculus

<400> SEQUENCE: 63
aacattatga tgacacagtc gccatcatct ctggctgtgt ctgcaggaga aaaggtcact      60
atgagctgta agtccagtca aagtgtttta tacagttcaa atcagaagaa ctacttggcc     120
tggtaccagc agaaaccagg gcagtctcct aaactgctga tctactggac ttccactagg     180
gaatcaggtg tcccggatcg cttcacaggc agtggatctg ggacagattt tactcttacc     240
atcagcagtg ttcaagctga agacctggca atttattact gtcatcaata tctctactcg     300
tacacgttcg gaggggggac caagctg                                         327

<210> SEQ ID NO 64
<211> LENGTH: 109
<212> TYPE: PRT
<213> ORGANISM: Mus musculus

<400> SEQUENCE: 64

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Thr Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys His Gln
                85                  90                  95

Tyr Leu Tyr Ser Tyr Thr Phe Gly Gly Gly Thr Lys Leu
            100                 105

<210> SEQ ID NO 65
<211> LENGTH: 17
<212> TYPE: PRT
<213> ORGANISM: Mus musculus

<400> SEQUENCE: 65

Lys Ser Ser Gln Ser Val Leu Tyr Ser Ser Asn Gln Lys Asn Tyr Leu
1               5                   10                  15

Ala

<210> SEQ ID NO 66
<211> LENGTH: 7
<212> TYPE: PRT
<213> ORGANISM: Mus musculus

<400> SEQUENCE: 66

Trp Thr Ser Thr Arg Glu Ser
1               5

<210> SEQ ID NO 67
<211> LENGTH: 8
<212> TYPE: PRT
<213> ORGANISM: Mus musculus

<400> SEQUENCE: 67

His Gln Tyr Leu Tyr Ser Tyr Thr
1               5

<210> SEQ ID NO 68
<211> LENGTH: 34
<212> TYPE: DNA
<213> ORGANISM: Artificial
<220> FEATURE:
<223> OTHER INFORMATION: An artificially synthesized primer sequence

<400> SEQUENCE: 68
cccaagctta ccatggaatg gagttggata tttc        34

<210> SEQ ID NO 69
<211> LENGTH: 25

```
<212> TYPE: DNA
<213> ORGANISM: Artificial
<220> FEATURE:
<223> OTHER INFORMATION: An artificially synthesized primer sequence

<400> SEQUENCE: 69
ccgctcgaga cggtgaccgt ggtcc                                    25

<210> SEQ ID NO 70
<211> LENGTH: 34
<212> TYPE: DNA
<213> ORGANISM: Artificial
<220> FEATURE:
<223> OTHER INFORMATION: An artificially synthesized primer sequence

<400> SEQUENCE: 70
cccaagctta ccatgagacc gtctattcag ttcc                          34

<210> SEQ ID NO 71
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 71
aatacgtacg tttgatttcc agcttggtcc c                             31

<210> SEQ ID NO 72
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 72

His Thr Ser Thr Leu Gln Pro
1               5

<210> SEQ ID NO 73
<211> LENGTH: 26
<212> TYPE: DNA
<213> ORGANISM: Artificial
<220> FEATURE:
<223> OTHER INFORMATION: An artificially synthesized primer sequence

<400> SEQUENCE: 73
cggaattctg tttggacact gcatcc                                   26

<210> SEQ ID NO 74
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 74
acgcgtcgac tggttgcgta aattttgg                                 28

<210> SEQ ID NO 75
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 75
```

```
acgcgtcgac aggaataaac tgacatcc                                          28

<210> SEQ ID NO 76
<211> LENGTH: 29
<212> TYPE: DNA
<213> ORGANISM: Artificial
<220> FEATURE:
<223> OTHER INFORMATION: An artificially synthesized primer sequence

<400> SEQUENCE: 76
acgcgtcgac tgctgttccg aggaggtgg                                         29

<210> SEQ ID NO 77
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 77
acgcgtcgac aggtggaggt tgagtaag                                          28

<210> SEQ ID NO 78
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 78
acgcgtcgac agtaagtttt ggaggacg                                          28

<210> SEQ ID NO 79
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 79
acgcgtcgac aggacgacct ttaggaat                                          28

<210> SEQ ID NO 80
<211> LENGTH: 54
<212> TYPE: DNA
<213> ORGANISM: Artificial
<220> FEATURE:
<223> OTHER INFORMATION: An artificially synthesized primer sequence

<400> SEQUENCE: 80
cgtcctccaa aactttgaag atctctcgag cggccgcatc gtgactgact gacg             54

<210> SEQ ID NO 81
<211> LENGTH: 53
<212> TYPE: DNA
<213> ORGANISM: Artificial
<220> FEATURE:
<223> OTHER INFORMATION: An artificially synthesized primer sequence

<400> SEQUENCE: 81
cgggatcctt tattcctaaa ggtcgtcctc caaaactttg aagatctctc gag              53

<210> SEQ ID NO 82
<211> LENGTH: 54
<212> TYPE: DNA
```

```
<213> ORGANISM: Artificial
<220> FEATURE:
<223> OTHER INFORMATION: An artificially synthesized primer sequence

<400> SEQUENCE: 82
actcaacctc caccttgaag atctctcgag cggccgcatc gtgactgact gacg        54

<210> SEQ ID NO 83
<211> LENGTH: 53
<212> TYPE: DNA
<213> ORGANISM: Artificial
<220> FEATURE:
<223> OTHER INFORMATION: An artificially synthesized primer sequence

<400> SEQUENCE: 83
cgggatcccg tcctccaaaa cttactcaac ctccaccttg aagatctctc gag         53

<210> SEQ ID NO 84
<211> LENGTH: 54
<212> TYPE: DNA
<213> ORGANISM: Artificial
<220> FEATURE:
<223> OTHER INFORMATION: An artificially synthesized primer sequence

<400> SEQUENCE: 84
cctcggaaca gcaattgaag atctctcgag cggccgcatc gtgactgact gacg        54

<210> SEQ ID NO 85
<211> LENGTH: 53
<212> TYPE: DNA
<213> ORGANISM: Artificial
<220> FEATURE:
<223> OTHER INFORMATION: An artificially synthesized primer sequence

<400> SEQUENCE: 85
cgggatccac tcaacctcca cctcctcgga acagcaattg aagatctctc gag         53

<210> SEQ ID NO 86
<211> LENGTH: 54
<212> TYPE: DNA
<213> ORGANISM: Artificial
<220> FEATURE:
<223> OTHER INFORMATION: An artificially synthesized primer sequence

<400> SEQUENCE: 86
gacctcaaaa acacttgaag atctctcgag cggccgcatc gtgactgact gacg        54

<210> SEQ ID NO 87
<211> LENGTH: 53
<212> TYPE: DNA
<213> ORGANISM: Artificial
<220> FEATURE:
<223> OTHER INFORMATION: An artificially synthesized primer sequence

<400> SEQUENCE: 87
cgggatcccc tcggaacagc aatgacctca aaaacacttg aagatctctc gag         53

<210> SEQ ID NO 88
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 88
aactgcaggc atcgtggtgt cacgctcgtc                                   30
```

<210> SEQ ID NO 89
<211> LENGTH: 480
<212> TYPE: DNA
<213> ORGANISM: Mus musculus

<400> SEQUENCE: 89

```
atggaatgga gttggatatt tctctttctc ctgtcaggaa ctgcaggtgt ccactctgag      60
gtccagctgc agcagtctgg acctgagctg gtaaagcctg ggcttcagt gaagatgtcc     120
tgcaaggctt ctggatacac attcactacc tatgttatgc actgggtgaa gcagaagcct    180
gggcagggcc ttgagtggat tggatatatt aatccttaca atgatggtac taagtacaat    240
gagaagttca aggcaaggc cacactgact tcagacaaat cctccagcac agcctacatg     300
gagctcagca gcctgacctc tgaggactct gcggtctatt actgtgcaag aggggccaat    360
tactacggta gtagctacaa ctggtccttc gatgtctggg gcgcaggga cacggtcacc     420
gtctcctcag ccaaaacgac accccatct gtctatccac tggcccctgg atctgctgcc     480
```

<210> SEQ ID NO 90
<211> LENGTH: 160
<212> TYPE: PRT
<213> ORGANISM: Mus musculus

<400> SEQUENCE: 90

```
Met Glu Trp Ser Trp Ile Phe Leu Phe Leu Leu Ser Gly Thr Ala Gly
  1               5                  10                  15

Val His Ser Glu Val Gln Leu Gln Gln Ser Gly Pro Glu Leu Val Lys
             20                  25                  30

Pro Gly Ala Ser Val Lys Met Ser Cys Lys Ala Ser Gly Tyr Thr Phe
         35                  40                  45

Thr Thr Tyr Val Met His Trp Val Lys Gln Lys Pro Gly Gln Gly Leu
     50                  55                  60

Glu Trp Ile Gly Tyr Ile Asn Pro Tyr Asn Asp Gly Thr Lys Tyr Asn
 65                  70                  75                  80

Glu Lys Phe Lys Gly Lys Ala Thr Leu Thr Ser Asp Lys Ser Ser Ser
                 85                  90                  95

Thr Ala Tyr Met Glu Leu Ser Ser Leu Thr Ser Glu Asp Ser Ala Val
            100                 105                 110

Tyr Tyr Cys Ala Arg Gly Ala Asn Tyr Tyr Gly Ser Ser Tyr Asn Trp
        115                 120                 125

Ser Phe Asp Val Trp Gly Ala Gly Thr Thr Val Thr Val Ser Ser Ala
    130                 135                 140

Lys Thr Thr Pro Pro Ser Val Tyr Pro Leu Ala Pro Gly Ser Ala Ala
145                 150                 155                 160
```

<210> SEQ ID NO 91
<211> LENGTH: 420
<212> TYPE: DNA
<213> ORGANISM: Mus musculus

<400> SEQUENCE: 91

```
atgagaccgt ctattcagtt cctggggctc ttgttgttct ggcttcatgg tgctcagtgt      60
gacatccaga tgacacagtc tccatcctca ctgtctgcat ctctgggagg caaagtcacc    120
atcacttgca aggcaagcca agacattaac aagtatatag cttggtacca acacaagcct    180
gggagaaggtc ctaggctact catacattac acatctacat tacagccagg catcccatca    240
```

```
aggttcagtg gaagtgggtc tgggagagat tattccttca gcatcagcaa cctggagcct      300
gaagatattg caacttatta ttgtctacag tatgattatc tgtggacgtt cggtggaggc      360
accaagctgg aaatcaaacg ggctgatgct gcaccaactg tatccatctt cccaccatcc      420
```

<210> SEQ ID NO 92
<211> LENGTH: 140
<212> TYPE: PRT
<213> ORGANISM: Mus musculus

<400> SEQUENCE: 92

```
Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asn Lys Tyr Ile Ala Trp Tyr Gln His Lys Pro Gly Glu Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Tyr Leu Trp Thr Phe Gly Gly Gly Thr Lys Leu Glu Ile Lys Arg Ala
        115                 120                 125

Asp Ala Ala Pro Thr Val Ser Ile Phe Pro Pro Ser
    130                 135                 140
```

<210> SEQ ID NO 93
<211> LENGTH: 480
<212> TYPE: DNA
<213> ORGANISM: Mus musculus

<400> SEQUENCE: 93

```
atggaatgga gttggatatt tctctttctc ctgtcaggaa ctgcaggtgt ccactctgag       60
gtccagctgc agcagtctgg acctgagctg gtaaagcctg ggcttcagt gaagatgtcc      120 tgcaaggctt ctggatacac attcactacc tatattatgc actgggtgaa gcagaagcct     180
gggcagggcc ttgagtggat tggatatatt aatccttaca atgatggtac aagtacaat      240 gagaagttca aggcgaggc cacactgact tcagacaaat cctccagtac agcctacatg      300
gagctcagca gcctgacctc tgaggactct gcggtctatt actgtgcaag aggggccaat     360
tactacggta gtaactacaa ctggtccttc gatgtctggg gcgcagggac cacggtcacc     420
gtctcctcag ccaaaacgac accccccatct gtctatccac tggcccctgg atctgctgcc   480
```

<210> SEQ ID NO 94
<211> LENGTH: 160
<212> TYPE: PRT
<213> ORGANISM: Mus musculus

<400> SEQUENCE: 94

```
Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30
```

Pro Gly Ala Ser Val Lys Met Ser Cys Lys Ala Ser Gly Tyr Thr Phe
            35                  40                  45

Thr Thr Tyr Ile Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Glu Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Gly Ala Asn Tyr Tyr Gly Ser Asn Tyr Asn Trp
            115                 120                 125

Ser Phe Asp Val Trp Gly Ala Gly Thr Thr Val Thr Val Ser Ser Ala
            130                 135                 140

Lys Thr Thr Pro Pro Ser Val Tyr Pro Leu Ala Pro Gly Ser Ala Ala
145                 150                 155                 160

<210> SEQ ID NO 95
<211> LENGTH: 420
<212> TYPE: DNA
<213> ORGANISM: Mus musculus

<400> SEQUENCE: 95
atgagaccgt ctattcagtt cctggggctc ttgttgttct ggcttcatgg tgctcagtgt    60
gacatccaga tgacacagtc tccatcctca ctgtctgcat ctctgggagg caaagtcacc   120
atcacttgca gggcaagcca agacattaac aagtatatag cttggtacca acacaagcct   180
ggaaaaggtc ctaggctgct catacatcac acatgtacat tacagccagg catcccatca   240
aggttcagtg gaagtgggtc tgggagagat tattccttca gcatcagcaa cctggagcct   300
gaagatattg caacttatta ttgtctacag tatgattatc tgtggacgtt cggtggaggc   360
accaagctgg aaatcaaacg ggctgatgct gcaccaactg tatccatctt cccaccatcc   420

<210> SEQ ID NO 96
<211> LENGTH: 140
<212> TYPE: PRT
<213> ORGANISM: Mus musculus

<400> SEQUENCE: 96

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Arg Ala Ser Gln Asp
            35                  40                  45

Ile Asn Lys Tyr Ile Ala Trp Tyr Gln His Lys Pro Gly Lys Gly Pro
    50                  55                  60

Arg Leu Leu Ile His His Thr Cys Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Tyr Leu Trp Thr Phe Gly Gly Gly Thr Lys Leu Glu Ile Lys Arg Ala
            115                 120                 125

Asp Ala Ala Pro Thr Val Ser Ile Phe Pro Pro Ser

<210> SEQ ID NO 97
<211> LENGTH: 61
<212> TYPE: PRT
<213> ORGANISM: Homo sapiens

<400> SEQUENCE: 97

Asn Pro Thr Gln Trp Gln Gln Lys Ile Ala Met Lys Met Glu Leu Leu
1               5                   10                  15

Gly Cys Gln Phe Ile Pro Lys Gly Arg Pro Pro Lys Leu Thr Gln Pro
            20                  25                  30

Pro Pro Pro Arg Asn Ser Asn Asp Leu Lys Asn Thr Thr Ala Pro Pro
        35                  40                  45

Lys Ile Ala Lys Gly Arg Ala Pro Lys Phe Thr Gln Pro
    50                  55                  60

<210> SEQ ID NO 98
<211> LENGTH: 22
<212> TYPE: PRT
<213> ORGANISM: Homo sapiens

<400> SEQUENCE: 98

Asn Pro Thr Gln Trp Gln Gln Lys Ile Ala Met Lys Met Glu Leu Leu
1               5                   10                  15

Gly Cys Gln Phe Ile Pro
            20

<210> SEQ ID NO 99
<211> LENGTH: 26
<212> TYPE: PRT
<213> ORGANISM: Homo sapiens

<400> SEQUENCE: 99

Asn Pro Thr Gln Trp Gln Gln Lys Ile Ala Met Lys Met Glu Leu Leu
1               5                   10                  15

Gly Cys Gln Phe Ile Pro Lys Gly Arg Pro
            20                  25

<210> SEQ ID NO 100
<211> LENGTH: 30
<212> TYPE: PRT
<213> ORGANISM: Homo sapiens

<400> SEQUENCE: 100

Asn Pro Thr Gln Trp Gln Gln Lys Ile Ala Met Lys Met Glu Leu Leu
1               5                   10                  15

Gly Cys Gln Phe Ile Pro Lys Gly Arg Pro Pro Lys Leu Thr
            20                  25                  30

<210> SEQ ID NO 101
<211> LENGTH: 34
<212> TYPE: PRT
<213> ORGANISM: Homo sapiens

<400> SEQUENCE: 101

Asn Pro Thr Gln Trp Gln Gln Lys Ile Ala Met Lys Met Glu Leu Leu
1               5                   10                  15

Gly Cys Gln Phe Ile Pro Lys Gly Arg Pro Pro Lys Leu Thr Gln Pro
            20                  25                  30

Pro Pro

<210> SEQ ID NO 102
<211> LENGTH: 38
<212> TYPE: PRT
<213> ORGANISM: Homo sapiens

<400> SEQUENCE: 102

Asn Pro Thr Gln Trp Gln Gln Lys Ile Ala Met Lys Met Glu Leu Leu
1               5                   10                  15

Gly Cys Gln Phe Ile Pro Lys Gly Arg Pro Pro Lys Leu Thr Gln Pro
            20                  25                  30

Pro Pro Pro Arg Asn Ser
        35

<210> SEQ ID NO 103
<211> LENGTH: 77
<212> TYPE: PRT
<213> ORGANISM: Homo sapiens

<400> SEQUENCE: 103

Gln Phe Ile Pro Lys Gly Arg Pro Pro Lys Leu Thr Gln Pro Pro Pro
1               5                   10                  15

Pro Arg Asn Ser Asn Asp Leu Lys Asn Thr Thr Ala Pro Pro Lys Ile
            20                  25                  30

Ala Lys Gly Arg Ala Pro Lys Phe Thr Gln Pro Leu Gln Pro Arg Ser
        35                  40                  45

Ser Asn Glu Phe Pro Ala Gln Thr Glu Gln Thr Thr Ala Ser Pro Asp
    50                  55                  60

Ile Arg Asn Thr Thr Val Thr Pro Asn Val Thr Lys Asp
65                  70                  75

<210> SEQ ID NO 104
<211> LENGTH: 420
<212> TYPE: DNA
<213> ORGANISM: Mus musculus

<400> SEQUENCE: 104
atgaaatgca gctgggtctt cttcttcctg atggcagtgg ttactggggt caattcagag      60
gttcagctgc agcagtctgg ggctgagctt gtgaggccag ggccttagt caagttgtcc      120 tgcaaagctt ctggcttcaa cattaaagac tactatatgc actgggtgaa gcagaggcct      180
gaacagggcc tggagtggat tggatggatt gatcctgaga atgataatac tatatatgac      240
ccgaagttcc agggcaaggc cagtataaca gcagacacgt cctccaacac agcctacctg      300
cacctcagca gcctgacatc tgaggacact gccgtctatt actgtgctag agcctatggt      360
tacgacgatt actatgctat ggaatactgg ggtcaaggaa cctcagtcac cgtctcctca      420

<210> SEQ ID NO 105
<211> LENGTH: 140
<212> TYPE: PRT
<213> ORGANISM: Mus musculus

<400> SEQUENCE: 105

Met Lys Cys Ser Trp Val Phe Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

```
Lys Asp Tyr Tyr Met His Trp Val Lys Gln Arg Pro Glu Gln Gly Leu
         50                  55                  60

Glu Trp Ile Gly Trp Ile Asp Pro Glu Asn Asp Asn Thr Ile Tyr Asp
 65                  70                  75                  80

Pro Lys Phe Gln Gly Lys Ala Ser Ile Thr Ala Asp Thr Ser Ser Asn
                 85                  90                  95

Thr Ala Tyr Leu His Leu Ser Ser Leu Thr Ser Glu Asp Thr Ala Val
            100                 105                 110

Tyr Tyr Cys Ala Arg Ala Tyr Gly Tyr Asp Asp Tyr Tyr Ala Met Glu
            115                 120                 125

Tyr Trp Gly Gln Gly Thr Ser Val Thr Val Ser Ser
130                 135                 140

<210> SEQ ID NO 106
<211> LENGTH: 387
<212> TYPE: DNA
<213> ORGANISM: Mus musculus

<400> SEQUENCE: 106
atggaatcac agactcaggt cttcctctcc ctgctgctct gggtatctgg tacctgtggg       60
aacattatga tgacacagtc gccatcatct ctggctgtgt ctgcaggaga aaaggtcact      120
atgagctgta gtccagtca aagtgtttta tacagttcaa atcagaagaa ctacttggcc       180
tggtaccagc agaaaccagg gcagtctcct aaactgctga tctactggac ttccactagg      240
gaatcaggtg tcccggatcg cttcacaggc agtggatctg ggacagattt tactcttacc      300
atcagcagtg ttcaagctga agacctggca atttattact gtcatcaata tctctactcg      360
tacacgttcg gaggggggac caagctg                                          387

<210> SEQ ID NO 107
<211> LENGTH: 129
<212> TYPE: PRT
<213> ORGANISM: Mus musculus

<400> SEQUENCE: 107

Met Glu Ser Gln Thr Gln Val Phe Leu Ser Leu Leu Leu Trp Val Ser
 1               5                   10                  15

Gly Thr Cys Gly Asn Ile Met Met Thr Gln Ser Pro Ser Ser Leu Ala
                 20                  25                  30

Val Ser Ala Gly Glu Lys Val Thr Met Ser Cys Lys Ser Ser Gln Ser
             35                  40                  45

Val Leu Tyr Ser Ser Asn Gln Lys Asn Tyr Leu Ala Trp Tyr Gln Gln
         50                  55                  60

Lys Pro Gly Gln Ser Pro Lys Leu Leu Ile Tyr Trp Thr Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Gln Ala Glu Asp Leu Ala Ile Tyr
            100                 105                 110

Tyr Cys His Gln Tyr Leu Tyr Ser Tyr Thr Phe Gly Gly Gly Thr Lys
            115                 120                 125

Leu

<210> SEQ ID NO 108
<211> LENGTH: 10
<212> TYPE: PRT
```

```
<213> ORGANISM: Homo sapiens

<400> SEQUENCE: 108

Phe Ile Pro Lys Gly Arg Pro Pro Lys Leu
1               5                   10

<210> SEQ ID NO 109
<211> LENGTH: 10
<212> TYPE: PRT
<213> ORGANISM: Homo sapiens

<400> SEQUENCE: 109

Arg Pro Pro Lys Leu Thr Gln Pro Pro Pro
1               5                   10

<210> SEQ ID NO 110
<211> LENGTH: 10
<212> TYPE: PRT
<213> ORGANISM: Homo sapiens

<400> SEQUENCE: 110

Thr Gln Pro Pro Pro Pro Arg Asn Ser Asn
1               5                   10

<210> SEQ ID NO 111
<211> LENGTH: 10
<212> TYPE: PRT
<213> ORGANISM: Homo sapiens

<400> SEQUENCE: 111

Pro Arg Asn Ser Asn Asp Leu Lys Asn Thr
1               5                   10

<210> SEQ ID NO 112
<211> LENGTH: 25
<212> TYPE: PRT
<213> ORGANISM: Homo sapiens

<400> SEQUENCE: 112

Phe Ile Pro Lys Gly Arg Pro Pro Lys Leu Thr Gln Pro Pro Pro
1               5                   10                  15

Arg Asn Ser Asn Asp Leu Lys Asn Thr
            20                  25
```

ANTI-HUMAN CLCP1 ANTIBODY AND USE THEREOF

RELATED APPLICATIONS

This application is a nationalization under 35 U.S.C. 371 of PCT/JP2009/062901, filed Jul. 16, 2009 and published as WO 2010/008051 A1 on Jan. 21, 2010, which claimed priority under 35 U.S.C. 119 to Japanese Patent Application No. 2008-185305, filed Jul. 16, 2008; which applications and publication are incorporated herein by reference in their entirety.

TECHNICAL FIELD

The present invention relates to antibodies against the extracellular domain of human CUB, LCCL-homology, coagulation factor V/VIII homology domains protein 1 (CLCP1), and uses thereof.

BACKGROUND ART

The CLCP1 molecule is also referred to as endothelial and smooth muscle cell-derived neuropilin-like molecule (ESDN) or discoidin, CUB and LCCL domain containing 2 (DCBLD2), which is a type I membrane protein of 775 amino acids with a single transmembrane region. An isoform of 743 amino acids, which is a splicing variant, has been reported, and it has a substantially identical extracellular functional domain. Back in 1999, Nadadur S. et al. isolated a gene fragment (Non-patent Document 1), and information on most of the amino acid sequence of CLCP1 (positions 106 to 775 in SEQ ID NO: 2) has been disclosed in Japanese Patent Application Kohyo Publication No. (JP-A) 2002-523076 (unexamined Japanese national phase publication corresponding to a non-Japanese international publication). The extracellular domain has as motifs, CUB domain, LCCL domain, and FA58C domain from the N-terminus. Subsequently, it has been reported that CLCP1 is expressed in the vascular smooth muscles of arteries and tunica media of carotid arteries after balloon injury, as well as in cells of coronary arteries and smooth muscles, and that CLCP1 is useful in the cardiovascular field such as for the treatment of restenosis after PTCA or arteriosclerosis (Patent Document 1).

On the other hand, Takahashi et al. (the present inventors) revealed that the CLCP1 molecule is highly expressed in cells of metastatic lung cancer sublines and expressed at a high rate in vivo in lung cancers. Furthermore, Takahashi et al. identified that cancer growth and metastasis was inhibited by constitutively expressing short hairpin RNAs (shRNAs) against CLCP1, which biosynthesize small interference RNAs (siRNAs) inside the cells (see, for example, Non-patent Documents 1 to 4).

The effects described above were demonstrated to be produced by inhibiting the expression of CLCP1 through constitutive expression of shRNAs that biosynthesize siRNAs inside the cells. The homology between mouse and human CLCP1 molecules is about 85% at the amino acid level. However, monoclonal antibodies that specifically bind to the molecule remain unavailable on the market. There is almost no scientific document reporting such monoclonal antibodies. Thus, such antibodies are still poorly understood in terms of their activity, function, and such. Moreover, the utility of the antibodies must await prospective studies.

PRIOR ART DOCUMENTS

Patent Documents

[Patent Document 1] Japanese Patent Application No. 2001-397725

Non-Patent Documents

[Non-patent Document 1] Biochim Biophys Acta. (1999) Dec. 23; 1489 (2-3): 433-439.
[Non-patent Document 2] Katstuni Koshikawa, et al., Journal of Japan Surgical Society, Vol. 104, No. Suppl. (20030430) p. 520, "Isolation and analysis of novel metastasis-related gene CLCP1 in human lung cancer".
[Non-patent Document 3] Koshikawa K, et al., Oncogene (2002) 21: 2822-2828, "Significant up-regulation of a novel gene, CLCP1, in a highly metastatic lung cancer subline as well as in lung cancers in vivo".
[Non-patent Document 4] Nagai H, et al., Oncogene (2007) 26: 4025-4031, "CLCP1 interacts with semaphorin 4B and regulates motility of lung cancer cells".

DISCLOSURE OF THE INVENTION

Problems to be Solved by the Invention

Under the above-described circumstances, an objective of the present invention is to provide antibodies having useful biological activity such as the activity of inhibiting lung cancer metastasis, invasion, migration, or cell growth, or cytotoxicity, and uses thereof. In detail, the objective of the present invention is to provide: novel antibodies that recognize an extracellular domain of human CLCP1 antigen; nucleic acids encoding the antibodies; vectors carrying the nucleic acids in an expressible manner; transformed cells carrying the vectors; methods for producing the antibodies; diagnostic methods for cancer and cancer prognosis using the antibodies; immunological methods for measuring cells or tissues; kits for detecting the expression levels of CLCP1 in cells or tissues; pharmaceutical compositions comprising the antibodies; pharmaceutical agents for use in treating or preventing cancers expressing CLCP1; agents for inhibiting the growth, migration, invasion, or metastasis of cancer cells expressing CLCP1; cytotoxic agents and immunostaining agents; and pharmaceutical agents for use in treating or preventing tumors expressing CLCP1. Another objective of the present invention is to provide methods of screening for candidate substances that inhibit the growth, invasion, migration, or metastasis of cancer cells, or candidate substances having cytotoxicity against cancer cell.

Means for Solving the Problems

The present inventors studied to achieve the above-described objectives by targeting human CLCP1. As a result, the present inventors discovered that the immunization efficiency was specifically increased by using partial fragments of the extracellular domain of human CLCP1. Thus, the present inventors successfully obtained anti-human CLCP1 monoclonal antibodies that specifically recognize the extracellular domain of human CLCP1, and identified preferable antibody sequences and epitopes.

Furthermore, the present inventors conducted various experiments using the antibodies and discovered that the antibodies have the effect of suppressing the metastasis of lung cancer cells. Specifically, the present inventors revealed that the antibodies have one or more of the five activities against lung cancer cells described below and confirmed the usefulness of the antibodies:

(1) the antibodies exert an effect of inhibiting the migration of lung cancer cells;
(2) the antibodies exert an effect of inhibiting the invasion of lung cancer cells;
(3) the antibodies exert an effect of inhibiting the metastasis of lung cancer cells;
(4) the antibodies exert an effect of inhibiting the growth of lung cancer cells; or
(5) the antibodies exert a cytotoxic effect against lung cancer cells.

Cancer metastasis occurs via the process of
detachment/migration of cancer cells from the primary lesion;
invasion into extracellular matrix/basement membrane:
invasion into blood vessels;
adhesion to distant sites;
extravasation from blood vessels;
invasion into basement membrane/extracellular matrix; and growth. Of these, invasion into extracellular matrix/basement membrane occurs twice, and therefore is thought to be highly important steps. Compositions comprising an antibody having the above-described inhibitory effect are very effective as a therapeutic agent for cancer.

Furthermore, the compositions comprising an antibody that has the above-described inhibitory effect by exerting an effect of inhibiting cancer cell growth suppress cancer progression and are very effective as therapeutic agents for cancer.

Moreover, the present inventors revealed that antibodies have antibody-dependent cell-mediated cytotoxicity (ADCC). ADCC is a mechanism in which the Fc portion of a therapeutic antibody binds to Fcγ receptors on the surface of killer cells which are capable of killing cancer cells; the killer cells are guided to the cancer cells by the cognitive effect of the therapeutic antibody variable regions; and as a result the killer cells kill the cancer cells via the therapeutic antibody. The present inventors first confirmed the effect against lung cancer (H460-LNM35, A549, etc.). In particular, the antibodies exerted the effect even against the CLCP1-expressing high metastatic lung cancer cell line H460-LNM35. Thus, the synergistic effect in combination with metastasis suppression described above can be expected to completely cure the cancer.

In addition, as described hereinbelow, the present inventors confirmed the various types of cancers expressing CLCP1 and suggested that the same effect on the cancers could also be expected. In particular, such target cancer types include kidney cancer, bladder tumor, prostate cancer, pancreas cancer, stomach cancer, large intestine cancer, and breast cancer.

Compositions comprising an antibody that exerts the above-described activity by producing ADCC against cancer cells actively kill cancers. Thus, the compositions are very effective as an anti-cancer therapeutic agent. The therapeutic agents for cancer were demonstrated to be applicable to various types of cancer.

Meanwhile, the present inventors assessed the obtained antibodies for their utility in the field of diagnosis. Specifically, lung cancer cells and tissues were immunostained with the antibodies. The result showed that the antibodies could specifically stain the metastatic/invasive state of lung cancer cells and tissues, and metastatic lymph node cancer. More specifically, normal lung, lung cancer cells and tissues or metastatic lymph node cancer, and metastasis/invasion could be stained discriminately by using the antibodies. This result suggests that prognosis, malignancy of lung cancer cells (tissues), and metastasis can be assessed by using the successfully obtained antibodies. Furthermore, the therapeutic effect of therapeutic agents that target the molecule can be assessed by the antibodies. As described above, the successfully obtained antibodies were revealed to be very useful in diagnosing lung cancer and the like. Thus, it was demonstrated that the antibodies were useful in the immunological staining of cancer cells, in particular, lung cancer tissue sections or metastatic lymph node cancer, and in diagnosing the progression of metastasis of lung cancer or metastatic lymph node cancer. In particular, they are preferably useful for assessing the prognosis of lung cancer.

In addition, the antibodies were assessed for their stainability on cancer cells. CLCP1 is a molecule that is not only expressed in lung cancer but also commonly expressed in various types of cancers, while it is hardly expressed in normal tissues. Thus, CLCP1 was expected to be applicable to assess the therapeutic effect. In particular, such target cancer types include kidney cancer, bladder tumor, prostate cancer, pancreas cancer, stomach cancer, large intestine cancer, and breast cancer.

Furthermore, the target diseases in the diagnosis of the therapeutic effect are not limited to lung cancer and metastatic lymph node cancer, and the diagnostic methods using the antibodies of the present invention are expected to be applicable to other CLCP1 expression diseases.

The present invention is based on the above-described findings. Thus, the present invention provides the following antibodies or antibody fragments, and uses thereof:

[1] an isolated antibody that recognizes a peptide consisting of the amino acid sequence of positions 456 to 470 in SEQ ID NO: 2;

[2] the antibody of [1], which recognizes a peptide consisting of the amino acid sequence of positions 461 to 470 in SEQ ID NO: 2 but does not recognize a peptide consisting of the amino acid sequence of positions 466 to 475 in SEQ ID NO: 2;

[3] the antibody of [1], which recognizes a peptide consisting of the amino acid sequence of positions 456 to 465 in SEQ ID NO: 2 but does not recognize a peptide consisting of the amino acid sequence of positions 451 to 460 in SEQ ID NO: 2;

[4] the isolated antibody of any one of [1] to [3], which has an activity of inhibiting the migration of a cancer cell expressing CLCP 1;

[5] the isolated antibody of any one of [1] to [3], which has an activity of inhibiting the invasion of a cancer cell expressing CLCP1;

[6] the isolated antibody of any one of [1] to [3], which has an activity of inhibiting the growth of a cancer cell expressing CLCP1;

[7] the isolated antibody of any one of [1] to [3], which has an activity of inhibiting the metastasis of a cancer cell expressing CLCP1.

[8] the isolated antibody of any one of [1] to [3], which has cytotoxicity against a cancer cell expressing CLCP1.

[9] the isolated antibody of any one of [4] to [8], wherein the cancer cell expressing CLCP1 is a kidney cancer cell, urinary bladder tumor cell, prostate cancer cell, pancreas cancer cell, stomach cancer cell, large intestine cancer cell, breast cancer cell, or lung cancer cell.

[10] the isolated antibody of any one of [1] to [9], wherein the amino acid sequences of each of the complementarity determining regions of heavy-chain variable region (VH CDR1, VH CDR2, and VH CDR3) and each of the complementarity determining regions of light-chain variable region (VL CDR1, VL CDR2, and VL CDR3) are selected from (A) to (C):

(A)
- (1) VH CDR1: the amino acid sequence of SEQ ID NO: 16 or an amino acid sequence substantially identical thereto;
- (2) VH CDR2: the amino acid sequence of SEQ ID NO: 17 or an amino acid sequence substantially identical thereto;
- (3) VH CDR3: the amino acid sequence of SEQ ID NO: 18 or an amino acid sequence substantially identical thereto;
- (4) VL CDR1: the amino acid sequence of SEQ ID NO: 21 or an amino acid sequence substantially identical thereto;
- (5) VL CDR2: the amino acid sequence of SEQ ID NO: 57 or an amino acid sequence substantially identical thereto;
- (6) VL CDR3: the amino acid sequence of SEQ ID NO: 22 or an amino acid sequence substantially identical thereto;

(B)
- (1) VH CDR1: the amino acid sequence of SEQ ID NO: 7 or an amino acid sequence substantially identical thereto;
- (2) VH CDR2: the amino acid sequence of SEQ ID NO: 8 or an amino acid sequence substantially identical thereto;
- (3) VH CDR3: the amino acid sequence of SEQ ID NO: 9 or an amino acid sequence substantially identical thereto;
- (4) VL CDR1: the amino acid sequence of SEQ ID NO: 12 or an amino acid sequence substantially identical thereto;
- (5) VL CDR2: the amino acid sequence of SEQ ID NO: 56 or an amino acid sequence substantially identical thereto;
- (6) VL CDR3: the amino acid sequence of SEQ ID NO: 13 or an amino acid sequence substantially identical thereto;

(C)
- (1) VH CDR1: the amino acid sequence of SEQ ID NO: 60 or an amino acid sequence substantially identical thereto;
- (2) VH CDR2: the amino acid sequence of SEQ ID NO: 61 or an amino acid sequence substantially identical thereto;
- (3) VH CDR3: the amino acid sequence of SEQ ID NO: 62 or an amino acid sequence substantially identical thereto;
- (4) VL CDR1: the amino acid sequence of SEQ ID NO: 65 or an amino acid sequence substantially identical thereto;
- (5) VL CDR2: the amino acid sequence of SEQ ID NO: 66 or an amino acid sequence substantially identical thereto;
- (6) VL CDR3: the amino acid sequence of SEQ ID NO: 67 or an amino acid sequence substantially identical thereto;

[11] the isolated antibody of any one of [1] to [10], wherein the amino acid sequences of the heavy-chain variable region (VH) and light-chain variable region (VL) are selected from (A) to (C):

(A)
- (1) VH: the amino acid sequence of SEQ ID NO: 45 or 15, or an amino acid sequence substantially identical thereto;
- (2) VL: the amino acid sequence of SEQ ID NO: 55 or 20, or an amino acid sequence substantially identical thereto;

(B)
- (1) VH: the amino acid sequence of SEQ ID NO: 6 or an amino acid sequence substantially identical thereto;
- (2) VL: the amino acid sequence of SEQ ID NO: 11 or an amino acid sequence substantially identical thereto;

(C)
- (1) VH: the amino acid sequence of SEQ ID NO: 59 or an amino acid sequence substantially identical thereto;
- (2) VL: the amino acid sequence of SEQ ID NO: 64 or an amino acid sequence substantially identical thereto;

[12] an isolated antibody that recognizes the same epitope as the antibody of any one of [1] to [11];

[13] the isolated antibody of any one of [1] to [12], which is an Fab, Fab', F(ab')$_2$, Fv, scFv, dsFv, diabody, or sc(Fv)2;

[14] the isolated antibody of any one of [1] to [13], which is an IgG antibody;

[15] the isolated antibody of any one of [1] to [14], which is a humanized antibody;

[16] an isolated nucleic acid encoding the isolated antibody of any one of [1] to [15];

[17] a vector that carries the nucleic acid of [16] in an expressible manner;

[18] a transformed cell comprising the vector of [17];

[19] a method for producing an antibody, which comprises the steps of:
- (a) culturing the transformed cell of [18]; and
- (b) isolating and purifying the antibody as an expression product;

[20] a pharmaceutical composition comprising the isolated antibody of any one of [1] to [15] and a pharmaceutically acceptable carrier;

[21] an agent for inhibiting cancer cell migration, which comprises an antibody that recognizes an extracellular domain of human CLCP1 antigen and has an activity of inhibiting the migration of a cancer cell expressing CLCP1;

[22] an agent for inhibiting cancer cell invasion, which comprises an antibody that recognizes an extracellular domain of human CLCP1 antigen and has an activity of inhibiting the invasion of a cancer cell expressing CLCP1;

[23] an agent for inhibiting cancer cell metastasis, which comprises an antibody that recognizes an extracellular domain of human CLCP1 antigen and has an activity of inhibiting the metastasis of a cancer cell expressing CLCP1;

[24] an agent for inhibiting cancer cell growth, which comprises an antibody that recognizes an extracellular domain of human CLCP1 antigen and has an activity of inhibiting the growth of a cancer cell expressing CLCP1;

[25] a cytotoxic agent against cancer cell, which comprises an antibody that recognizes an extracellular domain of human CLCP1 antigen and has cytotoxicity against a cancer cell expressing CLCP1;

[26] a pharmaceutical agent for use in treating or preventing tumor, which comprises an antibody that recognizes an extracellular domain of human CLCP1 antigen and has an activity of inhibiting the growth of a cancer cell expressing CLCP1;

[27] a pharmaceutical agent for use in treating or preventing cancer, which comprises an antibody that recognizes an extracellular domain of human CLCP1 antigen and has an activity of inhibiting the growth of a cancer cell expressing CLCP1;

[28] the pharmaceutical agent of [27] for use in treating or preventing CLCP1-expressing cancer, which has at least an inhibitory effect selected from migration inhibition, invasion inhibition, metastasis inhibition, and growth inhibition;

[29] a pharmaceutical agent for use in immunological detection of CLCP1 expression in a cell or tissue, which comprises an antibody that recognizes an extracellular domain of human CLCP1 antigen;

[30] a kit for use in immunological detection of CLCP1 expression in a cell or tissue, which comprises an antibody that recognizes an extracellular domain of human CLCP1 antigen;

[31] a diagnostic agent for prognosis of cancer, which comprises an antibody that recognizes an extracellular domain of human CLCP1 antigen;

[32] a diagnostic kit for prognosis of cancer, which comprises an antibody that recognizes an extracellular domain of human CLCP1 antigen;

[33] an immunological method comprising the steps of:
   (a) contacting an isolated cell or tissue with an antibody that recognizes an extracellular domain of human CLCP1 antigen; and
   (b) detecting CLCP1 expression in the cell or tissue;

[34] a method for diagnosing cancer, which comprises the steps of contacting an isolated pathological tissue with an antibody that recognizes an extracellular domain of human CLCP1 antigen, and immunologically detecting the expression of CLCP1 in a cell of the pathological tissue;

[35] a diagnostic method for cancer prognosis, which comprises the steps of contacting an isolated pathological tissue with an antibody that recognizes an extracellular domain of human CLCP1 antigen, and immunologically detecting the expression of CLCP1 in a cell of the pathological tissue;

[36] a method of screening for a candidate substance that inhibits cancer cell growth, invasion, migration, or metastasis, or a candidate substance having cytotoxicity against a cancer cell, which comprises the steps of:
   (a) contacting a test substance with an extracellular domain of human CLCP1 antigen;
   (b) detecting the binding between a test substance and the extracellular domain of human CLCP1 antigen; and
   (c) selecting a test substance that binds to the extracellular domain of human CLCP1 antigen;

[37] a method for inhibiting a migration of a cancer cell expressing CLCP1, which comprises the step of administering to a subject an antibody that recognizes an extracellular domain of human CLCP1 antigen and has an activity of inhibiting the migration of a cancer cell expressing CLCP1;

[38] a method for inhibiting an invasion of a cancer cell expressing CLCP1, which comprises the step of administering to a subject an antibody that recognizes an extracellular domain of human CLCP1 antigen and has an activity of inhibiting the invasion of the cancer cell expressing CLCP1;

[39] a method for inhibiting a metastasis of a cancer cell expressing CLCP1, which comprises the step of administering to a subject an antibody that recognizes an extracellular domain of human CLCP1 antigen and has an activity of inhibiting the metastasis of the cancer cell expressing CLCP1;

[40] a method for inhibiting a growth of a cancer cell expressing CLCP1, which comprises the step of administering to a subject an antibody that recognizes an extracellular domain of human CLCP1 antigen and has the activity of inhibiting the growth of the cancer cell expressing CLCP1;

[41] a method for damaging a cancer cell expressing CLCP1, which comprises the step of administering to a subject an antibody that recognizes an extracellular domain of human CLCP1 antigen and has cytotoxicity against the cancer cell expressing CLCP1;

[42] a method for treating or preventing a tumor expressing CLCP1, which comprises the step of administering to a subject an antibody that recognizes the extracellular domain of human CLCP1 antigen and has the activity of inhibiting the growth of a cancer cell expressing CLCP1;

[43] a method for treating or preventing a cancer expressing CLCP1, which comprises the step of administering to a subject an antibody that recognizes an extracellular domain of human CLCP1 antigen and has an activity of inhibiting the growth of a cancer cell expressing CLCP1;

[44] use of an antibody that recognizes an extracellular domain of human CLCP1 antigen and has an activity of inhibiting the migration of a cancer cell expressing CLCP1, in producing an agent for inhibiting the migration of the cancer cell expressing CLCP1;

[45] use of an antibody that recognizes an extracellular domain of human CLCP1 antigen and has an activity of inhibiting the invasion of a cancer cell expressing CLCP1, in producing an agent for inhibiting the invasion of the cancer cell expressing CLCP1;

[46] use of an antibody that recognizes an extracellular domain of human CLCP1 antigen and has an activity of inhibiting the metastasis of a cancer cell expressing CLCP1, in producing an agent for inhibiting the metastasis of the cancer cell expressing CLCP1;

[47] use of an antibody that recognizes an extracellular domain of human CLCP1 antigen and has an activity of inhibiting the growth of a cancer cell expressing CLCP1, in producing an agent for inhibiting the growth of the cancer cell expressing CLCP1;

[48] use of an antibody that recognizes an extracellular domain of human CLCP1 antigen and has cytotoxicity against a cancer cell expressing CLCP1, in producing a cytotoxic agent against the cancer cell expressing CLCP1;

[49] use of an antibody that recognizes an extracellular domain of human CLCP1 antigen and has an activity of inhibiting the growth of a cancer cell expressing CLCP1, in producing an agent for treating or preventing a tumor expressing CLCP1;

[50] use of an antibody that recognizes an extracellular domain of human CLCP1 antigen and has an activity of inhibiting the growth of a cancer cell expressing CLCP1, in producing an agent for treating or preventing a cancer expressing CLCP1;

[51] an antibody that recognizes an extracellular domain of human CLCP1 antigen and has an activity of inhibiting the migration of a cancer cell expressing CLCP1 for use in a method for inhibiting the migration of the cancer cell expressing CLCP1;

[52] an antibody that recognizes an extracellular domain of human CLCP1 antigen and has an activity of inhibiting the invasion of a cancer cell expressing CLCP1 for use in a method for inhibiting the invasion of the cancer cell expressing CLCP1;

[53] an antibody that recognizes an extracellular domain of human CLCP1 antigen and has an activity of inhibiting the metastasis of a cancer cell expressing CLCP1 for use in a method for inhibiting the metastasis of the cancer cell expressing CLCP1;

[54] an antibody that recognizes an extracellular domain of human CLCP1 antigen and has an activity of inhibiting the growth of a cancer cell expressing CLCP1 for use in a method for inhibiting the growth of the cancer cell expressing CLCP1;

[55] an antibody that recognizes an extracellular domain of human CLCP1 antigen and has cytotoxicity against a cancer cell expressing CLCP1 for use in a method for damaging the cancer cell expressing CLCP1;

[56] an antibody that recognizes an extracellular domain of human CLCP1 antigen and has an activity of inhibiting the growth of a cancer cell expressing CLCP1 for use in a method for treating or preventing a tumor expressing CLCP1; and

[57] an antibody that recognizes an extracellular domain of human CLCP1 antigen and has an activity of inhibiting the growth of a cancer cell expressing CLCP1 for use in a method for treating or preventing a cancer expressing CLCP1.

Effects of the Invention

The present invention provides anti-human CLCP1 monoclonal antibodies that specifically recognize the extracellular domain of human CLCP1, preferably isolated antibodies that recognize a peptide consisting of the amino acid sequence of positions 456 to 470 in SEQ ID NO: 2, more preferably isolated antibodies that recognize a peptide consisting of the amino acid sequence of positions 461 to 470 in SEQ ID NO: 2 but do not recognize a peptide consisting of the amino acid sequence of positions 466 to 475 in SEQ ID NO: 2, or isolated antibodies that recognize a peptide consisting of the amino acid sequence of positions 456 to 465 in SEQ ID NO: 2 but do not recognize a peptide consisting of the amino acid sequence of positions 451 to 460 in SEQ ID NO: 2, most preferably FA19-1, FA17-9, or 6AA_17-2, and even more preferably FA19-1 which is characterized by its specific recognition of the extracellular domain of CLCP1 and strong inhibition of the biological activity of CLCP1, for example, signaling activity or interaction with other molecules, by binding to the protein. The present invention for the first time provides effective monoclonal antibodies that inhibit cell growth, migration, invasion, or metastasis (in particular, lung cancer metastasis and lymph: node metastasis), in which CLCP1 is thought to be involved, and have cytotoxicity in cancer diseases.

According to the present invention, agents for inhibiting migration, invasion, growth, or metastasis of cancer cells expressing CLCP1, and cytotoxic agents for damaging cancer cells expressing CLCP1, as well as cancer therapeutic agents whose action mechanism is based on the above-described inhibition, can be readily produced by using the above-described antibody as an active ingredient. These agents can be used for treating cancer/preventing cancer metastasis.

Furthermore, the present invention for the first time provides monoclonal antibodies having cytotoxic activity against CLCP1 expression cancer diseases.

According to the present invention, cancer therapeutic agents whose mechanism is to damage CLCP1-expressing cancer cells can be readily produced by using the above-described antibody as an active ingredient. These agents can be used for treating/preventing cancer diseases.

Furthermore, it was demonstrated that CLCP1 was expressed at high levels in lung cancer and lymph node cancer, and that the frequency of invasion/metastasis was higher when the expression level of CLCP1 was higher or the proportion of CLCP1-expressing cells was larger in cancer tissues. It was also demonstrated that CLCP1 was hardly expressed in normal tissues while it was expressed at high levels in various types of cancers.

Thus, the above-described antibodies can be used to readily assess the CLCP1 expression by immunological staining of pathological specimens, and thus be applied in the diagnostic field. Specifically, the CLCP1 expression can be tested using immunostaining agents comprising the above-described antibody as an, active ingredient. In particular, the present invention enables one to readily produce immunostaining agents for diagnosing pathological symptoms/conditions associated with cancer metastasis, for example, immunostaining agents for assessing the effect of cancer therapeutic agents, prognosis, or malignancy.

Lung cancer tissues were observed after staining (cell membrane staining) with an anti-CLCP1 antibody. In particular, the survival rate analyzed by the Kaplan-Meier method one year (12 months) after surgery was 73% in the group of clinical cases strongly positive in histochemistry (strongly positive cell membrane staining), while the rate was 93% in the group of weakly positive or negative clinical cases (weakly positive or negative cell membrane staining). On the other hand, the survival rate three years (36 months) after surgery was 55% in the group of strongly positive cases, while the rate was 90% in the group of weakly positive or negative cases. The survival rate was constantly lower in the group of strongly positive cases. The differences were evaluated by the logrank test or generalized Wilcoxon test (Gehan-Wilcoxon test), which are commonly used to assess significant differences in the survival rate between two groups. The result was p=0.012 in the logrank test and p=0.0072 in the generalized Wilcoxon test, suggesting that the survival rate is statistically significantly lower in the group of strongly positive cases (FIG. 37A).

The immunohistochemical reactivity of antibodies of the present invention was categorized into three groups: strongly positive (+), weakly positive (±), and negative (−). Specifically, strongly positive means that the cell membrane is clearly stained in outline (the outline of cell membrane is visible under a microscope) as shown in the upper panel of FIG. 37B; weakly positive means that the cell membrane is only stained vaguely (the outline of cell membrane is invisible under a microscope) as shown in the lower panel of FIG. 37B; and negative means that the cell membrane is completely invisible.

More specifically, the present invention provides kits for predicting the prognosis of cancer which comprise an above-described antibody. Thus, the present invention is useful in that prompt treatment or new therapy can be performed for high-risk patients who are predicted to have shorter survival time. The preferred target cancer type is lung cancer.

The present invention also provides methods of screening for candidate substances that inhibit the growth, invasion, migration, or metastasis of cancer cells. Substances obtained by the screening methods can be candidate substances that can be used to treat or prevent cancer diseases by the mechanism of the above-described inhibition.

BRIEF DESCRIPTION OF THE DRAWINGS

Figure 9:
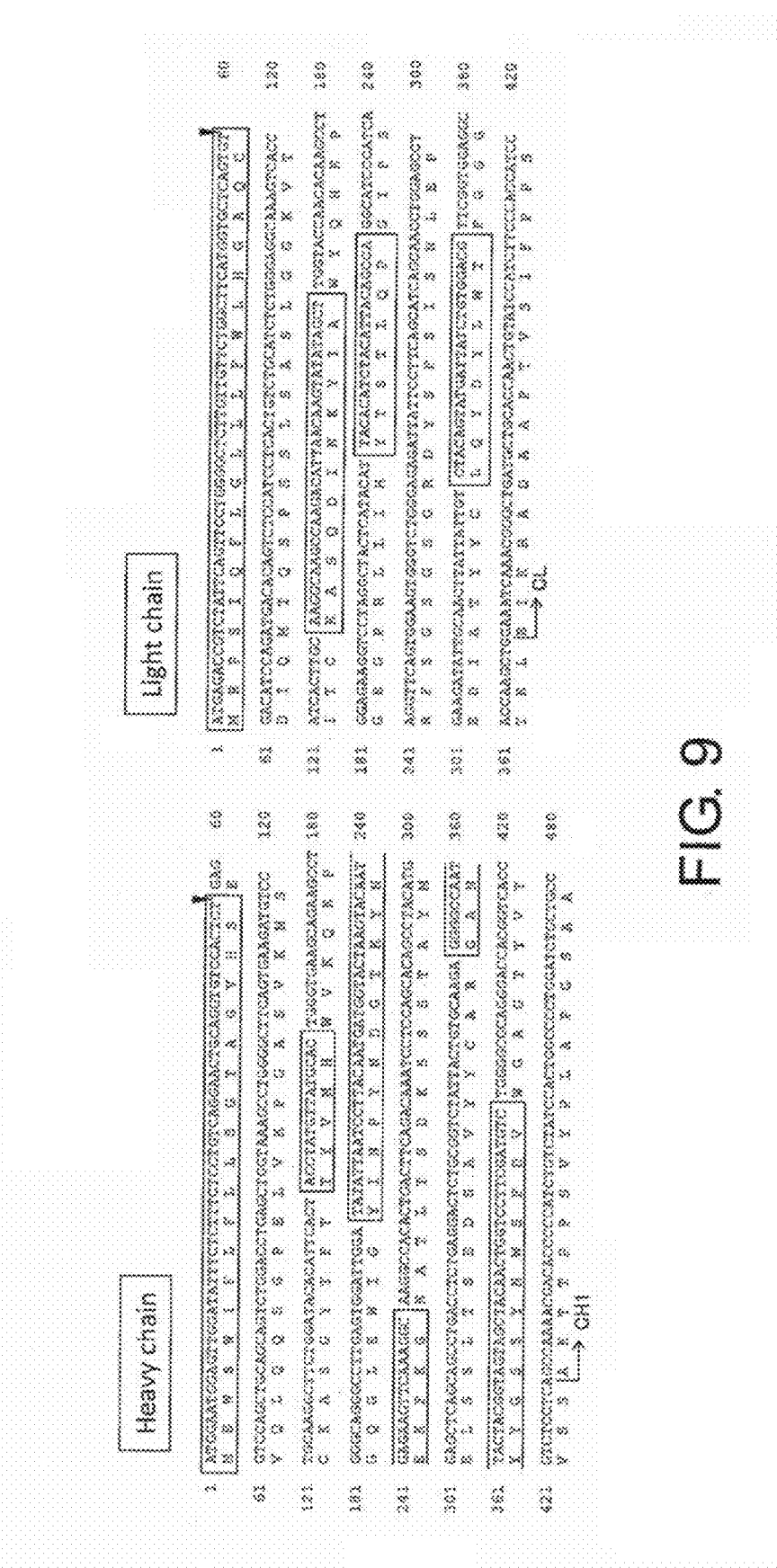

FIG. 9 shows in a diagram the nucleotide and amino acid sequences of antibody FA17-9. The nucleotide (SEQ ID NO: 89) and amino acid (SEQ ID NO: 90) sequences of the heavy chain (a portion of the variable region and constant region). The boxed regions correspond to the signal sequence, CDR1 (SEQ ID NO: 7), CDR2 (SEQ ID NO: 8), and CDR3 (SEQ ID NO: 9) from the top. Arrow indicates CH1. The nucleotide (SEQ ID NO: 91) and amino acid (SEQ ID NO: 92) sequences of the light chain (a portion of the variable and constant regions). The boxed regions correspond to the signal sequence, CDR1 (SEQ ID NO: 12), CDR2 (SEQ ID NO: 56), and CDR3 (SEQ ID NO: 13) from the top. Arrow indicates CL1.

Figure 10:
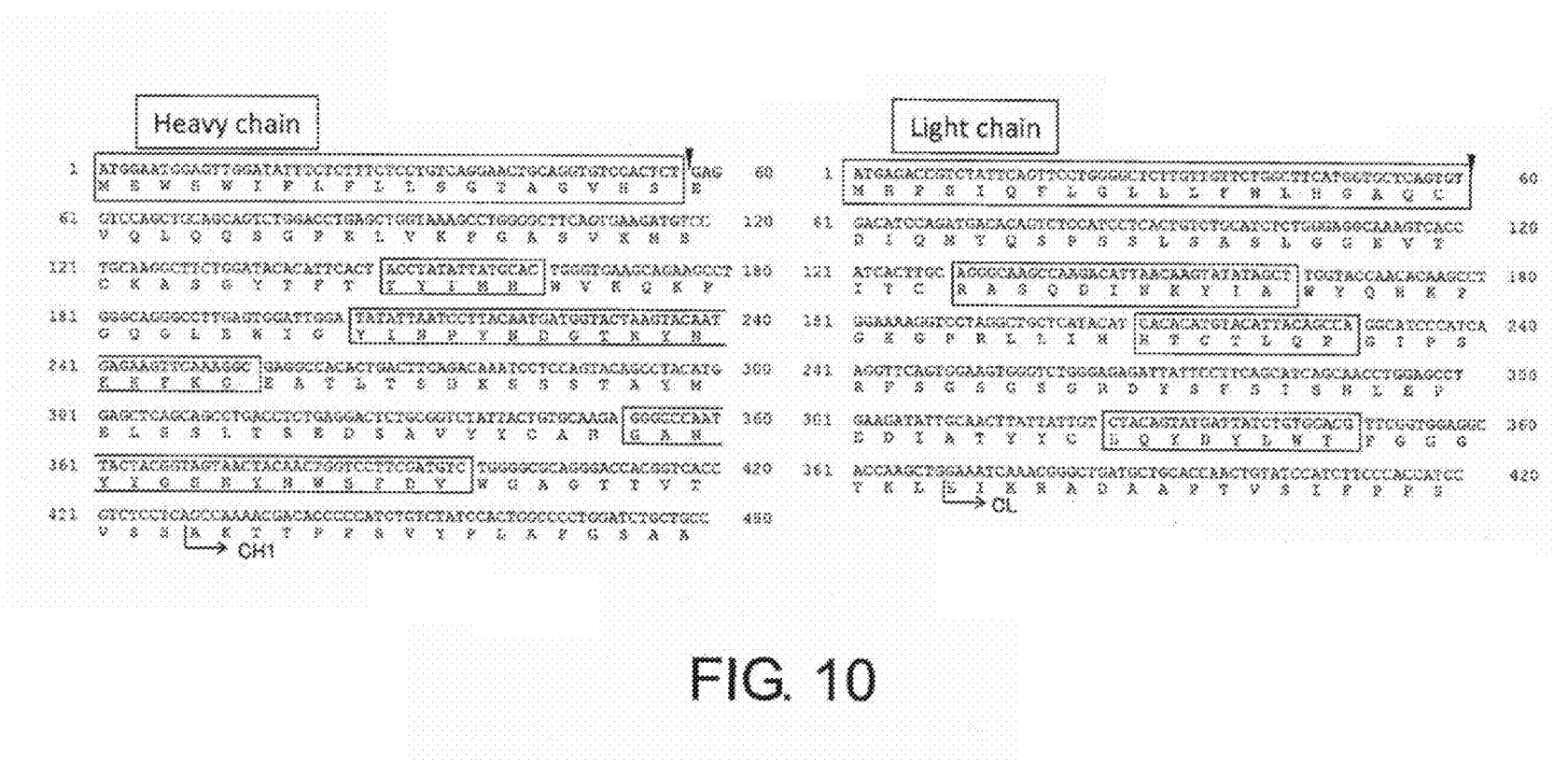

FIG. 10 shows in a diagram the nucleotide and amino acid sequences of antibody FA19-1. The nucleotide (SEQ ID NO: 93) and amino acid (SEQ ID NO: 94) sequences of the heavy chain (a portion of the variable and constant regions). The boxed regions correspond to the signal sequence, CDR1 (SEQ ID NO: 16), CDR2 (SEQ ID NO: 17), and CDR3 (SEQ ID NO: 18) from the top. Arrow indicates CHL The nucleotide (SEQ ID NO: 95) and amino acid (SEQ ID NO: 96) sequences of the light chain (a portion of the variable and constant regions). The boxed regions correspond to the signal sequence, CDR1 (SEQ ID NO: 21), CDR2 (SEQ ID NO: 57), and CDR3 (SEQ ID NO: 22) from the top. Arrow indicates CL1.

Tumor volume on day 10 (10 days after transplantation); (B) tumor volume on day 34 (34 days after transplantation); (C) tumor volume on day 41 (41 days after transplantation); and (D) tumor growth rate. The vertical axis indicates tumor volume (mm$^3$), and the horizontal axis indicates period after transplantation.

Figure 16:
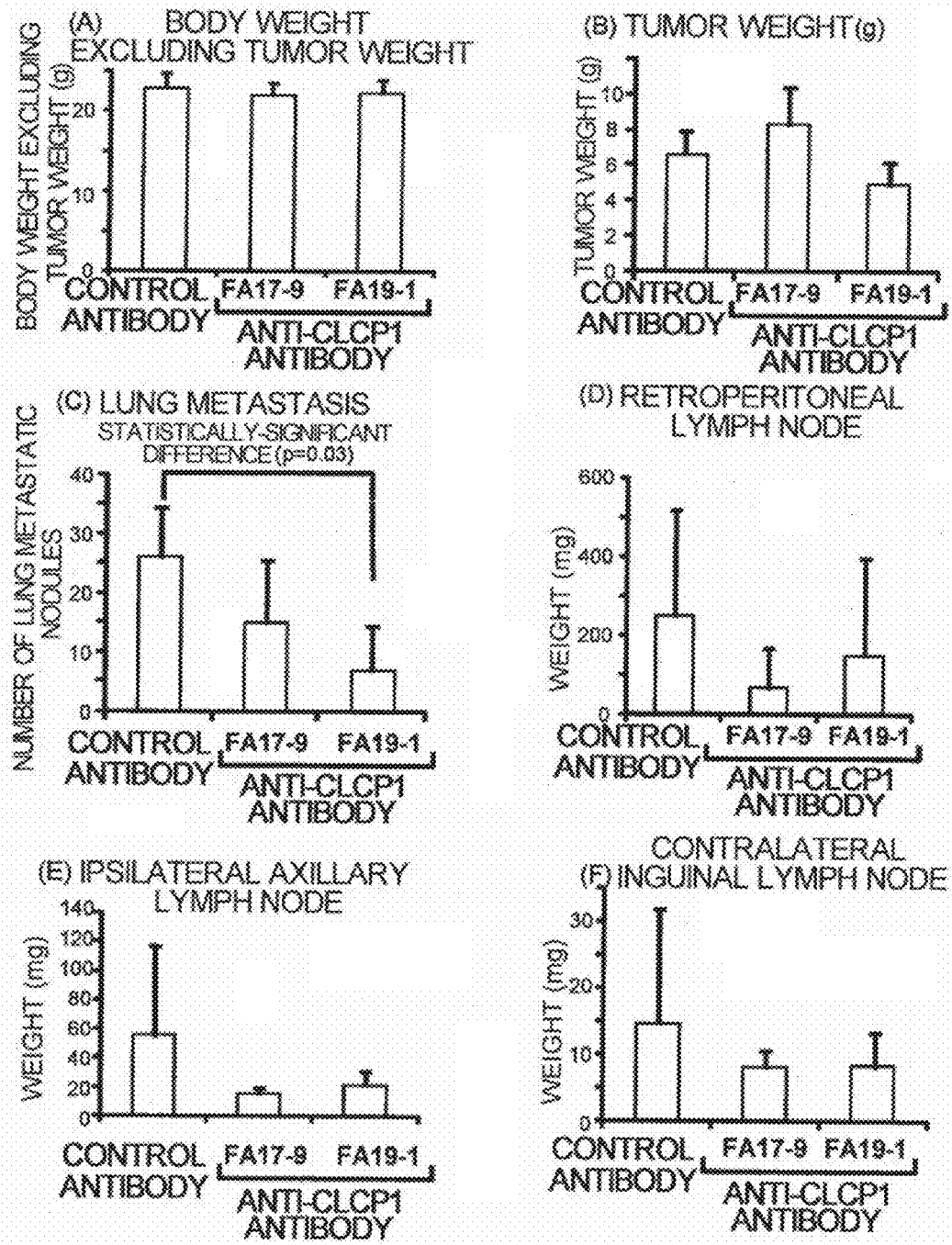

FIG. 16 shows in graphs the result 46 days after transplantation at the time of sacrifice. (A) There is no change in the body weight excluding tumor weight. (B) The tendency of FA19-1 is to suppress growth. Meanwhile, FA17-9 seems to promote growth, but there is no significant difference. (C) FA19-1 significantly suppresses metastasis. The tendency of FA17-9 is also to suppress metastasis. (D) Enlargement is commonly seen in all three groups, and is most evident in the control IgG group. (E) Although there is no significant difference due to variation in the control, lymph node enlargement caused by metastasis is hardly seen in the groups of FA17-9 and FA19-1. (F) Although there is no significant difference due to variation in the control, lymph node enlargement caused by metastasis is hardly seen in the groups of FA17-9 and FA19-1.

Figure 17:
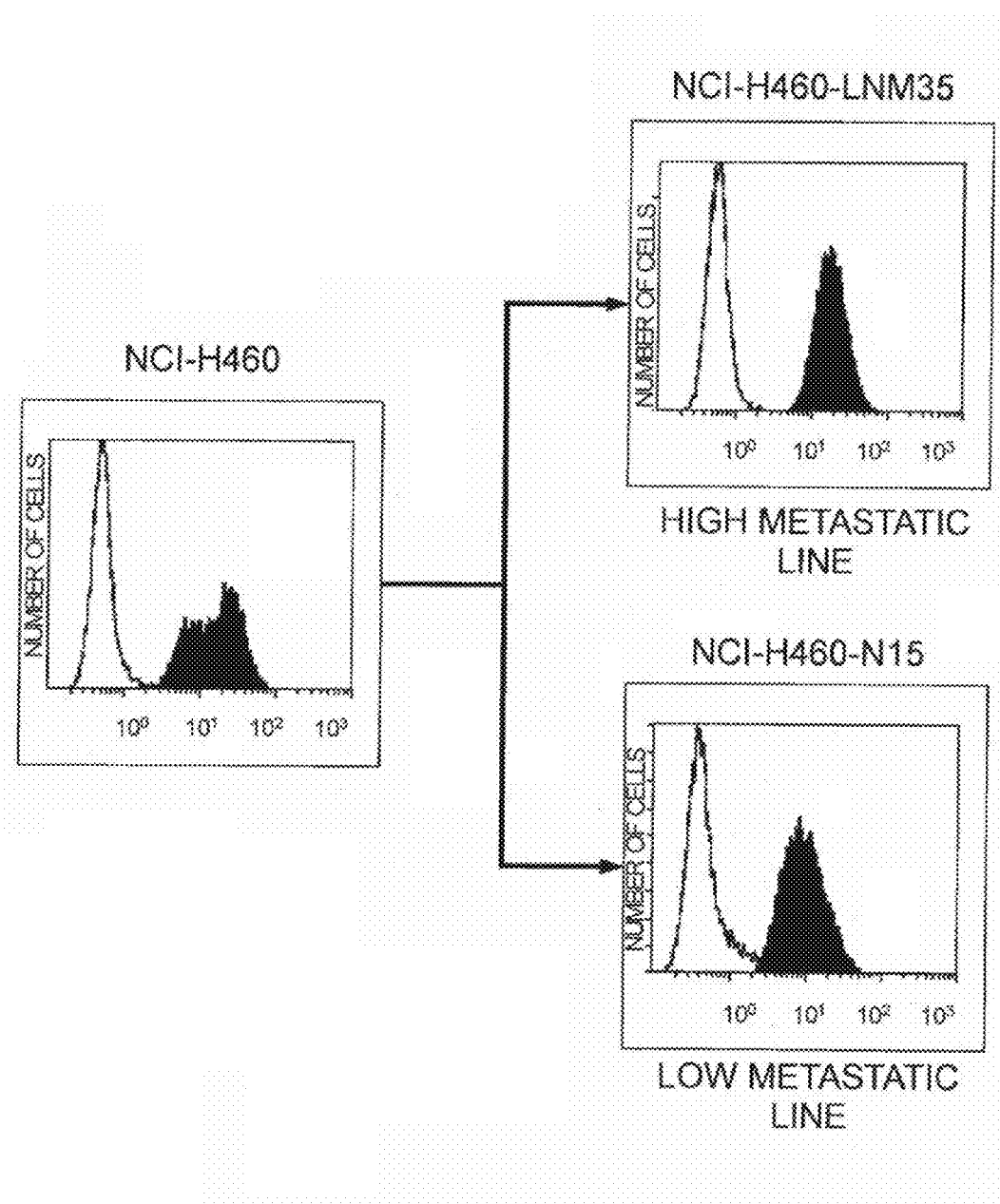

FIG. 17 shows in a diagram isolation of the high metastatic line NCI-H460-LNM35 and low metastatic line NCI-H460-N15, which are both derived from NCI-H460, and result of CLCP1 expression analysis. NCI-H460-LNM35 and NCI-H460-N15, both of which uniformly expressed CLCP1 on the cell membrane, could be isolated by cloning the parental line NCI-H460, which is a heterogeneous cell population, according to the strength of metastatic ability. This clarified the correlation between metastatic ability and the expression level on the cell membrane.

Figure 18:
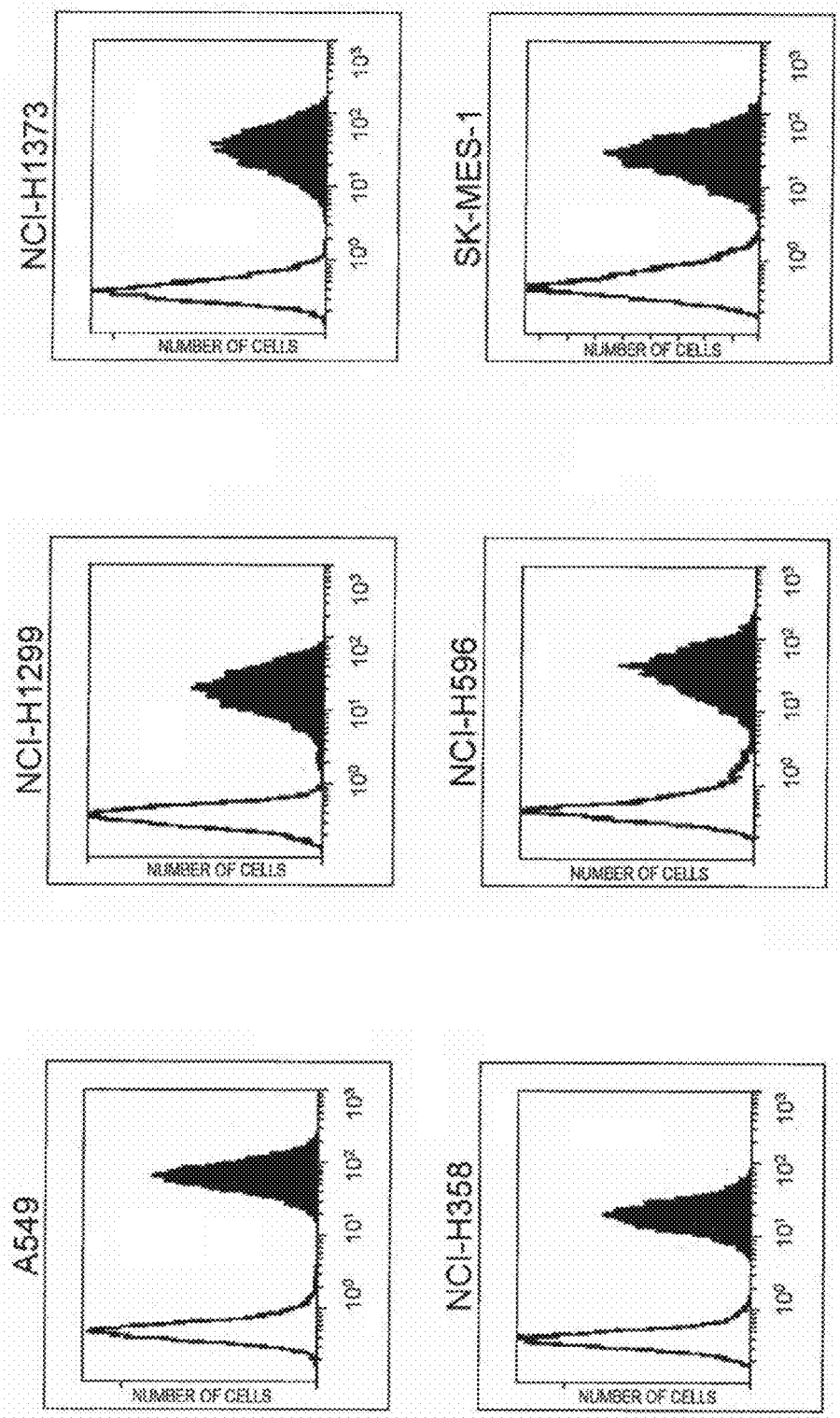

FIG. 18 shows in graphs flow cytometric analysis of lung cancer cell lines other than the NCI-H460 line using an anti-CLCP1 antibody (FA19-1). Mouse IgG1 was used as a control. Flow cytometric analysis was conducted after staining at an antibody concentration of 5 µg/ml.

Figure 19:
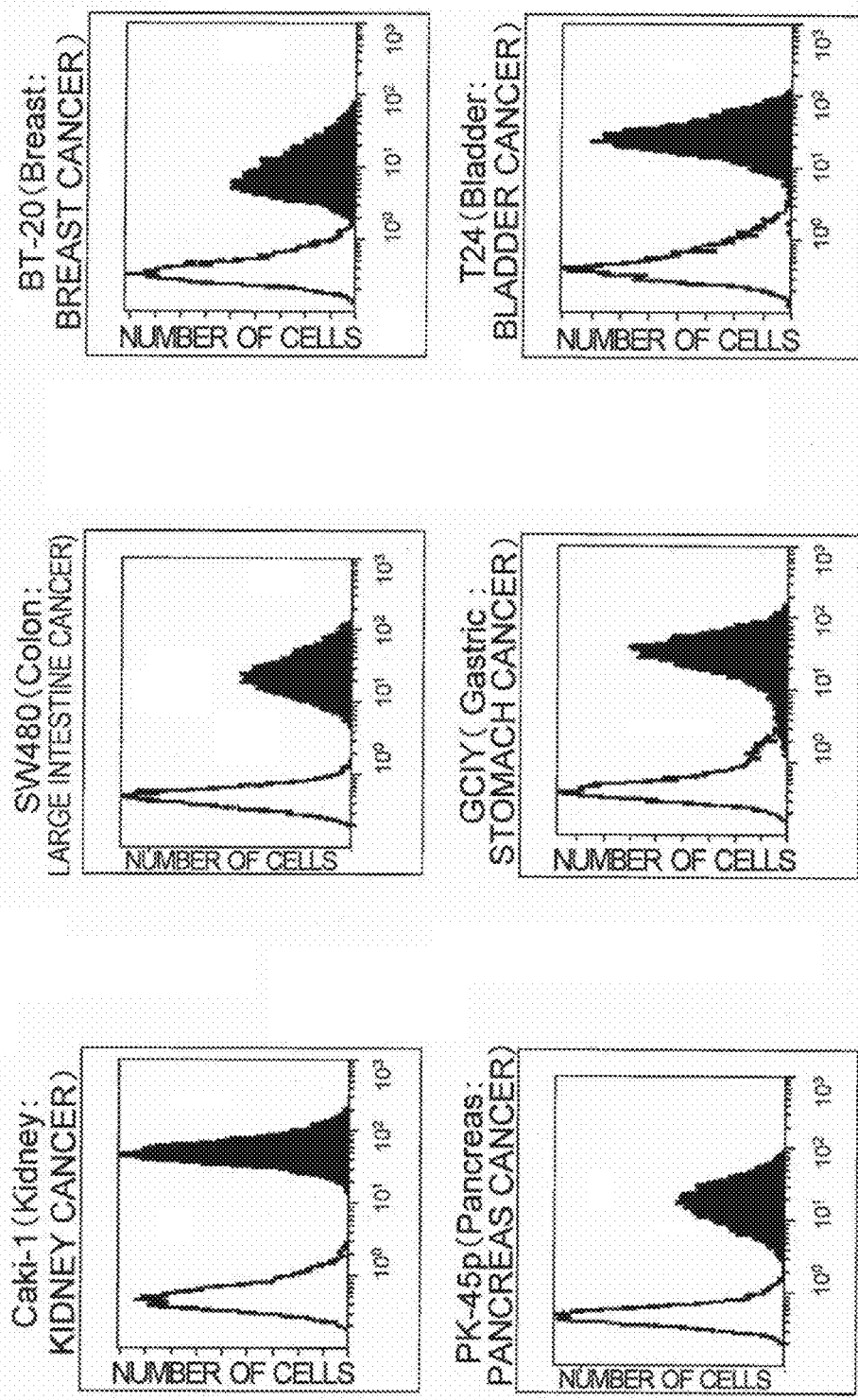

FIG. 19 shows in graphs flow cytometric analysis of various cancer cell lines using an anti-CLCP1 antibody (FA19-1). Mouse IgG1 was used as a control. Flow cytometric analysis was conducted after staining at an antibody-concentration of 5 µg/ml.

Figure 20:
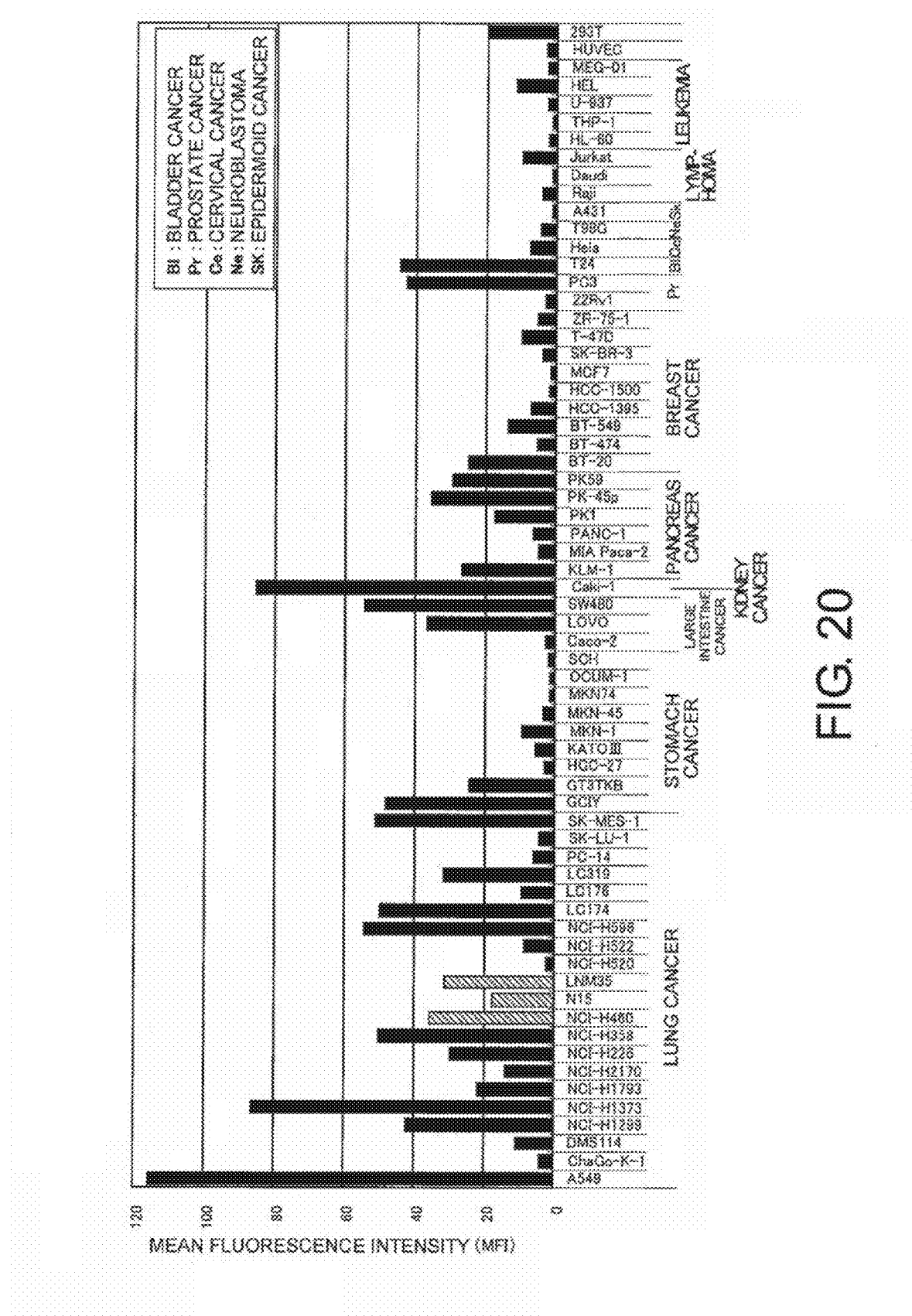

FIG. 20 is a graph showing the antigen expression level (mean fluorescence intensity) in various cancer cell lines. Various cancer cell lines (horizontal axis) were analyzed by flow cytometry using an anti-CLCP1 antibody (FA19-1) at a concentration of 5 µg/ml. The vertical axis of this graph indicates mean fluorescence intensity (MFI). CLCP1 was demonstrated to be expressed in cell lines of kidney cancer, bladder cancer, prostate cancer, pancreas cancer, stomach cancer, large intestine cancer, and breast cancer, in addition to lung cancer. Various cancer cell lines, and their origins and accession numbers are listed in Table 2.

Figure 21:
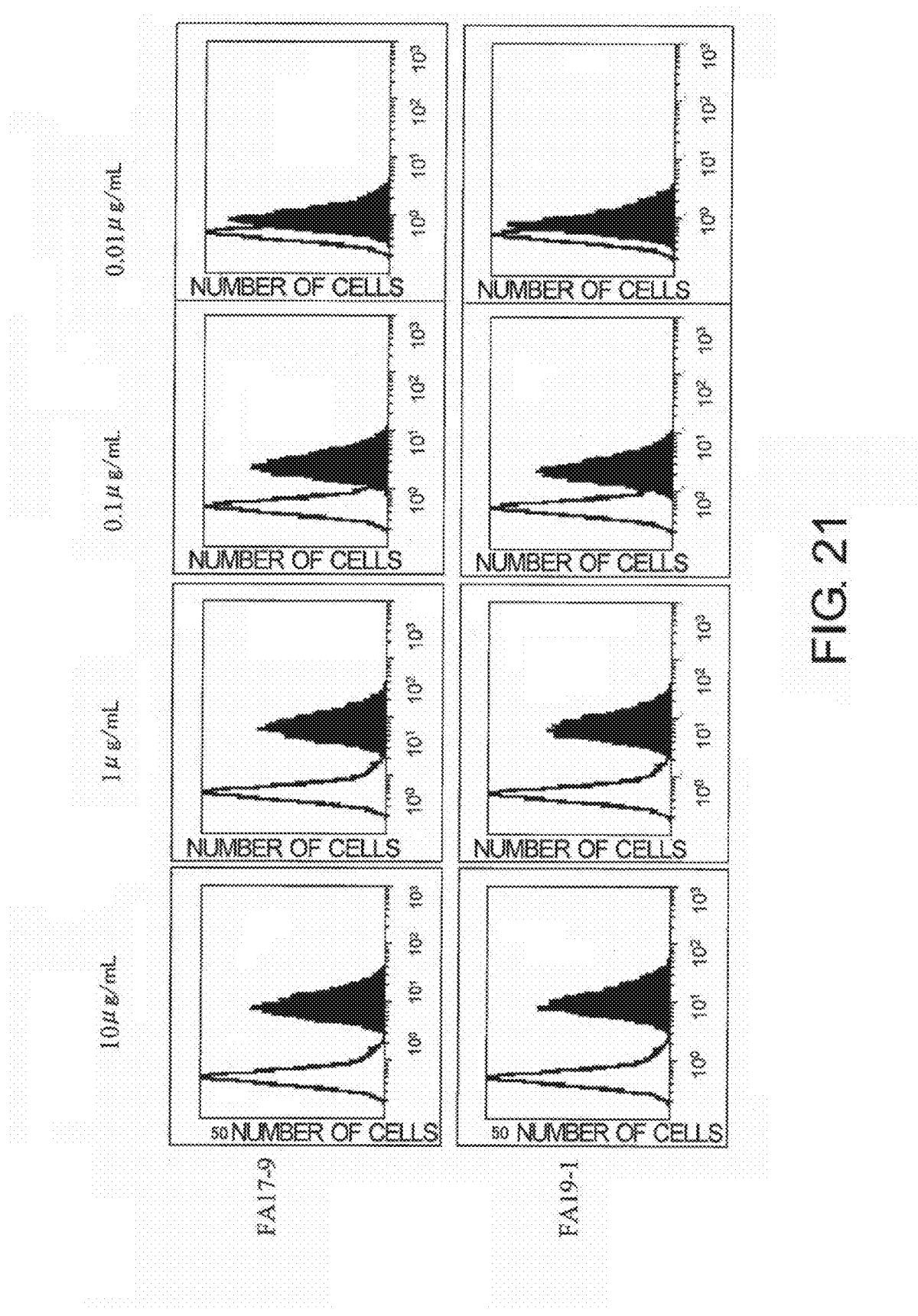

FIG. 21 shows in graphs the result of assessing the reactivity of chimeric FA17-9 antibody and chimeric FA19-1 antibody. The chimeric antibodies were produced to have constant regions derived from human IgG1 and variable regions derived from FA17-9 or FA19-1. Their binding activities to NCI-H460-LNM35 were assessed by flow cytometry.

FIG. 22 shows in graphs the result of assessing the ADCC activity of chimeric FA19-1 antibody or chimeric FA17-9 antibody against LNM35 cells. The ADCC of each chimeric antibody against NCI-H460-LNM35 cells was assessed by changing the antibody concentration (FIG. 22, upper panel (A)) or E/T ratio (effector/target ratio) (FIG. 22, lower panel (B)).

Figure 23:
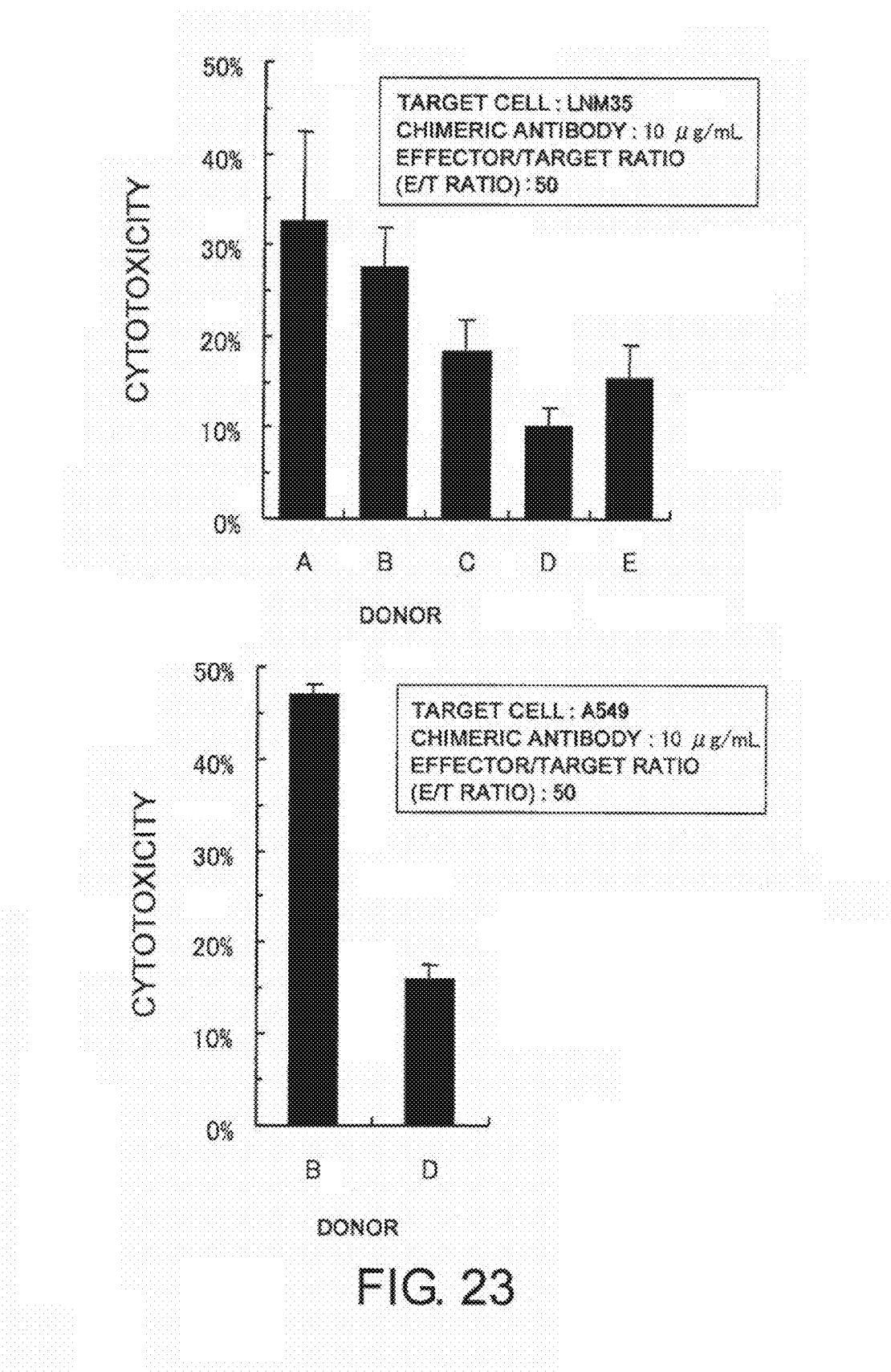

FIG. 23 shows in graphs results of assessing the ADCC activity of chimeric FA19-1 antibody against NCI-H460-LNM35 or A549. This result shows analysis of using different effector donors in the ADCC assay. The ADCC activity of chimeric FA19-1 antibody was confirmed against both NCI-H460-LNM35 (FIG. 23 upper panel) and A549 (FIG. 23 lower panel), although it varied to some extent depending on the type of donor (A to E). Chimeric FA19-1 antibody and chimeric FA17-9 antibody were demonstrated to mediate ADCC against the above-described lung cancer cells.

Figure 24:
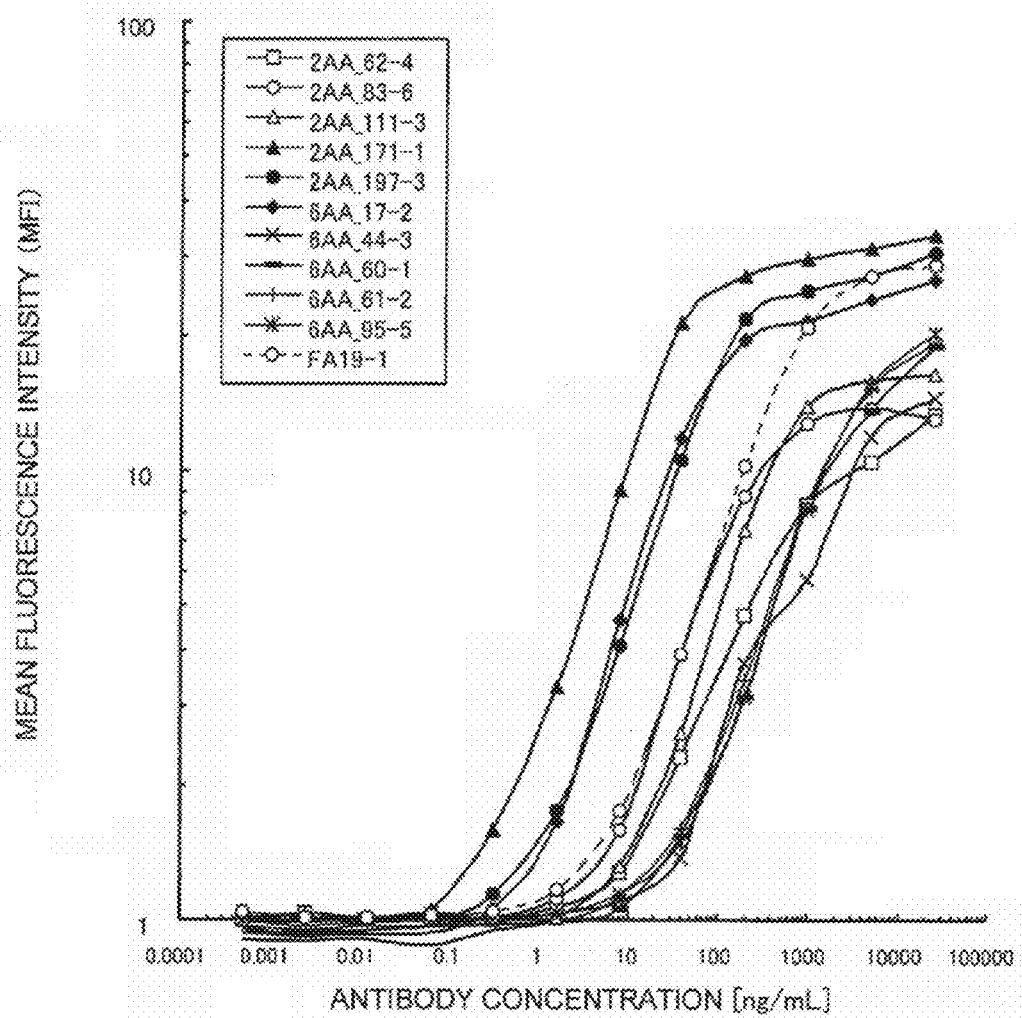

FIG. 24 shows in a graph the result of assessing the binding affinity of novel antibodies by FCM. The value of binding constant (affinity) can be determined from the antibody concentration and mean fluorescence intensity (MFI) determined by FCM analysis. The binding constant (affinity) was demonstrated to increase in the following order: 2AA_171-1>6AA_17-2≈2AA_197-3>FA19-1≈2AA_83-6>2AA_111-3>6AA_60-1.

Figure 25:
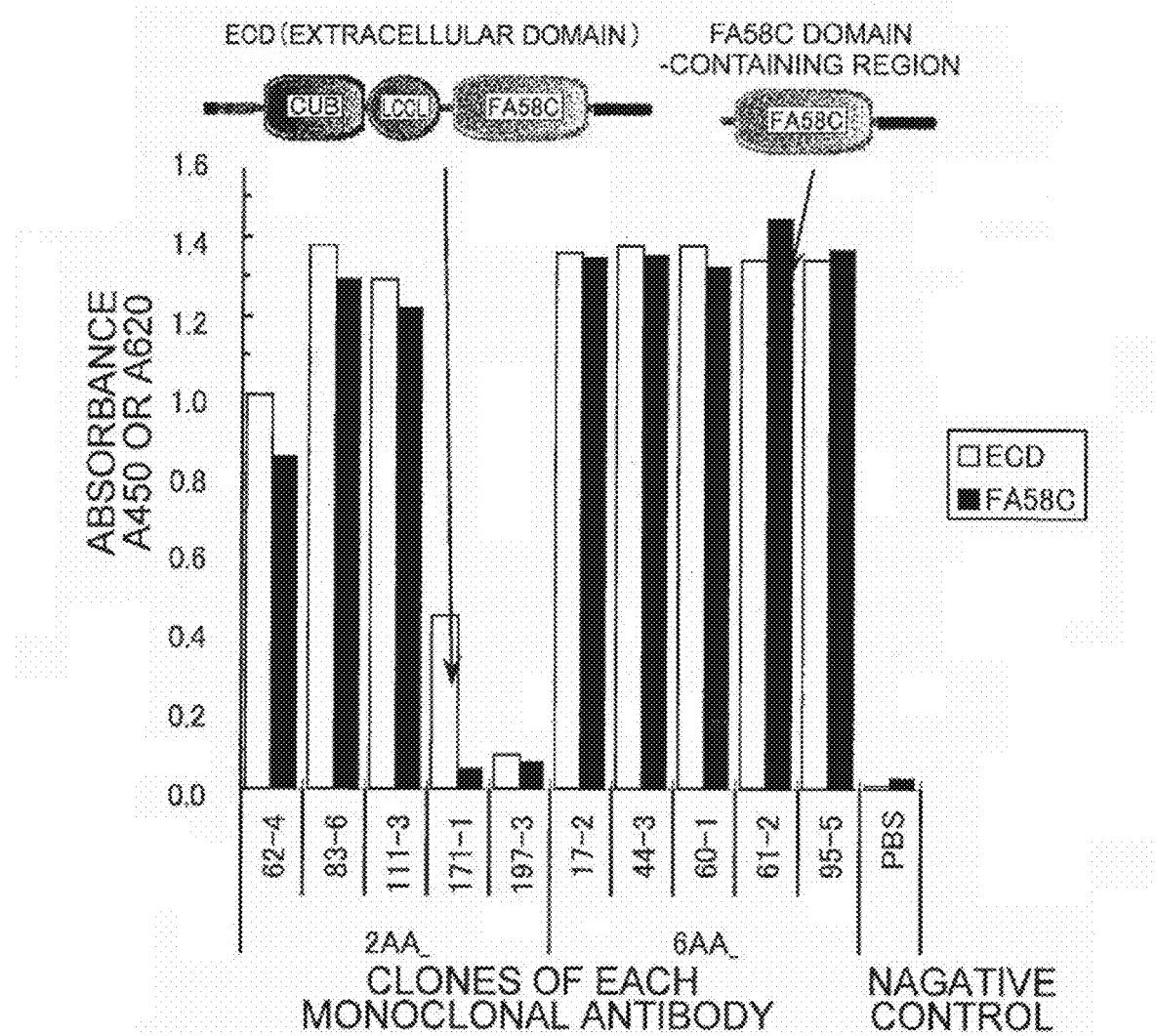

FIG. 25 shows in a diagram epitope mapping of novel antibodies. The recognition domains were estimated based on the ELISA reactivity to partial protein fragments. ELISA was carried out by sensitizing the whole extracellular domain (open bars) or a region containing FA58C (filled bars).

Figure 26:
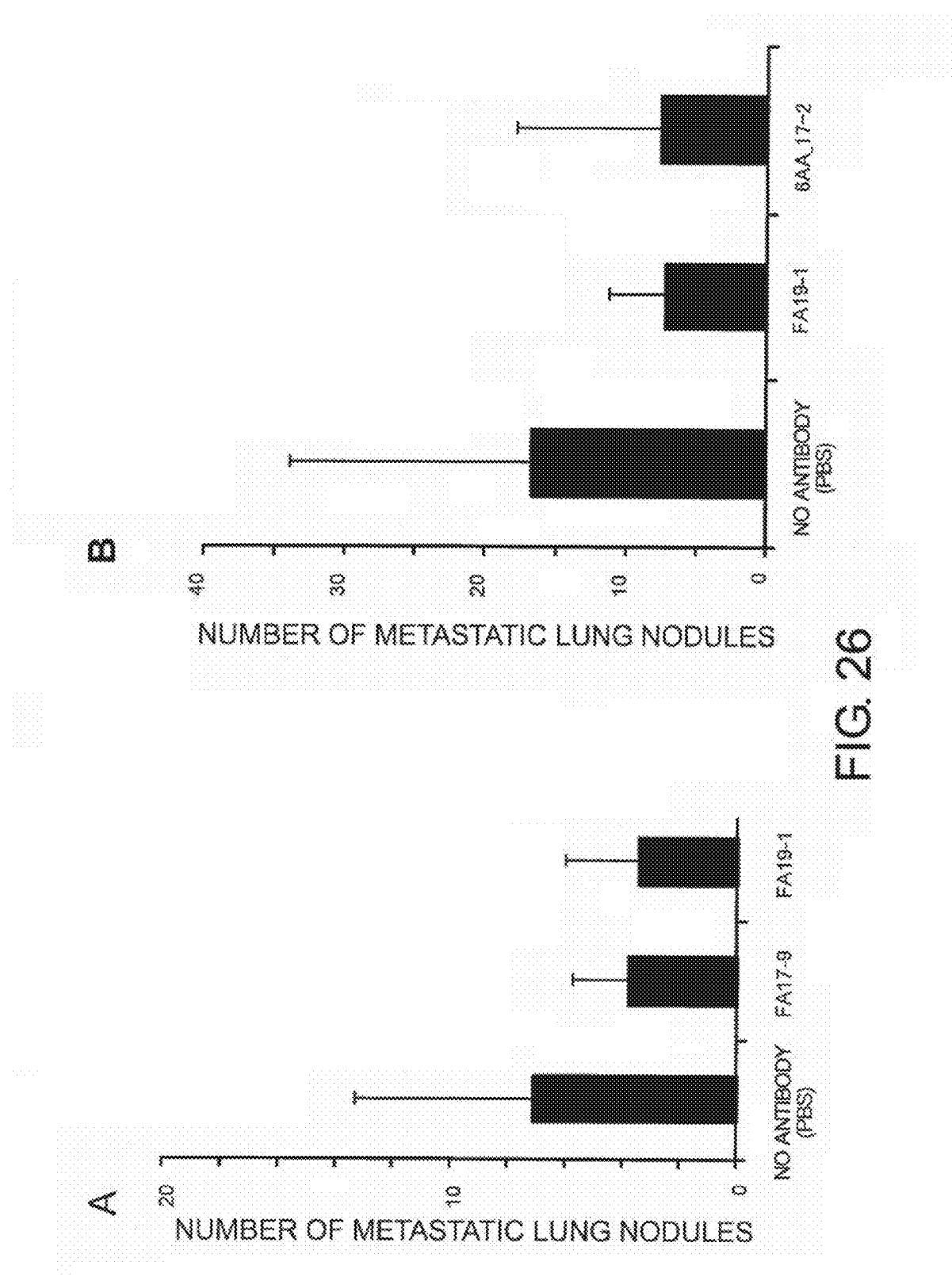

FIG. 26 shows in diagrams the result of suppressing lung metastasis 46 days after transplantation at the time of sacrifice, in the same manner as shown in FIG. 16(C). (A) FA19-1 significantly suppressed the metastasis. An additional experiment demonstrated that FA17-9 also suppressed the metastasis. (B) Both FA19-1 and 6AA_17-2 significantly suppressed the metastasis.

Figure 27:
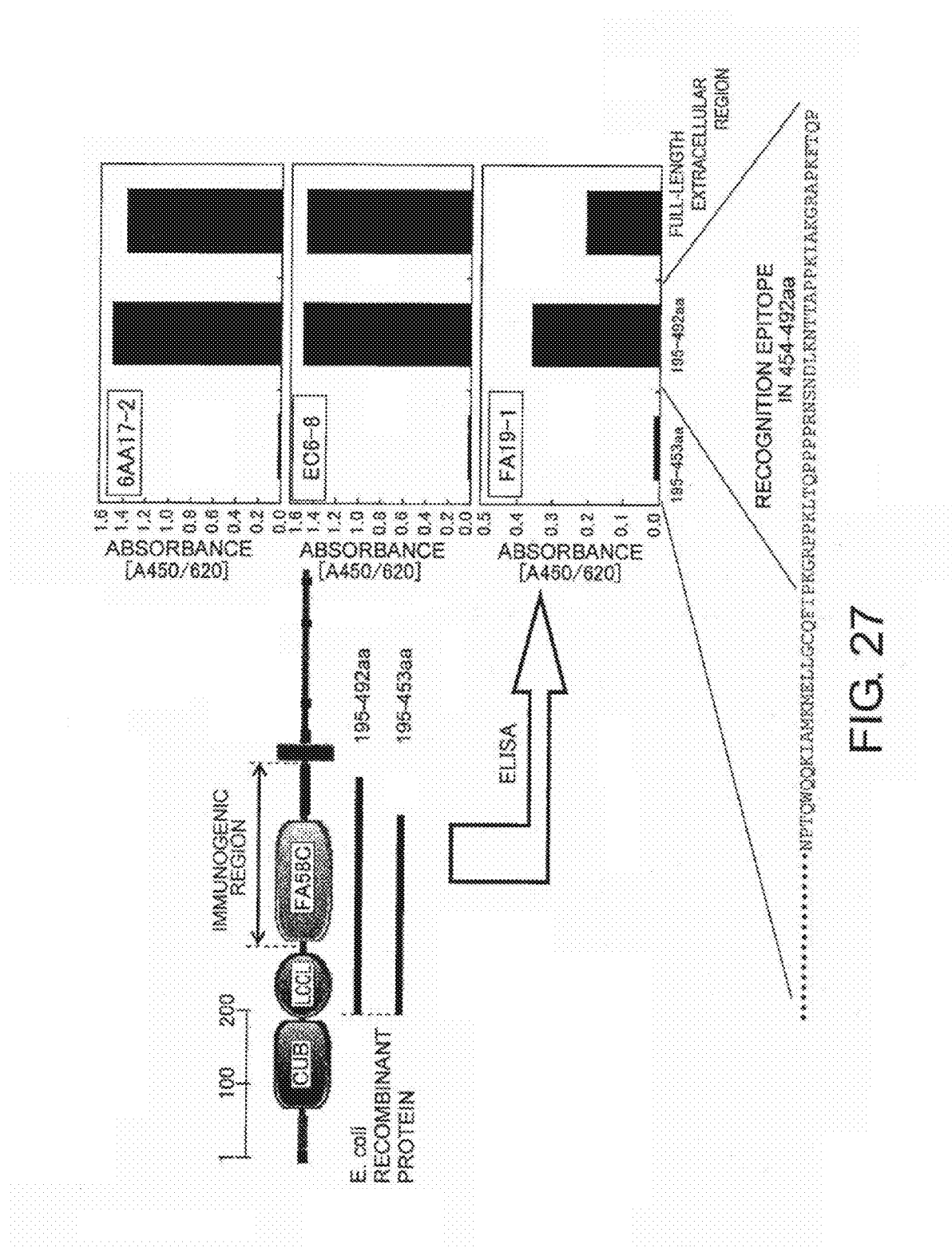

FIG. 27 shows in a diagram and graphs results obtained by narrowing down the epitope predicted to be recognized by novel antibodies (reactivity to an expressed partial antigen). To narrow down the binding site, the binding (reactivity) of antibodies 6AA_17-2, EC6-8, and FA19-1 to partial antigens was assessed by ELISA. The amino acid sequence in this FIG. is shown in SEQ ID NO: 97.

Figure 28:
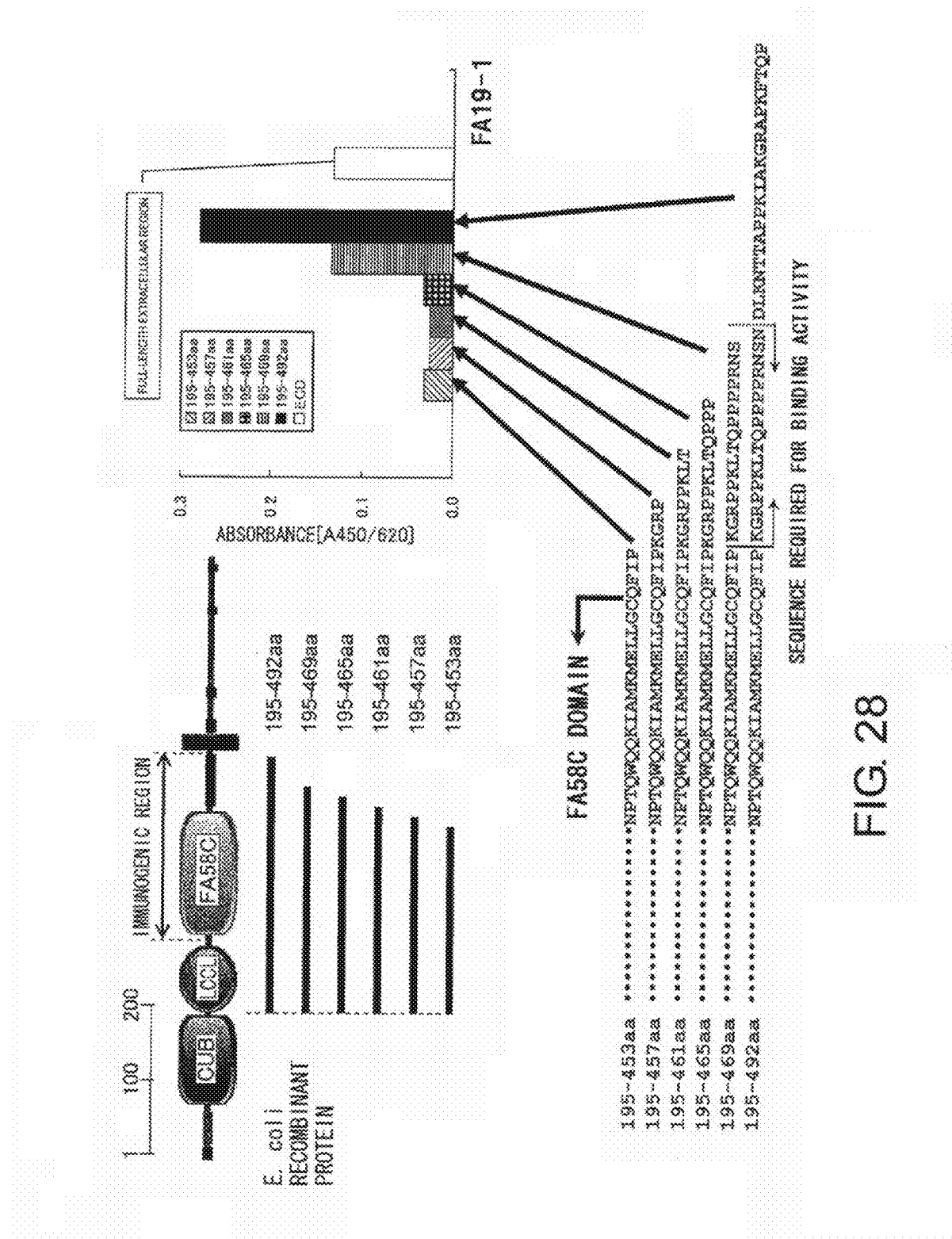

FIG. 28 shows in diagram and graphs results obtained by narrowing down the epitope predicted to be recognized by a novel antibody (reactivity to an expressed partial antigen). The binding (reactivity) of antibody FA19-1 to partial antigens was assessed by ELISA. The amino acid sequences of the partial regions of aa 195-aa 453, aa 195-aa 457, aa 195-aa 461, aa 195-aa 465, aa 195-aa 469, and aa 195-aa 492 in the sequence of SEQ ID NO: 2 are shown in SEQ ID NOs: 98-102 and 97, respectively.

Figure 29:
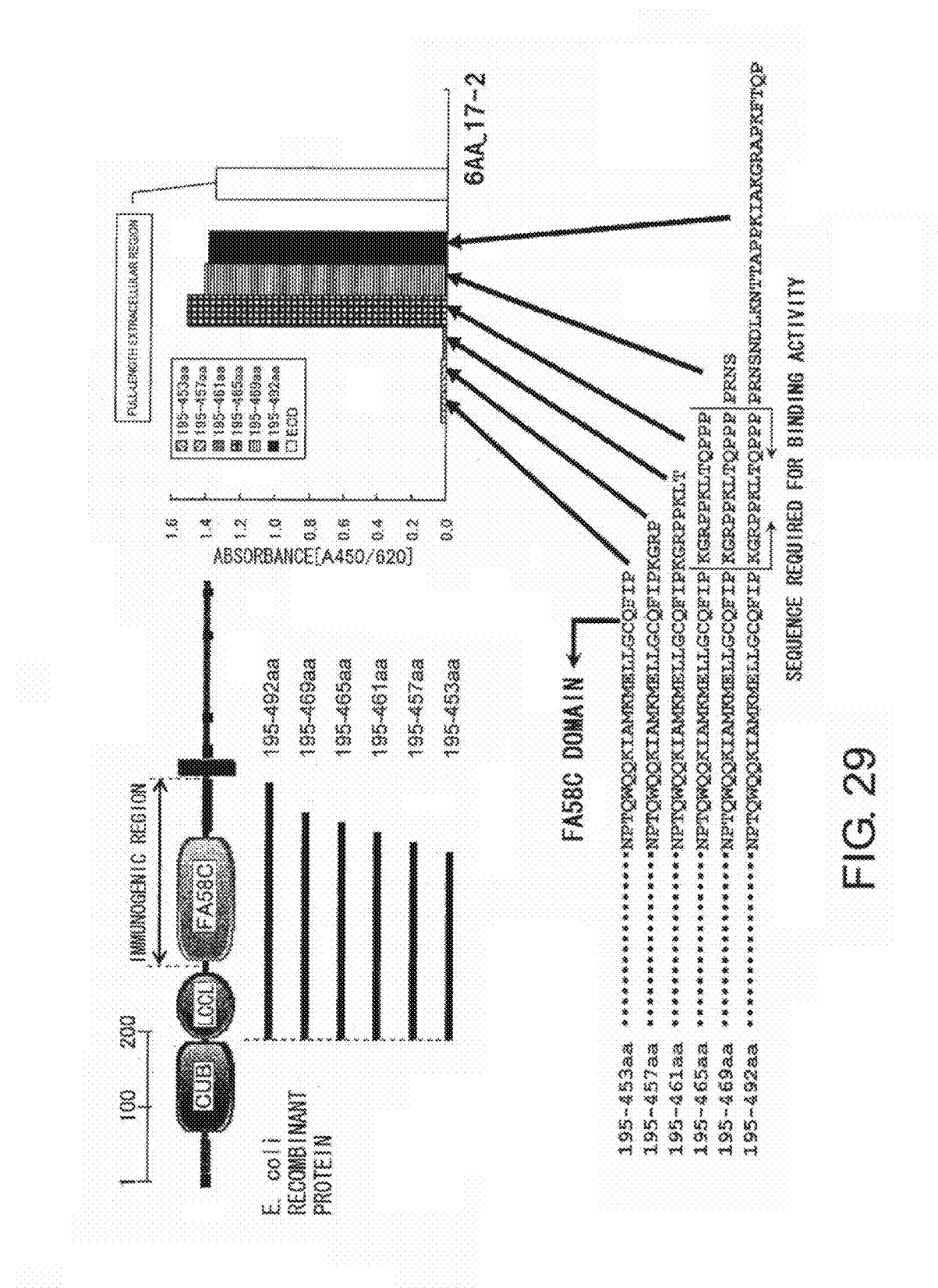

FIG. 29 shows in diagram and graphs results obtained by narrowing down the epitope predicted to be recognized by a novel antibody (reactivity to an expressed partial antigen). The binding (reactivity) of antibody 6AA_17-2 to partial antigens was assessed by ELISA. The amino acid sequences of the partial regions of aa 195-aa 453, aa 195-aa 457, aa 195-aa 461, aa 195-aa 465, aa 195-aa 469, and aa 195-aa 492 in the sequence of SEQ ID NO: 2 are shown in SEQ ID NOs: 98-102 and 97, respectively.

Figure 30:
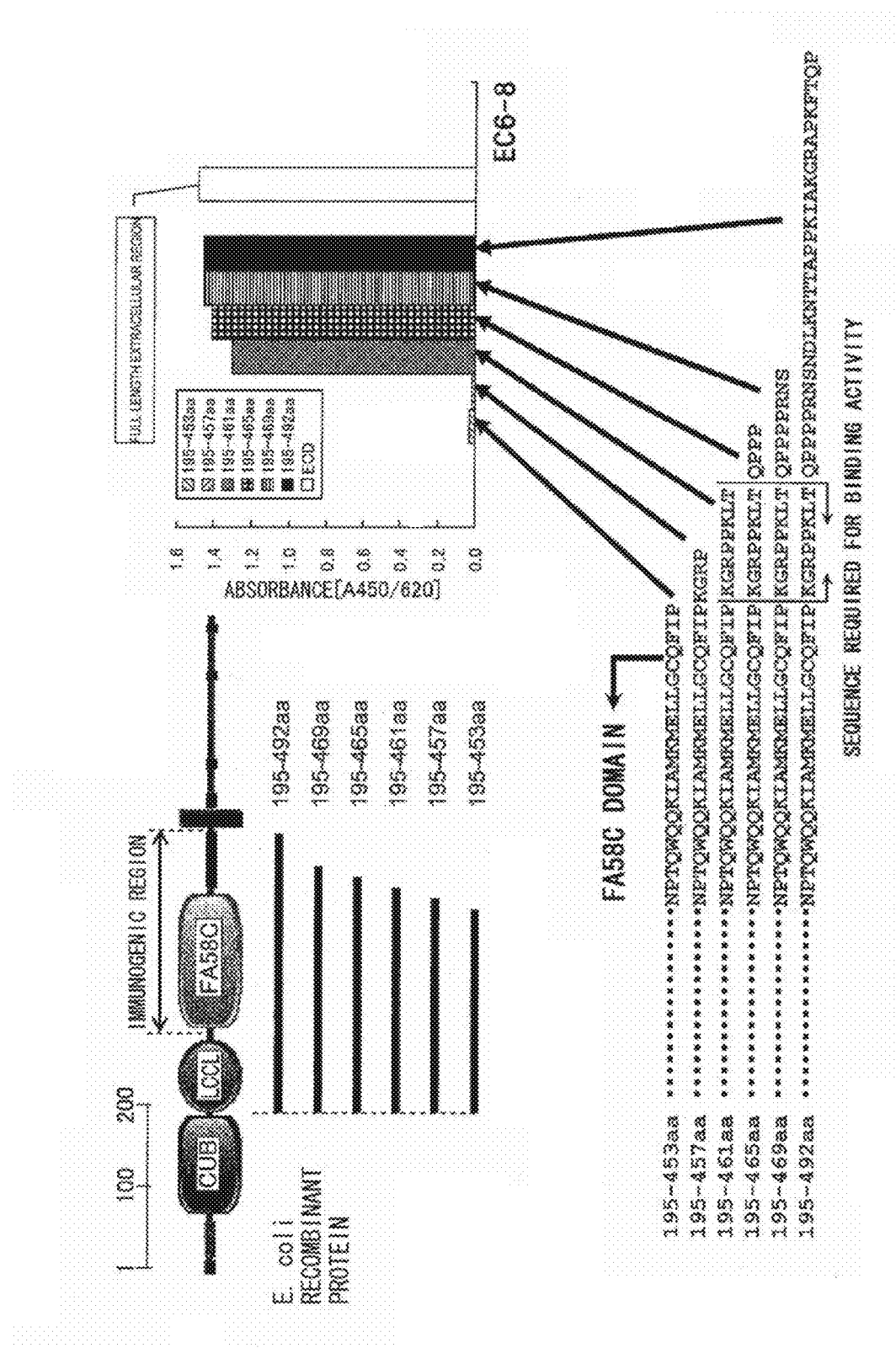

FIG. 30 shows in diagram and graphs results obtained by narrowing down the epitope predicted to be recognized by a novel antibody (reactivity to an expressed partial antigen). The binding (reactivity) of antibody EC6-8 to partial antigens was assessed by ELISA. The amino acid se uences of the artial re ions of aa 195-aa 453, aa 195-aa 457, aa 195-aa 461, aa 195-aa 465, aa 195-aa 469, and aa 195-aa 492 in the sequence of SEQ ID NO: 2 are shown in SEQ ID NOs: 98-102 and 97, respectively.

Figure 31:
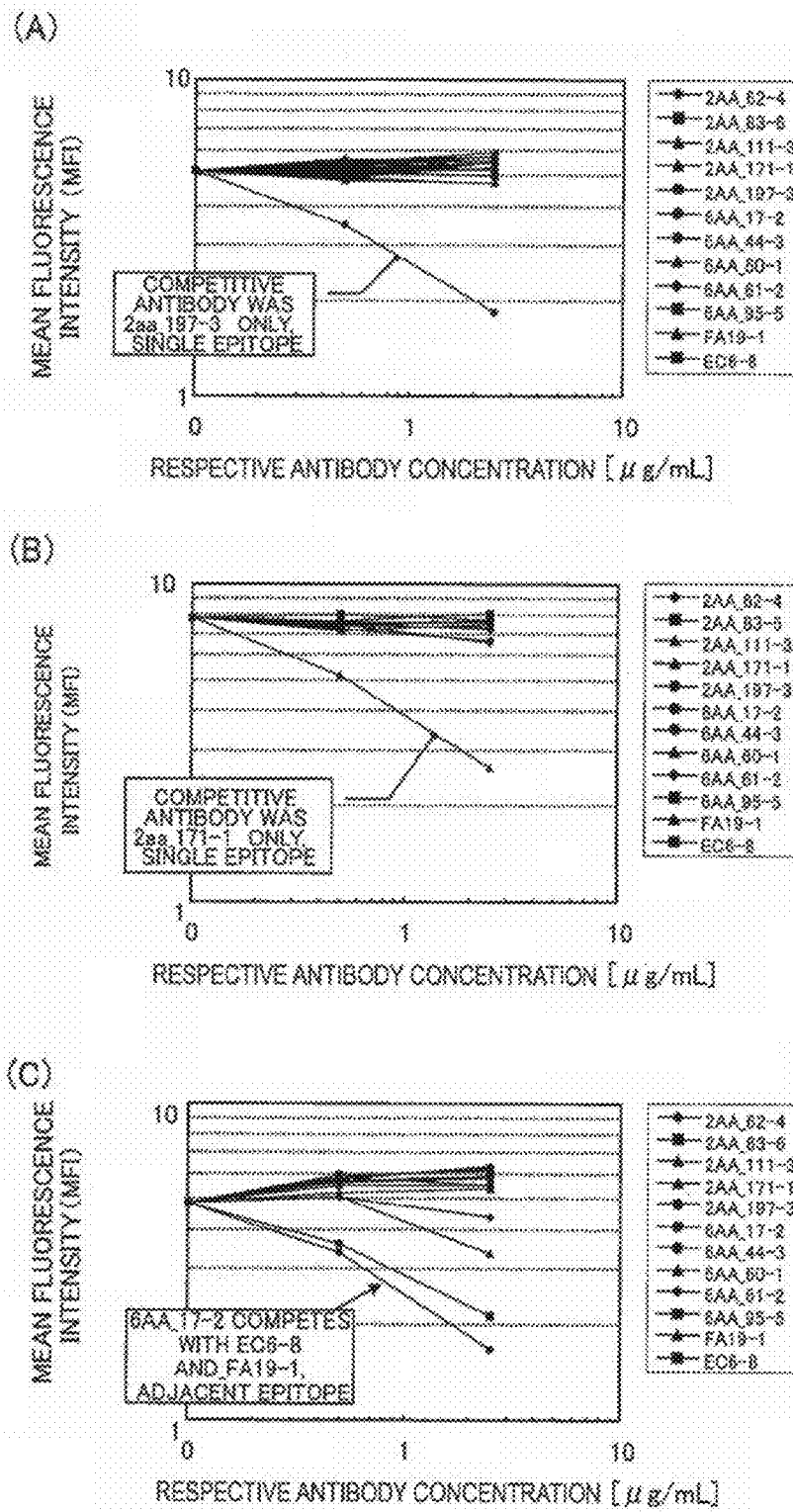

FIG. 31 shows in graphs epitope mapping of novel antibodies. Prediction based on a competitive inhibition experiments by FCM. (A) 2AA_197-3 inhibition assay: The only competing antibody is 2AA_197-3 itself, and thus the epitope was demonstrated to be unique and different from epitopes recognized by the other antibodies. (B) 2AA_171-1 inhibition assay: The only competing antibody is 2AA_171-1 itself, and thus the epitope was demonstrated to be unique and different from epitopes recognized by the other antibodies. (C) 6AA_17-2 inhibition assay: 6AA_17-2 competed with EC6-8 and FA19-1, and thus it became clear that it recognizes an epitope adjacent to the epitopes recognized by the other two clones.

Figure 3:
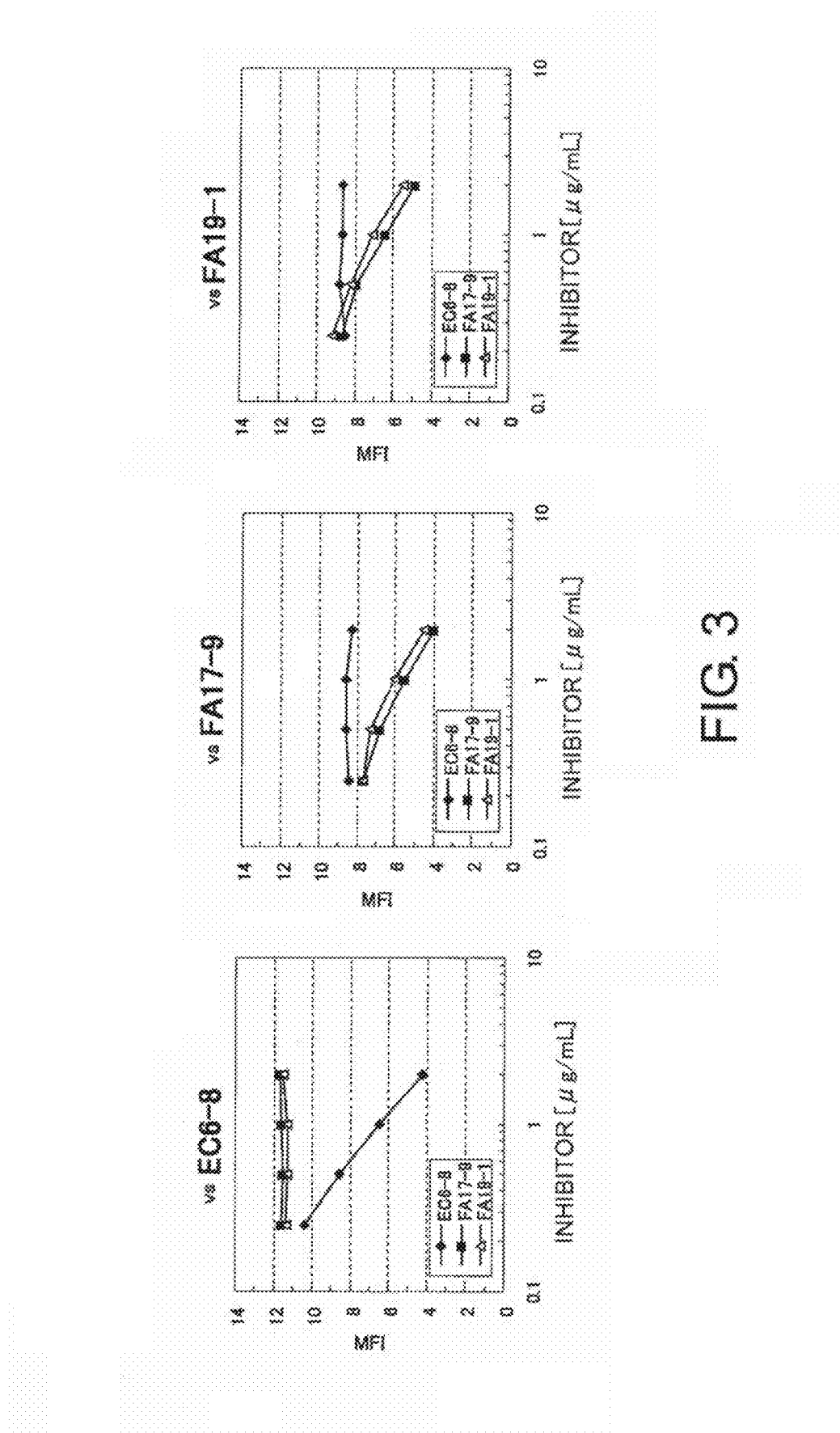
FIG. 3 shows in graphs an epitope analysis based on inhibition experiments. Three highly reactive clones were analyzed by FCM to assess the concentration-dependent inhibitory effect of each antibody in the presence of a constant concentration of biotinylated antibody. FA17-9 and FA19-1 were found to inhibit each other, suggesting that they share the same epitope or their epitopes are located very close to each other. EC6-8 inhibited neither FA17-9 nor FA19-1. Thus, EC6-8 is assumed to recognize an epitope that is different from those recognized by FA17-9 and FA19-1.
Figure 32:
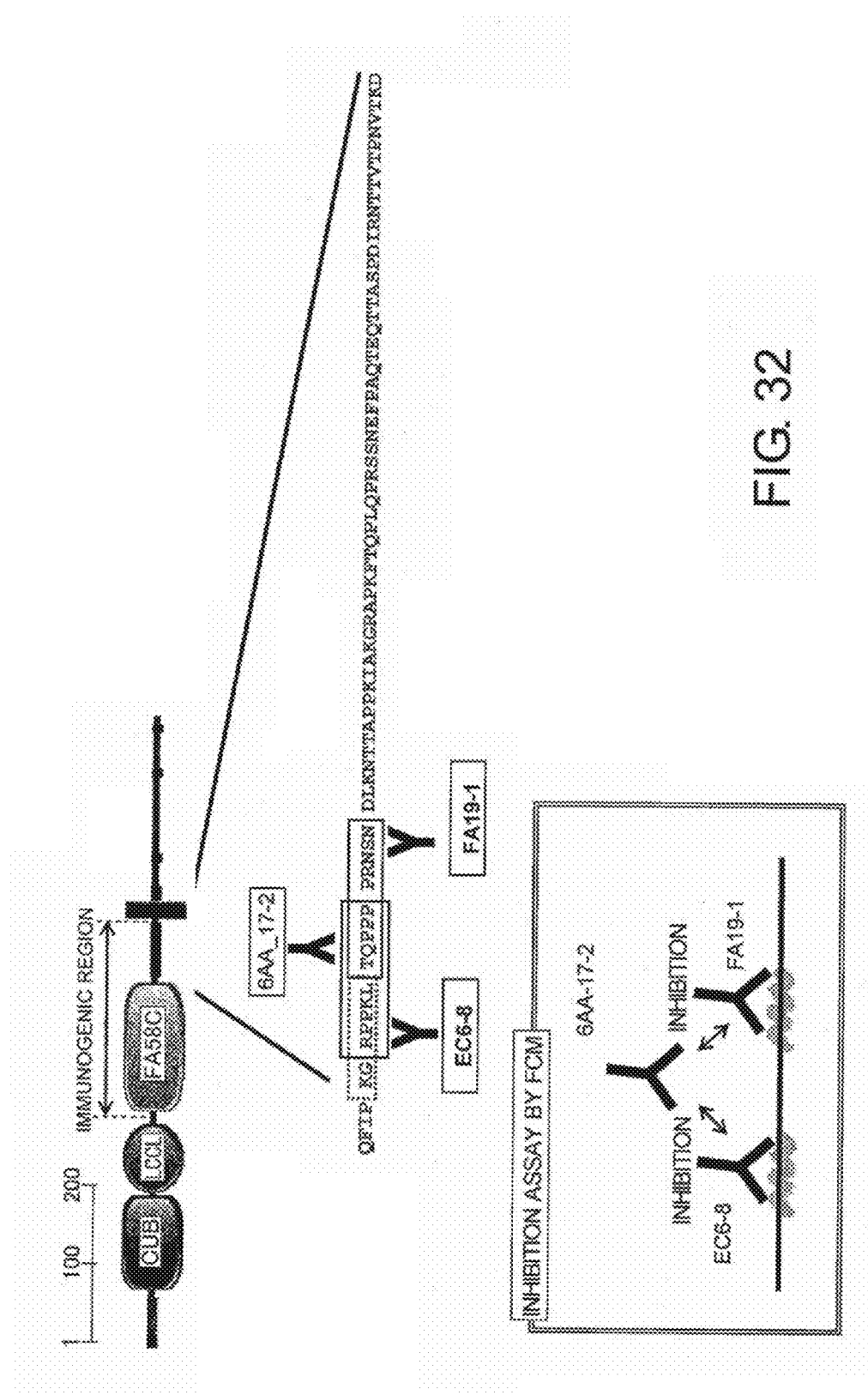

FIG. 32 shows speculation of epitopes based on summaries of the results of ELISA shown in FIGS. 27 to 30, and FCM competitive inhibition assays in FIGS. 3 and 31. 6AA_17-2, EC6-8, and FA19-1 were revealed to recognize epitopes adjacent to one another. Each epitope sequence was identified. The epitope recognized by EC6-8 is marked with broken lines. The amino acid sequence in this FIG. is shown in SEQ ID NO: 103.

Figure 33:
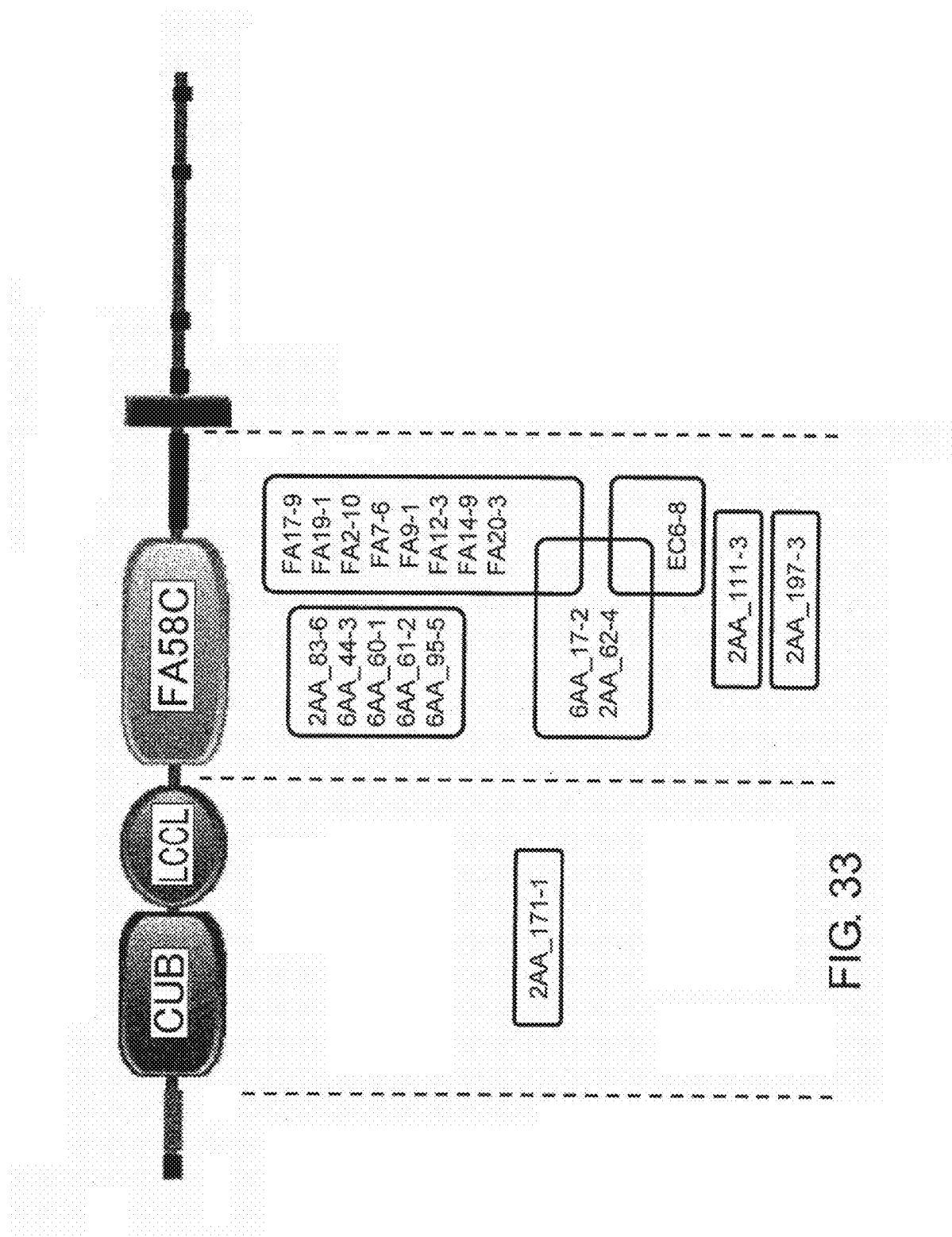

FIG. 33 shows the result of grouping epitopes based on summaries of the results of FCM competitive inhibition assay. Those in the same box competed with each other in the FCM competitive inhibition assay.

Figure 34:
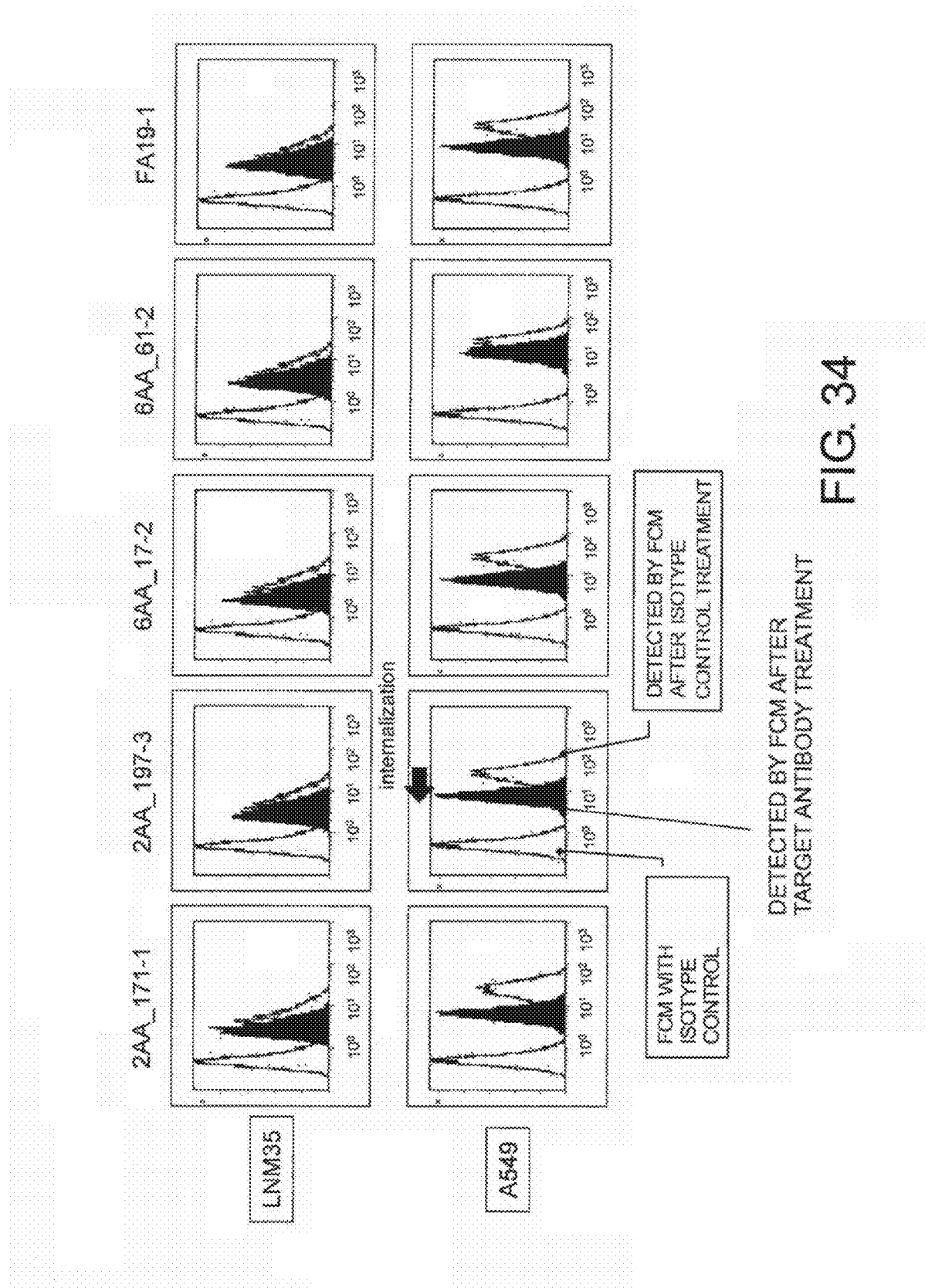

FIG. 34 shows in diagrams flow cytometric analysis after exposure to novel antibodies. LNM35 cells were exposed to novel antibodies at the indicated concentrations for 24 hours. After PBS wash, flow cytometric analysis was carried out using a biotinylated antibody. The result suggested that antibodies 2AA_171-1, 6AA_17-2, and 2AA_197-3 strongly induced CLCP1 degradation (internalization).

Figure 35:
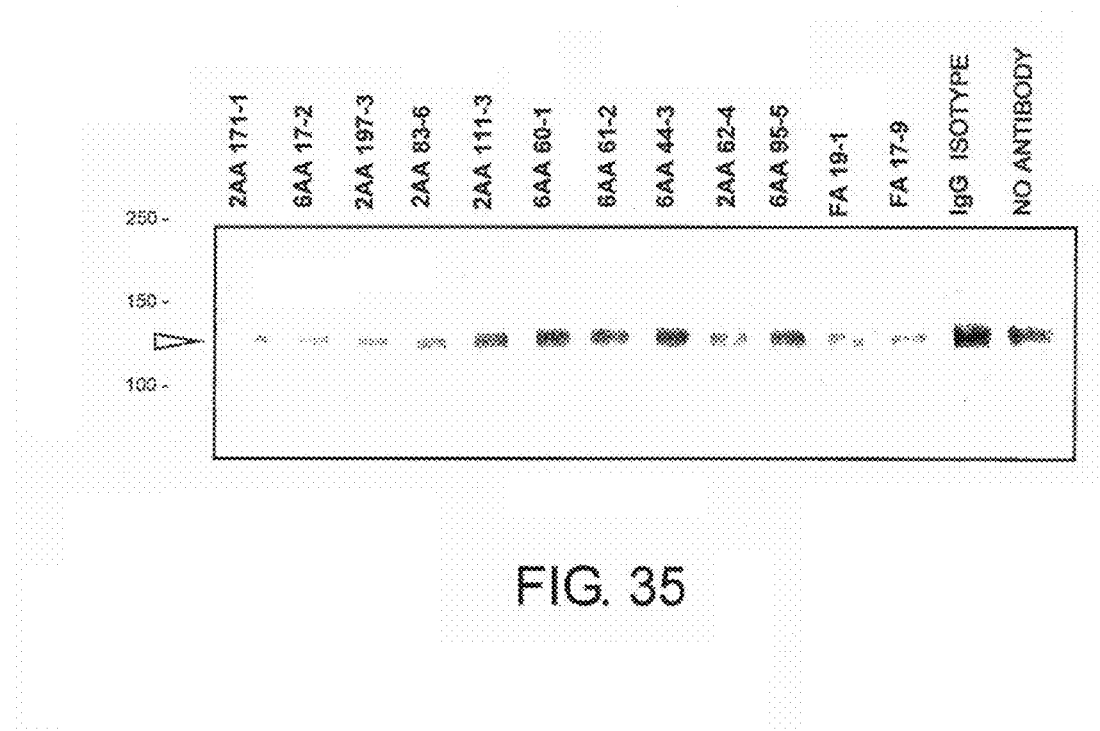

FIG. 35 shows in a photograph Western blot for CLCP1 in LNM35 after antibody exposure. Mouse IgG1 was used as a control antibody. After 24 hours of exposure to each antibody at a concentration of 5 µg/ml, equivalent amounts of cell lysates were assessed by Western blot analysis using FA19-1. The result suggested that similarly to FA17-9 and FA19-1, antibodies 2AA_171-1, 6AA_17-2, and 2AA_197-3 induced degradation (internalization) of CLCP1.

Figure 36:
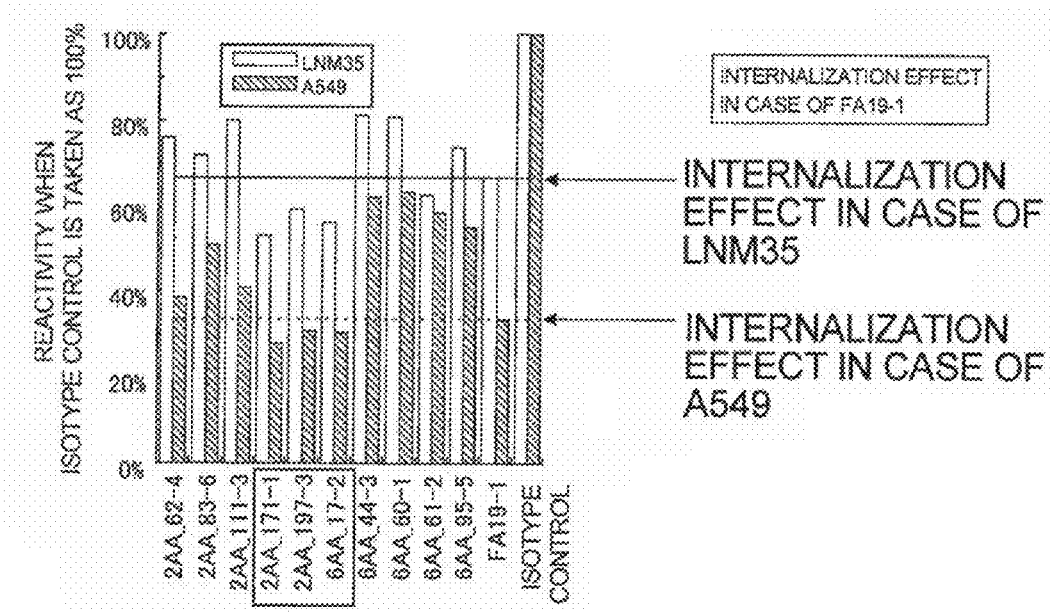

FIG. 36 shows in a diagram the effect of novel antibodies on internalization. The internalization effect is shown as percent activity when taking the internalization activity of the control antibody sample as 100%. The internalization effect of FA19-1 in NCI-H460-LNM35 and A549 is indicated by arrow. The amount of human CLCP1 antigen on the cell surface was reduced by reacting cells with the antibodies. It can be assumed that internalization of human CLCP1 into the cells was induced by antibody binding. This tendency can be observed with other type of cells.

Figure 37:
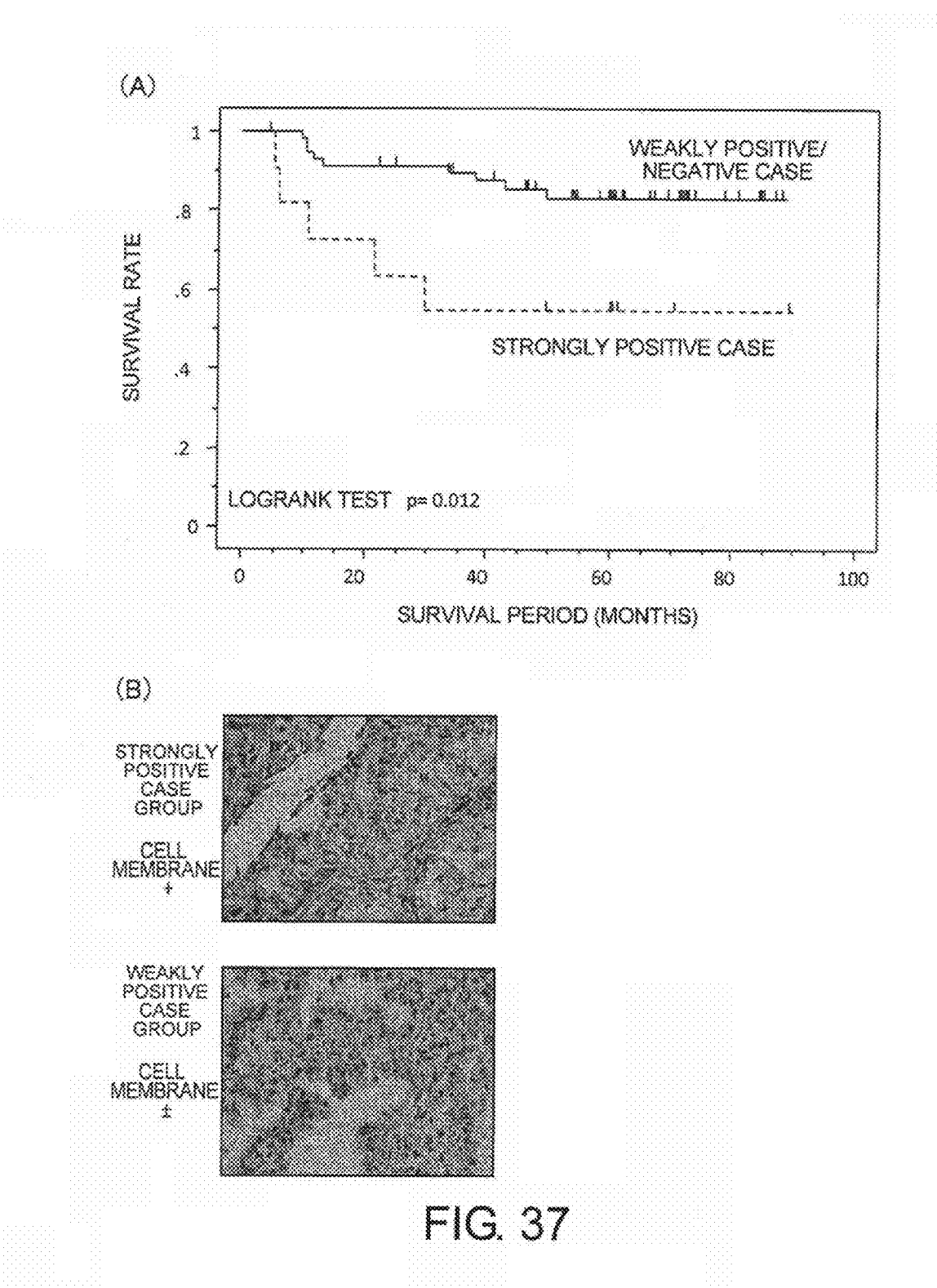

FIG. 37 shows in a graph and photographs prediction of prognosis by histological staining. (A) Lung cancer specimens were stained using antibody FA19-1 by the staining method described above. Based on the cell membrane staining, the specimens were grouped into strongly positive cases: 11, weakly positive cases: 7, and negative cases: 52. The group of strongly positive cases was compared to the groups of weakly positive/negative cases by Kaplan-Meier analysis. The prognosis in the strongly positive cases was p=0.012 in the logrank test, showing that the survival rate was statistically significantly low. The vertical bar indicates cases that could not reach the "end point=death" during observation periods (survival cases) (i.e., "censored case"). (B) shows the difference in staining between strongly positive cases and weakly positive cases. The immunohistological reactivities of the antibody were grouped into three groups: strongly positive (+), weakly positive (±), and negative (−). Specifically, cases where the cell membrane is clearly stained on the outline as shown in the upper panel are defined as strongly positive; cases where the cell membrane is only stained vaguely as shown in the lower panel are defined as weakly positive; and cases where the cell membrane is not stained are defined as negative (data not shown).

Figure 38:
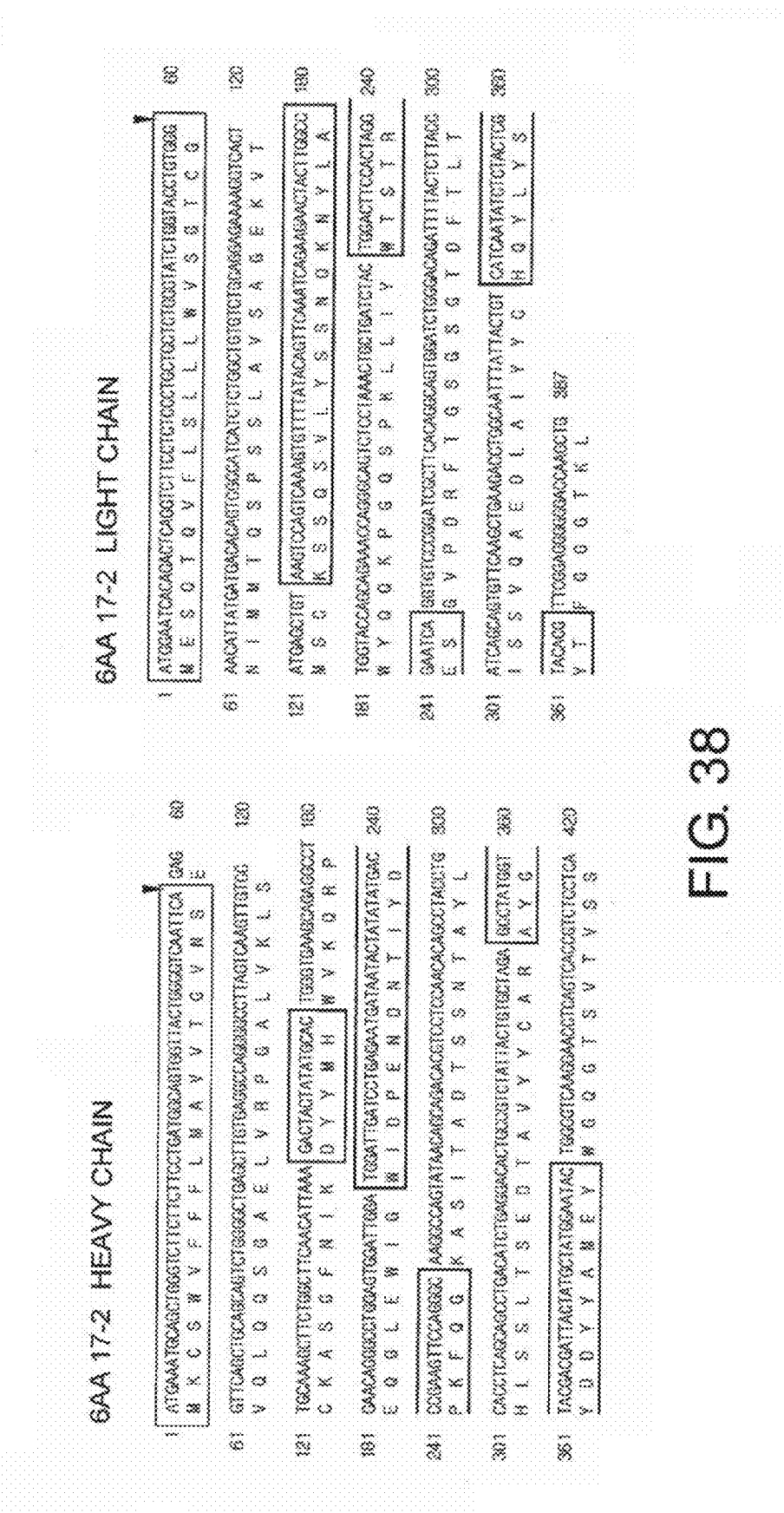

FIG. 38 shows in diagrams the nucleotide and amino acid sequences of variable regions of antibody 6AA_17-2. The nucleotide and amino acid sequences of the heavy chain (variable region comprising the signal sequence) are shown in SEQ ID NOs: 104 and 105, respectively. The boxed regions correspond to the signal sequence, CDR1 (SEQ ID NO: 60), CDR2 (SEQ ID NO: 61), and CDR3 (SEQ ID NO: 62) from the top. The nucleotide and amino acid sequences of the light chain (variable region comprising the signal sequence) (SEQ ID NOs: 106 and 107), respectively. The boxed regions correspond to the signal sequence, CDR1 (SEQ ID NO: 65), CDR2 (SEQ ID NO: 66), and CDR3 (SEQ ID NO: 67) from the top.

Figure 39:
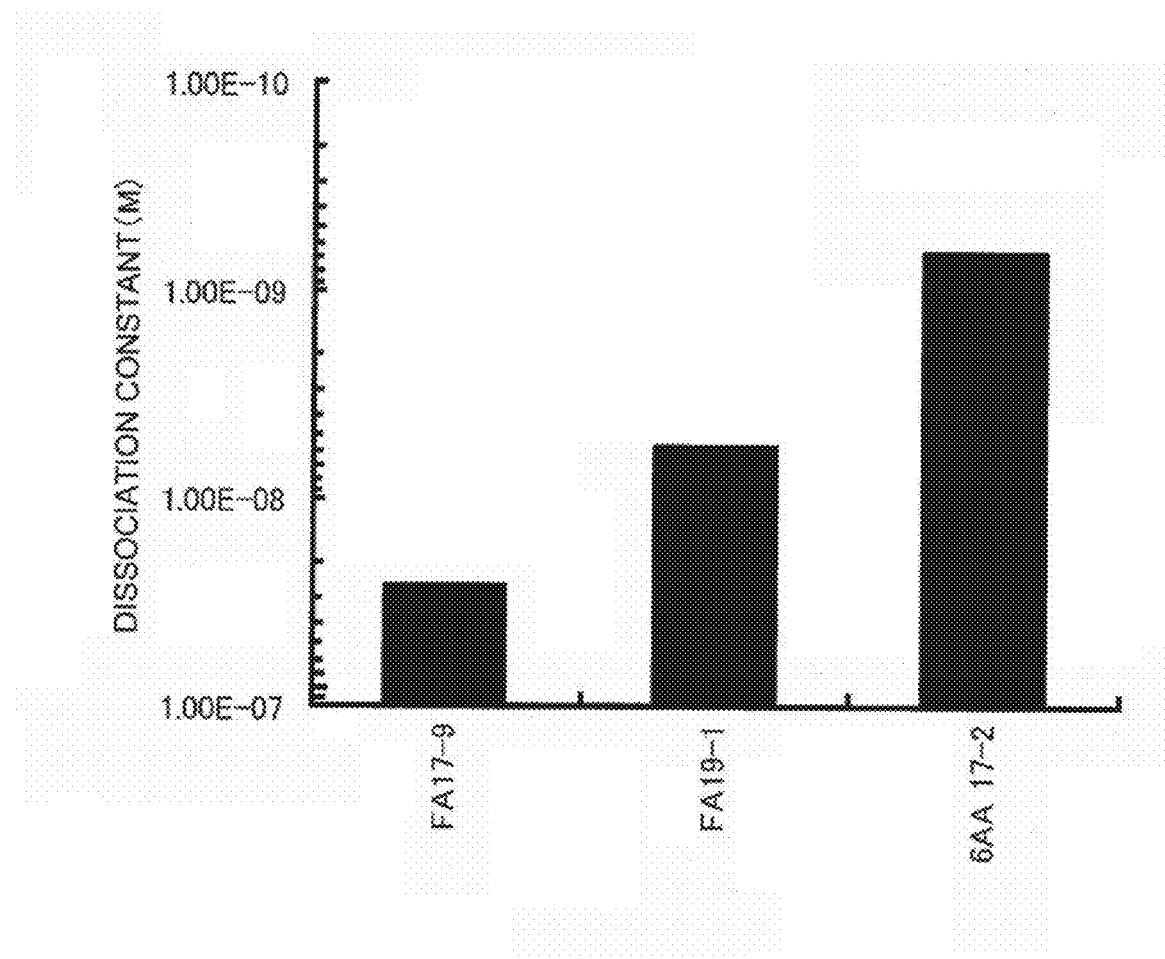

FIG. 39 shows in a graph the result of determining the dissociation constant of each antibody measured by Biacore assay.

Figure 40:
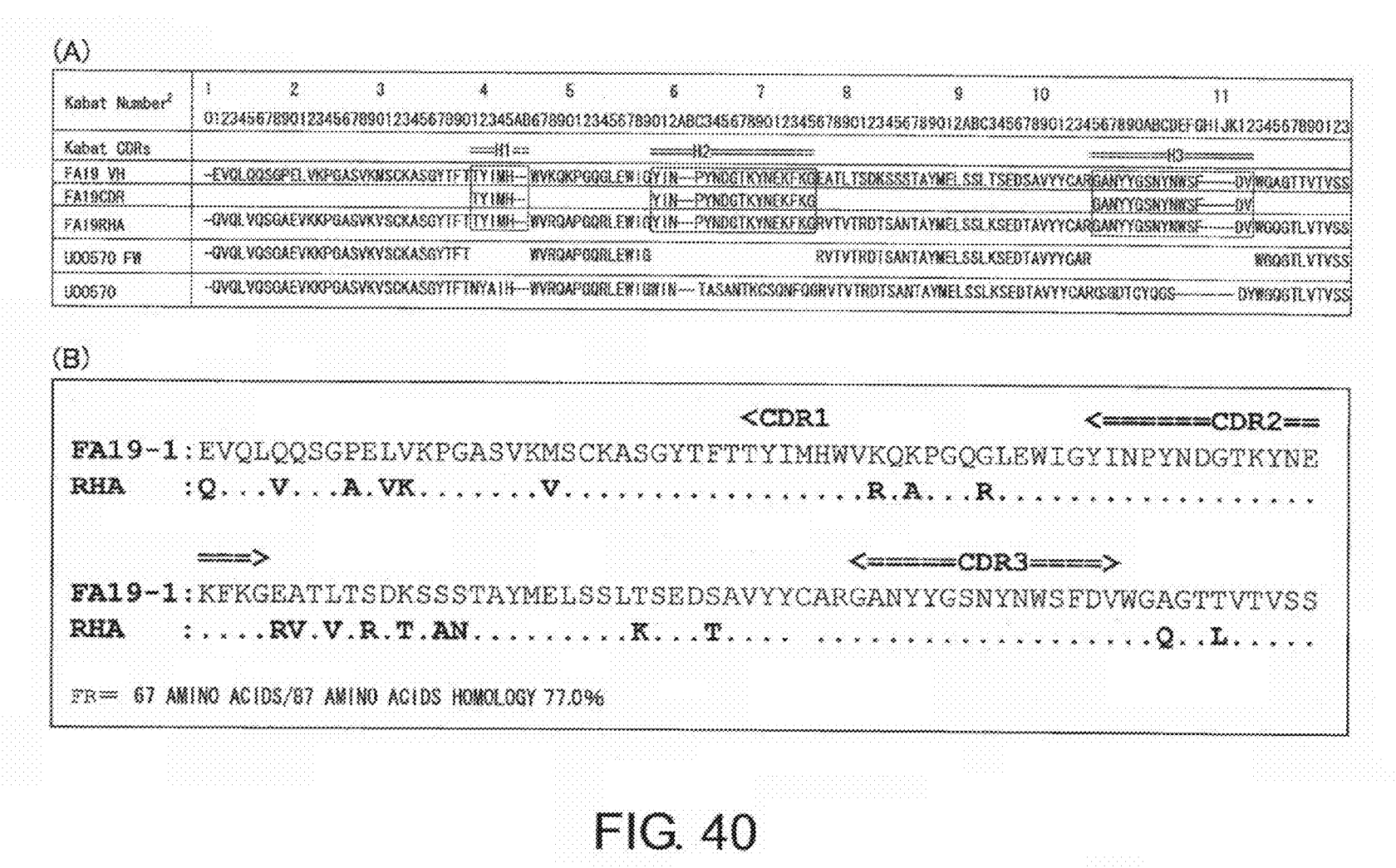

FIG. 40 shows in diagrams the process of humanizing a heavy chain. A shows FA19RHA (humanized) and the selected human antibody sequence. U00570 is the selected human antibody sequence. The CDR portions were converted into those of FA19-1. B shows % amino acid identity in framework. The constructed humanized antibody and FA19-1 have 77.0% amino acid identity in their frameworks. In (A), the amino acid sequences of FA19 VH, FA19 CDRs, FA19 RHA U00570 FWs and U00570 are shown in SEQ ID NO: 15, SEQ ID NOs: 16-18, SEQ ID NO: 45, SEQ ID NOs: 41-44, and SEQ ID NO: 40, respectively. In (B), the amino acid sequences of FA19-1 and RHA are shown in SEQ ID NO: 15 and SEQ ID NO: 45, respectively.

FIG. 41 shows in diagrams the process of humanizing a light chain. A shows FA19RKA (humanized) and the selected human antibody sequence. U96396 is the selected human antibody sequence. The CDR portions were converted into those of FA19-1. B shows % amino acid identity in framework. The constructed humanized antibody and FA19-1 have 78.8% amino acid identity in their frameworks. In (A), the amino acid sequences of FA19 VK, FA19 CDRs, FA19 RKA U96396 FWs and U96396 are shown in SEQ ID NO: 20, SEQ ID NOs: 21, 72, and 22; SEQ ID NO: 55; SEQ ID NOs: 51-54; and SEQ ID NO: 50, respectively. In (B), the amino acid sequences of FA19-1 and RKA are shown in SEQ ID NO: 20 and SEQ ID NO: 55, respectively.

Figure 42:
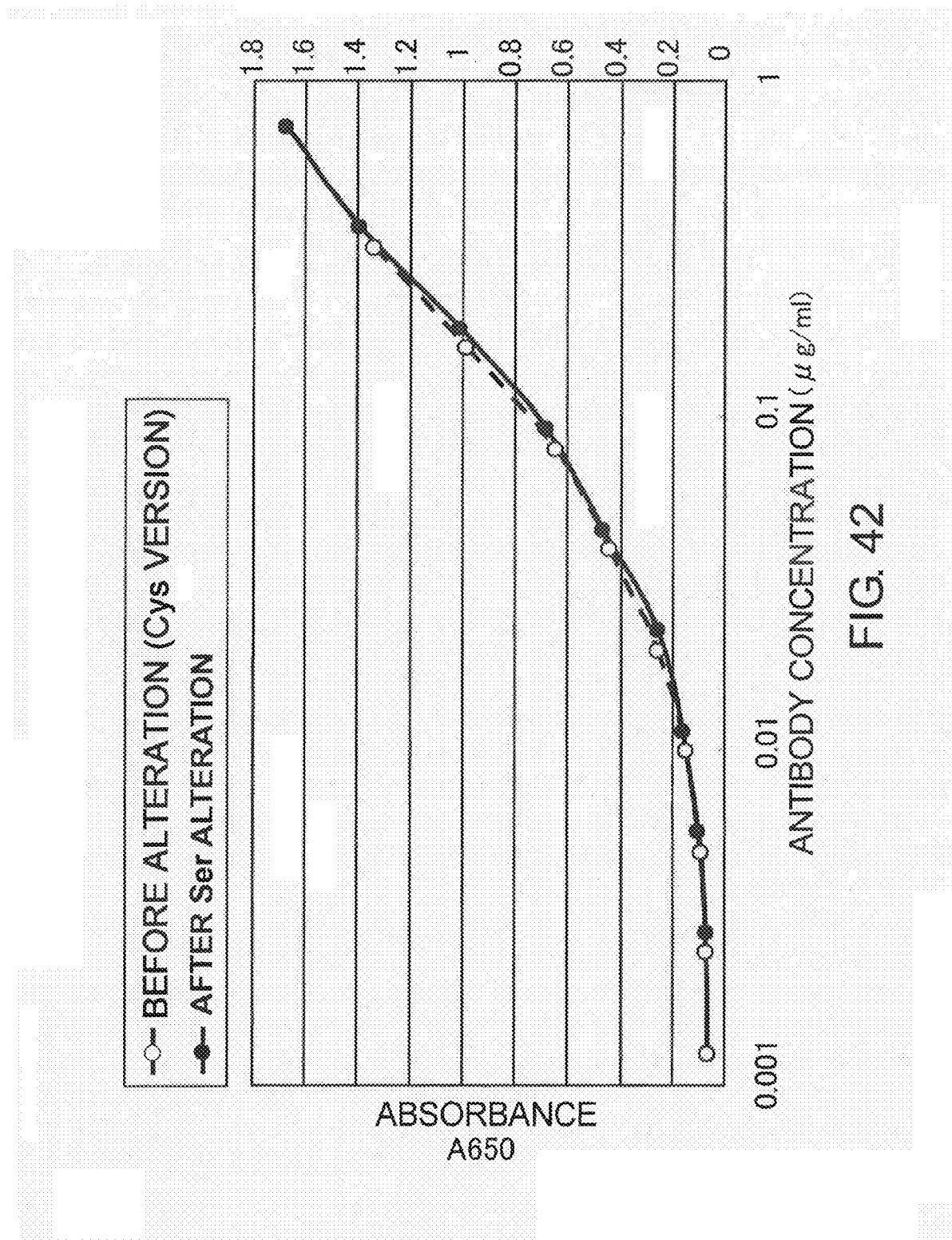

FIG. 42 shows in a graph the binding activity of the serine-substituted antibody to the extramembrane domain in ELISA. The binding activity of the antibody obtained by converting cysteine in the light chain CDR of antibody FA19-1 into serine was assessed. The constructed serine-substituted antibody exhibited a binding activity comparable to that of the antibody before conversion.

Figure 43:
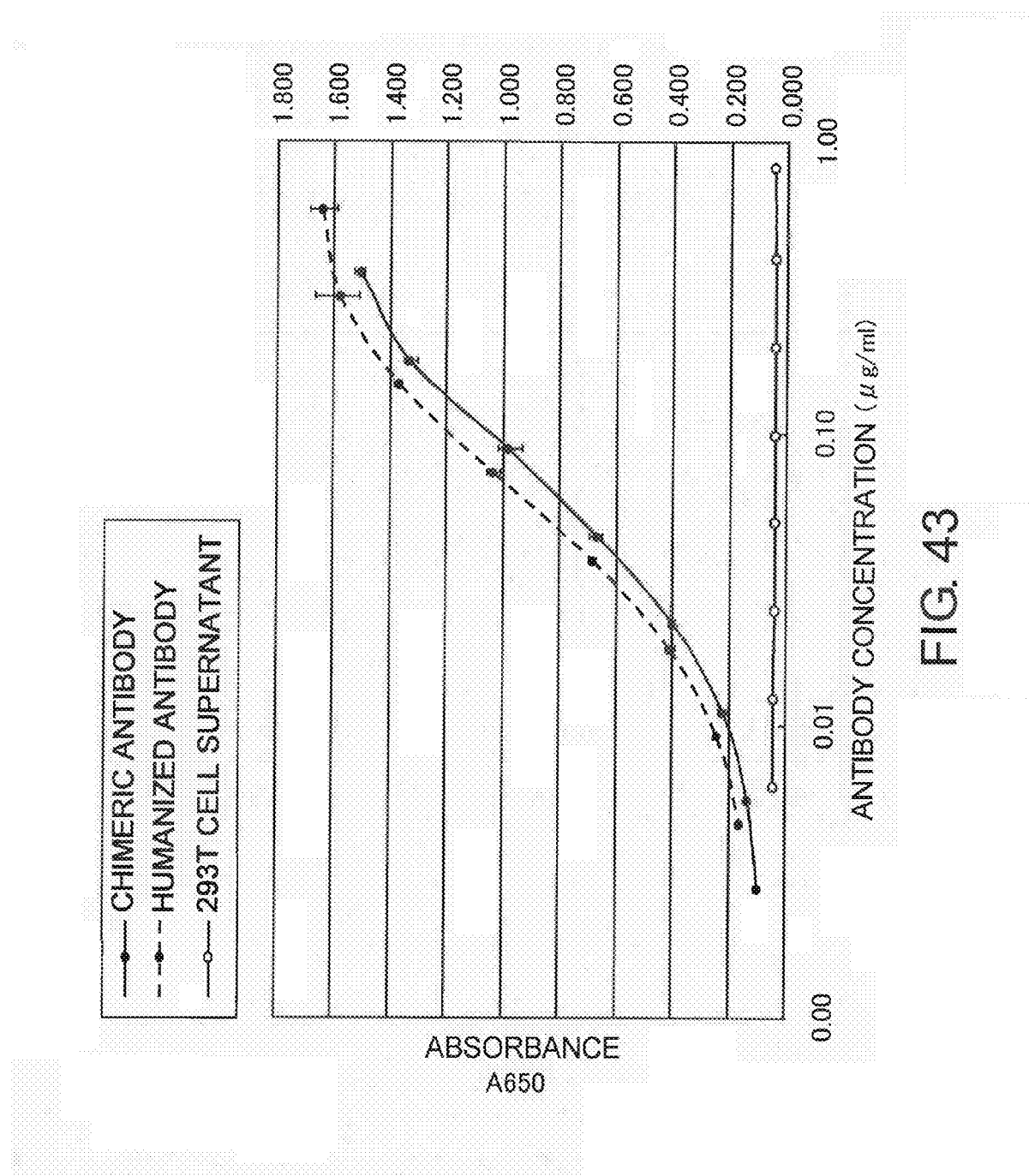

FIG. 43 shows in a graph the ELISA activity to the extramembrane domain (comparison of humanized IgG1 and chimeric IgG1). The binding activity of the prepared humanized antibody was assessed by ELISA. The prepared humanized antibody showed a binding activity comparable to that of the chimeric antibody.

Figure 44:
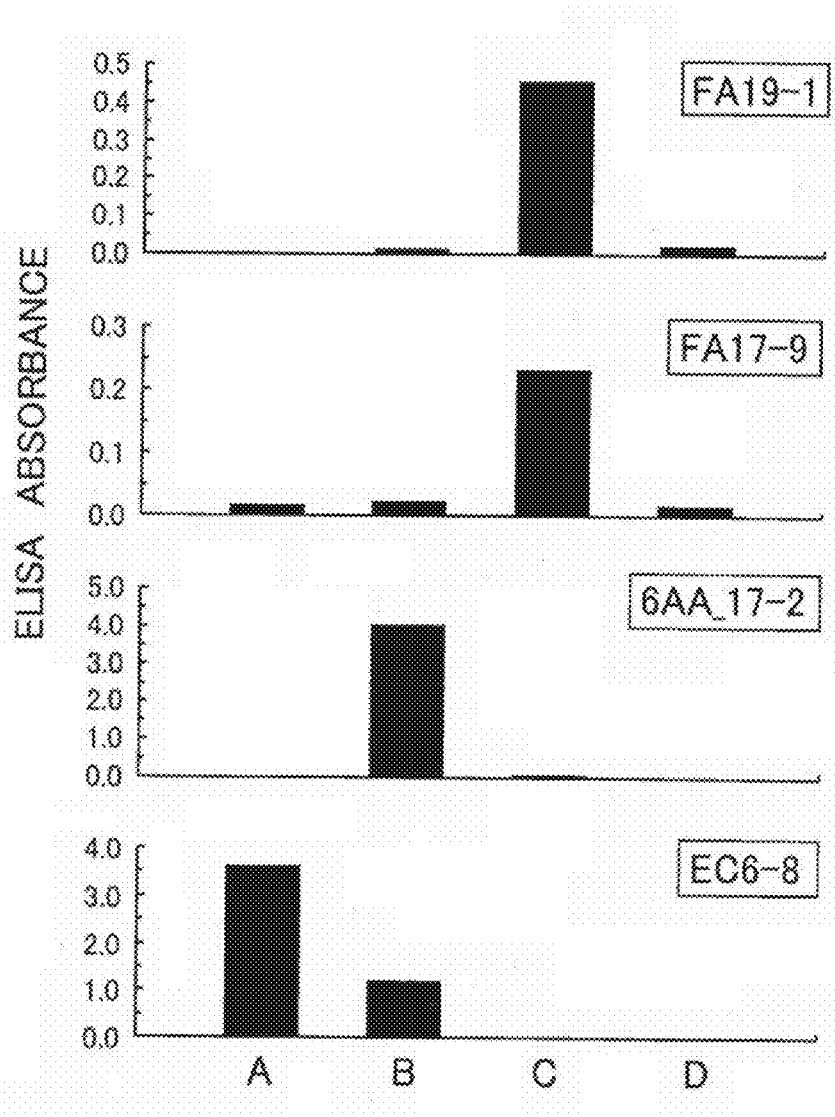

FIG. 44 shows in diagrams results of analyzing the reactivity of various antibodies to fusion proteins of GST and peptide sequences from dividing the region of aa 451-aa 475 of CLCP1 into four types of peptides by ELISA. The binding activities of FA17-9, FA19-1, 6AA_17-2, and EC6-8 were assessed by ELISA using plates immobilized with the obtained various GST proteins at 0.5 µg/ml. FA17-9 and FA19-1 exhibited binding activity to aa 461-aa 470 of SEQ ID NO: 2, while 6AA_17-2 showed binding activity to aa 456-aa 465 of SEQ ID NO: 2. The amino acid sequences of the regions of aa 451-aa 460, aa 456-aa 465, aa 461-aa 470, aa 466-aa 475, and aa 451-aa 475 in the sequence of SEQ ID NO: 2 are shown in SEQ ID NOs: 108-112, respectively.

MODE FOR CARRYING OUT THE INVENTION (Terms)

Herein, the term "isolated antibody" does not include natural antibodies that have not been externally manipulated (artificially manipulated), i.e., antibodies that are produced and remain in an individual. An isolated antibody typically exists alone (as a population of identical antibodies), and is not mixed with other types of antibodies.

With regards to terminology used to describe amino acid sequences, the term "substantially identical" means that the sequence difference between two amino acid sequences being compared is relatively small, and thus does not substantially affect the specific binding to an antigen. Substantially identical amino acid sequences are amino acid sequences that include partial alterations which do not substantially affect the specific binding to an antigen when compared to a standard amino acid sequence. Herein, "partial alteration of an amino acid sequence" means that an amino acid sequence is changed due to a deletion or substitution of one or more amino acids constituting the amino acid sequence, or addition or insertion of one or more amino acids in the amino acid sequence, or a combination thereof. The position of mutation in an amino acid sequence is not particularly limited; and the amino acid sequence may contain mutations at a plurality of positions. Herein, plurality means a number corresponding to, for example, 10% or less of the total amino acids constituting an amino acid sequence, preferably 5% or less of the total amino acids, and more preferably 1% or less of the total amino acids.

Whether two amino acid sequences are substantially identical to each other can be assessed by comparing the binding specificity of antibodies having each amino acid sequence (sequences of the other regions are the same) to an antigen (hereinafter, "specificity" means "specificity to the antigen", unless otherwise described). For example, when the dissociation constant (Kd) of a standard antibody to its antigen in physiological saline is A, an antibody being compared can be judged to be substantially identical when the Kd of the antibody being compared is within the range of $A \times 10^{-1}$ to $A \times 10$.

With regards to terminology used to describe the binding constant of an antibody, the term "substantially identical to or higher than" means that whether the binding constants of two antibodies are substantially identical to each other can be assessed by comparing the specificity of antigen binding between respective antibodies (hereinafter, "specificity" means "specificity to the antigen", unless otherwise described). For example, when the dissociation constant (Kd) of a standard antibody to its antigen in physiological saline is A, an antibody being compared can be judged to be substantially identical when the Kd of the antibody being compared is $0.9 \times A$ or greater.

Herein, the term "isolated nucleic acid" typically refers to a nucleic acid originally present in nature (for example, a nucleic acid in a human living body) to be in a state separated from other co-existing nucleic acids in nature. However, the nucleic acid may include part of another nucleic acid, for example, part of the adjacent nucleic acid sequence in the natural state. For example, in the case of genomic DNA, a preferred embodiment of the "isolated nucleic acid" in the case of genomic DNA, other coexisting DNA components in the natural state (including adjacent DNA sequence in the natural state) are not substantially contained.

For example, an "isolated nucleic acid" such as a cDNA molecule, which is produced by recombinant techniques, is preferably a nucleic acid that is substantially free of other cellular components, culture solution, and such. Likewise, when the "isolated nucleic acid" is produced by chemical synthesis, it is preferably a nucleic acid in a state that is substantially free of chemical precursors (raw materials) such as dNTPs or other chemicals used in the synthesis process.

A nucleic acid that is present as a part of a vector or composition, or a nucleic acid that is present in a cell as an exogenous molecule can be referred to as "isolated nucleic acid" as long as it is present as a result of artificial manipulation. Unless otherwise noted, "nucleic acid" in the present invention means "nucleic acid in an isolated state".

Herein, the term "nucleic acid" includes DNA (including cDNA and genomic DNA), RNA (including mRNA), DNA analogs, and RNA analogs. The form of the nucleic acid of the present invention is not limited, and specifically may be single-stranded or double-stranded. However, double-stranded DNA is preferred. The codon degeneracy is also considered. Specifically, nucleic acid encoding a protein may have any nucleotide sequence as long as the protein is obtained as an expression product of the nucleic acid. Herein, the "nucleic acid encoding a protein (for example, an antibody)" refers to a nucleic acid that is expressed to yield the protein, and includes not only nucleic acids having a nucleotide sequence corresponding to the amino acid sequence of the protein but also nucleic acids resulting from addition of a sequence that does not encode amino acid sequence to the nucleic acid described above (for example, DNA including one or more introns).

Herein, "lung cancer" is broadly interpreted, and includes pulmonary carcinoma and pulmonary sarcoma. Herein, the terms "cancer" and "tumor" are used interchangeably. Furthermore, "cancer" can include benign tumor, benign/malignant borderline pathological condition, and malignant tumor at a stage before pathological diagnosis is confirmed (i.e., before the benignancy and malignancy of a tumor is confirmed).

Herein, if necessary, the following abbreviations (inside the parentheses) are used according to practice.

Heavy chain (H chain), light chain (L chain), heavy-chain variable region (VH), light-chain variable region (VL), complementarity determining region (CDR), first complementarity determining region (CDR1), second complementarity determining region (CDR2), third complementarity determining region (CDR3), first complementarity determining region of heavy chain (VH CDR1), second complementarity determining region of heavy chain (VH CDR2), third complementarity determining region of heavy chain (VH CDR3), first complementarity determining region of light chain (VL CDR1), second complementarity determining region of light chain (VL CDR2), and third complementarity determining region of light chain (VL CDR3).

(Anti-Human CLCP1 Antibody)

In the first aspect, the present invention relates to isolated antibodies (hereinafter, also referred to as "antibodies of the present invention") that specifically recognize ("recognize" can be reworded as "bind"; "recognize" means recognizing an epitope in an antigen) the extracellular domain (SEQ ID NO: 3) of human CLCP1 (the nucleotide and amino acid sequences are shown in SEQ ID NOs: 1 and 2, respectively). It is particularly preferable that the antibodies recognize a region including the FA58C domain (SEQ ID NO: 4) in the extracellular domain of human CLCP1.

In another aspect, the present invention relates to isolated antibodies that recognize a peptide consisting of the amino acid sequence of positions 456 to 470 in SEQ ID NO: 2.

Preferably, the isolated antibodies recognize the peptide described in (c) below and do not recognize at least any one of the peptides described in (a), (b), and (d) below, or recognize the peptide described in (b) below and do not recognize at least any one of the peptides described in (a), (c), and (d) below.
 (a) a peptide consisting of the amino acid sequence of positions 451 to 460 in SEQ ID NO: 2
 (b) a peptide consisting of the amino acid sequence of positions 456 to 465 in SEQ II) NO: 2.
 (c) a peptide consisting of the amino acid sequence of positions 461 to 470 in SEQ ID NO: 2
 (d) a peptide consisting of the amino acid sequence of positions 466 to 475 in SEQ ID NO: 2

More preferably, the isolated antibodies recognize a peptide consisting of the amino acid sequence of positions 461 to 470 in SEQ ID NO: 2, but do not recognize a peptide consisting of the amino acid sequence of positions 466 to 475 in SEQ ID NO: 2. Alternatively, the isolated antibodies recognize a peptide consisting of the amino acid sequence of positions 456 to 465 in SEQ ID NO: 2, but do not recognize a peptide consisting of the amino acid sequence of positions 451 to 460 in SEQ ID NO: 2.

Even more preferably, the isolated antibodies bind to a peptide consisting of the amino acid sequence of positions 461 to 470 in SEQ ID NO: 2, but do not bind to a peptide consisting of the amino acid sequence of positions 466 to 475 in SEQ ID NO: 2 and a peptide consisting of the amino acid sequence of positions 456 to 465 in SEQ ID NO: 2. Alternatively, the isolated antibodies bind to a peptide consisting of the amino acid sequence of positions 456 to 465 in SEQ ID NO: 2, but not bind to a peptide consisting of the amino acid sequence of positions 451 to 460 and a peptide consisting of the amino acid sequence of positions 461 to 470.

Most preferably, the isolated antibodies recognize the peptide described in (c) below and do not recognize any of the peptides described in (a), (b), and (d) below, or recognize the peptide described in (b) below and do not recognize any of the peptides described in (a), (c), and (d) below.
 (a) a peptide consisting of the amino acid sequence of positions 451 to 460 in SEQ ID NO: 2
 (b) a peptide consisting of the amino acid sequence of positions 456 to 465 in SEQ ID NO: 2
 (c) a peptide consisting of the amino acid sequence of positions 461 to 470 in SEQ ID NO: 2
 (d) a peptide consisting of the amino acid sequence of positions 466 to 475 in SEQ ID NO: 2

The antibodies of the present invention exert the activity/effect by recognizing human CLCP1 antigen. Specifically, the antibodies of the present invention exert activity against human cancer cells expressing a human CLCP1 molecule on cell surface, preferably cancer cells expressing a human CLCP1 molecule at high levels, more preferably lung cancer cells, and especially metastatic lung cancer cells. Such activities of antibodies of the present invention include migration inhibitory activity, invasion inhibitory activity, metastasis inhibitory activity, and growth inhibitory activity. In another aspect, such activity is cytotoxicity (for example, ADCC).

The human CLCP1 molecule has been known to be expressed at high levels in lung cancer cells. However, little is known about the expression in other types of cancers and about functions of antibody against the extracellular domain of human CLCP1. As described below, interesting findings were obtained through studies by the present inventors.

The antibodies of the present invention exert:
 (1) migration inhibitory activity by recognizing human CLCP1 antigen expressed in human lung cancer cells;
 (2) invasion inhibitory activity by recognizing human CLCP1 antigen expressed in human lung cancer cells;
 (3) metastasis inhibitory activity by recognizing human CLCP1 antigen expressed in human lung cancer cells; and/or
 (4) growth inhibitory activity by recognizing human CLCP1 antigen expressed in human lung cancer cells. In another aspect, the antibodies of the present invention exert cytotoxicity by recognizing human CLCP1 antigen expressed in various cancer cells.

Herein, "migration inhibitory activity" refers to the activity of inhibiting the two- or three-dimensional migration of viable cells in vitro or in vivo. Herein, "invasion inhibitory activity" refers to the activity of inhibiting the migration of viable cells through basement membrane in vivo, or in vitro activity to inhibit the living cell migration from upper to lower chambers, which are separated with a membrane of extracellular matrix or matrigel. The "metastasis inhibitory activity" refers to the activity of inhibiting the in vivo spreading of cancer cells to other organs or different locations of the same organ by detaching/migrating from the primary lesion and invading into extracellular matrix/basement membrane. The "growth inhibitory activity" refers to the "activity of suppressing cancer cell division/cancer growth and thereby reducing the volume of cancer cells or suppressing the increase in weight as compared to a control IgG group", as a result of administration of an antibody of the present invention and subsequent observation. Herein, "cytotoxicity" refers to the "activity of reducing the number or volume of viable cancer cells as compared to a control IgG group" by damaging the cancer cells.

In the present invention, "inhibition of migration, invasion, metastasis; or growth" includes not only complete inhibition but also partial inhibition of migration, invasion, metastasis, or growth. "Cytotoxicity" includes not only complete damage but also partial damage of cancer cell populations. Non-patent Document 4 showed that the in vitro migration inhibitory activity and invasion inhibitory activity are correlated with the in vivo "metastasis inhibitory activity".

The level of human CLCP1 antigen on the cell surface was revealed to decrease when an antibody of the present invention was reacted with the cells. The reason can be assumed that binding of the antibody induced the internalization of human CLCP1 into cells. The tendency was observed with other type of cells.

Then, tests of migration inhibition and invasion inhibition were conducted to assess the correlation with the above finding. The result suggested that isolated antibodies that recognize a peptide consisting of the amino acid sequence of positions 456 to 470 in SEQ ID NO: 2, preferably isolated antibodies that recognize a peptide consisting of the amino acid sequence of positions 461 to 470 in SEQ ID NO: 2 but do not recognize a peptide consisting of the amino acid sequence of positions 466 to 475 in SEQ ID NO: 2, or isolated antibodies that recognize a peptide consisting of the amino acid sequence of positions 456 to 465 in SEQ ID NO: 2 but do not recognize a peptide consisting of the amino acid sequence of positions 451 to 460 in SEQ ID NO: 2, and most preferably antibodies FA19-1, FA17-9, and 6AA__17-2, in particular FA19-1, have migration inhibitory activity and invasion inhibitory activity, and thus have the effect of inhibiting metastasis in vivo.

Furthermore, as described below in the Examples, the present inventors conducted studies and as a result successfully identified epitopes recognized by antibodies that are obtained as anti-human CLCP1 antibodies.

Antibodies of the present invention that recognize epitopes in the extracellular domain of human CLCP1 described below could be further characterized based on this result. Herein, when two antibodies recognize an identical epitope, it means that the antibodies compete and the binding of a biotinylated antibody is inhibited by the other antibody in a competition experiment by FCM.

The successfully obtained antibody clones in the present invention were found to be grouped into seven types depending on the type of recognition epitope.

Specifically, such antibodies are isolated antibodies that recognize epitope A in a region containing the FA58C domain: (1) epitope located in the amino acid sequence of positions 456 to 470 in SEQ ID NO: 2 (hereinafter abbreviated as "aa 456-aa 470").

Such antibodies include, for example, (2) an isolated antibody (the first antibody) that recognizes an epitope in a partial sequence (aa 461-aa 470 in SEQ ID NO: 2) of the amino acid sequence of human CLCP1 antigen. The first antibody includes (corresponds to) antibody clones FA17-9 and FA19-1 which have been demonstrated to effectively inhibit metastasis, in particular, lung metastasis. The first antibody recognizes the same epitope as antibody clone FA17-9, i.e., "antibody that comprises heavy-chain variable region having the amino acid sequence of SEQ ID NO: 6 and light-chain variable region having the amino acid sequence of SEQ ID NO: 11", or the same epitope as antibody clone FA19-1, i.e., "antibody that comprises heavy-chain variable region having the amino acid sequence of SEQ ID NO: 15 and light-chain variable region having the amino acid sequence of SEQ ID NO: 20". Since the epitope recognized by the first antibody is identical to the epitope recognized by antibody clones FA17-9 and FA19-1, competition is confirmed when a test antibody is added to human CLCP1 in the reaction at the same as the first antibody and antibody clone FA17-9 or FA19-1. Thus, competency of the first antibody can be assessed by competition experiments by FCM using antibody clone FA17-9 or FA19-1, which is particularly preferable using FA19-1 (see Examples).

The competency of the first antibody can also be evaluated based on the cross reactivity between partial peptides. The competency can be tested by assessing whether an isolated antibody binds to a peptide consisting of the amino acid sequence of positions 461 to 470 in SEQ ID NO: 2, but does not bind to a peptide consisting of the amino acid sequence of positions 466 to 475 in SEQ ID NO: 2, and a peptide consisting of the amino acid sequence of positions 456 to 465 in SEQ ID NO: 2.

Several antibody clones were selected in the present invention, but it was identified that antibodies that recognize epitope A were repeatedly selected. As a result of examining the reason for this phenomenon, it is conceivable that the antigenicity of epitope A is extremely high and epitope overlapping occurs.

The first antibodies that recognize epitope A include monoclonal antibodies FA2-10, FA7-6, FA9-1, FA12-3, FA14-9, and FA20-3, as well as FA17-9 and FA19-1.

(1) The second antibody that recognizes an epitope in aa 456-aa 470 of SEQ ID NO: 2 and epitope A in a region containing the FA58C domain was demonstrated to effectively inhibit metastasis, and it corresponds to an isolated antibody (3) that recognizes an epitope in aa 456-aa 465 of SEQ ID NO: 2. Since the second antibody recognizes an epitope that is identical to the epitope recognized by antibody clone 6AA_17-2 or 2AA_62-4, competency is confirmed when a test antibody is added to human CLCP1 in the reaction at the same time as the second antibody and antibody clone 6AA_17-2 or 2AA_62-4. Competency of the second antibody can be confirmed as a competitive antibody by competition experiments with antibody clone 2AA_62-4 or 6AA_17-2 which is particularly preferable. Competency of the second antibody can also be evaluated based on the cross reactivity between partial peptides. Competency can be confirmed by assessing whether an isolated antibody binds to a peptide consisting of the amino acid sequence of positions 456 to 465 in SEQ ID NO: 2, but does not bind to a peptide consisting of the amino acid sequence of positions 451 to 460 in SEQ ID NO: 2, and a peptide consisting of the amino acid sequence of positions 461 to 470 in SEQ ID NO: 2.

Meanwhile, as a result of analyzing the amino acid sequences of the antibodies, the present inventors successfully identified not only the amino acid sequences of respective complementarity determining regions of heavy-chain variable region (VH CDR1, VH CDR2, and VH CDR3) and respective complementarity determining regions of light-chain variable region (VL CDR1, VL CDR2, and VL CDR3) but also the amino acid sequences of entire heavy-chain variable region (VH) and entire light-chain variable region (VL). Each amino acid sequence identified is described below.

Antibody 1: FA17-9
(1) VH CDR1: the amino acid sequence of SEQ ID NO: 7;
(2) VH CDR2: the amino acid sequence of SEQ ID NO: 8;
(3) VH CDR3: the amino acid sequence of SEQ ID NO: 9;
(4) VL CDR1: the amino acid sequence of SEQ ID NO: 12;
(5) VL CDR2: the amino acid sequence of SEQ ID NO: 56;
(6) VL CDR3: the amino acid sequence of SEQ ID NO: 13;
(7) VH: the amino acid sequence of SEQ ID NO: 6 (the nucleotide sequence encoding the amino acid sequence is SEQ ID NO: 5); and
(8) VL: the amino acid sequence of SEQ ID NO: 11 (the nucleotide sequence encoding the amino acid sequence is SEQ ID NO: 10);

Antibody 2: FA 19-1
(1) VH CDR1: the amino acid sequence of SEQ ID NO: 16;
(2) VH CDR2: the amino acid sequence of SEQ ID NO: 17;
(3) VH CDR3: the amino acid sequence of SEQ ID NO: 18;
(4) VL CDR1: the amino acid sequence of SEQ ID NO: 21;
(5) VL CDR2: the amino acid sequence of SEQ ID NO: 57;
(6) VL CDR3: the amino acid sequence of SEQ ID NO: 22;
(7) VH: the amino acid sequence of SEQ ID NO: 15 (the nucleotide sequence encoding the amino acid sequence is SEQ ID NO: 14); and
(8) VL: the amino acid sequence of SEQ ID NO: 20 (the nucleotide sequence encoding the amino acid sequence is SEQ ID NO: 19); and Antibody 3: 6AA_17-2
(1) VH CDR1: the amino acid sequence of SEQ ID NO: 60;
(2) VH CDR2: the amino acid sequence of SEQ ID NO: 61;
(3) VH CDR3: the amino acid sequence of SEQ ID NO: 62;
(4) VL CDR1: the amino acid sequence of SEQ ID NO: 65;
(5) VL CDR2: the amino acid sequence of SEQ ID NO: 66;
(6) VL CDR3: the amino acid sequence of SEQ ID NO: 67;
(7) VH: the amino acid sequence of SEQ ID NO: 59 (the nucleotide sequence encoding the amino acid sequence is SEQ ID NO: 58); and
(8) VL: the amino acid sequence of SEQ ID NO: 64 (the nucleotide sequence encoding the amino acid sequence is SEQ ID NO: 63).

The antibodies of the present invention can be further characterized based on the result described above. Thus, in one embodiment; an antibody of the present invention is specified by the respective CDR sequences. For example, such antibodies are isolated antibodies that recognize the extracellular domain of human CLCP1 antigen, in which the amino acid sequences of complementarity determining regions (VH CDR1, VH CDR2, VH CDR3, VL CDR1, VL CDR2, and VL CDR3) are selected from (A) to (C) below:

(A)
- (1) VH CDR1: the amino acid sequence of SEQ ID NO: 7 or an amino acid sequence substantially identical thereto;
- (2) VH CDR2: the amino acid sequence of SEQ ID NO: 8 or an amino acid sequence substantially identical thereto;
- (3) VH CDR3: the amino acid sequence of SEQ ID NO: 9 or an amino acid sequence substantially identical thereto;
- (4) VL CDR1: the amino acid sequence of SEQ ID NO: 12 or an amino acid sequence substantially identical thereto;
- (5) VL CDR2: the amino acid sequence of SEQ ID NO: 56 or an amino acid sequence substantially identical thereto; and
- (6) VL CDR3: the amino acid sequence of SEQ ID NO: 13 or an amino acid sequence substantially identical thereto;

(B)
- (1) VH CDR1: the amino acid sequence of SEQ ID NO: 16 or an amino acid sequence substantially identical thereto;
- (2) VH CDR2: the amino acid sequence of SEQ ID NO: 17 or an amino acid sequence substantially identical thereto;
- (3) VH CDR3: the amino acid sequence of SEQ ID NO: 18 or an amino acid sequence substantially identical thereto;
- (4) VL CDR1: the amino acid sequence of SEQ ID NO: 21 or an amino acid sequence substantially identical thereto;
- (5) VL CDR2: the amino acid sequence of SEQ ID NO: 57 or an amino acid sequence substantially identical thereto; and
- (6) VL CDR3: the amino acid sequence of SEQ ID NO: 22 or an amino acid sequence substantially identical thereto;

(C)
- (1) VH CDR1: the amino acid sequence of SEQ ID NO: 60 or an amino acid sequence substantially identical thereto;
- (2) VH CDR2: the amino acid sequence of SEQ ID NO: 61 or an amino acid sequence substantially identical thereto;
- (3) VH CDR3: the amino acid sequence of SEQ ID NO: 62 or an amino acid sequence substantially identical thereto;
- (4) VL CDR1: the amino acid sequence of SEQ ID NO: 65 or an amino acid sequence substantially identical thereto;
- (5) VL CDR2: the amino acid sequence of SEQ ID NO: 66 or an amino acid sequence substantially identical thereto; and
- (6) VL CDR3: the amino acid sequence of SEQ ID NO: 67 or an amino acid sequence substantially identical thereto.

The sequences of framework regions (FRs) in the variable regions of an antibody of the present invention are not particularly limited, as long as they do not substantially affect the specific binding activity to human CLCP1 antigen.

For example, when an antibody of the present invention is constructed as a humanized antibody, it is possible to use FRs of known human antibodies.

In another embodiment, an antibody of the present invention is specified by VH and VL sequences. For example, such antibodies are isolated antibodies that recognize the extracellular domain of human CLCP1 antigen, in which the amino acid sequences of variable regions (VH and VL) are selected from (A) to (C) below:

(A)
- (1) VH: the amino acid sequence of SEQ ID NO: 6 or an amino acid sequence substantially identical thereto; and
- (2) VL: the amino acid sequence of SEQ ID NO: 11 or an amino acid sequence substantially identical thereto;

(B)
- (1) VH: the amino acid sequence of SEQ ID NO: 45 or 15, or an amino acid sequence substantially identical thereto; and
- (2) VL: the amino acid sequence of SEQ ID NO: 55 or 20, or an amino acid sequence substantially identical thereto;

(C)
- (1) VH: the amino acid sequence of SEQ ID NO: 59 or an amino acid sequence substantially identical thereto; and
- (2) VL: the amino acid sequence of SEQ ID NO: 64 or an amino acid sequence substantially identical thereto.

In one embodiment, antibodies of the present invention have constant regions in addition to the variable regions (for example, in the case of IgG type antibody or the like). In this embodiment, the sequences of the constant regions are not particularly limited. For example, when antibodies of the present invention are constructed as a humanized antibody, it is possible to use constant regions of known human antibodies as described below The above-described antibodies of the present invention can be prepared by conventional immunological methods or other methods such as phage display methods.

Polyclonal antibodies can be prepared using an immunological method according to the following procedure. An antigen (CLCP1 or a portion thereof) is prepared, and animals such as rabbits are immunized with this antigen. The antigen may be human CLCP1 or CLCP1 of nonhuman animals such as mouse CLCP1. Such CLCP1 can be obtained from biological samples by purification. Alternatively, it is possible to use recombinant CLCP1. Recombinant human CLCP1 can be prepared, for example, by introducing a CLCP1-encoding gene (or a portion thereof) into host cells using an appropriate vector, and expressing the gene in the prepared recombinant cells.

As described above, the extracellular domain of CLCP1 (SEQ ID NO: 3) (or a portion thereof), preferably a region containing the FA58C domain (SEQ ID NO: 4) is expressed as a fusion protein with GST, β-galactosidase, maltose-binding protein, or histidine (His) tag, or the like and may also be used as an antigen to enhance the induction of immunity. Such fusion proteins can be readily purified by conventional methods.

Immunization may be repeated, if necessary. After the antibody titer is sufficiently elevated, the blood is collected and serum was obtained by centrifugation or such. Polyclonal antibody is prepared from the antiserum by affinity purification.

Meanwhile, monoclonal antibodies can be prepared by the following procedure. First, immunization is carried out by the same method as described above. Immunization may be repeated, if necessary. After the antibody titer is sufficiently elevated, antibody-producing cells are isolated from the immunized animals. Then, the prepared antibody-producing cells are fused with myeloma cells to give hybridomas. Clones that produce antibodies highly specific to a protein of interest are selected. After the hybridomas were single cloned, the antibodies of interest are purified from culture media of the selected clones. Alternatively, after hybridoma cells are expanded until they reach a desired number or more, the cells may be transplanted into peritoneal cavities of animals (for example, mice) and then the cells are grown as ascites. The antibody of interest can be purified from the ascites. Affinity chromatography using protein G, protein A, or such can be preferably used to purify the antibody from culture media or ascites. Alternatively, antigen-immobilized affinity chromatography can be used. Furthermore, it is possible to use ion exchange chromatography, gel filtration chromatography, ammonium sulfate fractionation, centrifugation, and such. These methods can be used alone or in any combination thereof.

The antibodies of the present invention also include humanized antibodies. Herein, "humanized antibody" refers to an antibody whose structure is similar to that of a human antibody. Such humanized antibodies include: humanized chimeric antibodies resulting from substituting the antibody constant regions with those of a human antibody; and CDR-grafted human-type antibodies whose constant and variable regions excluding the complementarity determining regions (CDRs) are substituted with those of a human antibody (P. T. Johons et al., Nature (1986) 321: 522). Improvement methods for enhancing the antigen binding activity of a CDR-grafted human-type antibody have been developed, which include: methods for selecting human antibody FRs that are highly homologous to the mouse antibody, methods for producing highly homologous humanized antibodies, and methods for substituting amino acids in FR after grafting mouse CDRs to human antibodies (see U.S. Pat. Nos. 5,585,089, 5,693,761, 5,693,762, and 6,180,370; EP Nos. 451216 and 682040; Japanese Patent No. 2828340). Such methods can be used to prepare human-type antibodies of the present invention.

Human-type chimeric antibodies can be produced, for example, by substituting a human anybody constant region for the constant region of an above-described antibody having the structure of an H-chain variable region and/or the structure of an L-chain variable region described above. Such human antibody constant regions include known human antibody constant regions. A method for producing human-type chimeric antibodies is described below as an example.

First, mRNA is extracted from hybridomas producing a mouse antibody of the present invention. cDNA is synthesized from the mRNA by a conventional method. The synthesized cDNA is inserted into a vector to construct a cDNA library. A vector carrying H-chain and L-chain genes is selected from the cDNA library using H-chain gene and L-chain gene fragments as a probe. The sequences of the H-chain variable region and L-chain variable region genes are determined by sequencing the insert in the selected vector. DNA encoding the H-chain variable region is constructed based on the sequence data obtained as described above by chemical synthesis, biochemical cleavage/ligation, or the like. The resulting DNA that encodes the H-chain variable region is ligated with a DNA encoding human H-chain constant region, and then inserted into an expression vector to construct an expression vector for H chain. Such expression vectors include, for example, SV40 virus-based vectors, EB virus-based vectors, and papilloma virus (BPV)-based vectors, but are not limited thereto. Furthermore, expression vectors for L chain are constructed by the same method. Host cells are co-transformed with the H-chain expression vectors and L-chain expression vectors. Preferred host cells include CHO cells (Chinese hamster ovary) (A. Wright & S. L. Morrison, J. Immunol. 160, 3393-3402 (1998)) and SP2/0 cells (mouse myeloma) (K. Motmans et al., Eur. J. Cancer Prey. 5, 512-519 (1996); R. P. Junghans et al., Cancer Res. 50, 1495-1502 (1990)). Transformation can be preferably carried out by using electroporation, a lipofectin method (R. W. Malone et al., Proc. Natl. Acad. Sci. USA 86, 6077 (1989); P. L. Feigner et al., Proc. Natl. Acad. Sci. USA 84, 7413 (1987)), calcium phosphate method (F. L. Graham & A. J. van der Eb, Virology 52, 456-467 (1973)), DEAE-Dextran method, and the like.

The transformants are cultured, and then human-type chimeric antibodies are isolated from the transformants or culture media. Antibodies can be isolated or purified by an appropriate combination of methods such as centrifugation, ammonium sulfate fractionation, salting out, ultrafiltration, affinity chromatography, ion exchange chromatography, and gel filtration chromatography.

Meanwhile, human-type CDR-grafted antibodies can be produced, for example, by the following method. First, the amino acid sequences of H-chain and L-chain variable regions of a mouse anti-human CLCP1 antibody, and nucleotide sequences encoding them are determined by the methods for producing chimeric antibodies as described above. The amino acid sequences of each CDR are determined as well.

Next, framework regions (FRs) which sandwich CDRs are selected. Three methods are available for selecting FRs. The first method uses human antibody frames with known three dimensional structures, such as NEWM and REI (Riechmann L. et al., Nature 332, 323-3Z7 (1988); Tempst, P R. et al., Protein Engineering 7, 1501-1507 (1994); Ellis J H. et al., J. Immunol 155, 925-937 (1995)). The second method uses FRs of a human antibody variable region that is most homologous to a mouse antibody variable region of interest, in which the human antibody variable region is selected from databases (Queen C. et al., Proc Natl Acad Sci USA 86, 10029-10033 (1989); Rozak M J. et al., J Biol Chem 271, 22611-22618 (1996); Shearman C W. et al., J. Immunol 147, 4366-4373 (1991)). In the third method, amino acids most commonly shared by human antibody FRs are selected (Sato K. et al., Mol Immunol 31, 371-381 (1994); Kobinger F. et al., Protein Engineering 6, 971-980 (1993); Kettleborough C A. et al., Protein Engineering 4, 773-783 (1991)). All of these methods can be used in the present invention.

Furthermore, FR amino acid sequences to be used also include amino acid sequences resulting from modification of the amino acid sequence of a selected human FR, as long as the human-type CDR-grafted antibody produced from it has the activity of specifically binding to human CLCP1. In particular, when a portion of the amino acid sequence of a selected human FR is replaced with the amino acid sequence of an FR of the antibody from which CDR is derived, the resulting antibody is very likely to retain the antibody properties. The number of amino acids to be modified is preferably 30% or less in a whole FR, more preferably 20% or less in a whole FR, and still more preferably 10% or less in a whole FR.

Next, DNAs encoding H-chain and L-chain variable regions are designed by combining the above-described CDRs with FRs selected by any one of the methods described above. Based on this design, DNAs encoding H-chain variable regions and DNAs encoding L-chain variable regions are prepared by chemical synthesis, biochemical cleavage/ligation, or the like. Then, an H-chain expression vector is constructed by inserting into an expression vector the H-chain variable region-encoding DNA, along with a DNA encoding an H-chain constant region of human immunoglobulin. Likewise, an L-chain expression vector is constructed by inserting into an expression vector the L-chain variable region-encoding DNA, along with a DNA encoding an L-chain constant region of human immunoglobulin. Expression vectors include, for example, SV40 virus-based vectors, EB virus-based vectors, and papilloma virus (BPV)-based vectors, but are not limited thereto.

Host cells are co-transformed with the H-chain expression vectors and L-chain expression vectors prepared by the method described above. Such preferred host cells include CHO cells (Chinese hamster ovary) (A. Wright & S. L. Morrison, J. Immunol. 160, 3393-3402 (1998)) and SP2/0 cells (mouse myeloma) (K. Motmans et al., Eur. J. Cancer Prev. 5, 512-519 (1996); R. P. Junghans et al., Cancer Res. 50, 1495-1502 (1990)). Transformation can be preferably carried out by using electroporation, a lipofectin method (R. W. Malone et al., Proc. Natl. Acad. Sci. USA 86, 6077 (1989); P. L. Feigner et al., Proc. Natl. Acad. Sci. USA 84, 7413 (1987)), calcium phosphate method (F. L. Graham & A. J. van der Eb, Virology 52, 456-467 (1973)), DEAE-Dextran method, and the like.

The transformants are cultured, and then human-type CDR-grafted antibodies are isolated from the transformants or culture media. Antibodies can be isolated or purified by an appropriate combination of methods such as centrifugation, ammonium sulfate fractionation, salting out, ultrafiltration, affinity chromatography, ion exchange chromatography, and gel filtration chromatography.

The antibodies of the present invention also include functional antibody fragments such as Fab, Fab', F(ab')$_2$, Fv, scFv, dsFv, diabodies, and sc(Fv)2. Multimers (for example, dimers, trimers, tetramers, and polymers) of such a functional antibody fragment are also included in the antibodies of the present invention.

Fab is a fragment with a molecular weight of about 50,000 that consists of L-chain and H-chain variable regions, and an H chain fragment containing $C_H1$ domain and a portion of hinge region. Fab is obtained by digesting IgG with papain in the presence of cysteine. In the present invention, an antibody described above can be digested with papain to prepare such Fab. Alternatively, a DNA encoding a portion of H chain and the L chain of an antibody described above is inserted into an appropriate vector. Fab can be prepared from transformants obtained by transformation using the vector.

Fab' is a fragment with a molecular weight of about 50,000 obtained by cleaving the disulfide bond between the H chains of F(ab')$_2$ described below. In the present invention, such F(ab')$_2$ can be obtained by treating an above-described antibody by pepsin digestion, followed by cleavage of disulfide bond with a reducing agent. Alternatively, like Fab, Fab' can be prepared by genetic engineering using DNA encoding Fab'.

F(ab')$_2$ is a fragment with a molecular weight of about 100,000 obtained by digesting IgG with pepsin. F(ab')$_2$ is constituted by two (Fab') fragments linked together via disulfide bond, each of which consists of L-chain and H-chain variable regions, and an H chain fragment containing $C_H1$ domain and a portion of hinge region. In the present invention, F(ab')$_2$ can be prepared by digesting an above-described antibody with pepsin. Alternatively, like Fab, F(ab')$_2$ can be prepared by genetic engineering using F(ab')$_2$-encoding DNAs.

Fv can be prepared by digesting an antibody into antibody fragments with an enzyme, for example, papain or pepsin. Alternatively, genes encoding antibody fragments are constructed and inserted into an expression vector. Fv can be expressed in appropriate host cells using the vector (see, for example, Co, M. S. et al., J. Immunol. 152, 2968-2976 (1994); Better, M. and Horwitz, A. H. Methods in Enzymology 178, 476-496 (1989); Plueckthun, A. and Skerra, A. Methods in Enzymology 178, 476-496 (1989); Lamoyi, E., Methods in Enzymology 121, 652-663 (1989); Rousseaux, J. et al., Methods in Enzymology 121, 663-669 (1989); Bird, R. E. et al., TIBTECH 9, 132-137 (1991)).

scFv is a single-chain antibody fragment in which the C terminus of one Fv chain consisting of H-chain and L-chain variable regions is linked via an appropriate peptide linker to the N terminus of the other chain Fv chain. Such peptide linkers include, for example, flexible (GGGGS (SEQ ID NO: 23))$_3$. For example, a DNA encoding an scFv antibody is constructed using DNAs encoding the H-chain variable region and L-chain variable region of an above-described antibody and a DNA encoding a peptide linker, and then inserted into an appropriate vector. Transformants are obtained by transformation with the resulting vector. scFv can be prepared from the transformants.

dsFv is an Fv fragment whose H-chain and L-chain variable regions are stabilized with a disulfide bond formed by introducing Cys residues at appropriate positions in the H-chain and L-chain variable regions. In each chain, the position at which Cys residue is to be introduced is determined based on the conformation predicted by molecular modeling. In the present invention, for example, the conformation is predicted from the amino acid sequences of H-chain and L-chain variable regions of an above-described antibody. DNAs are constructed to encode H-chain and L-chain variable regions that have been introduced with mutations based on the prediction, and inserted into an appropriate vector. Transformants are obtained by transformation with the resulting vector. dsFv can be prepared from the transformants.

Furthermore, multimers of antibody fragments can be prepared by linking scFv antibodies, dsFv antibodies, and the like via appropriate linkers, or fusing them to streptavidin. Fusion antibodies or labeled antibodies can be prepared from the antibodies (including antibody fragments) of the present invention by fusing or linking the antibodies with low molecular weight compounds, proteins, labeling substance, or the like. Such labeling substances include radioactive substances such as $^{125}I$.

Diabody refers to a bivalent antibody fragment constructed by gene fusion (Holliger P et al., Proc. Natl. Acad. Sci. USA, 90: 6444-6448 (1993); EP 404,097; WO 93/11161). Diabodies are dimers consisting of two polypeptide chains, where each polypeptide chain has a VL and a VH linked via a linker short enough to prevent interaction of these two domains, for example, a linker of about five residues. The VL and VH linked together in a single polypeptide chain will form a dimer because the linker between them is too short to form a single-chain variable region fragment. As a result, the polypeptide chains form a dimer, and thus the diabody has two antigen binding sites. Diabodies can be prepared by treating an antibody with an enzyme, for example, papain or pepsin, to generate antibody fragments, or by constructing DNAs encoding those antibody fragments and introducing them into expression vectors, followed by expression in an appropriate host cell (see, for example, Co, M. S. et al., J. Immunol. 152, 2968-2976 (1994); Better, M. and Horwitz, A. H., Methods Enzymol. 178, 476-496 (1989); Pluckthun, A. and Skerra, A., Methods Enzymol. 178, 497-515 (1989); Lamoyi, E., Methods Enzymol. 121, 652-663 (1986); Rousseaux, J. et al., Methods Enzymol. 121, 663-669 (1986); Bird, R. E. and Walker, B. W., Trends Biotechnol. 9, 132-137 (1991)).

sc(Fv)2 is a single-chain minibody produced by linking two VHs and two VLs using linkers and such (Hudson et al., J Immunol. Methods 231: 177-189 (1999)). sc(Fv)2 can be produced, for example, by linking scFvs via a linker.

When the cytotoxic effect of the present invention is used, antibodies linked with constant regions are used. Antibodies of the present invention include isotypes IgG1, IgG2, IgG3, and IgG4. Antibody isotype is determined by the structure of the constant region. The constant regions of isotypes IgG1, IgG2, IgG3, and IgG4 are referred to as Cγ1, Cγ2, Cγ3, and Cγ4, respectively. Although the effect may vary on one level or another, it is possible to use any of the constant regions in embodiments that use the cytotoxic effect of the present invention. In terms of the cytotoxic effect, a preferred constant region is that of IgG1.

(Nucleic Acid Molecules Encoding an Anti-Human CLCP1 Antibody or a Portion Thereof)

In another aspect, the present invention relates to nucleic acid molecules encoding an antibody of the present invention (hereinafter also referred to as "nucleic acids of the present invention").

The nucleic acids of the present invention can be prepared by conventional methods such as chemical synthesis and biochemical cleavage/ligation. The nucleic acids of the present invention are used to prepare antibodies of the present invention, but are not limited thereto.

(Vectors)

In another aspect, the present invention relates to vectors carrying nucleic acids of the present invention in an expressible manner (hereinafter also referred to as "vectors of the present invention") and cells transformed with the vectors (hereinafter also referred to as "transformed cells of the present invention"). Expression vectors that are used to express antibodies of the present invention in host cells can be prepared by inserting a nucleic acid or a nucleic acid that is attached with a signal sequence known to those skilled in the art (see, for example, a nucleic acid described in the Examples) into an appropriate vector. Any vector may be used as long as the vector can carry a nucleic acid of the present invention in an expressible manner and can express the carried nucleic acid in host cells. Nucleic acids of the present invention can be inserted into vectors by conventional methods such as methods using restriction enzymes and DNA ligase (Molecular Cloning, Third Edition, 1.84, Cold Spring Harbor Laboratory Press, New York). Appropriate host cells are selected depending on the vector type to be used. Host cells include, for example, bacteria such as *Escherichia coli*; yeasts such as *Saccharomyces cerevisiae*; and animal cells such as COS and CHO cells.

In another aspect, the present invention relates to methods for producing antibodies of the present invention, which comprise the steps of:
(a) culturing transformed cells of the present invention; and
(b) isolating/purifying an antibody as the expression product.

Antibodies of the present invention can be expressed in transformed cells or its culture medium by culturing the transformed cells prepared by transforming host cells with a vector carrying the nucleic acid of the present invention. Then, the antibodies of the present invention can be prepared by isolating/purifying the expression product. The purification/isolation is achieved by an appropriate combination of methods such as centrifugation, ammonium sulfate fractionation, salting out, ultrafiltration, affinity chromatography, ion exchange chromatography, and gel filtration chromatography.

(Pharmaceutical Compositions)

In another aspect, the present invention relates to pharmaceutical compositions comprising antibodies of the present invention and pharmaceutically acceptable carriers.

(Formulations Comprising Antibodies and Use Thereof)

In additional aspect, the present invention provides pharmaceutical agents comprising antibodies of the present invention for treating or preventing cancer expressing CLCP1, therapeutic or preventive methods using the agents, agents for inhibiting the migration, invasion, metastasis, or growth of cancer cells expressing CLCP1, and cytotoxic agents against cancer cells expressing CLCP1, and pharmaceutical agents for treating or preventing tumor expressing CLCP1.

The present invention also provides:
(a) agents for inhibiting cancer cell migration, which comprise antibodies that recognize the extracellular domain of human CLCP1 antigen and have an activity of inhibiting the migration of cancer cells expressing CLCP1;
(b) agents for inhibiting cancer cell invasion, which comprise antibodies that recognize the extracellular domain of human CLCP1 antigen and have an activity of inhibiting the invasion of cancer cells expressing CLCP1;
(c) agents for inhibiting cancer cell metastasis, which comprise antibodies that recognize the extracellular domain of human CLCP1 antigen and have an activity of inhibiting the metastasis of cancer cells expressing CLCP1;
(d) agents for inhibiting cancer cell growth, which comprise antibodies that recognize the extracellular domain of human CLCP1 antigen and have an activity of inhibiting the growth of cancer cells expressing CLCP1;
(e) cytotoxic agents against cancer cells, which comprise antibodies that recognize the extracellular domain of human CLCP1 antigen and have cytotoxicity against cancer cells expressing CLCP1;
(f) agents for treating or preventing tumor, which comprise antibodies that recognize the extracellular domain of human CLCP1 antigen and have at least one selected from the activities of inhibiting migration, invasion, metastasis, and growth of cancer cells expressing CLCP1, and cytotoxic activity against cancer cells expressing CLCP1; and
(g) agents for use in treating or preventing cancer, which comprise antibodies that recognize the extracellular domain of human CLCP1 antigen and have at least one selected from the activities of inhibiting the migration, invasion, metastasis, and growth of cancer cells expressing CLCP1, and cytotoxic activity against cancer cells expressing CLCP1.

Herein, cancer type is not particularly limited, as long as the cancer expresses CLCP1. Examples of such cancer specifically include lung cancer, and metastatic lymph node cancer. Meanwhile, pharmaceutical agents for treating or preventing such cancers have at least one inhibitory activity selected from the activities of inhibiting the migration, cell invasion, metastasis, and cell growth, and/or cytotoxic activity. The agents may be administered to prevent cancer metastasis.

The type and origin of an anti-CLCP1 antibody to be used in antibody-comprising formulations are not particularly limited, as long as it has a specific binding activity to CLCP1. Anti-CLCP1 antibodies may be polyclonal antibodies, oligoclonal antibodies (mixtures of several to several tens of antibodies), and monoclonal antibodies. Preferably, such polyclonal antibodies or oligoclonal antibodies are expressed as a recombinant antibody (humanized antibody or chimeric antibody) by genetic engineering using antibody genes isolated from hybridomas prepared from immunized animals. The expressed antibodies can be used after purification. Alternatively, it is possible to use recombinant human antibodies having complete human variable regions prepared by using phage display technology or the like. The anti-CLCP1 antibodies may be antibody fragments such as Fab, Fab', F(ab')$_2$, Fv, scFv, dsFv, diabody, and sc(Fv)2, and genetic recombinants thereof. Anti-CLCP1 antibodies can be prepared by the methods described above.

Antibodies prepared by the methods described above may be variously altered as long as they retain a specific binding activity to CLCP1. Such altered antibodies can be used in the present invention.

Agents for treating or preventing cancer expressing CLCP1 and agents for inhibiting the migration, invasion, metastasis, or growth of cancer cells expressing CLCP1, which comprise an antibody of the present invention, can be formulated by conventional methods. The agents can be formulated by adding other pharmaceutically acceptable components (for example, carriers, excipients, disintegrants, buffers, emulsifiers, suspending agents, analgesics, stabilizers, preservatives, antiseptics, and physiological saline). Excipients include, for example, lactose, starch, sorbitol, D-mannitol, and sucrose. Disintegrants include, for example, starch, carboxymethyl cellulose, and calcium carbonate. Buffers include, for example, phosphate, citrate, and acetate. Emulsifiers include, for example, gum arabic, sodium alginate, and tragacanth. Suspending agents include, for example, glyceryl monostearate, aluminum monostearate, methyl cellulose, carboxymethyl cellulose, hydroxymethyl cellulose, and sodium lauryl sulfate. Analgesics include, for example, benzyl alcohol, chlorobutanol, and sorbitol. Stabilizers include, for example, propylene glycol, diethylin sulfite, and ascorbic acid. Preservatives include, for example, phenol, benzalkonium chloride, benzyl alcohol, chlorobutanol, and methylparaben. Antiseptics include, for example, benzalkonium chloride, paraoxybenzoic acid, and chlorobutanol.

The dosage form when formulating is not particularly limited. The dosage form includes, for example, tablets, powders, subtle granules, granules, capsules, syrups, injections, external preparations, and suppositories.

Also, the administration route of the above-described preparation of the present invention is not particularly limited. Specifically, the above-described preparation of the present invention can be administered orally or parenterally (intravenous, intraarterial, subcutaneous, intramuscular, or intraperitoneal injection, or direct introduction into target cells) to subjects (patients) depending on the dosage form.

The dosage of an above-described preparation of the present invention varies depending on patient's symptoms, age, sex, and weight, and such. Those skilled in the art can appropriately select a proper dosage. For example, when the subject is an adult (body weight of about 60 kg), the dosage can be selected so that the amount of active ingredient is about 0.001 to 100,000 mg for each administration. The administration schedule may be determined, for example, from administration once to several times a day, once every two days, once every three days, once a week, and once a month. The administration schedule may be determined by considering the patient's condition, duration of efficacy, and such.

(Immunological Methods)

In another aspect, the present invention relates to immunological methods comprising the steps of:
  (a) contacting an antibody of the present invention with isolated cells or tissues; and
  (b) detecting the expression of CLCP1 in the cells or tissues.

Immunological methods include, for example, immunohistochemical staining method, ELISA method, radioimmunoassay, FCM, immunoprecipitation methods, and immunoblotting. For example, of the above immunological methods, an immunohistochemical staining method for detecting the expression level of CLCP1 in physiological tissues such as cells and tissues is carried out by the typical procedure of (1) to (10) described hereinafter.

Such immunological method can be referred to as an agent comprising an antibody of the present invention for detecting the expression level of CLCP1 in cells and tissues by the immunological method. Furthermore, the immunological method can be used, for example, in a diagnostic method for lung cancer, which is described below.

The cells or tissues are not particularly limited, and include, for example, cancer cells, cancer tissues, and potential cancer cells or tissues.

(Agents for Detecting CLCP1 by Immunological Techniques)

In another aspect, the present invention relates to agents comprising an antibody of the present invention for detecting CLCP1 expression in cells or tissues by an immunological technique.

The agents may contain carriers known to those skilled in the art. The agents can be used, for example, in methods for lung cancer diagnosis, as described below.

(Kits)

In another aspect, the present invention relates to kits comprising an antibody of the present invention for detecting CLCP1 expression in cells or tissues by an immunological technique. Specifically, such kits can be produced by combining an antibody of the present invention with substrates needed for label detection, a strong positive control and a negative control, buffers for washing or diluting samples, and so on.

The kits can be used, for example, in diagnostic methods for lung cancer, as described below.

(Immunostaining Diagnostic Test for Assessing the Degree of Invasion or Metastasis of Human Lung Cancer)

In still another aspect, the present invention provides diagnostic methods for assessing the site and degree of lung cancer invasion (severity of invasion), or metastatic state and site based on the particularly excellent stainability of lung cancer by an antibody of the present invention (hereinafter also referred to as "diagnostic methods of the present invention"). The diagnostic methods of the present invention comprise the step of contacting an antibody of the present invention with an isolated pathological tissue, and detecting the expression of CLCP1 in a pathological tissue by an immunological method.

Herein, "detecting the expression of CLCP1" means determining the expression level of CLCP1 per CLCP1-expressing cell, or the proportion of CLCP1-expressing cells. There is a strong correlation between CLCP1 expression and the possibility of a cell being cancer, or between CLCP1 expression and the degree of tissue invasion by cancer or site of cancer metastasis, wherein CLCP1 expression can also be presented as staining intensity or proportion of strongly stained cancer cells determined by an immunological method.

The diagnostic methods of the present invention enable visual understanding of the site and state of metastasis or the pattern of occurrence of cancer cells invading into new tissues.

The diagnostic methods of the present invention are described in more detail below.

First, tissues suspected of cancer invasion or metastasis are isolated from a living body.

Information (detection result) obtained by the methods is used to assess the degree of invasion or site of metastasis of lung cancer cells in pathological tissues.

In this context, as described in the Examples below, a plurality of lung cancer tissues and lung carcinomas, which were different in the degree of invasion, were immunologically stained with an anti-CLCP1 antibody. The staining patterns were significantly different, and the intensely stained areas were found to be consistent with the pathologically determined cancer areas. Consequently, there is a strong correlation between the degree of invasion or metastasis of lung cancer cells and the expression level of CLCP1 or frequency of CLCP1 expression in cells. The diagnostic methods of the present invention enable visual understanding of the site and state of metastasis or pattern of occurrence of cancer cells invading into new tissues. Specifically, CLCP1 was revealed to be effective as a marker for assessing the degree of invasion of lung cancer cells.

Furthermore, the expression level of CLCP1 is significantly higher in lung cancer than in normal lung (staining intensity or frequency of cellular expression in tissues).

In another embodiment, based on the finding described above, the present invention provides methods for assessing the malignancy in a pathological tissue by using the detection result obtained in the above step, specifically methods for assessing the malignancy of cancer cells.

Detection results obtained by the methods of the present invention are useful in diagnosing cancer. For example, information obtained by testing cancer patients using an above-described method can be used to monitor or assess the pathological condition of the patient or therapeutic effect. For example, when the method of the present invention is conducted in parallel to cancer treatment, the resulting information can be used to assess the therapeutic effect. Specifically, the method of the present invention is carried out to evaluate the change in stainability in pathological tissues after administration of pharmaceutical agents. The therapeutic effect can be assessed based on the time-dependent changes in the degree of invasion or the number of sites of metastasis. Thus, methods of the present invention may be used to monitor therapeutic effects.

Meanwhile, when the subject is not a patient but a person who is not yet diagnosed as having cancer, the resulting information can be used to assess or judge the presence of cancer invasion or metastasis, or such. The methods of the present invention can be said to be highly valuable, because they can be used to diagnose cancer based on stainability which is a highly objective indicator.

When the subject (person being tested, living individual, or patient) is a human, in general, cancer diagnosis is performed by medical practitioners including persons who are instructed by medical practitioners (the same is applied hereinafter). Data on the expression level of CLCP1 in pathological tissues, which are obtained by the diagnostic methods of the present invention, are useful for medical practitioners to diagnose the subjects. Thus, the diagnostic methods of the present invention can be expressed as a method of collecting and providing data that are useful for medical practitioners to diagnose subjects.

The type of cancer as the target of the diagnostic methods of the present invention is not particularly limited; however, such cancer includes, for example, kidney cancer, bladder tumor, prostate cancer, pancreas cancer, stomach cancer, large intestine cancer, breast cancer, and lung cancer, particularly preferably lung cancer.

Hereinbelow, the configuration of the present invention is described in detail below.

Cells are prepared from subjects (persons being tested or living individuals). The subjects may include healthy persons (including persons that are suspected to have cancer) as well as cancer patients. Portions of organs or tissues collected from the subjects by biopsy can be used as test cancer cells in the methods of the present invention.

Herein, the "pathological tissue" refers to a tissue that is used as a sample (target) in detection by the methods of the present invention. Such pathological tissues are isolated from living individuals. Specifically, the present invention is applied to pathological tissues isolated from living individuals. "Isolated from a living individual" means that cancer cells to be tested are completely isolated from the living individual from which the cells originate by excising a portion of biological tissue that contains the pathological tissue.

When contacting with an antibody or antibody fragment, in general, the pathological tissue is prepared in the same state as in the living individual, i.e., attached with adjacent cells (as a tissue fragment), and then subjected to the methods of the present invention. However, the pathological tissue in the methods of the present invention may also be used after its separation (isolation) from surrounding cells. Herein, "contacting" means that the a cancer tissue or cells are soaked in a solution containing the antibody, or the solution is sufficiently dropped or sprayed onto the cancer tissue or cells, and then the cancer tissue or cells are left in physiological conditions that allow the antibody to recognize CLCP1 in the cancer tissue or cells.

When the detection result is used to assess the degree of invasion or site of metastasis, preferred pathological tissues include cells that are judged to be cancer cells by other diagnostic methods, cells that are strongly suspected to be cancer cells, and cells that are assumed to be potential cancer cells, more preferably cells that are judged to be cancer cells by other diagnostic methods and cells that are strongly suspected to be cancer cells. Such other diagnostic methods include, for example, X-ray contrast examination, endoscopic examination, ultrasonic examination, CT examination, MRI examination, PET examination, and diagnostic examination using tumor markers. In general, test cancer cells are collected from tissues that are suspected to have cancer by one or more of the above-described examination methods.

Then, detection of CLCP1 is carried out using prepared test pathological tissues as targets. "Detection of CLCP1" means assessing whether CLCP1 is expressed (presence or absence of expression), or determining the absolute or relative expression level of CLCP1. Standard of the relative expression level may be, for example, the level of CLCP1 in a standard sample prepared depending on the degree of invasion or site of metastasis. Herein, "standard sample" refers to a CLCP1-expressing sample that corresponds to the degree of cancer invasion or site of cancer metastasis. For example, a pathological tissue for which the degree of cancer invasion or site of cancer metastasis has been already determined can be used as the standard sample of the present invention. Alternatively, tissues that are not affected with cancer may be used as a standard sample in the present invention.

In general, pathological tissues are assessed for the presence of CLCP1 expression, and, when CLCP1 is expressed, the level of expression level is assayed. In the detection of CLCP1, accurate quantitation of CLCP1 is not essential. For example, when CLCP1 is detected to assess the degree of invasion or site of metastasis in pathological tissues, the CLCP1 level may be determined with such accuracy to allow assessment of the degree of invasion or site of metastasis in pathological tissues, by comparing the level of CLCP1 with that in the standard sample as an indicator for the degree of invasion or site of metastasis.

According to the diagnostic methods of the present invention, a pathological tissue is diagnosed to be potentially cancer if a portion of the isolated tissue is stained more intensely than its surrounding area.

The type of cancer is not particularly limited. Such cancers include, for example, kidney cancer, bladder tumor, prostate cancer, pancreas cancer, stomach cancer, large intestine cancer, and breast cancer, preferably lung cancer. As described below in the Examples, lung cancer tissue specimens were immunostained with an antibody of the present invention. The result showed that the lung cancer portion in the lung cancer tissue specimens was stained more intensely than the non-cancer area in the same specimens.

In particular, CLCP1 is detected preferably by immunological methods (for example, immunohistochemistry, ELISA, radioimmunoassay, FCM, immunoprecipitation, and immunoblotting). An anti-CLCP1 antibody is used in such immunological methods, and the CLCP1 protein is detected using the binding activity of the antibody (the amount of the bound antibody) as an indicator. Such immunological methods enable rapid and sensitive detection. In addition, the procedures of the methods are simple.

Such immunohistochemical methods enable rapid and sensitive detection of CLCP1. In addition, the procedures of the methods are simple. Thus, the immunohistochemical methods reduce the burden of CLCP1 detection for subjects (patients).

In immunohistochemical staining, generally, the first step of contacting a test pathological tissue with an anti-CLCP1 antibody is carried out, and the amount of bound anti-CLCP1 antibody is determined. Specifically, the method of the present invention can be carried out according to the immunohistochemical staining method described below.

In general, biological tissues are immunohistochemically stained by the procedure described below in (1) to (10). Various documents and books are available on immunohistochemical staining of biological tissues (for example, "Kouso Koutai Hou (Enzyme labeled antibody method) Revised 3rd edition", eds., Keiichi Watanabe and Kazuho Nakane, Gakusai Kikaku).

(1) Fixation and Paraffin Embedding

Biological tissues surgically collected from a living body are fixed in formalin, formaldehyde, anhydrous ethyl alcohol, or such. Then, the tissues are embedded in paraffin. In general, after dehydration with alcohol, the tissues are treated with xylene, and finally embedded in paraffin. The paraffin-embedded samples are sliced into sections of a desired thickness (for example, 3 to 5 µm), and placed flat onto glass slides. Sometimes, alcohol-fixed samples, dried and mounted samples, frozen samples, and the like are used instead of paraffin-embedded samples.

(2) Deparaffinization

In general, samples were treated with xylene, alcohol, and purified water in succession.

(3) Pre-Treatment (Unmasking of Antigen)

If needed, enzyme treatment, thermal treatment, pressure treatment, and/or the like are carried out to unmask antigens.

(4) Blocking of Endogenous Peroxidase

When peroxidase is used as a labeling substance in the staining, the endogenous peroxidase activity should be blocked in advance by the treatment with a hydrogen peroxide solution.

(5) Blocking of Non-Specific Reaction

The sections are treated with a bovine serum albumin solution (for example, 1% solution) for about several minutes to several tens of minutes to inhibit non-specific reaction. However, this step may be omitted when the primary antibody reaction is carried out using an antibody solution containing bovine serum albumin.

(6) Primary Antibody Reaction

The antibody is diluted to an appropriate concentration and dripped onto sections on glass slides. Then, the sections are incubated for several tens of minutes to several hours. After incubation, the sections are washed with an appropriate buffer such as phosphate buffer.

(7) Addition of Labeling Reagent

Peroxidase is commonly used as a labeling substance. A secondary antibody conjugated with peroxidase is dripped onto sections on glass slides. Then, the sections are incubated for several tens of minutes to several hours. After incubation, the sections are washed with an appropriate buffer such as phosphate buffer.

(8) Chromogenic Reaction

DAB (3,3'-diaminobenzidine) is dissolved in Tris buffer, and then a hydrogen peroxide solution is added thereto. The resulting chromogenic solution is allowed to permeate into the sections for several minutes (for example, five minutes) to develop color. After color development, the sections are sufficiently washed with tap water to remove DAB.

(9) Nuclear Staining

Nuclear staining is carried out by reacting Mayer's Hematoxylin for several seconds to several tens of seconds. The sections are allowed to develop color with washing under running water (generally, several minutes).

(10) Dehydration, Clearance, and Mounting

After dehydrated with alcohol and cleared with xylene, the sections are finally mounted in synthetic resins, glycerin, gum syrup, or such.

The type and source of an anti-CLCP1 antibody to be used in immunological staining are not particularly limited, as long as the antibody has a specific binding activity to CLCP1. The anti-CLCP1 antibody may be a polyclonal, oligoclonal (a mixture of several to several tens of antibodies), or monoclonal antibody. Such polyclonal and oligoclonal antibodies may be. IgG fractions derived from antisera obtained by immunizing animals or antibodies that are affinity-purified using the antigen. The anti-CLCP1 antibodies include antibody fragments such as Fab, Fab', F(ab')$_2$, Fv, scFv, dsFv, diabody, and sc(Fv)2.

The anti-CLCP1 antibodies can be prepared according to the methods described above.

Antibodies prepared by the methods described above may be modified variously as long as they retain a specific binding activity to CLCP1. Such modified antibodies can be used in the present invention.

When a labeled antibody is used as an anti-CLCP1 antibody, the amount of bound antibody can be directly determined using the amount of the label as an indicator. Such a method is simpler but has problems. The detection sensitivity of the method is in general lower, and it is necessary to prepare a labeling substance-linked anti-CLCP1 antibody. Thus, indirect detection methods are more preferably used, which include methods using a secondary antibody linked to a labeling substance and methods using a polymer linked to a secondary antibody and labeling substance. The secondary antibody refers to an antibody that has the activity of specifically binding to the anti-CLCP1 antibody. For example, an anti-rabbit IgG antibody can be used when the prepared anti-CLCP1 antibody is a rabbit antibody. Labeled secondary antibodies that can be used to detect antibodies of various animal species such as rabbit, goat, and mouse are available on the market. Thus, appropriate antibodies may be selected and used depending on the type of anti-CLCP1 antibody of the present invention.

Any one selected from peroxidase, β-D-galactosidase, microperoxidase, horseradish peroxidase (HRP), fluorescein isothiocyanate (FITC), Rhodamine isothiocyanate (RITC), alkaline phosphatase, biotin, and radioactive substances is used preferably as the labeling substance. In particular, high sensitivity detection can be achieved by methods in which biotin is used as the labeling substance and reacted in combination with avidin peroxidase.

The above-described antibodies of the present invention can be used as an anti-CLCP1 antibody here. Specifically, for example, it is possible to use antibodies that have been successfully isolated by the present inventors. As described in the Examples below, of the successfully isolated antibodies, in particular, antibody FA19-1 and such unambiguously stained different invading or metastasizing cancers in a distinguishable manner. Thus, the antibodies are particularly valuable when used in methods for determining the invasion or metastasis site of cancer cells (for example, lung cancer cells).

In still another aspect, the present invention also provides methods for predicting cancer prognosis (hereinafter, also referred to as "diagnostic methods for cancer prognosis of the present invention"). The diagnostic methods for cancer prognosis of the present invention can be said as a method of collecting and providing data that are useful for medical practitioners to predict the prognosis.

The type of target cancer in the diagnostic methods for cancer prognosis of the present invention is not particularly limited; however, such cancers include, for example, kidney cancer, bladder tumor, prostate cancer, pancreas cancer, stomach cancer, large intestine cancer, breast cancer, and lung cancer, particularly preferably lung cancer.

The diagnostic methods for cancer prognosis of the present invention comprise the steps of contacting an antibody of the present invention with an isolated pathological tissue and detecting the expression of CLCP1 in a pathological tissue by an immunological method. The steps are described in detail above in the examples of diagnostic methods of the present invention.

In the diagnostic methods for cancer prognosis of the present invention, the survival rate is predicted to be lower for the group of clinical cases where the isolated pathological tissues are strongly positive in the histological staining than for the group of clinical cases where the isolated pathological tissues are weakly positive or negative in the histological staining.

For example, the Kaplan-Meier survival rate one year (12 months) after surgery is 73% in the group of clinical cases strongly positive in the histological staining, while the rate is 93% in the group of weakly positive or negative clinical cases. On the other hand, the survival rate three years (36 months) after surgery is 55% in the group of strongly positive clinical cases, while the rate is 90% in the group of weakly positive or negative clinical cases.

Strong positive histological staining means a staining result where the cell membrane is clearly stained (the outline of cell membrane is visible under a microscope) in an isolated pathological tissue, as shown in the upper panel of FIG. 37B. On the other hand, weak positive histological staining means a staining result where the cell membrane is only stained vaguely (the outline of cell membrane is invisible under a microscope) in an isolated pathological tissue, as shown in the lower panel of FIG. 37B. Alternatively, negative histological staining means a staining result where the cell membrane is completely invisible in an isolated pathological tissue.

Furthermore, the present invention provides agents and kits comprising an antibody of the present invention to be used in the above-described diagnostic methods for cancer prognosis.

(Screening Method)

In another aspect, the present invention relates to methods of screening for candidate substances that inhibit the growth, invasion, migration, or metastasis of cancer cells, or candidate substances that have cytotoxic activity towards cancer cells, which comprise the steps of:

(a) contacting a test substance with the extracellular domain of a human CLCP1 antigen;

(b) detecting the binding between a test substance and the extracellular domain of the human CLCP1 antigen; and (c) selecting a test substance that binds to the extracellular domain of the human CLCP1 antigen.

The respective steps are achieved by using known methods or methods described above.

Candidate substances in the screening methods of the present invention include, but are not limited to, purified proteins (including antibodies), expression products of gene libraries, synthetic peptide libraries, DNA or RNA libraries (including functional nucleic acids such as aptamers and siRNAs), cell extracts, cell culture supernatants, and libraries of synthetic low-molecular-weight compounds.

Test substances that bind to the extracellular domain of a human CLCP1 antigen, which are selected by the screening methods of the present invention, are candidate substances for of agents for treating or preventing CLCP1-expressing cancer, or agents for inhibiting the growth, migration, invasion, or metastasis of cancer cells, or candidate substances having cytotoxic activity towards cancer cells. Specifically, the present invention provides agents for treating or preventing CLCP1-expressing cancer, agents for inhibiting the growth, migration, invasion, or metastasis of cancer cells, and cytotoxic agents against cancer cells, which comprise as an active ingredient a substance selected from screening according to the present invention. The present invention also relates to the use of substances selected by the screening methods of the present invention, in producing agents for treating or preventing CLCP1-expressing cancer, agents for inhibiting the growth, migration, invasion, or metastasis of cancer cells, or cytotoxic agents against cancer cells. When a substance isolated by the screening methods of the present invention is used as an agent for treating or preventing cancer expressing CLCP1, it can be formulated using known pharmaceutical production methods. For example, the agent is administered to patients in combination with pharmaceutically acceptable carriers or media (physiological saline, vegetable oils, suspending agents, surfactants, stabilizers, etc.). The agent is administered transdermally, nasally, transbronchially, intramuscularly, intravenously, or orally, according to the properties of the substance. The dose varies depending on the patient's age, weight, symptoms, administration method, and so on; however, those skilled in the art can appropriately select a proper dose.

Hereinbelow, the present invention will be described more specifically with reference to the Examples, but is not to be construed as being limited to the embodiments described in the Examples.

All prior art documents cited in the specification are incorporated herein by reference.

EXAMPLES

Example 1

Preparation of Human CLCP1 cDNA

ESTs corresponding to CLCP1 were selected from the NCBI EST database. The 3' end was determined by 3'-RACE. The full-length cDNA sequence of human CLCP1 was determined and deposited in a database (GenBank database, Accession No. AB073146; Koshikawa K, et al., Oncogene 21:2822-2828 (2002)). Primers were designed based on this human CLCP1 cDNA sequence (GenBank database, Accession No. AB073146 (the same sequence as that of NM_080927)). The primer 5'-CCCAAGCTTT GCAGGCA-GAC TGCCGGC-3' (SEQ ID NO: 25) was prepared based on the nucleotide sequence of positions 336 to 356 (5'-CTATG-CAGGC AGACTGCCGG C-3' (SEQ ID NO: 24)) immediately before the first nucleotide (position 364) of the ORF. This primer contains an ATG-to-TTG mutation (underlined) to prevent the initiation of translation from ATG (underlined) in a different reading frame. The primer also has a HindIII recognition sequence (AAGCTT) at the 5' end. The primer 5'-CGAGGTACCAAGGATTECTTTAAAAACATCACAT-3' (SEQ ID NO: 26) was prepared by adding a KpnI recognition sequence (GGTACC) to the 5' end of a sequence complementary to the nucleotide sequence of positions 2664 to 2688 immediately before the stop 1.5 codon. RNA was prepared from normal lung tissue using the RNAeasy Kit (Qiagen), and then processed by RT-PCR using the above-described primers to amplify human CLCP1 cDNA. The PCR product was cloned into a cloning vector, pBSSKII (Stratagene), between the HindIII and KpnI sites. The nucleotide sequence was determined (about 2362 by including the additional sequence; translated region of 2331 bp; 777 codons (CLCP 1 HindIII -KpnI)) using an automatic sequencer (Applied Biosystems). After sequencing, CLCP1 was excised with HindIII and KpnI, and then inserted into an HA-tag protein expression vector pcDNA3-HA (a gift from Dr. N. Inohara in the Department of Medicine, Michigan University) between HindIII and KpnI sites, thereby yielding an expression vector pcDNA3-CLCP1-HA for HA-tag-attached full-length CLCP1.

Example 2

Preparation of Cells Expressing Human CLCP1

The animal cell expression vector pQCXIPG was used to express the full-length human CLCP1 (amino acid positions 1 to 775) or the whole extracellular domain of human CLCP1 (amino acid positions 1 to 526). pQCXIPG is under the control of CMV promoter, and its IRES sequence allows simultaneous expression of a puromycin-EGFP fusion protein and a gene of interest. On the other hand, the animal expression vector lyssig-pQCXIPG was used to express partial human CLCP1 containing the human FA58C domain (amino acid positions 284 to 526) in animal cells. The secretory signal sequence of chicken egg white lysozyme [amino acid sequence: MRSLLILVLCFLPLAALG|AAA (SEQ ID NO: 27), gene sequence: ATGAGGTCTTTGCTAATCTTGGT-GCTTTGCTTCCTGCCCCTGGCTGCT-CTGGGG|GCGG CCGCC (SEQ ID NO: 28), whereas "|" indicates the border between the signal sequence and structural protein] is added upstream of the multicloning site of pQCXIPG above. The vector lyssig-pQCXIPG is used to enable forced secretion of the translated product of the introduced gene to outside of the cells. The vectors pQCXIPG and lyssig-pQCXIPG were constructed by the present inventors from modification based on pQCXIP which is one of "BD Retro-XTM Q Vectors".

In every case, PCR amplification of genes of interest was carried out with KOD-Plus-(TOYOBO) using the above-described pcDNA3-CLCP1-HA as a template.

Full-length human CLCP1 was amplified by PCR [34 cycles of (99° C. for 30 seconds, 61° C. for 30 seconds, and 68° C. for two minutes)] using 5' primer 5'-AATAGCGGC-CGCACCATGGCGAGCCGGGCGGTG-3' (SEQ ID NO: 29; NotI site is underlined) and 3' primer 5'-ACGCGTCGA-CAAGGATTTCTITAAAAACATCACATTC-3' (SEQ ID NO: 30; SalI site is underlined). The whole extracellular domain of human CLCP1 was amplified by PCR [34 cycles of (99° C. for 30 seconds, 61° C. for 30 seconds, and 68° C. for two minutes)] using 5' primer 5'-AATAGCGGCCGCAC-CATGGCGAGCCGGGCGGTG-3' (SEQ ID NO: 29; NotI site is underlined) and 3' primer 5'-ACGCGTCGACTA-CATCTTTGGTTACATTTGGAG-3' (SEQ ID NO: 31; SalI site is underlined). Both of the amplified PCR products were digested with restriction enzymes NotI and SalI, and the resulting fragments were each inserted into pQCXIPG between the NotI and XhoI sites. This yielded expression vectors, pQCXIPG-full and pQCXIPG-EC. Meanwhile, partial human CLCP1 containing the FA58C domain was amplified by PCR [34 cycles of (99° C. for 30 seconds, 61° C. for 30 seconds, and 68° C. for two minutes)] using 5' primer 5'-AATAGCGGCCGCTCTTTTTACATTTAA-GACAAGTGG-3' (SEQ ID NO: 32; NotI site is underlined) and 3' primer 5'-ACGCGTCGACAAGGATTTCTT-TAAAAACATCACATTC-3' (SEQ ID NO: 30; SalI site is underlined). The amplified PCR product was digested with restriction enzymes NotI and SalI, and then inserted into lyssig-pQCXIPG between the NotI and XhoI sites. This yielded expression vector pQCXIPG-FA.

The Pantropic Retroviral Expression System (Clontech: K1063-1) was used to establish antigen-expressing cell lines. GP2-293 (Clontech; K1063-1) grown to 80% to 90% confluency in 100 mm collagen-coated dishes were co-transfected using Lipofectamine 2000 with 11.2 μg each of pVSV-G (Clontech; K1063-1) and a constructed expression vector described above (pQCXIPG-full, pQCXIPG-EC, or pQCX-IPG-FA). After 48 hours, the virion-containing supernatants were collected, and the virions were precipitated by ultracentrifugation (18,000 rpm, 1.5 h, 4° C.). The precipitates were suspended in 30 μl of TNE (50 mM Tris-HCl (pH 7.8), 130 mM NaCl, 1 mM EDTA) to prepare retroviral vector concentrates.

5 μl of the retroviral vector concentrate was diluted with 150 μl of DMEM (SIGMA; D5796)/10% FBS containing 8 μg/ml hexadimethrine bromide (SIGMA; H-9268) to prepare a virion-containing medium. The medium of 293T grown to about 40% confluency in 96 well microplates was replaced with the prepared virion-containing medium to introduce pQCXIPG-full, pQCXIPG-EC, or pQCXIPG-FA. After gene transfer, the cultures were expanded using DMEM (SIGMA; D5796)/10% FBS containing 5 μg/ml Puromycin (SIGMA; P-8833) to establish antigen-expressing cell lines (hCLCP1-full/293T, hCLCP1-EC/293T, and hCLCP1-FA/293T).

Example 3

Preparation of Immunization Antigen

The established cell lines described above (hCLCP1-EC/293T and hCLCP1-FA/293T) were cultured in DMEM/10%

FBS (5 μg/ml puromycin) or CD293 (Invitrogen). About one liter each of the supernatants were collected, and myc-His Tag-attached recombinant proteins were purified from them using the TALON Purification Kit (Clontech; K1253-1) or an affinity column filled with carriers chemically modified with an anti-myc-tag antibody. Then, the purified proteins were dialyzed against PBS, and assessed by SDS-PAGE and Western blotting. The protein concentrations were determined using Protein Assay Kit II (BioRad; 500-0002JA). The resulting protein samples were used as immunization antigens.

Example 4

Antigen Immunization

The purified protein of the extracellular domain of human CLCP1 or the purified partial protein containing the FA58C domain of human CLCP1 was combined with an equal volume of complete adjuvant (SIGMA; F5881). Using the resulting emulsion, BALB/c mice (female) were immunized at 5 to 50 μg/head several times every three to seven days. Three to five days after final immunization, lymphocytes were collected from the mice, and fused with cells of a mouse myeloma line P3U1 (P3-X63Ag8U1).

Example 5

Cell Fusion, and Selection and Preparation of Monoclonal Antibody-Producing Cells Cell fusion was carried out basically according to the following conventional method. In every case, the fetal bovine serum (FBS) to be added to culture medium was inactivated by heating at 56° C. for 30 minutes. P3U1 cells were prepared by culturing in RPMI1640/10% FBS (containing penicillin and streptomycin).

The collected mouse lymphocytes and P3U1 cells were mixed at a ratio of 10:1 to 2:1. After centrifugation, 50% polyethylene glycol 4000 (Merck; 1.09727.0100) as a fusion-enhancing agent was added little by little to the precipitated cells while the mixture was gently stirred to achieve cell fusion. Then, the mixture was gently stirred while adding RPMI1640 thereto little by little. The resulting mixture was centrifuged, and the precipitated, fused cells were appropriately diluted with HAT medium [RPMI1640, HAT-supplement (Invitrogen; 11067-030), penicillin, and streptomycin] supplemented with 15% FBS, and plated at 200 μl/well in 96-well microplates.

The fused cells were cultured in a $CO_2$ incubator (5% $CO_2$, 37° C.). After formation of sufficiently large colonies, the cells were screened by sampling the culture supernatants.

In this screening, hybridomas reactive to 293T with forced expression of full-length CLCP1 (hCLCP1-full/293T) were selected by flow cytometry from cells positive in ELISA using 96-well plates sensitized with the same CLCP1 antigen used in the immunization. After expansion culture in HT medium [RPMI1640, HT-supplement (Invitrogen; 21060-017), Penicillin, and Streptomycin] supplemented with 15% FBS, the cells were cloned into single clones by the limiting dilution method. Eleven hybridoma clones producing anti-human CLCP1 antibody were obtained by the method described above. Of the 11 clones, one clone (antibody No. EC6-8) was obtained by using as an immunogen the complete extracellular domain protein (amino acid positions 1 to 526), and 10 clones (antibody Nos. FA2-10, FA7-6, FA9-1, FA10-3, FA12-3, FA14-9, FA16-3, FA17-9, FA19-1, and FA20-3) were obtained by using the partial protein containing FA58C domain (amino acid positions 284 to 526).

Example 6

Antibody Reactivity to Cells Expressing Human CLCP1 (FCM)

Figure 1:
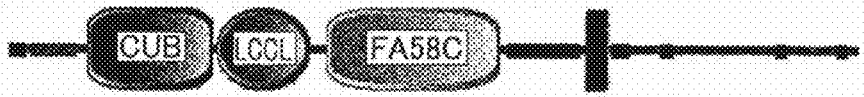
FIG. 1 shows in diagrams the structure of CLCP1 molecule.
Figure 2:
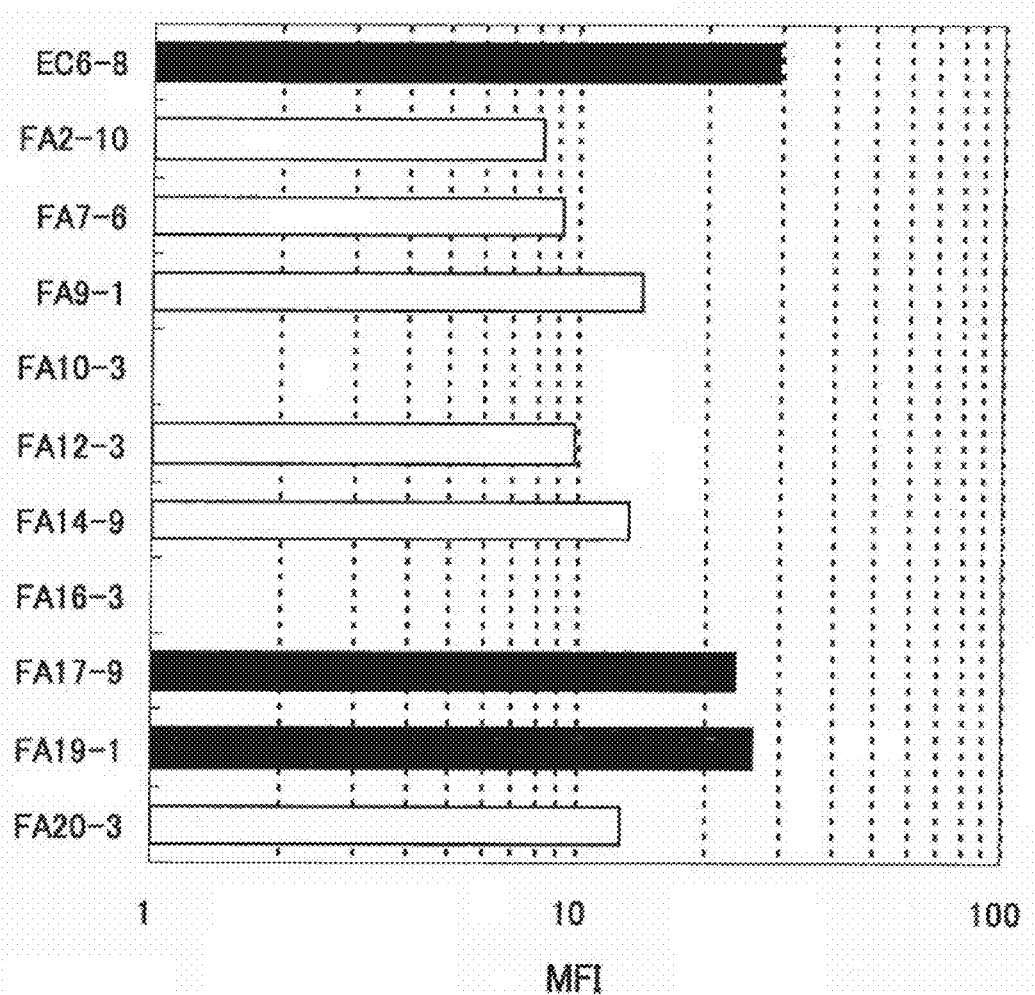
FIG. 2 shows in a diagram the reactivity of anti-human CLCP1 antibodies to CLCP1-expressing cells. A result of flow cytometric (FCM) analysis of H460-LNM35 cells (each monoclonal antibody was detected using a PE-labeled anti-mouse IgG antibody).

The antibodies prepared as described above were assessed for the reactivity to endogenous human CLCP1 by testing their reactivity to cells of high CLCP1-expressing line H460-LNM35 according to the following method. Anti-human CLCP1 antibody was purified from culture supernatant of each hybridoma clone by a conventional affinity purification method using Protein A-Sepharose. The purified antibodies were each diluted to 5 μg/ml, and the reaction intensity to H460-LNM35 was assessed by flow cytometry. In this assay, the anti-CLCP1 monoclonal antibody bound on the cell surface was detected by using a phycoerythrin-labeled anti-mouse IgG antibody. All samples were processed under the same conditions. As seen in FIG. 2, the result showed that except antibody clones Nos. FA10-3 and FA16-3, nine clones (antibody Nos. EC6-8, FA2-10, FA7-6, FA9-1, FA12-3, FA14-9, FA17-9, FA19-1, and FA20-3) were reactive. Thus, the nine clones were demonstrated to be reactive to endogenous human CLCP1. In particular, three clones, EC6-8, FA17-9, and FA19-1, were suggested to be very highly reactive.

Example 7

Analysis of Epitope Recognized by Monoclonal Antibodies (Inhibition Test Using Biotinylated Antibodies)

The anti-human CLCP1 antibodies of nine established clones were biotinylated by a conventional method. A non-labeled antibody was combined at 2, 1, 0.5, or 0.25 μg/ml with a biotinylated antibody at a constant concentration (1 μg/ml). An inhibition experiment was carried out by incubating cells of the H460-LNM35 line in the reaction mixture, and determining the amount of biotinylated antibody bound on the cell surface by flow cytometry using phycoerythrin-labeled StreptAvidin. In this experimental system, when the epitope recognized by the biotinylated antibody being tested is close to the epitope recognized by the non-labeled antibody added, the binding of biotinylated antibody is inhibited and as a result the reaction is altered depending on the added concentration of the non-labeled antibody. Epitope analysis (epitope grouping) was achieved by performing this assay using all possible combinations of the isolated monoclonal antibodies. FIG. 3 shows an analysis result on three clones that exhibit significantly higher reactivity. The vertical axis indicates the amount of bound biotinylated antibody (phycoerythrin-labeled StreptAvidin) (mean fluorescence intensity; MFI), while the horizontal axis indicates the added amount of non-labeled antibody (μg/ml). The result on each clone suggested that other than EC6-8, eight clones (antibody Nos. FA2-10, FA7-6, FA9-1, FA12-3, FA14-9, FA17-9, FA19-1, and FA20-3) all recognized an adjacent epitope.

Example 8

Analysis of Epitope Recognized by EC6-8 Monoclonal Antibody (Immunoprecipitation)

Figure 4:
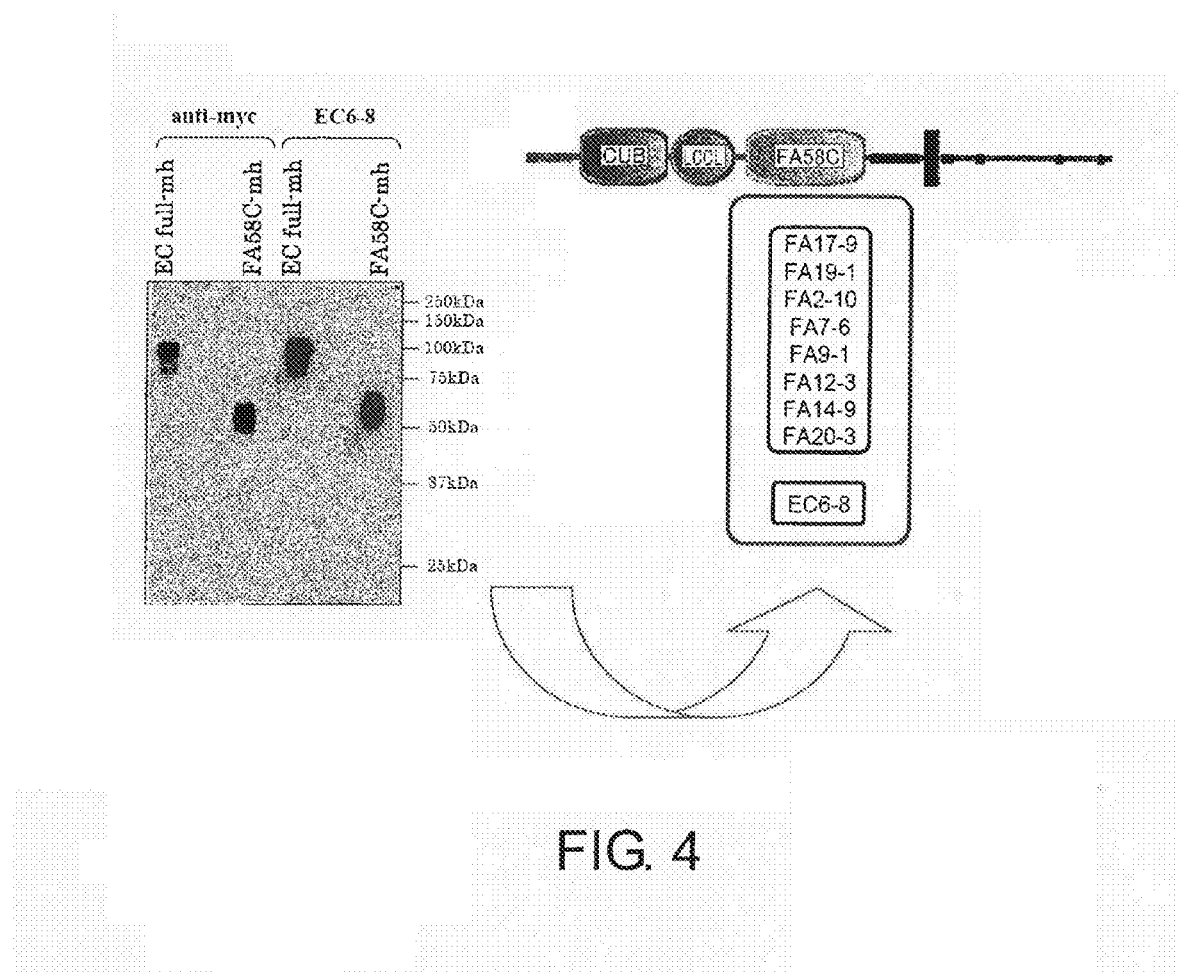
FIG. 4 shows in a photograph and a diagram an experiment to identify the epitope recognized by antibody EC6-8. FA58C domain was successfully immunoprecipitated with EC6-8. Thus, EC6-8 was demonstrated to recognize the FA58C domain.

The epitope recognized by EC6-8 alone is different from the others in the above-described inhibition experiment using biotinylated antibodies. Thus, the location of the distinct epitope was analyzed by immunoprecipitation. Target proteins used were the whole extracellular domain protein (amino acid positions 1 to 526) and the partial protein containing the FA58C domain (amino acid positions 284 to 526). These target proteins were individually reacted with EC6-8-bound Protein G-Sepharose. Samples resulting from immunoprecipitation were subjected to Western blotting using an anti-myc tag antibody to detect the binding of EC6-8 to the target proteins. As shown in FIG. 4, the result showed that both the whole extracellular domain protein (amino acid positions 1 to 526) and the partial protein containing the FA58C domain (amino acid positions 284 to 526) were immunoprecipitated, suggesting that the epitope recognized by EC6-8 is located within the region of amino acid positions 284 to 526. FIG. 4 also shows the result of epitope grouping of nine clones of anti-CLCP1 antibodies (antibody Nos. EC6-8, FA2-10, FA7-6, FA9-1, FA12-3, FA14-9, FA17-9, FA19-1, and FA20-3) reactive to endogenous CLCP1, which was elucidated together with the result of the above-described inhibition experiment using the biotinylated antibodies.

Example 9

Antibody Affinity

Figure 5:
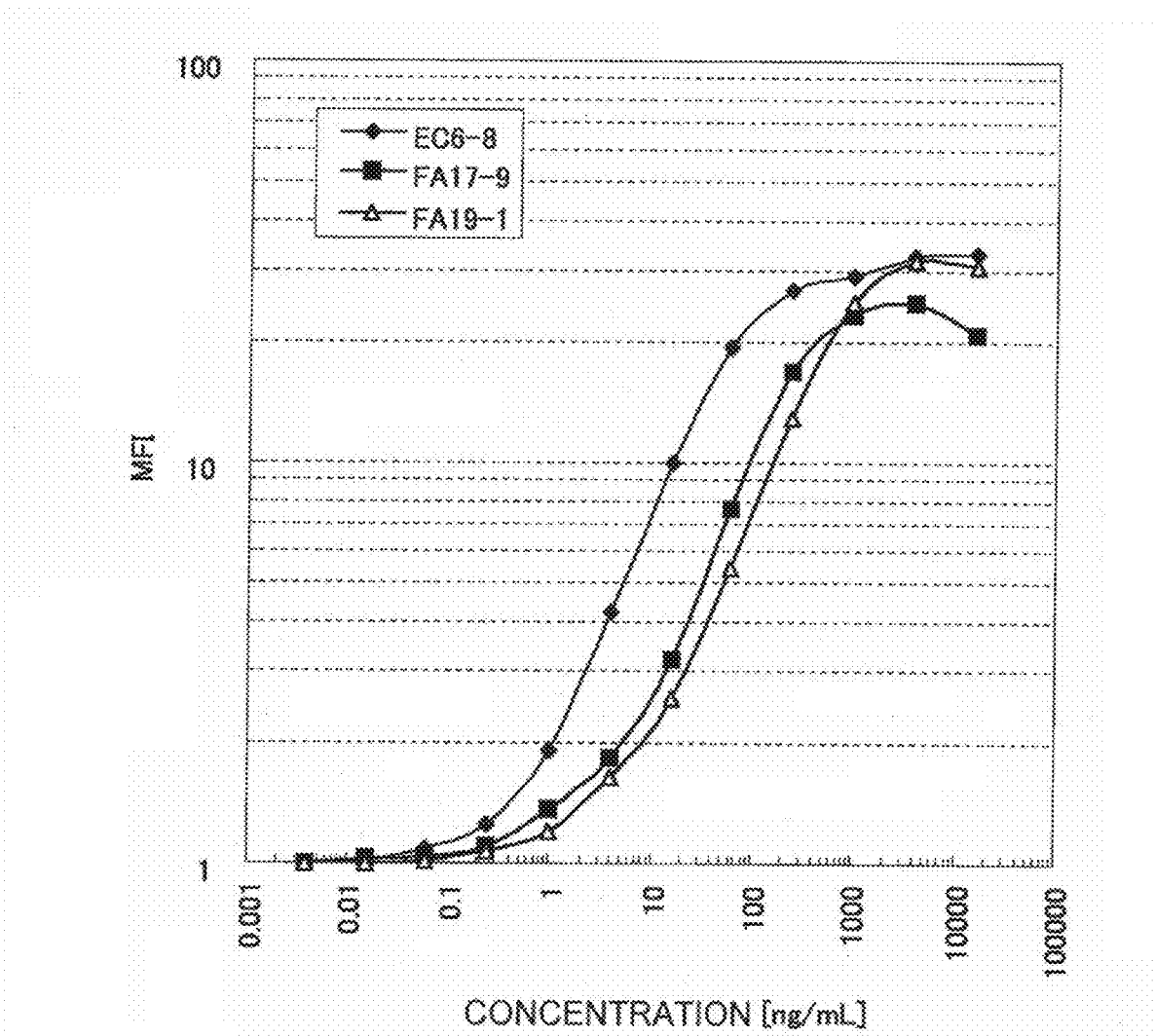
FIG. 5 shows in a graph affinity analysis by FCM.

The three clones exhibiting significantly higher reactivity were analyzed for their relative affinity by the following method. Each purified antibody was analyzed by flow cytometry under the same conditions (same number of 11460-LNM35 cells ($1 \times 10^5$ cells); same concentration of each of the purified antibodies; same concentration of secondary (detection) antibody) to determine the mean fluorescence intensity. Furthermore, the relative affinity was assessed by collecting data on the antibody concentration-dependent changes in mean fluorescence intensity and analyzing detection limits at lower concentrations. The result is shown as a graph in FIG. 5. The horizontal axis of the graph indicates the concentration (ng/ml) of used antibodies, and the vertical axis indicates the mean fluorescence intensity (MFI) determined by flow cytometry. The result showed that the relative affinity was: EC6-8>FA17-9>FA19-1.

Example 10

Assessment of Antibody Reactivity (Western Blotting and Immunoprecipitation)

The antibodies prepared as described above were further assessed and confirmed to recognize CLCP1 by testing the reactivity to endogenous CLCP1 using Western blotting and immunoprecipitation by the following procedure.

Figure 8:
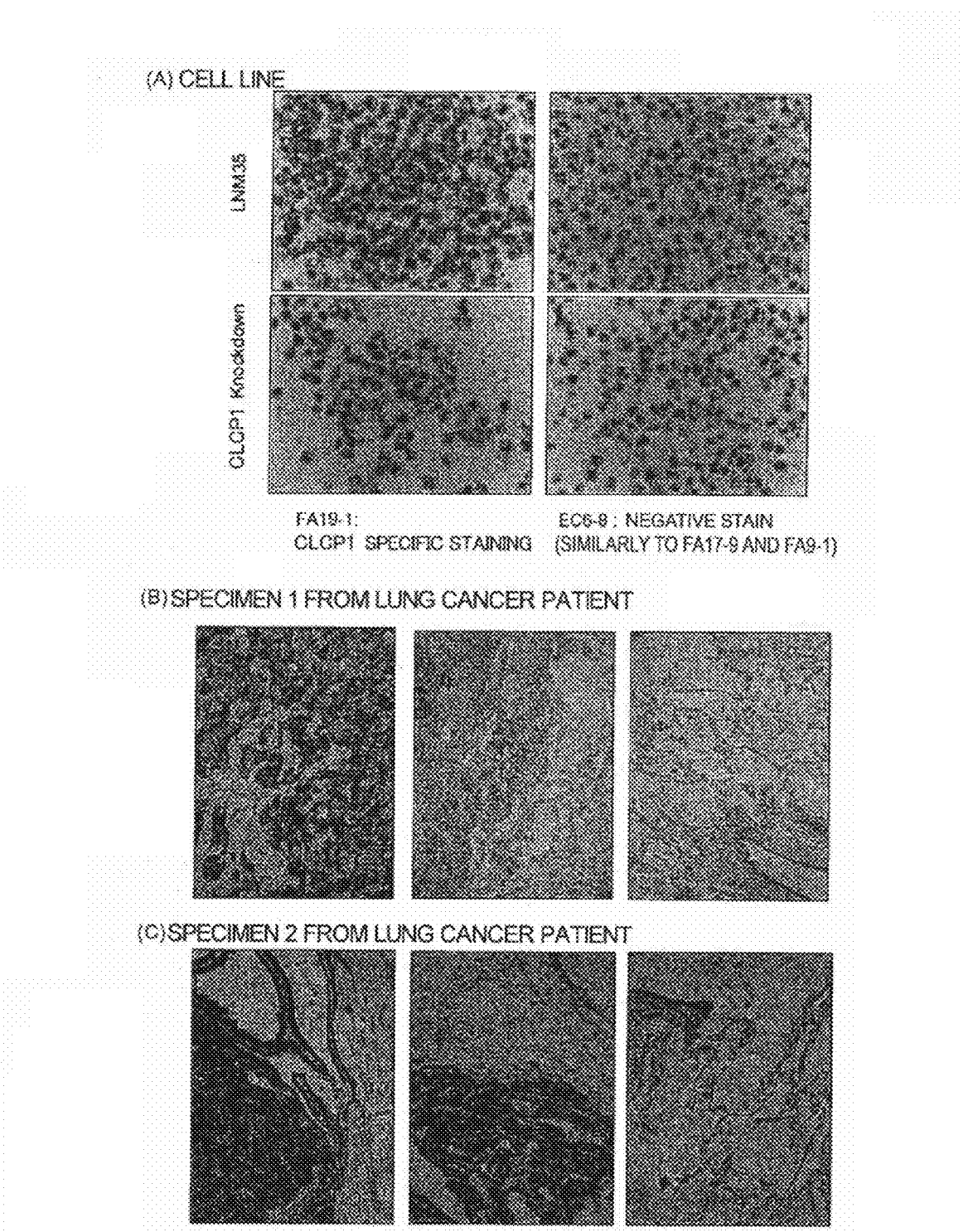
FIG. 8 shows in photographs assessment of the stainability of monoclonal antibodies. A, cell staining; B and C, staining of cancer tissue. A: it was demonstrated that only FA19-1 could be used in immunohistochemistry of paraffin-embedded samples under the experimental conditions used in the present invention. B: cell membrane was stained in the cancer tissue (lung squamous cell carcinoma) of specimen 1. B left panel: histochemistry of lung squamous cell carcinoma. The lung cancer was uniformly positive for cell membrane staining. This result is consistent with the pathologically identified cancer area. B middle panel: the area of cancer invasion in normal region was stained positive, and the normal region was stained negative. Thus, the normal and invaded areas were clearly discriminated by staining. This result is consistent with the pathologically identified cancer area. B right panel: staining image for the normal lung tissue: stain negative. The black dots visible in the panel are sites of iron grain deposition. Cell membrane was stained also in the specimen 2 cancer tissue (lung adenocarcinoma), where the cytoplasm was also stained. C left panel: staining of the lung cancer tissue was uniformly positive. Cell surface staining was strongly positive. The cytoplasm was also stained. C middle panel: other portions of the lung cancer tissue were mostly stained positive. However, the staining was slightly non-uniform. C right panel: an area of the normal lung tissue distant from cancer was stained negative. The black dots visible in the panel are sites of iron grain deposition.
Figure 11:
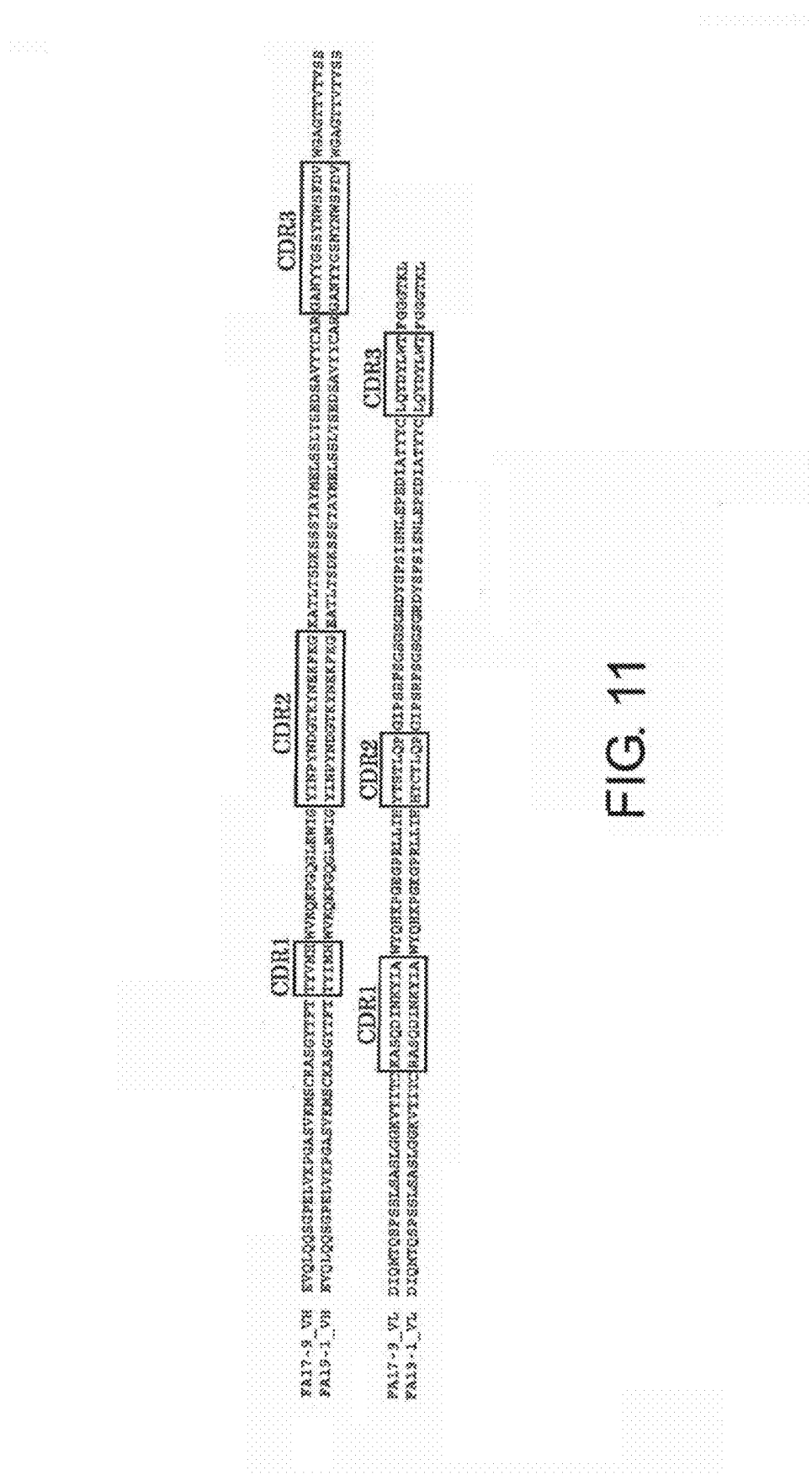
FIG. 11 shows in a diagram comparison of antibody sequences (FA17-9 VH and FA19-1 VH are shown in SEQ ID NOs: 6 and 15, respectively). FA17-9 and FA19-1 are derived from the same germline, and differ in only some amino acids due to somatic mutation.

As described in the reference, Nagai H, et al., Oncogene 26: 4025-4031 (2007), a subline that constitutively expresses a CLCP1 siRNA as a short hairpin RNA (shRNA) biosynthesized in cells has been established from the high expressing CLCP1 cell line H460-LNM35. The expression level of CLCP1 mRNA was demonstrated to be significantly reduced in the cells of the subline (siCLCP1-3 #9 cell line; Nagai H, et al., Oncogene 26: 4025-4031 (2007)). Western blotting was carried out using siCLCP1-3 #9 cells (CLCP1 Knockdown in FIG. 8) and H460-LNM35 cells.

Figure 12:
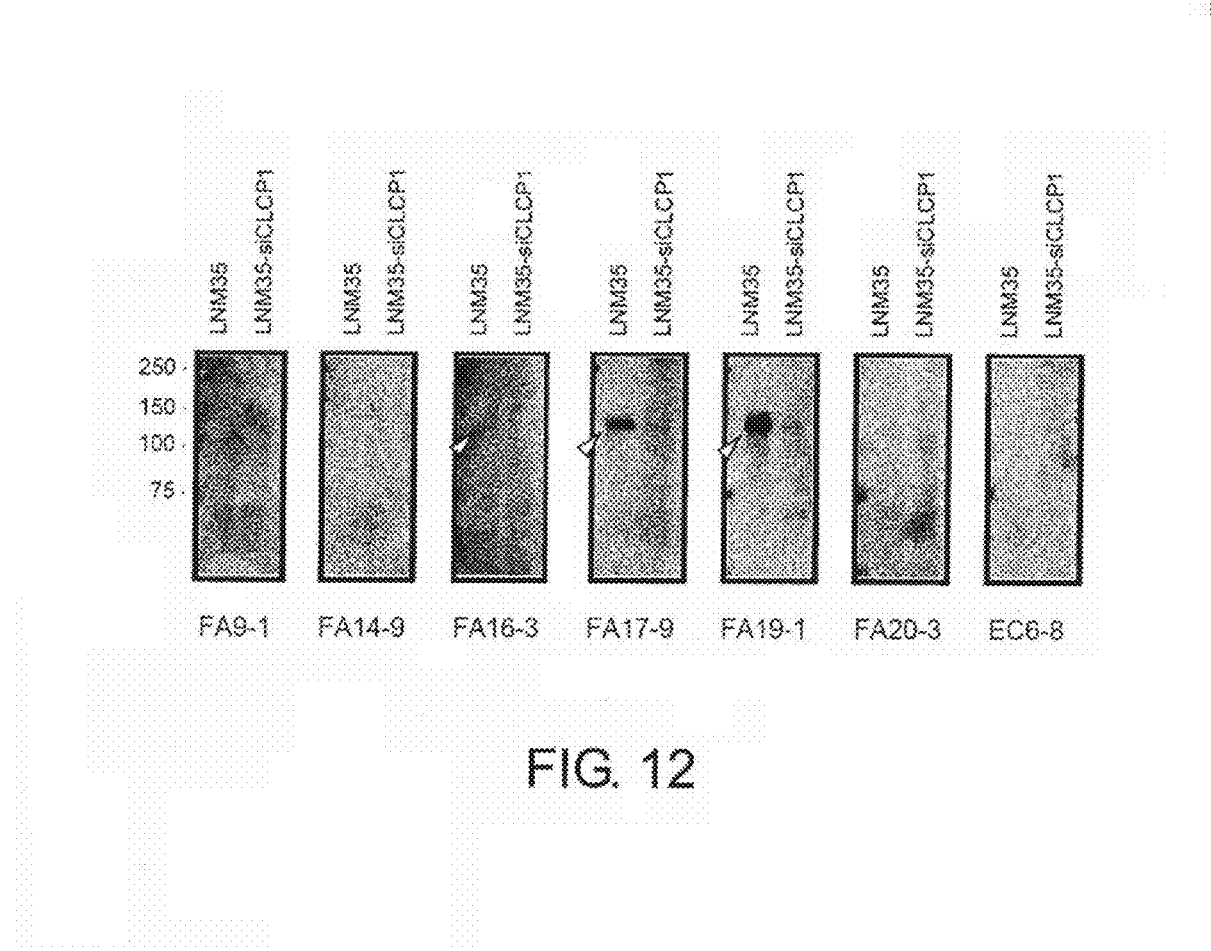
FIG. 12 shows in photographs Western blot analysis of each antibody for endogenous CLCP1. Cell lysates were prepared from parental line H460-LNM35 and the H460-LNM35 subline which constitutively expresses short hairpin RNA (shRNA) biosynthesized intracellularly to siRNA against CLCP1 (siCLCP1-3 #9 cell; Nagai H, et al., Oncogene (2007) 26: 4025-4031) (lane, LNM35-siCLCP1). The expression level of CLCP1 mRNA was demonstrated to be significantly reduced in siCLCP1-3 #9 cells. Western blot was carried out using the cell lysates and each of the indicated antibodies. As a result, FA19-1, FA17-9, and FA16-3 gave signals of an identical size. However, the signal was very weak with FA16-3. The Western blot results showed that FA19-1 and FA17-9 could specifically and efficiently recognize endogenous CLCP1.

$2 \times 10^6$ cells of the high expressing CLCP1 cell line H460-LNM35 and siCLCP1-3 #9 line were each suspended in lysis buffer [50 mM Tris (pH 6.8), 5% glycerol, 2% SDS], and the protein concentration was determined using the DC Protein Assay Kit (Bio-Rad). Then, 2-mercaptoethanol was added at 5.3% to the lysates. After heating, 20 µg each of the lysates were subjected to SDS-PAGE, followed by Western blotting with each of the antibodies and an HRP-labeled anti-mouse or anti-rabbit antibody. The result showed that both FA19-1 and FA17-9 gave signals of an identical size (signal intensity: FA19-1>FA17-9) (FIG. 12). Meanwhile, there was almost no detectable signal in siCLCP1-3 #9 cells. Thus, Western blotting demonstrated that FA19-1 and FA17-9 specifically recognized CLCP1.

Figure 7:
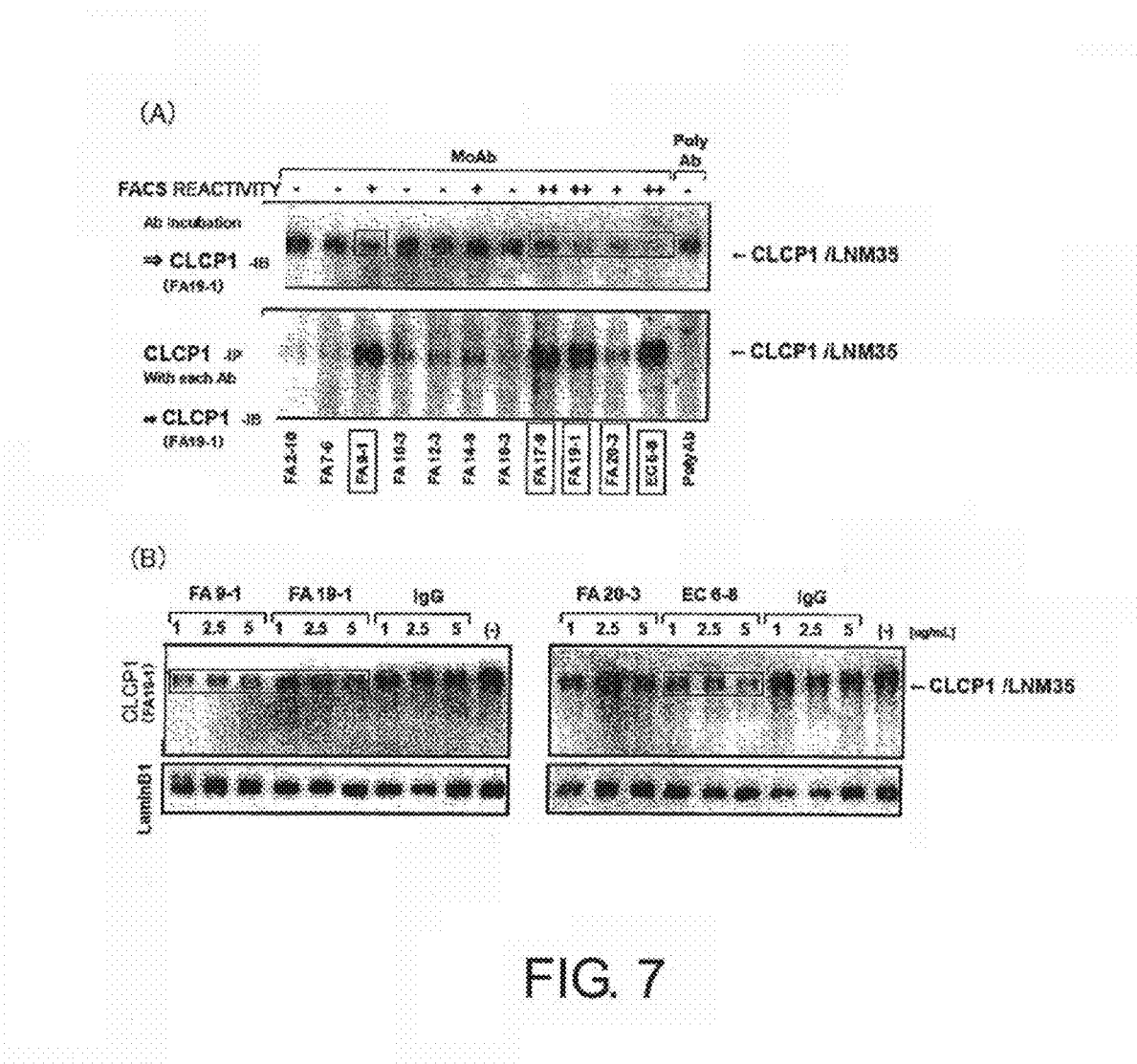
FIG. 7 shows in photographs functional assessment of the monoclonal antibodies. (A) upper panel: Western blot of H460-LNM35 cell lysates after exposure to each antibody; (A) lower panel: Western blot of immunoprecipitates prepared using each antibody; (B): Western blot of H460-LNM35 cell lysates after exposure to each antibody at the indicated concentrations. In each experiment, CLCP1 was detected using FA19-1 and an HRP-labeled anti-mouse IgG antibody.

$1 \times 10^7$ cells of high expressing CLCP1 cell line H460-LNM35 were suspended in lysis buffer for immunoprecipitation [10 mM HEPES (pH 7.5), 300 mM NaCl, 0.5% NP-40, 5 mM EDTA, 0.5 mM DTT, ×1 Protease Inhibitor Cocktail Complete (Roche)]. Then, 1/10-aliquots were added to microcentrifuge tubes (Eppendorf tubes), and 1 µg each of antibodies FA2-10, FA7-6, FA9-1, FA12-3, FA14-9, FA17-9, FA19-1, FA20-3, and EC6-8 (and rabbit polyclonal antibody) were added thereto. The resulting mixtures were stirred at 4° C. for two hours. 20 µl of Protein G-sepharose (GE Healthcare) was added and the mixtures were stirred for one hour. The Protein G-sepharose was precipitated by centrifugation at 3,000 rpm for one minute. The precipitates were washed four times with lysis buffer for immunoprecipitation. The resulting precipitates were subjected to SDS-PAGE, followed by Western blotting with antibody FA19-1 and an HRP-labeled anti-mouse antibody. The result showed that except the rabbit polyclonal antibody, all monoclonal antibodies gave signals of the same size as that given by FA19-1 and FA17-9 described above. Thus, the monoclonal antibodies were demonstrated to specifically recognize CLCP1 (lower panel of FIG. 7(A)). Furthermore, FA9-1, FA17-9, FA19-1, and EC6-8 gave significantly higher signals, suggesting that the monoclonal antibodies exhibit very high reactivity.

Example 11

Assessment of Histopathological Staining Pattern with Antibodies (Immunostaining)

The above-described siCLCP1-3 #9 cells (lower panel of FIG. 8(A); CLCP1 knockdown) and H460-LNM35 cells (upper panel of FIG. 8(A)) were immunohistochemically stained with four antibodies FA9-1, FA17-9, FA19-1, and EC6-8, each of which as described above, gave a strong signal for CLCP1 protein in immunoprecipitation. The result showed that signals on the cell surface were obtained in a H460-LNM35 cell-specific manner only with FA19-1. Thus, it was demonstrated that only FA19-1 could be used to detect CLCP1 in immunohistochemistry of paraffin-embedded specimens under the experimental conditions used in the present invention (FIG. 8(A)).

Then, lung cancer tissues were stained with FA19-1 as a test. It was revealed that some clinical cases of lung cancer were strongly positive with FA19-1 (FIGS. 8(B) and (C)).

The antibody obtained as described above was tested to evaluate whether it could also be used to assess tissue metastasis. Specifically, the test was carried out by the following procedure.

(1) Preparation of Sections

Each clinical specimen of lung cancer (pulmonary squamous carcinoma or lung adenocarcinoma) was fixed with formalin and then embedded in paraffin. The paraffin-embedded tissue specimens were sliced into 3-µm thin sections with a microtome, and mounted on coated anti-detachment glass slides (MAS-GP, type A, MATSUNAMI).

(2) Staining

Hereinafter unless otherwise noted, sections were treated at room temperature. After deparaffinizing sections on glass slides, the sections were soaked in Immunosaver (NISSHIN EM CO.; Immunosaver was 200 times diluted with distilled water) and heated in an electric pot at 98° C. for 50 minutes to unmask the antigen. Then, to inactive endogenous peroxidase, the sections were treated with methanol containing 3% hydrogen peroxide for 20 minutes. After washing three times with PBS for five minutes each, the sections were incubated for one hour with the anti-CLCP1 antibody (FA19-1) as the primary antibody, which was 250 times diluted with 1% BSA/1% thimerosal/PBS. After washing three times with PBS for five minutes each, the sections were incubated for 30 minutes with a biotin-labeled horse anti-mouse immunoglobulin antibody (Vectastain ABC Kit, Vector Lab.) as the secondary antibody. The ABC reagent (Vectastain ABC Kit, Vector Lab.) was added in a drop, and the sections were incubated for 60 minutes according to the ABC method, followed by washing three times with PBS for five minutes each. The DAB (3,3'-diaminobenzidine) reaction mixture (20 mg of DAB/100 ml) was prepared by dissolving two DAB Tris tablets (Muto Pure Chemicals) in 100 ml of distilled water, and adding three or four drops of hydrogen peroxide thereto. The chromogenic reaction was carried out by soaking the sections in the DAB reaction solution for 12 minutes. After washing with tap water and distilled water, the sections were treated with hematoxylin for nuclear staining, followed by dehydration, clearance, and mounting. Then, the sections were observed under a microscope. The results obtained by staining the lung cancer tissues are shown in FIGS. 8(B) and (C).

The staining results of the specimens derived from two lung cancer patients are shown.

In specimen 1 (FIG. 8(B): pulmonary squamous carcinoma), cancer tissue was stained positive.

Left panel of FIG. 8(B): in the lung cancer tissue, the cell surface was stained positive in a uniform fashion, while the surrounding non-cancer area (so-called stromal area) was negative in this staining.

Middle panel of FIG. 8(B): in the area that cancer invades in the normal lung tissue, the invading cancer cells were stained positive while the remaining normal lung area was negative in this staining.

Right panel of FIG. 8(B): the normal lung tissue area distant from cancer was negative in this staining. The dark dot-like appearance represents deposits of iron grain.

As described above, cancer and non-cancer tissues were stained discriminately. This result is consistent with the pathologically identified cancer area.

In specimen 2 (FIG. 8(C): lung adenocarcinoma), cancer tissue was stained positive as well. However, this specimen was stained slightly weaker (perhaps, due to a lower expression level of the CLCP1 gene than in specimen 1), and the stain was less uniform in some areas, when compared to specimen 1.

Left panel of FIG. 8(C): the lung cancer tissue was stained positive in a uniform fashion. The cell surface was stained strongly positive, and the cytoplasm was stained positive as well. The surrounding non-cancer area (so-called stromal area) was stained negative.

Middle panel of FIG. 8(C): the other portions of the same lung cancer tissue were mostly stained positive. However, the stain was slightly less uniform. There were negative cancer cells in this staining. In the surrounding non-cancer area (so-called stromal area), only a small population of stromal cells were stained exceptionally positive, while most of the surrounding non-cancer area was stained negative.

Right panel of FIG. 8(C): the normal lung tissue area distant from cancer was stained negative. The dark dot-like appearance represents deposits of iron grain.

As described above, cancer and non-cancer tissues were also stained discriminately in specimen 2. This result is consistent with the pathologically identified cancer area.

The above-described result demonstrates that FA19-1 can be used in immunohistochemistry of paraffin-embedded specimens. When the intensity of stain in a pathological tissue is stronger than that of the non-cancer area in the lung tissue specimens shown in FIG. 8, the pathological tissue is diagnosed to be potentially affected with lung cancer. The areas stained positive by the antibody of the present invention were consistent with those pathomorphologically suspected as lung cancer. Areas stained negative with the antibody of the present invention are consistent with those assumed to be normal. The result generally agreed with the pathological finding based on microscopic observation.

Example 12

Assessment of the Antibody Staining (Immunostaining) Pattern of Normal Tissue

Sections of the normal tissues described below were tested for the FA19-1 staining pattern by the same method as described in Example 11.

The result showed that there was no specific, intense stain, except in the cytoplasm of follicular epithelium.

TABLE 1

HUMAN NOMARL TISSUE STAINING USING ANTIBODY FA19-1

|  | CELL MEMBRANE STAINING | CYTOPLASM STAINING | NOTES |
|---|---|---|---|
| CEREBRUM | — | — |  |
| BRONCHI | — | — | PSEUDO-POSITIVE STAINED IMAGE AT BRONCHI CILIATED EPITHELIUM/MUCOSAL GLAND |
| HEART | — | — |  |
| ESOPHAGUS | — | — |  |
| STOMACH | — | — | PSEUDO-POSITIVE STAINED IMAGE AT PYLORIC GLANDS |
| LARGE INTESTINE | — | — | PSEUDO-POSITIVE STAINED IMAGE AT CRYPT MUCOSAL EPITHELIUM |
| KIDNEY | — | — | PSEUDO-POSITIVE STAINED IMAGE AT RENAL TUBULE |
| PANCREAS | — | — | PSEUDO-POSITIVE STAINED IMAGE AT SMALL AMOUNT OF UNKNOWN ORIGIN CELLS |

TABLE 1-continued

HUMAN NOMARL TISSUE STAINING USING ANTIBODY FA19-1

| | CELL MEMBRANE STAINING | CYTOPLASM STAINING | NOTES |
|---|---|---|---|
| LIVER | — | — | PSEUDO-POSITIVE STAINED IMAGE AT LIVER CELL AND BILE DUCT |
| SPLEEN | — | — | |
| THYROID GLAND | — | — | PSEUDO-POSITIVE STAINED IMAGE AT FOLLICLE EPITHELIUM |

Example 13

Prediction of the Prognosis of Lung Cancer Patients by Histochemistry

The correlation between the prediction of prognosis and the staining pattern of lung cancer specimen was assessed by staining lung cancer specimens with the anti-CLCP1 antibody FA19-1 by the same histochemical method described above.

Lung cancer tissues were stained (cell membrane staining) with the anti-CLCP1 antibody. The result showed that the Kaplan-Meier survival rate one year (12 months) after surgery was 73% in the group of clinical cases strongly positive in histological staining by the anti-CLCP1 antibody (strongly positive for cell membrane staining), while the rate was 93% in the group of weakly positive or negative clinical cases (weakly positive or negative for cell membrane staining). The survival rate three years (36 months) after surgery was 55% in the group of strongly positive cases, while the rate was 90% in the group of weakly positive or negative cases. The survival rate was constantly lower in the group of strongly positive cases. The differences were evaluated by logrank test or generalized WilcoxOn test (Gehan-Wilcoxon test), which are commonly used to assess significant differences in the survival rate between two groups. The result was p=0.012 in the logrank test and p=0.0072 in the generalized Wilcoxon test, suggesting that the survival rate is statistically significantly lower in the group of strongly positive cases (FIG. 37A).

The immunohistological reactivity of the antibody was categorized into three groups: strongly positive (+), weakly positive (±), and negative (−). Specifically, strongly positive means that the cell membrane is clearly stained in outline (the outline of cell membrane is visible) as shown in the upper panel of FIG. 37B; weakly positive means that the cell membrane is only stained vaguely (the outline of cell membrane is invisible) as shown in the lower panel of FIG. 37B; and negative means that the cell membrane is not stained at all.

Example 14

Assessment of Invasion Inhibitory Activity

The cells were exposed to each antibody as follows. First, H460-LNM35 cells were suspended at a concentration of $5 \times 10^4$ to $2 \times 10^5$ cells/ml in RPMI1640 medium (0.25% FCS). Then, the prepared cell suspension was aliquoted into microcentrifuge tubes (Eppendorf tubes), and each antibody was added at a concentration of 1.5 to 5 μg/ml thereto. The tubes were allowed to stand at room temperature for 30 minutes. Then, the processed cells were used in the subsequent invasion assay according to a method described in a reference (Kozaki K et al., Cancer Res. 60: 2535-40 (2000)). Specifically, 1 ml of RPMI1640 (5% FCS) was added to each well (bottom chamber) of a 24-well plate, and then a cell culture insert with 8-μm pores, coated with 10 μg of reconstituted basement membrane matrix matrigel, or a "Matrigel Invasion Chamber (Becton Dickinson)" with the coating of reconstituted basement membrane matrix matrigel was placed at each well of the 24-well plate. The H460-LNM35 cell suspension ($5 \times 10^4$ to $2 \times 10^5$ cells/ml) after antibody exposure in RPMI1640 (0.25% FCS) was aliquoted (0.5 ml) into each upper chamber ($2.5 \times 10^4$ to $1 \times 10^5$ cells/chamber). Then, the cells were incubated at 37° C. under 5% $CO_2$ for 48 hours. The remaining cells and matrigel were thoroughly removed from the upper chambers with cotton swabs. After fixing with 70% ethanol solution, the cells in the bottom wells were stained with a Giemsa staining solution. The cells in the bottom wells were counted under a microscope. The percent invasion inhibitory activity relative to that of the antibody non-treated group was determined for each antibody according to the formula shown below. The result is shown in FIG. 6(A).

Invasion inhibitory activity (%)=(Number of invading cancer cells in the presence of an antibody/Number of invading cancer cells in the absence of antibody)×100

Figure 6:
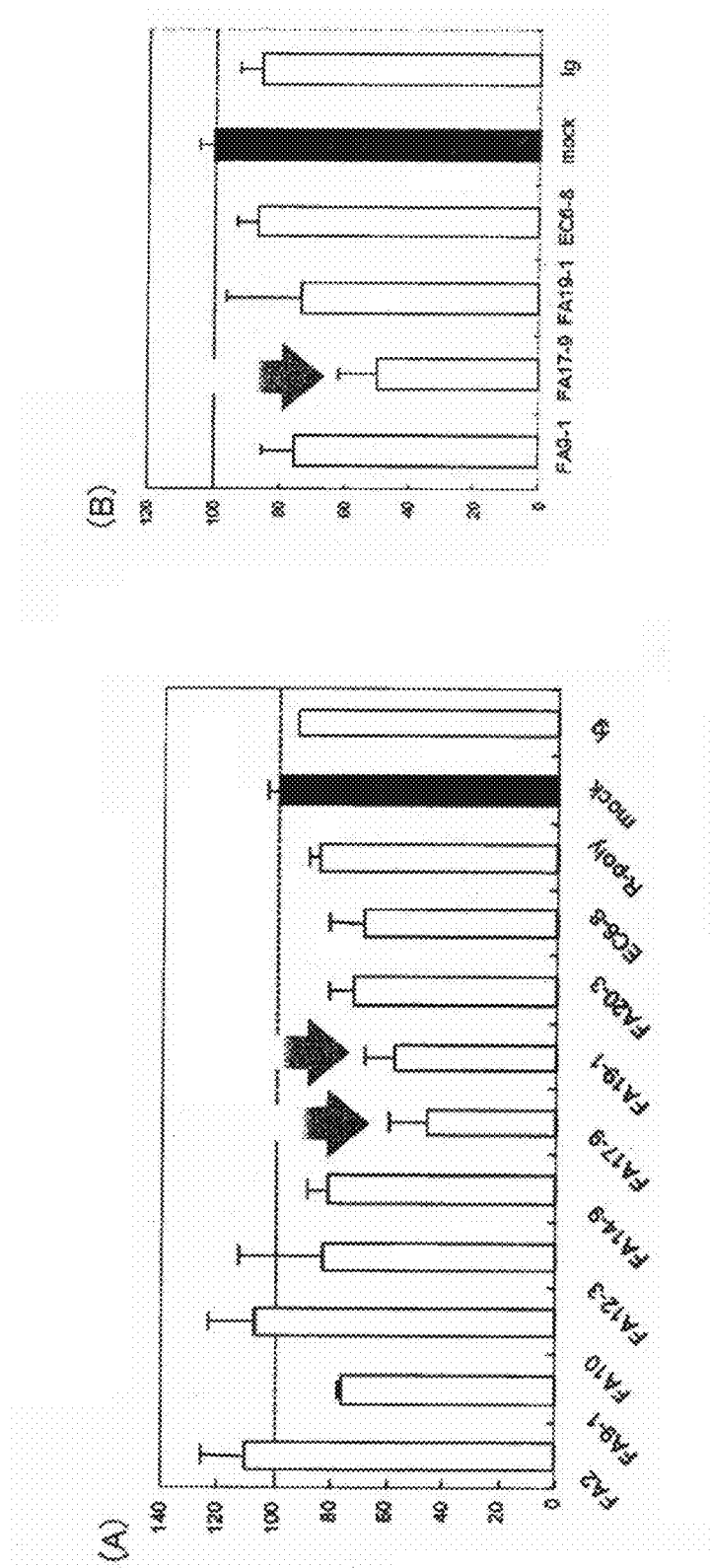
FIG. 6: A shows in a graph activity of the antibodies to inhibit cell invasion. The horizontal axis indicates antibody number and the vertical axis indicates the activity of inhibiting cell invasion when the activity of negative control (mock) is taken as 100%. Open bar indicates detection result in the test group using IgG antibody fractions, while filled bar (mock) indicates detection in the control group. B shows in a graph activity of the antibodies to inhibit cell migration. The horizontal axis indicates antibody number and the vertical axis indicates the activity of inhibiting cell migration when the activity of negative control (mock) is taken as 100%. Open bars indicate detection result in the test group using IgG antibody fractions, while filled bars (mock) indicate detection in the control group.

The result shown in FIG. 6(A) demonstrates that antibodies FA17-9 and FA19-1, in particular, have the stronger activity of inhibiting the invasion of cells of the high metastatic human lung cancer cell line H460-LNM35 than the control antibody (mouse IgG).

Example 15

Assessment of Migration Inhibitory Activity

In the same manner described above, the cells were exposed to each antibody as follows. First, H460-LNM35 cells were suspended at a concentration of $5 \times 10^4$ to $2 \times 10^5$ cells/ml in RPMI1640 medium (0.25% FCS). Then, the prepared cell suspension was aliquoted into microcentrifuge tubes (Eppendorf tubes), and each antibody was added at a concentration of 1.5 to 5 μg/ml thereto. The tubes were allowed to stand at room temperature for 30 minutes. Then, the processed cells were used in the subsequent motility assay according to a method described in a reference (Kozaki K et al., Cancer Res. 60: 2535-40 (2000)). Specifically, 1 ml of RPM11640 (5% FCS) was added to each well (bottom chamber) of a 24-well plate, and then a cell culture insert with 8-μm pores (Becton Dickinson) was placed at each well of the 24-well plate. The H460-LNM35 cell suspension ($5 \times 10^4$ to $2 \times 10^5$ cells/ml) after antibody exposure in RPMI1640 (0.25% FCS) was aliquoted (0.5 ml) into each upper chamber ($2.5 \times 10^4$ to $1 \times 10^5$ cells/chamber). Then, the cells were incubated at 37° C. under 5% $CO_2$ for 24 hours. The remaining cells were thoroughly removed from the upper chambers with cotton swabs. After fixing with 70% ethanol solution, the cells in the bottom wells were stained with a Giemsa staining solution. The cells in the bottom wells were counted under a microscope. The percent motility relative to the antibody non-treated group was determined for each antibody according to the formula shown below. The result is shown in FIG. 6(B).

Motility (%)=(Number of migrating cancer cells in the presence of antibody/Number of migrating cancer cells in the absence of antibody)×100

The result shown in FIG. 6(B) demonstrates that antibodies FA17-9 and FA19-1, in particular, have a stronger activity of inhibiting the migration of cells of the high metastatic human lung cancer cell line H460-LNM35 than the control antibody (mouse IgG).

Example 16

Analysis of CLCP1 Expression in Cells of High Metastatic and Low Metastatic Cell Lines Derived from NCI-H460

Previously, the present inventors isolated two types of sublines from the parental line NCI-H460 based on the degree of metastatic activity of the cells transplanted into mice. FA19-1 staining showed that the expression level of CLCP1 on the cell surface of NCI-H460-LNM35, a high metastatic line, was higher than that of NCI-H460-N15, a low metastatic line (FIG. 17). The parental line NCI-H460 was also stained with FA19-1 by the same method. The result demonstrated that the cells are a heterogeneous cell population. Thus, for the first time, CLCP1 expressed on the cell surface was suggested in some way to be involved in the metastatic activity (FIG. 17).

Example 17

Expression Pattern of the CLCP1 Antigen in Various Cancer Cell Lines (FCM)

The CLCP1 expression pattern in various cancer cell lines was assessed by FCM using an anti-CLCP1 antibody (FA19-1; 5 µg/ml). The cell lines used and their origins are listed in Tables 2-1 and 2-1.

TABLE 2-1

| CELL NAME | ORIGIN OF CANCER | NUMBER |
|---|---|---|
| A549 | LUNG CANCER | CCL-185 |
| ChaGo-K-1 | LUNG CANCER | HTB-168 |
| DMS114 | LUNG CANCER | CRL-2066 |
| NCI-H1299 | LUNG CANCER | CRL-5803 |
| NCI-H1373 | LUNG CANCER | CRL-5866 |
| NCI-H1793 | LUNG CANCER | CRL-5896 |
| NCI-H2170 | LUNG CANCER | CRL-5928 |
| NCI-H226 | LUNG CANCER | CRL-5826 |
| NCI-H358 | LUNG CANCER | CRL-5807 |
| NCI-H460 | LUNG CANCER | HTB-177 |
| NCI-H520 | LUNG CANCER | HTB-182 |
| NCI-H522 | LUNG CANCER | CRL-5810 |
| NCI-H596 | LUNG CANCER | HTB-178 |
| LC174 | LUNG CANCER | Aichi Cancer Center |
| LC176 | LUNG CANCER | Aichi Cancer Center |
| LC319 | LUNG CANCER | Aichi Cancer Center |
| PC-14 | LUNG CANCER | ECACC90071810 |
| SK-LU-1 | LUNG CANCER | HTB-57 |
| SK-MES-1 | LUNG CANCER | HTB-58 |
| GCIY | STOMACH CANCER | RCB0555 |
| HGC-27 | STOMACH CANCER | RCB0500 |
| KATO III | STOMACH CANCER | HTB-103 |
| MKN-1 | STOMACH CANCER | JCRB0252 |
| MKN-45 | STOMACH CANCER | JCRB0254 |
| MKN74 | STOMACH CANCER | JCRB0255 |
| OCUM-1 | STOMACH CANCER | JCRB0192 |

TABLE 2-1-continued

| CELL NAME | ORIGIN OF CANCER | NUMBER |
|---|---|---|
| SCH | STOMACH CANCER | JCRB0251 |
| Caco-2 | LARGE INTESTINE CANCER | HTB-37 |
| LOVO | LARGE INTESTINE CANCER | CCL-229 |
| SW480 | LARGE INTESTINE CANCER | CCL-228 |
| Caki-1 | KIDNEY CANCER | HTB-46 |
| KLM-1 | PANCREAS CANCER | RCB2138 |
| MIA Paca-2 | PANCREAS CANCER | CRL-1420 |
| PANC-1 | PANCREAS CANCER | CRL-1469 |
| PK1 | PANCREAS CANCER | RCB1972 |

TABLE 2-2

| PK-45p | PANCREAS CANCER | RCB2141 |
|---|---|---|
| PK59 | PANCREAS CANCER | RCB1901 |
| BT-20 | BREAST CANCER | HTB-19 |
| BT-474 | BREAST CANCER | HTB-20 |
| BT-549 | BREAST CANCER | HTB-122 |
| HCC1395 | BREAST CANCER | CRL-2324 |
| HCC1500 | BREAST CANCER | CRL-2329 |
| MCF7 | BREAST CANCER | HTB-22 |
| SK-BR-3 | BREAST CANCER | HTB-30 |
| T-47D | BREAST CANCER | HTB-133 |
| ZR-75-1 | BREAST CANCER | CRL-1500 |
| 22Rv1 | PROSTATE CANCER | CRL-2505 |
| PC3 | PROSTATE CANCER | CRL-1435 |
| T24 | BLADDER CANCER | HTB-4 |
| Hela | CERVICAL CANCER | CCL-2 |
| T98G | NEUROBLASTOMA | CRL-1690 |
| A431 | EPIDERMOID CANCER | CRL-1555 |
| Raji | LYMPHOMA | CCL-86 |
| Daudi | LYMPHOMA | CCL-213 |
| Jurkat, clone E6-1 | LYMPHOMA | TIB-152 |
| HL-60 | LYMPHOMA | CCL-240 |
| THP-1 | LEUKEMIA | TIB-202 |
| U-937 | LEUKEMIA | CRL-1593.2 |
| HEL | LEUKEMIA | ACC11 |
| MEG-01 | LEUKEMIA | CRL-2021 |
| HUV-EC-C | VASCULAR ENDOTHELIAL CELL | CRL-1730 |
| 293T | FETAL KIDNEY CELL | RCB2202 |

The result showed that CLCP1 was expressed at high levels, as seen in FIGS. 18 and 19. The mean fluorescence intensities (MFI) are shown in FIG. 20.

In addition to lung cancer, cancer cell lines expressing CLCP1 at high levels include, in particular, kidney cancer (for example, Caki-1 cell line), bladder cancer (for example, T24 cell line), prostate cancer (for example, PC3 cell line), pancreas cancer (for example, PK-45p cell line), stomach cancer (for example, GCIY cell line), large intestine cancer (for example, SW480 cell line), and breast cancer (for example, BT-20 cell line). In particular, when MFI is 20 or greater in FIG. 20, the expression can be said to be significantly enhanced.

Example 18

Functional Analysis of Monoclonal Antibodies (WB and FCM)

Figure 13:
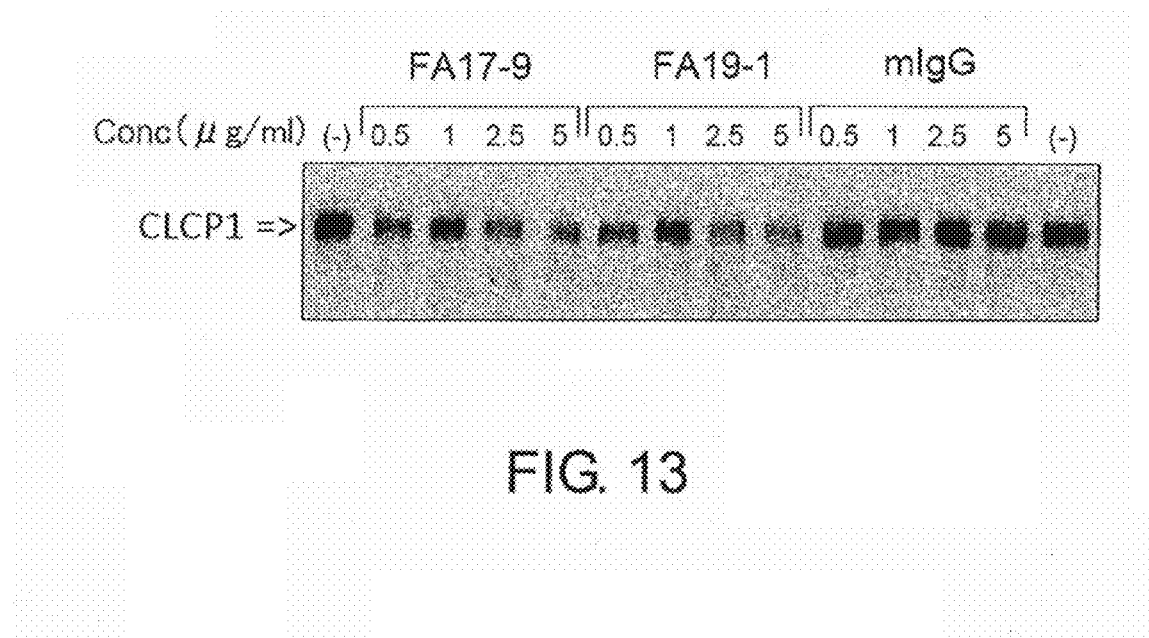
FIG. 13 shows in a photograph Western blot for CLCP1 in LNM35 after exposure to FA17-9 or FA19-1. LNM35 cells were exposed to FA17-9 or FA19-1 at the indicated concentrations for 24 hours, and then equal amounts of cell lysates were used for Western blot analysis by FA19-1 in the same manner as described in FIG. 7(B). The result suggested that the degradation (internalization) of CLCP1 was induced by FA17-9 and FA19-1 at a concentration of 0.5 μg/ml.

In the same manner described above, the cells were exposed to each antibody as follows. First, H460-LNM35 cells were suspended at a concentration of $6 \times 10^4$ cells/ml in RPMI1640 medium (10% FCS). The prepared cell suspension was aliquoted (0.5 ml) into 6-well culture plates (Becton Dickinson) ($3 \times 10^4$ cells/well). Then, the indicated antibodies were added at the indicated concentrations to each well (FIG. 7(B): 1, 2.5, and 5 µg/ml; FIG. 13: 0.5, 1, 2.5, and 5 µg/ml), and the wells were incubated at 37° C. under 5% $CO_2$ for 24 hours. After washing with PBS, 200 µl of lysis buffer (50 mM Tris (pH 6.8), 5% glycerol, 2% SDS) was added to each well to prepare cell lysates. In the same manner described above, the protein concentrations of the cell lysates were determined using the DC Protein Assay Kit (Bio-Rad). Then, 2-mercaptoethanol was added at 5.3% to the lysates. After heating, 5 µg each of the lysates were subjected to SDS-PAGE, followed by Western blotting with antibody FA19-1 and an HRP-labeled anti-mouse antibody. The result showed that FA9-1, FA17-9, FA19-1, and EC6-8 reduced the CLCP1 signal as compared to the untreated cells or cells exposed to the control mouse IgG (FIGS. 7(B) and 13). The exposure to an anti-CLCP1 antibody was demonstrated to induce CLCP1 degradation, Similarly to that induced by SEMA4B exposure which has been reported in Nagai H, et al., Oncogene 26: 4025-4031 (2007).

Figure 14:
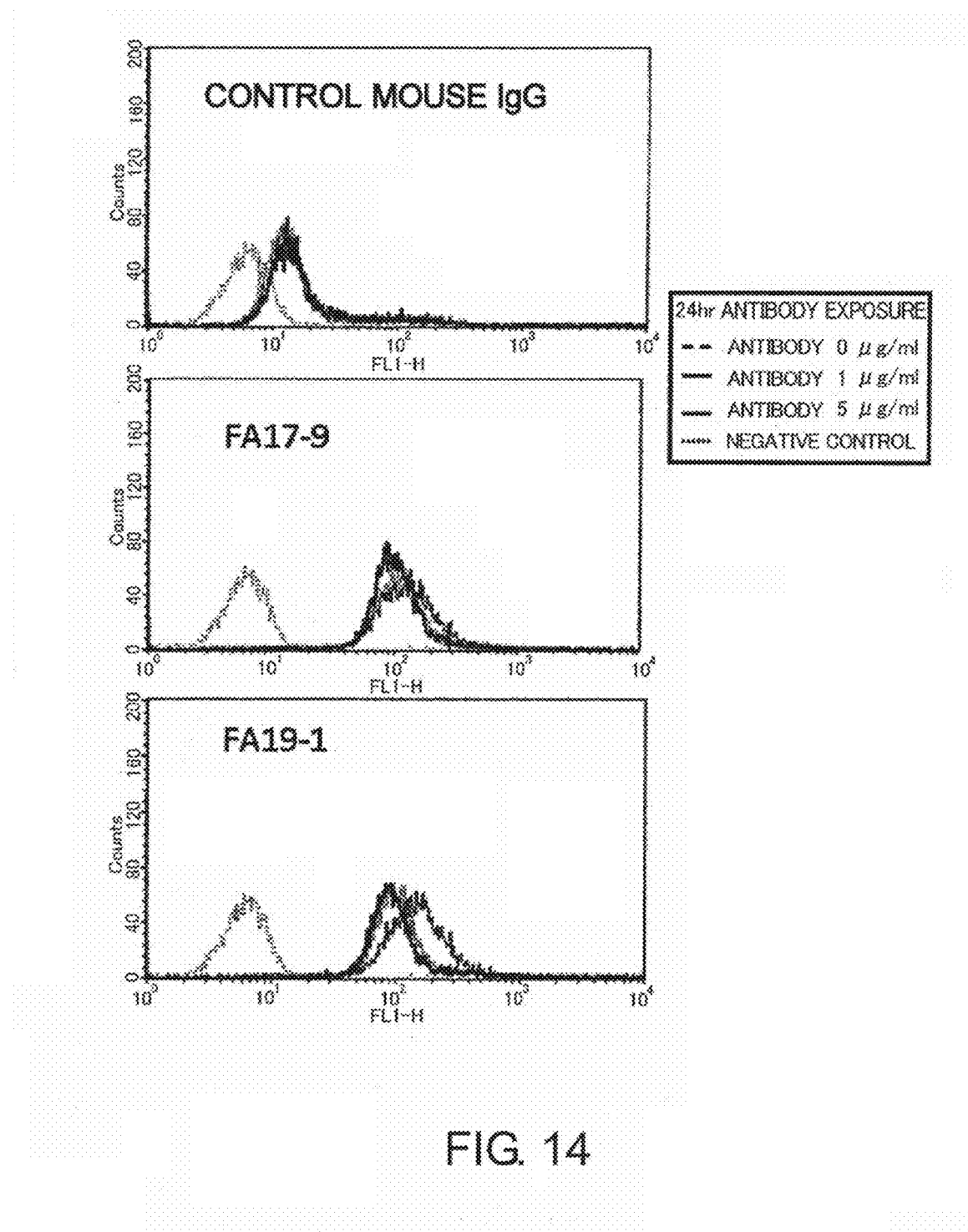
FIG. 14 shows in graphs flow cytometric analysis after exposure to each antibody. Flow cytometric analysis was performed for each of control mouse IgG; FA17-9, and FA19-1 after 24 h exposure at a concentration of 1 or 5 μg/ml, followed by PBS wash. The exposure to FA19-1 reduced the reactivity to cell surface CLCP1. This suggests that CLCP1 degradation (internalization) was induced on the cell surface.

In the same manner, H460-LNM35 cells were exposed to FA17-9, FA19-1, or control mouse IgG (at a concentration of 1 µg/ml or 5 µg/ml) in 6-well culture plates, and incubated at 37° C. under 5% $CO_2$ for 24 hours. After washing with PBS, the cells were detached using PBS/0.5 mM EDTA to prepare cell suspensions. Then, the cells were analyzed by flow cytometry with FACS Caliber (Becton Dickinson) using the same antibodies used in the above treatment and an Alexa Flour 488-labeled anti-mouse antibody (Molecular Probe) (FIG. 14). The result showed that the FA19-1 exposure reduced the expression level of CLCP1 on the cell surface. Thus, the exposure to anti-CLCP1 antibody FA19-1 was demonstrated to induce the degradation of CLCP1 on the cell surface or internalization of CLCP1 into cells.

Example 19

Preparation of Novel Antibodies

Clones of novel antibodies 2AA_62-4, 2AA_83-6, 2AA_111-3, 2AA_171-1, and 2AA_197-3 were isolated using as an immunogen a purified protein of the extracellular domain (ECD: extra-cellular domain) of human CLCP1, which was prepared as described in Example 3. Furthermore, clones of novel antibodies 6AA_17-2, 6AA44-3, 6AA_60-1, 6AA_61-2, and 6AA_95-5 were isolated using as an immunogen a purified partial protein (FA) containing the FA58C domain of human CLCP1, which was prepared as described in Example 3.

Example 20

Assessment of Novel Antibodies for Their Binding Affinity by FCM

The novel antibodies were assessed for their binding affinity by FCM using the same method described in Example 9. Three clones (2AA_171-1, 6AA_17-2, and 2AA_197-3) were shown to be more reactive than FA19-1 (FIG. 24).

Example 21

Epitope Mapping of Novel Antibodies (1) Prediction of Recognized Domains Based on the Reactivity to Partial Protein Fragments in ELISA The domains recognized by the antibodies were predicted by ELISA using the immunizing antigens prepared as described in Example 3. The purified protein of the extracellular domain of human CLCP1 and purified partial protein containing the human CLCP1 FA58C domain were each diluted to 0.5 µg/ml with PBS. The resulting solutions were added at 50 µl/well to plates (NUNC; MaxiSorp). The plates were allowed to stand at room temperature for four hours or more to immobilize the proteins. After blocking with BSA, each antibody diluted to 1 µg/ml with PBS was added to the plates for the first reaction. The plates were allowed to stand at room temperature for one hour. An HRP-labeled anti-mouse antibody was added for the second reaction according to a conventional method. The antibodies bound to each immobilized protein were detected by this reaction. The result showed that 2AA_171-1 recognized the extracellular domain but not the partial protein containing the FA58C domain (FIG. 25).

(2) Prediction Based on a Competitive Inhibition Experiment by FCM (Specific Description on the Procedure of the Experimental Method)

Competitive inhibition experiments on the novel antibodies were carried out by FCM using the same method described in Example 7. The inhibition experiments were achieved by using all combinations of biotinylated antibodies and non-labeled antibodies. As an example, the result on three clones (2AA_171-1, 6AA_17-2, and 2AA_197-3) which were found to be more reactive than FA19-1 by FCM, is shown in Table 3 and FIG. 31. 6AA_17-2 and 2AA_62-4 competed with both EC6-8 and FA19-1.

TABLE 3

| | | INHIBITION ANTIBODY | | | | | |
|---|---|---|---|---|---|---|---|
| | | 2AA_62-4 | 2AA_83-6 | 2AA_111-3 | 2AA_171-1 | 2AA_197-3 | 6AA_17-2 |
| (A) | | | | | | | |
| CONCENTRATION OF | 0 | 5.16 | 5.16 | 5.16 | 5.16 | 5.16 | 5.16 |
| INHIBITION ANTIBODY | 0.5 | 5.63 | 5.39 | 5.40 | 4.81 | 3.50 | 5.55 |
| [µg/mL] | 2.5 | 5.53 | 5.74 | 5.92 | 4.74 | 1.84 | 5.74 |
| (B) | | | | | | | |
| CONCENTRATION OF | 0 | 7.82 | 7.82 | 7.82 | 7.82 | 7.82 | 7.82 |
| INHIBITION ANTIBODY | 0.5 | 7.54 | 8.04 | 7.49 | 5.18 | 7.27 | 7.51 |
| [µg/mL] | 2.5 | 7.65 | 7.75 | 7.61 | 2.64 | 6.65 | 7.27 |
| (C) | | | | | | | |
| CONCENTRATION OF | 0 | 4.87 | 4.87 | 4.87 | 4.87 | 4.87 | 4.87 |
| INHIBITION ANTIBODY | 0.5 | 5.03 | 5.94 | 5.23 | 5.49 | 5.86 | 3.38 |
| [µg/mL] | 2.5 | 4.39 | 6.13 | 5.36 | 5.52 | 5.57 | 1.67 |

TABLE 3-continued

| | | INHIBITION ANTIBODY | | | | | | |
|---|---|---|---|---|---|---|---|---|
| | | 6AA_35-4 | 6AA_44-3 | 6AA_60-1 | 6AA_61-2 | 6AA_95-5 | FA19-1 | EC6-8 |
| (A) | | | | | | | | |
| CONCENTRATION | 0 | 5.16 | 5.16 | 5.16 | 5.16 | 5.16 | 5.16 | 5.16 |
| OF INHIBITION | 0.5 | 5.10 | 5.23 | 5.08 | 5.11 | 4.87 | 5.10 | 5.23 |
| ANTIBODY [µg/mL] | 2.5 | 5.03 | 5.21 | 5.28 | 5.24 | 5.49 | 5.29 | 4.95 |
| (B) | | | | | | | | |
| CONCENTRATION | 0 | 7.82 | 7.82 | 7.82 | 7.82 | 7.82 | 7.82 | 7.82 |
| OF INHIBITION | 0.5 | 7.15 | 7.44 | 7.14 | 7.46 | 7.35 | 7.62 | 7.67 |
| ANTIBODY [µg/mL] | 2.5 | 7.75 | 7.33 | 7.49 | 6.55 | 7.72 | 7.59 | 8.11 |
| (C) | | | | | | | | |
| CONCENTRATION | 0 | 4.87 | 4.87 | 4.87 | 4.87 | 4.87 | 4.87 | 4.87 |
| OF INHIBITION | 0.5 | 5.37 | 5.63 | 5.86 | 5.78 | 5.74 | 5.08 | 3.61 |
| ANTIBODY [µg/mL] | 2.5 | 5.29 | 5.81 | 6.26 | 6.34 | 5.92 | 3.37 | 2.12 |

(3) Epitope Grouping

Epitope grouping was carried out based on the results described in (1) and (2). The prediction result is shown in FIG. 33. Only 2AA_171-1 recognizes the outside of the region containing FA58C and the others recognize the region containing FA58C. 6AA_17-2 and 2AA_62-4 compete with both EC6-8 and FA19-1, and recognize an epitope adjacent to the epitope recognized by the two. 2AA_83-6, 6AA_44-3, 6AA_60-1, 6AA_61-2, and 6AA_95-5 recognize an identical epitope, but the epitope was different from that for EC6-8 and FA19-1. 2AA_111-3 and 2AA_197-3 did not compete with any antibodies.

Example 22

Assessment of Cellular Internalization by FCM

By the same method described in Example 18, NCI-H460-LNM35 or A549 cells cultured in 6-well plates were exposed to each of non-labeled antibodies (5 µg/ml) for 24 hours, and then detached with PBS/0.5 mM EDTA. The remaining CLCP1 molecule on the cell membrane was detected by FCM (FIG. 34) or WB (FIG. 35) using the biotinylated antibodies. The result showed strong internalization activity.

FIG. 36 shows the analysis results of converting the portion of the remaining molecules into an MFI value by taking the level of CLCP1 detected on the cell membrane in the presence of the control antibody in FIG. 34 to be 100%. When comparing to the internalization-inducing activity of FA19-1 which has high metastasis inhibitory activity, three clones were found to be functional antibodies having higher internalization-inducing activity than FA19-1 (FIG. 36).

Example 23

Biacore

To analyze the binding activity kinetically, a binding activity assay was carried out using Biacore. Biacore 3000 (GE Healthcare Bio-Sciences) was used throughout the process described below. The evaluation system employed was the capture method using an anti-mouse antibody as a capture.

An anti-mouse antibody (GE Healthcare Bio-Sciences) was immobilized onto the CMS sensor chip (GE Healthcare Bio-Sciences) by the amino-coupling method. Various monoclonal antibodies diluted to 2 µg/ml with HBS EP Buffer (GE Healthcare Bio-Sciences) were injected at 10 µl/min over the chip. Then, a purified protein of the whole extracellular domain of CLCP1 derived from 293T was diluted in a two-fold dilution series up to five stages, and injected as an analyte at a rate of 20 µl/min. The concentrations of dilutes of each monoclonal antibody as an analyte were determined as follows. First, the KD value (M) for each antibody was calculated at a prefixed analyte concentration of 5 µg/ml, and then starting at a concentration 10 times higher than the concentration (M) corresponding to the KD value, the analyte was diluted in a two-fold dilution series up to five stages. The resulting sensorgrams were analyzed to calculate the association and dissociation rate constants for each antibody. The KD value was determined from the rate constants (FIG. 39).

Example 24

Isolation of Antibody VH and VL Genes, and Identification of CDRs

The positive hybridomas that were selected were cultured, and total RNAs were prepared from them by a conventional method. Then, cDNAs were isolated by 5'-RACE using the GeneRacer™ kit (Invitrogen). The VH genes (cDNAs) were isolated by PCR [35 cycles of (94° C. for 30 seconds, 57° C. for 30 seconds, and 72° C. for 50 seconds)] using the cDNAs as a template with Plutinum Taq High Fidelity (Invitrogen) and GeneRacer™ 5' primer [5'-CGACTGGAGCACGAG-GACACTGA-3' (SEQ ID NO: 33)] and CHI [mouse IgG1 constant region 1) 3' primer (5'-AATTTTCTTGTCCAC-CTGG-3' (SEQ ID NO: 34)]. Similarly, the VL genes (cDNAs) were also isolated by PCR using GeneRacer™ 5' primer and Cκ (κ constant region) 3' primer [5'-CTAACACTCAT-TCCTGTTGAAGCTCT-3' (SEQ ID NO: 35)].

The VH and VL genes were each subcloned into the pT7Blue vector, and then their sequences were determined using an automatic sequencer (Applied Biosystems) or an automatic fluorescence sequencer. The amino acid sequences of VH and VL, and respective CDR sequences were deduced from die obtained nucleotide sequences encoding VH and VL (FIGS. 9 to 11, and FIG. 38).

The respective sequences identified are shown below.
(Amino Acid Sequence of FA17-9)
VH CDR1: the amino acid sequence, of SEQ ID NO: 7
VH CDR2: the amino acid sequence of SEQ ID NO: 8
VH CDR3: the amino acid sequence of SEQ ID NO: 9
VL CDR1: the amino acid sequence of SEQ ID NO: 12
VL CDR2: the amino acid sequence of SEQ ID NO: 56

VL CDR3: the amino acid sequence of SEQ ID NO: 13
VH: the amino acid sequence of SEQ ID NO: 6
VL: the amino acid sequence of SEQ ID NO: 11
(Nucleotide Sequence of FA17-9)
VH: the nucleotide sequence of SEQ ID NO: 5
VL: the nucleotide sequence of SEQ ID NO: 10
(Amino Acid Sequence of FA19-1)
VH CDR1: the amino acid sequence of SEQ ID NO: 16
VH CDR2: the amino acid sequence of SEQ ID NO: 17
VH CDR3: the amino acid sequence of SEQ ID NO: 18
VL CDR1: the amino acid sequence of SEQ ID NO: 21
VL CDR2: the amino acid sequence of SEQ ID NO: 57
VL CDR3: the amino acid sequence of SEQ ID NO: 22
VH: the amino acid sequence of SEQ ID NO: 15
VL: the amino acid sequence of SEQ ID NO: 20
(Nucleotide Sequence of FA19-1)
VH: the nucleotide sequence of SEQ ID NO: 14
VL: the nucleotide sequence of SEQ ID NO: 19.
(Amino Acid Sequence of 6AA_17-2)
VH CDR1: the amino acid sequence of SEQ ID NO: 60
VH CDR2: the amino acid sequence of SEQ ID NO: 61
VH CDR3: the amino acid sequence of SEQ ID NO: 62
VL CDR1: the amino acid sequence of SEQ ID NO: 65
VL CDR2: the amino acid sequence of SEQ ID NO: 66
VL CDR3: the amino acid sequence of SEQ ID NO: 67
VH: the amino acid sequence of SEQ ID NO: 59
VL: the amino acid sequence of SEQ ID NO: 64
(Nucleotide Sequence of 6AA_17-2)
VH: the nucleotide sequence of SEQ ID NO: 58
VL: the nucleotide sequence of SEQ ID NO: 63

Example 25

Preparation and Assessment of Chimeric Antibodies (FA19-1 and FA17-9)

Primers for PCR amplification were designed based on the identified gene sequences. The primers are shown below. FA17-9 and FA19-1 are antibodies derived from the same genome sequence. Thus, the same primers were used for these antibodies.

```
Heavy chain forward primer:
                                    (SEQ ID NO: 68)
5'-CCCaagcttACCATGGAATGGAGTTGGATATTTC-3'

Heavy chain reverse primer:
                                    (SEQ ID NO: 69)
5'-CCGctcgagACGGTGACCGTGGTCC-3'

Light chain forward primer:
                                    (SEQ ID NO: 70)
5'-CCCaagcttACCATGAGACCGTCTATTCAGTTCC-3'

Light chain reverse primer:
                                    (SEQ ID NO: 71)
5'-AATAcgtacgTTTGATTTCCAGCTTGGTCCC-3'
```

(lowercase letters indicate restriction enzyme sequence)
By a conventional method, the PCR products amplified using the primers described above were inserted into an antibody production vector (LONZA) carrying the constant region of human IgG1 as an insert. After establishing chimeric antibody-producing cell lines, the chimeric antibodies were purified from the culture supernatants using Protein A according to the protocol recommended by LONZA Co.
Chimeric FA17-9 antibody and chimeric FA19-1 antibody were assessed for their reactivity by FCM. At concentrations 10 to 0.01 µg/ml, the antibodies exhibited a binding activity comparable to those of the original mouse antibodies (FIG. 21).

Example 26

ADCC (Antibody-Dependent Cellular Cytotoxicity) Test

ADCC assay was performed while changing the antibody concentration from 0.1 to 10 µg/ml or the E/T ratio (effector/target ratio) from 100 to 5. The antibodies used were chimeric FA17-9 antibody and chimeric FA19-1 antibody whose binding activities were confirmed in Example 25. The target cells used were cancer cell lines, for example, NCI-H460-LNM35. The effector cells used were PBMC prepared from human peripheral blood by a conventional method using density gradient centrifugation.

ADCC was assessed by lactate dehydrogenase release assay. Cytotoxicity (%) was calculated according to the following formula:

$$[\% \text{ Cytotoxicity}] = 100 \times (E - S_E - S_T)/(M - S_T)$$

where E represents "experimental release", which means the activity of lactate dehydrogenase released from target cells during co-incubation of target cells with antibody and effector cells; $S_E$ represents the activity of lactate dehydrogenase spontaneously released from effector cells; $S_T$ represents the activity of lactate dehydrogenase spontaneously released from target cells; and M represents the activity of lactate dehydrogenase maximally released from target cells upon addition of lysis solution (9% Triton X-100).

(1) ADCC of Chimeric FA19-1 Antibody and Chimeric FA17-9 antibody on NCI-H460-LNM35 Cells ADCC assay was performed using as a target NCI-H460-LNM35 cells while changing the antibody concentration (FIG. 22A) or E/T ratio (effector/target ratio) (FIG. 22B). ADCC against $10^4$ target cells (NCI-H460-LNM35) was determined by adding chimeric antibody at 10 µg/ml, 1 µg/ml, or 0.1 µg/ml under the fixed condition of $2 \times 10^5$ effector cells, and calculated according to the above formula. The result showed that chimeric FA19-1 antibody has higher ADCC than chimeric FA17-9 antibody. The cytotoxic effect was strongest at an antibody concentration of 10 µg/ml. Then, to test the influence of E/T ratio, ADCC against $10^4$ target cells was assessed at a fixed antibody concentration of 10 µg/ml in the presence of varying number of effector cells: 100 times greater ($10^6$ cells), 50 times greater ($5 \times 10^5$ cells), 20 times greater ($2 \times 10^5$ cells), 10 times greater ($10^5$ cells), and 5 times greater ($5 \times 10^4$ cells) number of effector cells. The result showed that ADCC was strongest at an E/T ratio of 50 and the cytotoxicity was 32.4% in the presence of chimeric FA19-1 antibody.

(2) ADCC Against NCI-H460-LNM35 or A549 in the Presence of Chimeric FA19-1 Antibody (Various Donors)

ADCC against NCI-H460-LNM35 and A549 target cells was assessed in the presence of effector cells derived from each of five donors (A to E) under the conditions in which maximal ADCC was observed in the assay described above (in the presence of 10 µg/ml chimeric antibody at E/T ratio of 50). The result showed that the cytotoxicity was observed with each donor and was particularly strong (47.1%) against A549 high-expressing CLCP1 (FIG. 23). Thus, the present inventors for the first time discovered the cytotoxicity induced by using antibodies against CLCP1.

Example 27

Production of Humanized Antibody (FA19-1)

Human frameworks were selected and the CDRs were replaced with those of mouse monoclonal antibody FA19-1 according to the CDR grafting method.

Specifically, homology search was carried out separately for the heavy chain variable region framework and light chain variable region framework. The result revealed that the framework regions of antibody FA19-1 heavy chain variable region [hereinafter, FR1 to FR4 regions (SEQ ID NOs: 36 to 39); hereinafter, collectively FR] were highly homologous to FR regions (SEQ ID NOs: 41 to 44) of the human antibody of accession number U00570 (SEQ ID NO: 40) (see FIG. 40). The homology between the heavy chain FRs of mouse antibody FA19-1 and CDR-grafted human antibody was 67/87=77.0%. The amino acid sequence was designed to adequately graft the CDR1, CDR2, and CDR3 of FA19-1 heavy chain (SEQ ID NOs: 16 to 18) to the FR region of the human antibody of accession number U00570. Thus, the amino acid sequence was designed for the humanized antibody heavy chain variable region (SEQ ID NO: 45). Hereinafter, the humanized heavy chain is abbreviated as "FA19RHA".

Likewise, the FR1 to FR4 (SEQ ID NOs: 46 to 49; hereinafter, collectively FR) of antibody FA19-1 light chain was found to be highly homologous to the FR regions (SEQ ID NOs: 51 to 54) of the human antibody of accession number U96396 (SEQ ID NO: 50) (see FIG. 41). The homology of light chain FR between mouse antibody FA19-1 and CDR-grafted human antibody was 63/80=78.8%. The amino acid sequence was designed to adequately graft the light chain and heavy chain CDR1, CDR2, and CDR3 (SEQ ID NOs: 21, 57, and 22) of FA19-1 to the FR region of the human antibody of accession number U96396. Thus, the amino acid sequence was designed for the humanized antibody light chain variable region (SEQ ID NO: 55). Hereinafter, the humanized light chain is abbreviated as "FA19RKA".

Meanwhile, the light chain CDR2 of FA19-1 contains a cysteine. This may cause an antibody stability problem due to aggregation or such. Thus, a variant was also designed by substituting serine, which is adopted in the mouse germline, for the cysteine in the humanized FA19-1 antibody designed as described above. HTCTLQP (SEQ ID NO: 57) in the light chain CDR2 of FA19-1 was converted into HTSTLQP (SEQ ID NO: 72) in serine-substituted light chain CDR2. Hereinafter, the modified light chain is referred to as "serine-substituted light chain".

To construct the genes for the heavy chain and light chain variable region of humanized antibody, synthetic oligo DNAs of about 50 nucleotides were designed to be able to hybridize to each other in a region of about 20 nucleotides. The synthetic oligo DNAs were assembled together by PCR to prepare the genes encoding each variable region. After cleaving at the HindIII restriction enzyme site at the end of the 5' synthetic oligo DNA and at the XhoI (RHA) or BsiWI (RICA; serine-substituted light chain) site at the end of the 3' synthetic oligo DNA, the digested DNAs were each inserted into a pEE6.4 vector carrying the human IgG1 constant region or a pEE14.4 vector carrying the human κ chain constant region, both of which are from Lonza.

By a conventional method using lipofectamine 2000, 293T cells were co-transfected using the constructed expression vectors for serine-substituted light chain, FA19RHA, and FA19RKA in the combinations of FA19RHA and FA19RKA, and FA19RHA and serine-substituted light chain. After 48 hours, the culture supernatants were collected and the IgG concentrations in the culture supernatants were determined by sandwich ELISA using a goat anti-human IgG antibody, Fcγ fragment-specific (Stratech Scientific) and goat anti-human kappa light chain peroxidase conjugate (Sigma). The concentrations were calculated from a standard curve prepared using purified human IgG (Cappel) available on the market.

Using the culture supernatants whose IgG concentrations had been determined, the activities of the chimeric antibody, humanized antibody, and serine-substituted humanized antibody were assessed and compared by ELISA for the purified protein of the extracellular domain of CLCP1 described in Example 21. The result showed that the activity was comparable between the chimeric antibody and serine-substituted humanized antibody, and between the humanized antibody and serine-substituted humanized antibody. Thus, humanized FA19-1 was successfully designed (FIGS. 42 and 43).

Example 28

Tumor Treatment by Monoclonal Antibody and Its Effect of Suppressing Cancer Cell Growth and Metastasis H460-LNM35 cells were transplanted to KSN/slc nude mice (obtained from Japan SLC, Inc.) under the skin in the left inguinal region. Then, an antibody was administered to the mice, and they were monitored for lung and lymph node metastasis. Each group contained four mice. The dose was 10 μg/g (BW) and the number of times of administration was 10.

Figure 15:
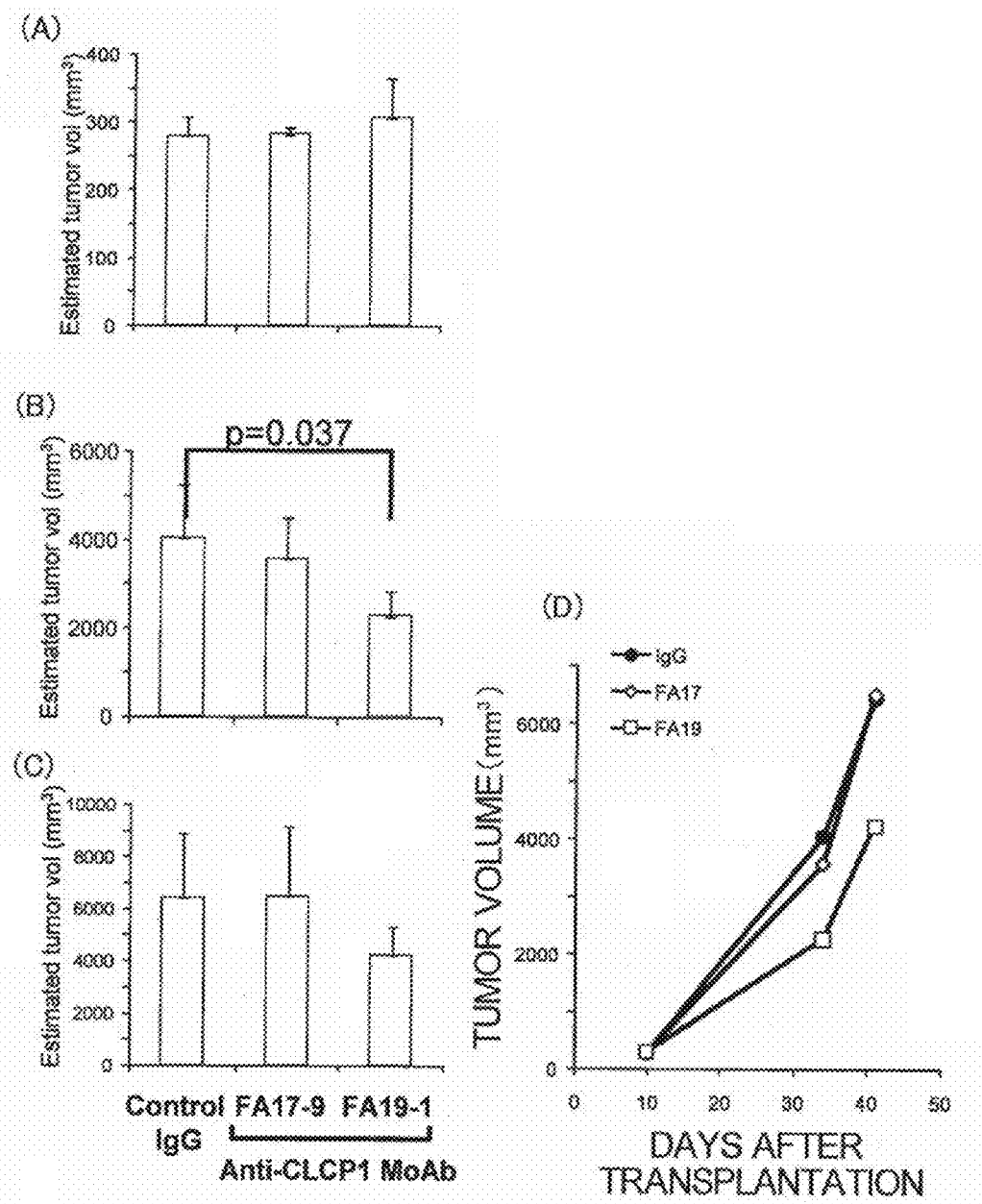
FIG. 15 shows in graphs results of observing changes in the lung and lymph node metastasis as a result of antibody administration after KSN/slc nude mice was transplanted with LNM35 cells under the skin in the left inguinal region. (A)

The volume of transplanted tumor was measured on day 10 (ten days) after transplantation of H460-LNM35 cells ($5\times10^6$ cells). Mice with the closest tumor volumes were selected and divided into three groups each containing four (FIG. 15A).

On day 10 to day 37 (ten to 37 days after transplantation), an antibody was administered once every three days for a total of ten times (10 μg/g (BW)). On day 46 (46 days after transplantation), the mice were sacrificed to measure the body weight, tumor volume, and tumor weight. Statistical analysis used was t-test for the body weight, tumor volume, and tumor weight, or Mann-Whitney U test for the number of lung metastasis sites and lymph node weight.

The tumor volume is shown in FIGS. 15A-D. Various weights (body weight excluding tumor weight, tumor weight, retroperitoneal lymph node, ipsilateral axillary lymph node, and contralateral inguinal lymph node) and the number of lung metastatic nodules at the time of sacrifice are shown in FIG. 16.

Regarding the therapeutic effect against the tumor, the administration of FA19-1 had a tendency of suppressing tumor growth as compared to the control IgG group. There was a significant difference on day 34 (34 days after transplantation). However, no significant difference was noted on day 41 (41 days after transplantation).

On the other hand, FA17-9 showed a tendency of suppressing tumor growth to some extent on day 34 (34 days after transplantation). However, there was no difference in the effect on day 41 (41 days after transplantation). The weight at the time of sacrifice seemed to be heavier than that of the control; however, there was no significant difference. Furthermore, the growth rate was elevated after termination of administration of antibody FA17-9 (data not shown).

The effect of suppressing cancer cell metastasis is summarized as follows. Administration of FA 19-1 was demonstrated to significantly suppress metastasis, in particular, lung metastasis. FA17-9 also had a tendency of suppressing metastasis, although the effect was weaker as compared to FA19-1 (FIG. 16C). Furthermore, in the groups administered with FA19-1 or FA17-9 (FIGS. 16D-F), lymph node enlargement due to metastasis was hardly seen in any lymph node. However, there was no significant difference due to variation in the control antibody administration group.

Antibody administration did not weaken any animal. There was no change in body weight excluding the tumor weight (FIG. 16A).

Specifically, this experiment demonstrated that these antibodies had the activity of inhibiting cell growth, in addition to the activity of inhibiting metastasis.

The data on the metastasis suppression by FA17-9 or FA19-1, in particular, suppression of lung metastasis, were highly reproducible. In addition, the data obtained demonstrated that 6AA_17-2 administration also suppressed lung metastasis (FIG. 26).

Example 29

Identification of Site Recognized by Monoclonal Antibodies

Monoclonal antibodies FA19-1, 6AA_17-2, EC6-8, and FA17-9 were examined for their recognition sites in CLCP1. FA17-9 is highly homologous to FA19-1 in both heavy chain and light chain, and their usage is same. Thus, the sites recognized by them were assumed to be identical. For this reason, FA17-9 was excluded from the procedure of narrowing down the recognition sites.

First, to narrow down the recognition sites, recombinant proteins corresponding to the portions of aa 195-aa 492 (aa: amino acid residue) and aa 195-aa 453 in SEQ ID NO: 2 were produced in *E. coli*. The reactivity of each antibody to the proteins was assessed by ELISA. To produce the recombinant proteins in *E. coli*, which correspond to aa 195-aa 492 and aa 195-aa 453 in SEQ ID NO: 2, *E. coli* expression vectors were constructed. Specifically, partial CLCP1 fragments were amplified by PCR using the primers described below. The fragments were digested with EcoRI and SalI, and then inserted into pET28a between the EcoRI and XhoI sites. BL21 was transformed with the constructed expression vectors. The expression was induced with 1 mM IPTG. The insoluble fractions were solubilized with 8 M Urea. The proteins were purified using TALON column.

```
Common 5' primer:
                                        (SEQ ID NO: 73)
CGGAATTCTGTTTGGACACTGCATCC aa 195-aa 492 3' primer:
                                        (SEQ ID NO: 74)
ACGCGTCGACTGGTTGCGTAAATTTTGG aa 195-aa 453 3' primer:
                                        (SEQ ID NO: 75)
ACGCGTCGACAGGAATAAACTGACATCC
EcoRI and SalI cleavage sites are underlined.
```

Each antibody was assayed by ELISA using the purified proteins prepared described above. A recombinant protein of the whole extracellular domain produced in *E. coli* was also used as a control. The result showed that all three types of antibodies tested were reactive to the *E. coli*-produced recombinant protein corresponding to aa 195-aa 492 in SEQ ID NO: 2 but not to the *E. coli*-produced recombinant protein corresponding to aa 195-aa 453 (FIG. 27). This suggests that the sites recognized by the antibodies are located within the region of aa 454-aa 492 in SEQ ID NO: 2, which only exists in the purified protein of aa 195-aa 492 in SEQ ID NO: 2.

Then, four proteins which start from aa 195 in SEQ ID NO: 2 on the N terminal side, and differ from one another in C terminus were prepared to further narrow down the recognition sites. The respective proteins correspond to the regions of aa 195-aa 469, aa 195-aa 465, aa 195-aa 461, and aa 195-aa457 in SEQ ID NO: 2. The proteins were produced and purified by the same method as described using the pET28a expression system. The 3' primers used are shown below. The 5' primer used was the same as the common 5' primer shown above.

```
aa 195-aa 469 3' primer:
                                        (SEQ ID NO: 76)
ACGCGTCGACTGCTGTTCCGAGGAGGTGG aa 195-aa 465 3' primer:
                                        (SEQ ID NO: 77)
ACGCGTCGACAGGTGGAGGTTGAGTAAG aa 195-aa 461 3' primer:
                                        (SEQ ID NO: 78)
ACGCGTCGACAGTAAGTTTTGGAGGACG aa 195-aa 457 3' primer:
                                        (SEQ ID NO: 79)
ACGCGTCGACAGGACGACCTTTAGGAAT
SalI cleavage site is underlined.
```

Each antibody was assayed by ELISA using the purified proteins prepared described above. The result on FA19-1, 6AA_17-2, and EC6-8 is shown in FIGS. 28, 29, and 30. The purified proteins corresponding to aa 195-aa 492 and aa 195-aa 453 in SEQ ID NO: 2, prepared in the narrowing down process described above, were also used.

FA19-1 was reactive to the purified protein of aa 195-aa 469 in SEQ ID NO: 2, but not to the protein of aa 195-aa 465 and the smaller proteins (FIG. 28). However, the reactivity seemed to be slightly weaker than that to aa 195-aa 492. Thus, the sequence around aa 465 in SEQ ID NO: 2 was suspected to have an influence on the antibody binding. On the other hand, the absorbance in the presence of any protein other than those described above was comparable to that in the absence of an antibody. Thus, FA19-1 was demonstrated to be non-reactive to the proteins.

6AA_17-2 was reactive to aa 195-aa 465 in SEQ ID NO: 2 but not to aa 195-aa 461. This suggests that the binding requires at least the sequence of aa 461-aa 465 in SEQ ID NO: 2 (FIG. 29).

EC6-8 was reactive to aa 195-aa 461 in SEQ ID NO: 2 but not at all to aa 195-aa 457. This suggests that the binding requires at least the sequence of aa 457-aa 461 in SEQ ID NO: 2 (FIG. 30).

Next, partial sequences of CLCP1 were inserted into pGEX4T-1, an expression vector for GST fusion protein, to produce recombinant proteins in *E. coli*. The binding activity to the recombinant proteins was analyzed by ELISA to more accurately identify the sites recognized by FA17-9, FA19-1, 6AA_17-2, and EC6-8. The four partial sequences inserted were: aa 451-aa 460 (hereinafter GST451-60), aa 456-aa 465 (hereinafter GST456-65), aa 461-aa 470 (hereinafter GST461-70), and aa 466-aa 475 (hereinafter GST466-75) in SEQ ID NO: 2. The genes encoding these sequences, which were inserted into pGEX4T-1, were prepared by PCR using the following primers:

```
GST451-60/F1 primer:
                                       (SEQ ID NO: 80)
cgtcctccaaaactttgaagatctctcgagCGGCCGCAT
CGTGACTGACTGACG GST451-60/F2 primer:
                                       (SEQ ID NO: 81)
CGGGATCCTTTATTCCTAAAGGTcgtcctccaaaacttt
gaagatctctcgag GST456-65/F1 primer:
                                       (SEQ ID NO: 82)
actcaacctccaccttgaagatctctcgagCGGCCGCAT
CGTGACTGACTGACG GST456-65/F2 primer:
                                       (SEQ ID NO: 83)
CGGGATCCCGTCCTCCAAAACTTactcaacctccaccTT
gaagatctctcgag GST461-70/F1 primer:
                                       (SEQ ID NO: 84)
cctcggaacagcaattgaagatctctcgagCGGCCGCAT
CGTGACTGACTGACG GST461-70/F2 primer:
                                       (SEQ ID NO: 85)
CGGGATCCACTCAACCTCCACCTcctcggaacagcaatt
gaagatctctcgag GST466-75/F1 primer:
                                       (SEQ ID NO: 86)
gacctcaaaaacacttgaagatctctcgagCGGCCGCAT
CGTGACTGACTGACG GST466-75/F2 primer:
                                       (SEQ ID NO: 87)
CGGGATCCCCTCGGAACAGCAATgacctcaaaaacactt
gaagatctctcgag GST-peptide/R primer:
                                       (SEQ ID NO: 88)
AACTGCAGGCATCGTGGTGTCACGCTCGTC
BamHI and PstI sites are underlined.
```

Lowercase letters indicate the annealing sequence in the F1 or F2 primer. The sequence starting from the 5' BamHI site in the F2 primer up to the 3' end of the F1 primer encodes a partial CLCP1.

Using pGEX4T-1 as a template, the BamHI-PstI region of pGEX4T-1 additionally containing a portion of the gene encoding each partial sequence was amplified by PCR with a set of primers: F1 primer corresponding to each partial sequence and GST-peptide/R primer containing the PstI cleavage sequence of pGEX4T-1. Then, using the amplified fragment as a template, the BamHI-PstI fragment additionally containing the entire partial sequence to be inserted was amplified by PCR with a set of primers: F2 primer corresponding to each partial sequence and GST-peptide/R primer. The final product was digested with BamHI and PstI, and substituted for the BamHI-PstI region in pGEX4T-1 to construct an expression vector for each GST fusion protein. BL21 was transformed with the resulting expression vectors. The expression was induced with 1 mM IPTG The GST fusion proteins were purified from the soluble fractions using a glutathione column.

FA17-9, FA19-1, 6AA_17-2, and EC6-8 were assayed by ELISA using the prepared various GST fusion proteins to assess their binding activities. The result showed that FA17-9 and FA19-1 were reactive to GST461-70 while 6AA_17-2 was reactive to GST456-65 (FIG. 44). EC6-8 exhibited a strong binding activity to GST451-60 but weak reactivity to GST456-65.

(Sites Recognized by FA19-1 and FA17-9)

The result shown in FIG. 28 indicates that the recognition site is located at aa 454-aa 469 and a small region immediately adjacent to its C terminal side. The result shown in FIG. 44 demonstrates that the two antibodies are sufficiently reactive to aa 461-aa 470 but do not bind to other regions (the absorbance is comparable to the background level with other peptides). On the whole, the recognition site is located at aa 461-aa 470 in SEQ ID NO 2. Alternatively, the antibodies can be defined as isolated antibodies that bind to a peptide consisting of the amino acid sequence of positions 461 to 470 in SEQ ID NO: 2, but do not bind to a peptide consisting of the amino acid sequence of positions 466 to 475 in SEQ ID NO: 2, and a peptide consisting of the amino acid sequence of positions 456 to 465 in SEQ ID NO: 2.

(Site Recognized by 6AA_17-2)

The result shown in FIG. 29 indicates that the recognition site is located within aa 454-aa 465 in SEQ ID NO: 2. The result shown in FIG. 44 demonstrates that 6AA_17-2 is highly reactive to aa 456-aa 465 inside the region of aa 454-aa 465 but does not bind to other regions (the absorbance is comparable to the background level with other peptides). Thus, the site recognized by the antibody is located at aa 456-aa 465 in SEQ ID NO: 2. Alternatively, the antibody can be defined as an isolated antibody that binds to a peptide consisting of the amino acid sequence of positions 456 to 465 in SEQ ID NO: 2, but does not bind to a peptide consisting of the amino acid sequence of positions 451 to 460 in SEQ ID NO: 2, and a peptide consisting of the amino acid sequence of positions 461 to 470 in SEQ ID NO: 2.

(Site Recognized by EC6-8)

The result shown in FIG. 30 demonstrates that the recognition site is located within aa 454-aa 461 in SEQ ID NO: 2. The antibody is highly reactive to aa 451-aa 460, as seen in FIG. 44. The antibody is not reactive to aa 461-aa 470. Thus, the site recognized by the antibody is assumed to be located at the common site aa 454-aa 460. Alternatively, the antibody can be defined as an isolated antibody that binds to a peptide consisting of the amino acid sequence of positions 451 to 465 in SEQ ID NO: 2 but does not bind to a peptide consisting of the amino acid sequence of positions 461 to 470 in SEQ ID NO: 2.

The results described above are summarized in a diagram in FIG. 32. The sites recognized by the three antibodies (FA19-1, FA17-9, and 6AA_17-2), which were demonstrated to have metastasis-suppressing activity, are located within aa 456-aa 470. Thus, aa 456-aa 470 of CLCP1 (SEQ ID NO: 2) is an essential sequence as a binding site for antibodies with metastasis-suppressing activity.

Industrial Applicability

The antibodies and antibody fragments of the present invention bind to human CLCP1 and have the activity of inhibiting migration, invasion, metastasis, or cell growth, and/or cytotoxic activity. In another aspect, the antibodies have ADCC against cancer cells. Thus, the antibodies of the present invention are highly expected to be applicable in treating cancer diseases such as malignant tumor.

The present invention is not to be construed as being limited to any particular examples and embodiments described herein. Various variations and modifications of the invention apparent to those skilled in the art without departing from the scope of the claimed invention are also included in the present invention. The content of all research reports, published patent applications, and patent publications expressly cited herein are hereby incorporated by reference in their entirety.

The invention claimed is:

1. An isolated antibody that recognizes a peptide consisting of the amino acid sequence of positions 456 to 470 in SEQ ID NO: 2.

2. The antibody of claim 1, which recognizes a peptide consisting of the amino acid sequence of positions 461 to 470 in SEQ ID NO: 2 but does not recognize a peptide consisting of the amino acid sequence of positions 466 to 475 in SEQ ID NO: 2.

3. The antibody of claim 1, which recognizes a peptide consisting of the amino acid sequence of positions 456 to 465 in SEQ ID NO: 2 but does not recognize a peptide consisting of the amino acid sequence of positions 451 to 460 in SEQ ID NO: 2.

4. The isolated antibody of claim 1, which has an activity of inhibiting the migration of a cancer cell expressing CLCP1.

5. The isolated antibody of claim 1, which has an activity of inhibiting the invasion of a cancer cell expressing CLCP1.

6. The isolated antibody of claim 1, which has an activity of inhibiting the growth of a cancer cell expressing CLCP1.

7. The isolated antibody of claim 1, which has an activity of inhibiting the metastasis of a cancer cell expressing CLCP1.

8. The isolated antibody of claim 1, which has cytotoxicity against a cancer cell expressing CLCP1.

9. The isolated antibody of claim 4, wherein the cancer cell expressing CLCP1 is a kidney cancer cell, urinary bladder tumor cell, prostate cancer cell, pancreas cancer cell, stomach cancer cell, large intestine cancer cell, breast cancer cell, or lung cancer cell.

10. The isolated antibody of claim 1, wherein the amino acid sequences of each of the complementarity determining regions of heavy-chain variable region (VH CDR1, VH CDR2, and VH CDR3) and each of the complementarity determining regions of light-chain variable region (VL CDR1, VL CDR2, and VL CDR3) are selected from (A), (B) or (C):

(A)
 (1) VH CDR1: the amino acid sequence of SEQ ID NO: 16 or an amino acid sequence substantially identical thereto;

(2) VH CDR2: the amino acid sequence of SEQ ID NO: 17 or an amino acid sequence substantially identical thereto;

(3) VH CDR3: the amino acid sequence of SEQ ID NO: 18 or an amino acid sequence substantially identical thereto;

(4) VL CDR1: the amino acid sequence of SEQ ID NO: 21 or an amino acid sequence substantially identical thereto;

(5) VL CDR2: the amino acid sequence of SEQ ID NO: 57 or 72 or an amino acid sequence substantially identical thereto;

(6) VL CDR3: the amino acid sequence of SEQ ID NO: 22 or an amino acid sequence substantially identical thereto;

(B)
(1) VH CDR1: the amino acid sequence of SEQ ID NO: 7 or an amino acid sequence substantially identical thereto;

(2) VH CDR2: the amino acid sequence of SEQ ID NO: 8 or an amino acid sequence substantially identical thereto;

(3) VH CDR3: the amino acid sequence of SEQ ID NO: 9 or an amino acid sequence substantially identical thereto;

(4) VL CDR1: the amino acid sequence of SEQ ID NO: 12 or an amino acid sequence substantially identical thereto;

(5) VL CDR2: the amino acid sequence of SEQ ID NO: 56 or an amino acid sequence substantially identical thereto;

(6) VL CDR3: the amino acid sequence of SEQ ID NO: 13 or an amino acid sequence substantially identical thereto;

(C)
(1) VH CDR1: the amino acid sequence of SEQ ID NO: 60 or an amino acid sequence substantially identical thereto;

(2) VH CDR2: the amino acid sequence of SEQ ID NO: 61 or an amino acid sequence substantially identical thereto;

(3) VH CDR3: the amino acid sequence of SEQ ID NO: 62 or an amino acid sequence substantially identical thereto;

(4) VL CDR1: the amino acid sequence of SEQ ID NO: 65 or an amino acid sequence substantially identical thereto;

(5) VL CDR2: the amino acid sequence of SEQ ID NO: 66 or an amino acid sequence substantially identical thereto;

(6) VL CDR3: the amino acid sequence of SEQ ID NO: 67 or an amino acid sequence substantially identical thereto.

11. The isolated antibody of claim 1, wherein the amino acid sequences of the heavy-chain variable region (VH) and light-chain variable region (VL) are selected from (A), (B) or (C):

(A)
(1) VH: the amino acid sequence of SEQ ID NO: 45 or 15, or an amino acid sequence substantially identical thereto;

(2) VL: the amino acid sequence of SEQ ID NO: 55 or 20, or an amino acid sequence substantially identical thereto;

(B)
(1) VH: the amino acid sequence of SEQ ID NO: 6 or an amino acid sequence substantially identical thereto;

(2) VL: the amino acid sequence of SEQ ID NO: 11 or an amino acid sequence substantially identical thereto;

(C)
(1) VH: the amino acid sequence of SEQ ID NO: 59 or an amino acid sequence substantially identical thereto;

(2) VL: the amino acid sequence of SEQ ID NO: 64 or an amino acid sequence substantially identical thereto.

12. An isolated antibody that recognizes the same epitope as the antibody of claim 1.

13. The isolated antibody of claim 1, which is an Fab, Fab', F(ab')$_2$, Fv, scFv, dsFv, diabody, or sc(Fv)2.

14. The isolated antibody of claim 1, which is an IgG antibody.

15. The isolated antibody of claim 1, which is a humanized antibody.

16. An isolated nucleic acid encoding the isolated antibody of claim 1.

17. A vector that carries the nucleic acid of claim 16 in an expressible manner.

18. A transformed cell comprising the vector of claim 17.

19. A method for producing an antibody, which comprises the steps of:
(a) culturing the transformed cell of claim 18; and
(b) isolating and purifying the antibody as an expression product.

20. A pharmaceutical composition comprising the isolated antibody of claim 1 and a pharmaceutically acceptable carrier.

21. An agent which comprises an antibody of claim 1, wherein the agent is selected from the group consisting of:
(i) an agent for inhibiting cancer cell migration, wherein the antibody has an activity of inhibiting the migration of a cancer cell expressing CLCP1;
(ii) an agent for inhibiting cancer cell invasion, wherein the antibody has an activity of inhibiting the invasion of a cancer cell expressing CLCP1;
(iii) an agent for inhibiting cancer cell metastasis, wherein the antibody has an activity of inhibiting the metastasis of a cancer cell expressing CLCP1;
(iv) an agent for inhibiting cancer cell growth, wherein the antibody has an activity of inhibiting the cell growth of a cancer cell expressing CLCP1; and
(v) a cytotoxic agent against cancer cell, wherein the antibody has cytotoxicity against a cancer cell expressing CLCP1.

22. A kit for use in immunological detection of CLCP1 expression in a cell or tissue, which comprises an antibody of claim 1.

23. A diagnostic agent for prognosis of cancer, which comprises an antibody of claim 1.

24. A diagnostic kit for prognosis of cancer, which comprises an antibody of claim 1.

25. An immunological method comprising the steps of:
(a) contacting an isolated cell or tissue with an antibody of claim 1; and
(b) detecting CLCP1 expression in the cell or tissue.

26. A method for diagnosing cancer, which comprises the steps of contacting an isolated pathological tissue with an antibody of claim 1, and immunologically detecting the expression of CLCP1 in a cell of the pathological tissue.

27. A diagnostic method for cancer prognosis, which comprises the steps of contacting an isolated pathological tissue with an antibody of claim 1, and immunologically detecting the expression of CLCP1 in a cell of the pathological tissue, wherein the survival rate is predicted to be lower for the group of clinical cases where the isolated pathological tissues are strongly positive in the histological staining than for the group of clinical cases where the isolated pathological tissues are weakly positive or negative in the histological staining.

28. A method of screening for a candidate substance that inhibits cancer cell growth, invasion, migration, or metastasis, or a candidate substance having cytotoxicity against a cancer cell, which comprises the steps of:
 (a) contacting a test substance with a peptide consisting of the amino acid sequence of positions 456 to 470 in SEQ ID NO: 2;
 (b) detecting the binding between a test substance and the peptide; and
 (c) selecting a test substance that binds to the peptide.

29. A method for inhibiting a migration of a cancer cell expressing CLCP1, which comprises the step of administering to a subject an antibody of claim 1 and has an activity of inhibiting the migration of a cancer cell expressing CLCP1.

30. A method for inhibiting an invasion of a cancer cell expressing CLCP1, which comprises the step of administering to a subject an antibody of claim 1 and has an activity of inhibiting the invasion of the cancer cell expressing CLCP1.

31. A method for inhibiting a metastasis of a cancer cell expressing CLCP1, which comprises the step of administering to a subject an antibody of claim 1 and has an activity of inhibiting the metastasis of the cancer cell expressing CLCP1.

32. A method for inhibiting a growth of a cancer cell expressing CLCP1, which comprises the step of administering to a subject an antibody of claim 1 and has the activity of inhibiting the growth of the cancer cell expressing CLCP1.

33. A method for damaging a cancer cell expressing CLCP1, which comprises the step of administering to a subject an antibody of claim 1 and has cytotoxicity against the cancer cell expressing CLCP1.

34. A method for treating a tumor expressing CLCP1 or a cancer expressing CLCP1, which comprises the step of administering to a subject an antibody of claim 1 and has the activity of inhibiting the growth of a cancer cell expressing CLCP1.

* * * * *